(12) United States Patent
Sin et al.

(10) Patent No.: US 7,323,447 B2
(45) Date of Patent: Jan. 29, 2008

(54) HEPATITIS C VIRUS INHIBITORS

(75) Inventors: Ny Sin, East Hampton, CT (US); Andrew Charles Good, Wallingford, CT (US); Brian Lee Venables, Durham, CT (US); Paul Michael Scola, Glastonbury, CT (US); Nicholas A. Meanwell, East Hampton, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 102 days.

(21) Appl. No.: 11/348,721

(22) Filed: Feb. 6, 2006

(65) Prior Publication Data

US 2006/0183694 A1  Aug. 17, 2006

Related U.S. Application Data

(60) Provisional application No. 60/650,798, filed on Feb. 8, 2005.

(51) Int. Cl.
*A61K 38/00* (2006.01)
*C07D 215/00* (2006.01)
*C07D 207/00* (2006.01)

(52) U.S. Cl. .................. 514/19; 546/153; 548/531
(58) Field of Classification Search .................. None
See application file for complete search history.

(56) References Cited

U.S. PATENT DOCUMENTS

| | | | | |
|---|---|---|---|---|
| 6,268,207 | B1 * | 7/2001 | Bailey | 435/280 |
| 2005/0153877 | A1 | 7/2005 | Miao et al. | |
| 2006/0172950 | A1 | 8/2006 | Wang et al. | |
| 2006/0199773 | A1 | 9/2006 | Sausker et al. | |

FOREIGN PATENT DOCUMENTS

| | | |
|---|---|---|
| WO | WO 98/17679 | 4/1998 |
| WO | WO 98/46597 * | 10/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 2004/103996 | 2/2000 |
| WO | WO 00/59929 | 10/2000 |
| WO | WO 02/060926 | 8/2002 |
| WO | WO 03/064416 A1 * | 1/2003 |
| WO | WO 03/053349 | 7/2003 |
| WO | WO 03/064416 | 7/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/096652 | 9/2006 |
| WO | WO 2006/119061 | 11/2006 |
| WO | WO 2006/122188 | 11/2006 |

OTHER PUBLICATIONS

U.S. Appl. No. 11/415,722, filed May 2, 2006, Wenying Li.
U.S. Appl. No. 11/481,536, filed Jul. 6, 2006, Hewawasam, et al.
Lauer, G.M. and Walker, B.D., "Hepatitis C Virus Infection", *N. Engl. J. Med.*, 2001, 345, 41-52.
Poupart, M.-A., Cameron, D.R., Chabot, C., Ghiro, E., Goudreau, N., Boulet, S., Poirier, M., and Tsantrizos, Y.S., "Solid-Phase Synthesis of Peptidomimetic Inhibitors for the Hepatitis C Virus NS3 Protease", *J. Org. Chem.*, 2001, 66, 4743-4751.
U.S. Appl. No. 11/591,253, filed Nov. 1, 2006, D'Andrea, et al.
Montse Llinas-Brunet, et al, "A Systematic Approach to the Optimization of Substrate-Based Inhibitors of the Hepatitis C Virus NS3 Protease: Discovery of Potent and Specific Tripeptide Inhibitors," *J. Med. Chem.*, 47, pp. 6584-6594, 2004.

* cited by examiner

*Primary Examiner*—Cscilia J. Tsang
*Assistant Examiner*—Thomas S. Heard
(74) *Attorney, Agent, or Firm*—Pamela A. Mingo

(57) ABSTRACT

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

26 Claims, No Drawings

HEPATITIS C VIRUS INHIBITORS

CROSS REFERENCE TO RELATED APPLICATION

The non-provisional application claims priority from the provisional application U.S. Ser. No. 60/650,798 filed Feb. 8, 2005.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. *N. Engl. J. Med.* 2001, 345, 41-52).

Presently, the most effective HCV therapy employs a combination of alpha-interferon and ribavirin, leading to sustained efficacy in 40% of patients. (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

A first aspect of the present disclosure provides a compound of formula (I)

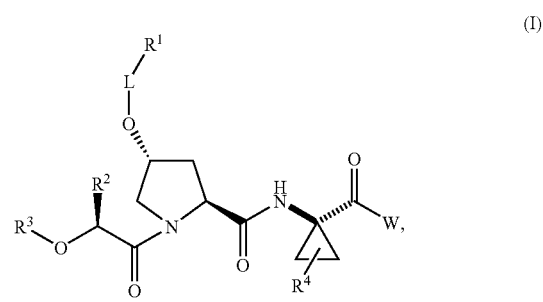

or a pharmaceutically acceptable salt thereof, wherein

L is absent or —C(O)—;

$R^1$ is heteroaryl or heterocyclyl wherein the heteroaryl and the heterocyclyl are optionally substituted with one, two, three, four, five, or six substituents independently selected from alkoxy, alkoxycarbonyl, alkoxycarbonyloxy, alkyl, alkylsulfanyl, aryl, arylalkoxy, carboxy, cyano, cycloalkyl, halo, haloalkoxy, haloalkyl, heteroaryloxy, heteroaryl, heteroarylcarbonyl, heterocyclyl, hydroxy, mercapto, —$NR^aR^b$, ($NR^aR^b$)alkyl, and ($NR^cR^d$)carbonyl;

$R^2$ is selected from hydrogen, alkenyl, alkoxyalkyl, alkoxycarbonylalkyl, alkyl, alkylaminoalkyl, aminoalkyl, aryl, arylalkyl, cycloalkyl, (cycloalkyl)alkyl, dialkylaminoalkyl, haloalkoxyalkyl, haloalkyl, heteroaryl, heteroarylalkyl, heterocyclyl, and heterocyclylalkyl;

$R^3$ is selected from hydrogen and $R^5$—NH—C(O)—;

$R^4$ is selected from hydrogen, alkenyl, alkyl, cycloalkyl, haloalkenyl, and haloalkyl;

$R^5$ is selected from alkyl, aryl, arylalkyl, carboxyalkyl, cycloalkyl, (cycloalkyl)alkyl, haloalkoxyalkyl, haloalkyl, heteroaryl, heteroarylalkyl, heterocyclyl, and heterocyclylalkyl;

one of $R^a$ and $R^b$ is selected from hydrogen, alkoxycarbonyl, alkyl, alkylcarbonyl, alkylsulfonyl, arylalkyl, arylcarbonyl, arylsulfonyl, cycloalkyl, formyl, and ($NR^cR^d$)carbonyl and the other is selected from hydrogen, alkyl, and cycloalkyl;

$R^c$ and $R^d$ are each independently selected from hydrogen and alkyl; and

W is selected from hydroxy and —NH—$SO_n$—$R^6$, wherein n is 1 or 2 and $R^6$ is selected from alkyl, aryl, cycloalkyl, (cycloalkyl)alkyl, heteroaryl, heterocyclyl, and —$NR^aR^b$.

In one embodiment of the first aspect the present disclosure provides a compound of formula (I) wherein $R^3$ is hydrogen.

In another embodiment of the first aspect the present disclosure provides a compound of formula (I) wherein $R^3$ is $R^5$—NH—C(O)—.

In another embodiment of the first aspect the present disclosure provides a compound of formula (I) wherein $R^3$ is $R^5$—NH—C(O)—; and W is —NH—$SO_n$—$R^6$.

In another embodiment of the first aspect the present disclosure provides a compound of formula (I) wherein $R^3$ is $R^5$—NH—C(O)—; W is —NH—SO$_n$—R$^6$; and L is —C(O)—.

In another embodiment of the first aspect the present disclosure provides a compound of formula (I) wherein $R^3$ is $R^5$—NH—C(O)—; W is —NH—SO$_n$—R$^6$; L is —C(O)—; and $R^1$ is

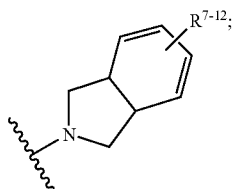

wherein
$R^7$, $R^8$, $R^9$, $R^{10}$, $R^{11}$, and $R^{12}$ are independently selected from hydrogen, alkoxy, alkoxycarbonyl, alkoxycarbonyloxy, alkyl, alkylsulfanyl, aryl, arylalkoxy, carboxy, cyano, cycloalkyl, halo, haloalkoxy, haloalkyl, heteroaryloxy, heteroaryl, heteroarylcarbonyl, heterocyclyl, hydroxy, mercapto, —NR$^a$R$^b$, (NR$^a$R$^b$)alkyl, and (NR$^c$R$^d$)carbonyl.

In another embodiment of the first aspect the present disclosure provides a compound of formula (I) wherein $R^3$ is $R^5$—NH—C(O)—; W is —NH—SO$_n$—R$^6$; L is —C(O)—; and $R^1$ is

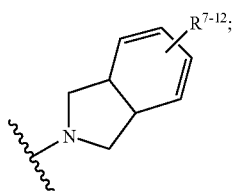

wherein one of $R^7$, $R^8$, $R^9$, $R^{10}$, $R^{11}$, and $R^{12}$ is halo and the rest are hydrogen.

In another embodiment of the first aspect the present disclosure provides a compound of formula (I) wherein $R^3$ is $R^5$—NH—C(O)—; W is —NH—SO$_n$—R$^6$; and L is absent.

In another embodiment of the first aspect the present disclosure provides a compound of formula (I) wherein $R^3$ is $R^5$—NH—C(O)—; W is —NH—SO$_n$—R$^6$; L is absent; and $R^1$ is

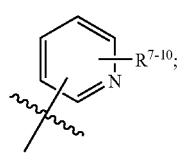

wherein $R^7$, $R^8$, $R^9$, and $R^{10}$ are independently selected from hydrogen, alkoxy, alkoxycarbonyl, alkoxycarbonyloxy, alkyl, alkylsulfanyl, aryl, arylalkoxy, carboxy, cyano, cycloalkyl, halo, haloalkoxy, haloalkyl, heteroaryloxy, heteroaryl, heteroarylcarbonyl, heterocyclyl, hydroxy, mercapto, —NR$^a$R$^b$, (NR$^a$R$^b$)alkyl, and (NR$^c$R$^d$)carbonyl.

In another embodiment of the first aspect the present disclosure provides a compound of formula (I) wherein $R^3$ is $R^5$—NH—C(O)—; W is —NH—SO$_n$—R$^6$; L is absent; and $R^1$ is

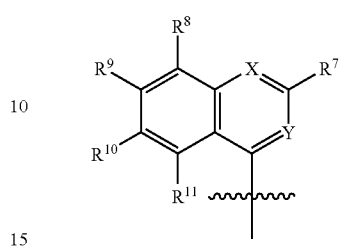

wherein
X is selected from N and CR$^{12}$;
Y is selected from N and CH; and
$R^7$, $R^8$, $R^9$, $R^{10}$, $R^{11}$ and $R^{12}$ are independently selected from hydrogen, alkoxy, alkoxycarbonyl, alkoxycarbonyloxy, alkyl, alkylsulfanyl, aryl, arylalkoxy, carboxy, cyano, cycloalkyl, halo, haloalkoxy, haloalkyl, heteroaryloxy, heteroaryl, heteroarylcarbonyl, heterocyclyl, hydroxy, mercapto, —NR$^a$R$^b$, (NR$^a$R$^b$)alkyl, and (NR$^c$R$^d$)carbonyl.

A second aspect of the present disclosure provides a compound of formula (II)

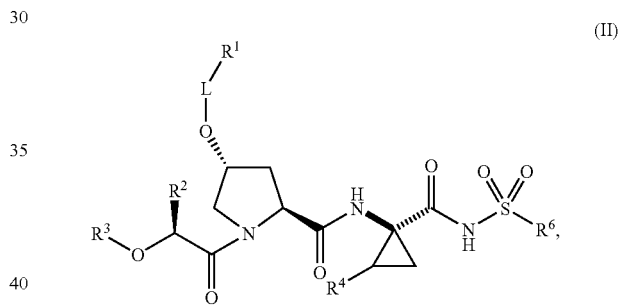

(II)

or a pharmaceutically acceptable salt thereof, wherein
$R^1$ is selected from

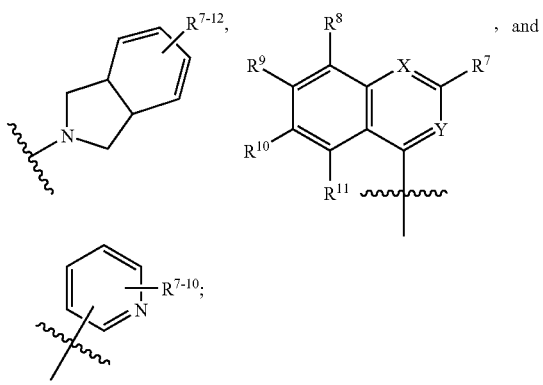

L is absent or —(O)—;
X is selected from N and CR$^{12}$;
Y is selected from N and CH; and
$R^7$, $R^8$, $R^9$, $R^{10}$, $R^{11}$ and $R^{12}$ are each independently selected from hydrogen, alkoxy, aryl, halo, and heteroaryl;

$R^2$ is selected from alkoxyalkyl, alkyl, aryl, cycloalkyl, (cycloalkyl)alkyl, and heteroarylalkyl;

$R^3$ is selected from hydrogen and $R^5$—NH—C(O)—;

$R^4$ is alkenyl or alkyl;

$R^5$ is selected from alkenyl, alkyl, aryl, cycloalkyl, and heteroarylalkyl;

$R^6$ is selected from aryl, cycloalkyl, heteroaryl, and —$NR^aR^b$; and $R^a$ and $R^b$ are alkyl.

In one embodiment of the second aspect the present disclosure provides a compound of formula (II) wherein $R^3$ is hydrogen.

In another embodiment of the second aspect the present disclosure provides a compound of formula (II) wherein $R^3$ is $R^5$—NH—C(O)—.

In a third aspect the present disclosure provides a composition comprising a compound of formula (I), or a pharmaceutically acceptable salt thereof, and a pharmaceutically acceptable carrier.

In another embodiment of the third aspect the present disclosure provides a composition comprising a compound of formula (I), or a pharmaceutically acceptable salt thereof, a pharmaceutically acceptable carrier, an interferon, and ribavirin.

In another embodiment of the third aspect the present disclosure provides a composition comprising a compound of formula (I), or a pharmaceutically acceptable salt thereof, a pharmaceutically acceptable carrier, and a second compound having anti-HCV activity.

In another embodiment of the third aspect the second compound having anti-HCV activity is an interferon.

In another embodiment of the third aspect the interferon is selected from interferon alpha 2B, pegylated interferon alpha, consensus interferon, interferon alpha 2A, and lymphoblastiod interferon tau.

In another embodiment of the third aspect the second compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fourth aspect the present disclosure provides a method of inhibiting the function of HCV serine protease comprising contacting the HCV serine protease with a compound of formula (I), or a pharmaceutically acceptable salt thereof.

In a fifth aspect the present disclosure provides a method of treating an HCV infection in a patient, comprising administering to the patient a therapeutically effective amount of a compound of formula (I), or a pharmaceutically acceptable salt thereof.

In one embodiment of the fifth aspect the compound is effective to inhibit the function of the HCV serine protease.

In another embodiment of the fifth aspect the method further comprises administering a second compound having anti-HCV activity prior to, after or simultaneously with the compound of formula (I), or a therapeutically acceptable salt thereof.

In another embodiment of the sixth aspect the second compound having anti-HCV activity is an interferon.

In another embodiment of the sixth aspect the interferon is selected from interferon alpha 2B, pegylated interferon alpha, consensus interferon, interferon alpha 2A, and lymphoblastiod interferon tau.

In another embodiment of the sixth aspect the method further comprises administering a second compound having anti-HCV activity prior to, after or simultaneously with the compound of formula (I), or a therapeutically acceptable salt thereof, wherein the second compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a seventh aspect the present disclosure provides the use of a compound of formula (I), or a pharmaceutically acceptable salt thereof, for the manufacture of a medicament for treating HCV infection in a patient.

In an eighth aspect the present disclosure provides the use of a composition comprising a compound of formula (I), or a pharmaceutically acceptable salt thereof, and a pharmaceutically acceptable carrier for the manufacture of a medicament for treating HCV infection in a patient.

Unless otherwise specifically noted herein, the terms set forth below will have the following definitions.

As used herein, the singular forms "a", "an", and "the" include plural reference unless the context clearly dictates otherwise.

The term "alkenyl," as used herein, refers to a straight or branched chain group of two to eight carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkoxycarbonyloxy," as used herein, refers to an alkoxycarbonyl group attached to the parent molecular moiety through an oxygen atom.

The term "alkyl," as used herein, refers to a group derived from a straight or branched chain saturated hydrocarbon containing from one to eight carbon atoms.

The term "alkylamino," as used herein, refers to —$NR^xR^y$, wherein one of $R^x$ and $R^y$ is hydrogen and the other is an alkyl group.

The term "alkylaminoalkyl," as used herein, refers to an alkyl group substituted with one, two, or three alkylamino groups.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "amino," as used herein, refers to —$NH_2$.

The term "aminoalkyl," as used herein, refers to an alkyl group substituted with one, two, or three amino groups.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group.

Representative examples of aryl groups include, but are not limited to, indanyl, indenyl, naphthyl, phenyl, and tetrahydronaphthyl. The aryl groups of the present disclosure can be optionally substituted with one, two, three, four, or five substituents independently selected from alkoxy, alkyl, a second aryl, carboxy, carboxyalkoxy, carboxyalkyl, cyano, halo, haloalkoxy, haloalkyl, heteroaryl, heterocyclyl, hydroxy, hydroxyalkyl, nitro, —$NR^aR^b$, ($NR^aR^b$)alkoxy, ($NR^aR^b$)alkyl, ($NR^cR^d$)carbonyl, and oxo; wherein the second aryl, the heteroaryl, and the heterocyclyl can be further optionally substituted with one, two, three, four, or five substituents independently selected from alkoxy, alkyl, cyano, halo, haloalkoxy, and nitro.

The term "arylalkoxy," as used herein, refers to an arylalkyl group attached to the parent molecular moiety through an oxygen atom.

The term "arylalkyl," as used herein, refers to an alkyl group substituted with one, two, or three aryl groups.

The term "arylcarbonyl," as used herein, refers to an aryl group attached to the parent molecular moiety through a carbonyl group.

The term "arylsulfonyl," as used herein, refers to an aryl group attached to the parent molecular moiety through a sulfonyl group.

The term "carbonyl," as used herein, refers to —C(O)—.

The term "carboxy," as used herein, refers to —$CO_2H$.

The term "carboxyalkoxy," as used herein, refers to a carboxyalkyl group attached to the parent molecular moiety through an oxygen atom.

The term "carboxyalkyl," as used herein, refers to an alkyl group substituted with one, two, or three carboxy groups.

The term "cyano," as used herein, refers to —CN.

The term "cycloalkyl," as used herein, refers to a saturated monocyclic, bicyclic, or tricyclic hydrocarbon ring system having three to seven carbon atoms and zero heteroatoms. Representative examples of cycloalkyl groups include, but are not limited to, cyclopropyl, cyclobutyl, cyclopentyl, cyclohexyl, and bicyclo[3.1.1]heptyl. The cycloalkyl groups of the present disclosure can be optionally substituted with one or two unsubstituted (cycloalkyl)alkyl groups or a haloalkyl group.

The term "(cycloalkyl)alkyl," as used herein, refers to an alkyl group substituted with one, two, or three cycloalkyl groups.

The term "dialkylamino," as used herein, refers to —$NR^xR^y$, wherein $R^x$ and $R^y$ are the same or different alkyl groups.

The term "dialkylaminoalkyl," as used herein, refers to an alkyl group substituted with one, two, or three dialkylamino groups.

The term "formyl," as used herein, refers to —C(O)H.

The terms "halo" and "halogen," as used herein, refer to F, Cl, Br, or I.

The term "haloalkenyl," as used herein, refers to an alkenyl group substituted by one, two, three, or four halogen atoms.

The term "haloalkoxy," as used herein, refers to a haloalkyl group attached to the parent molecular moiety through an oxygen atom.

The term "haloalkoxyalkyl," as used herein, refers to an alkyl group substituted with one, two, or three haloalkoxy groups.

The term "haloalkyl," as used herein, refers to an alkyl group substituted by one, two, three, or four halogen atoms.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a four- to six-membered aromatic or non-aromatic ring containing zero, one, or two additional heteroatoms selected from N, O, and S. The heteroaryl groups are attached to the parent molecular moiety through any substitutable carbon or nitrogen atom in the group. Representative examples of heteroaryl groups include, but are not limited to, benzimidazolyl, benzofuranyl, benzothienyl, furanyl, imidazolyl, indolyl, isoquinolinyl, isothiazolyl, isoxazolyl, naphthyridinyl, oxadiazolyl, oxazolyl, pyrazinyl, pyrazolyl, pyridazinyl, pyridinyl, pyrimidinyl, pyrrolyl, quinolinyl, thiazolyl, thienyl, and triazolyl. Unless otherwise specified, the heteroaryl groups of the present disclosure can be optionally substituted with one, two, three, four, or five substituents independently selected from alkoxy, alkoxycarbonyl, alkyl, alkylcarbonyl, aryl, cyano, halo, haloalkoxy, haloalkyl, a second heteroaryl, heterocyclyl, nitro, —$NR^aR^b$, and oxo; wherein the aryl, the second heteroaryl, and the heterocyclyl can be further optionally substituted with one, two, three, four, or five substituents independently selected from alkoxy, alkyl, cyano, halo, haloalkyl, haloalkoxy, and nitro.

The term "heteroarylalkyl," as used herein, refers to an alkyl group substituted with one, two, or three heteroaryl groups.

The term "heteroarylcarbonyl," as used herein, refers to a heteroaryl group attached to the parent molecular moiety through a carbonyl group.

The term "heteroaryloxy," as used herein, refers to a heteroaryl group attached to the parent molecular moiety through an oxygen atom.

The term "heterocyclyl," as used herein, refers to a cyclic, non-aromatic, saturated or partially unsaturated three-, four-, five-, six-, or seven-membered ring where at least one atom is selected from oxygen, nitrogen, and sulfur. The term "heterocyclyl" also includes bicyclic systems where a heterocyclyl ring is fused to a four- to six-membered aromatic or non-aromatic carbocyclic ring or a four- to six-membered non-aromatic ring containing one, or two heteratoms selected from nitrogen, oxygen, and sulfur. The heterocyclyl groups of the disclosure are attached to the parent molecular group through any substitutable carbon or nitrogen atom in the group. Representative examples of heterocyclyl groups include, but are not limited to, azetidinyl, benzodioxolyl, benzothiazolyl, diazepinyl, dihydrobenzodioxinyl, dihydrobenzofuranyl, dihydroindolyl, dihydropyridinyl, 1,3-dioxanyl, 1,4-dioxanyl, morpholinyl, piperazinyl, piperidinyl, pyrrolidinyl, tetrahydropyridinyl, tetrahydroisoquinolinyl, and thiomorpholinyl. Unless otherwise specified, the heterocyclyl groups of the present disclosure can be optionally substituted with one, two, three, four, or five substituents independently selected from alkoxy, alkyl, aryl, arylalkoxy, cyano, cycloalkyl, halo, haloalkoxy, haloalkyl, heteroaryl, a second heterocyclyl, hydroxy, nitro, —$NR^aR^b$, and oxo; wherein the aryl, the aryl part of the arylalkoxy, the heteroaryl, and the second heterocyclyl can be further optionally substituted with one, two, three, four, or five substituents independently selected from alkoxy, alkyl, cyano, halo, haloalkoxy, haloalkyl, and nitro.

The term "heterocyclylalkyl," as used herein, refers to an alkyl group substituted with one, two, or three heterocyclyl groups.

The term "hydroxy," as used herein, refers to —OH.

The term "hydroxyalkyl," as used herein, refers to an alkyl group substituted with one, two, or three hydroxy groups.

The term "mercapto," as used herein, refers to —SH.

The term "nitro," as used herein, refers to —NO$_2$.

The term "—NR$^a$R$^b$," as used herein, refers to two groups, R$^a$ and R$^b$, which are attached to the parent molecular moiety through a nitrogen atom. R$^a$ and R$^b$ are independently selected from hydrogen, alkoxycarbonyl, alkyl, alkylcarbonyl, alkylsulfonyl, arylsulfonyl, cycloalkyl, formyl, and (NR$^c$R$^d$)carbonyl.

The term "(NR$^a$R$^b$)alkoxy," as used herein, refers to an (NR$^a$R$^b$)alkyl group attached to the parent molecular moiety through an oxygen atom.

The term "(NR$^a$R$^b$)alkyl," as used herein, refers to an alkyl group substituted with one, two, or three —NR$^a$R$^b$ groups.

The term "—NR$^c$R$^d$," as used herein, refers to two groups, R$^c$ and R$^b$ which are attached to the parent molecular moiety through a nitrogen atom. R$^c$ and R$^d$ are each independently selected from hydrogen and alkyl.

The term "(NR$^c$R$^d$)carbonyl," as used herein, refers to an —NR$^c$R$^d$ group attached to the parent molecular moiety through a carbonyl group.

The term "oxo," as used herein, refers to (=O).

The term "sulfonyl," as used herein, refers to —SO$_2$—.

The description of the disclosure herein should be construed in congruity with the laws and principals of chemical bonding. For example, it may be necessary to remove a hydrogen atom in order accommodate a substitutent at any given location.

Additionally, structures depicted in the present disclosure are understood to convey proper valency for all atoms. For example, the following structure is understood to depict the compound dimethylamine, though the hydrogen atoms are not shown:

Likewise, where a structure is depicted in the following manner:

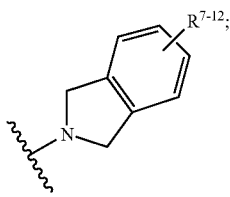

it should be understood that the substituents, i.e., R$^7$, R$^8$, R$^9$, R$^{10}$, R$^{11}$, and R$^{12}$ may be attached to any substitutable atom in either ring of the bicyclic system.

It should also be understood that a substituent may be attached at any and all suitable points of attachment on the substituent unless otherwise specified.

It should also be understood that the compounds encompassed by the present disclosure are those that are chemically stable.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydrojodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is a nucleoside analog and/or is effective to inhibit the function of one or more targets selected from HCV metalloprotease, HCV serine protease, HCV polymerase, HCV helicase, HCV NS4B protein, HCV entry, HCV assembly, HCV egress, HCV NS5A protein, and IMPDH.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18th ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

The term "residue" with reference to an amino acid or amino acid derivative means a radical derived from the corresponding α-amino acid by eliminating the hydroxy of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e., N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

The following figure shows the designations for the compounds of the present disclosure.

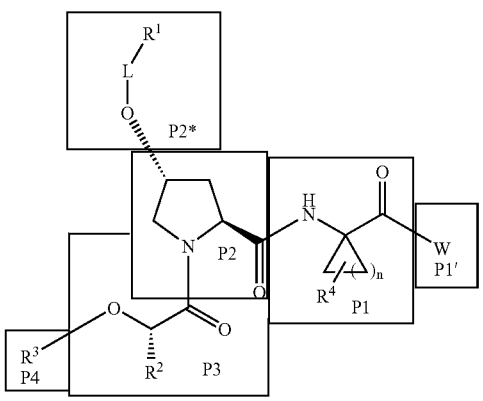

Asymmetric centers exist in the compounds of the present disclosure. For example, the compounds may include P1 cyclopropyl element of formula

wherein $C_1$ and $C_2$ each represent an asymmetric carbon atom at positions 1 and 2 of the cyclopropyl ring. Notwithstanding other possible asymmetric centers at other segments of the compounds, the presence of these two asymmetric centers means that the compounds can exist as racemic mixtures of diastereomers, such as the diastereomers wherein $R^4$ is configured either syn to the amide or syn to the carbonyl as shown below.

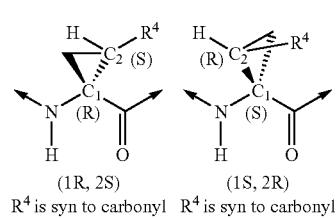

(1R, 2S)   (1S, 2R)
$R^4$ is syn to carbonyl   $R^4$ is syn to carbonyl

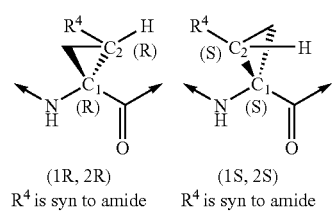

(1R, 2R)   (1S, 2S)
$R^4$ is syn to amide   $R^4$ is syn to amide

It should be understood that the disclosure encompasses all stereochemical isomeric forms, or mixtures thereof, which possess the ability to inhibit HCV protease. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrastemal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I), and pharmaceutically acceptable salts thereof, may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutionis which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The abbreviations used in the present application, including particularly in the Schemes and Examples which follow, are well-known to those skilled in the art. Some of the abbreviations used are as follows: Acca for 1-aminocyclopropylcarboxylic acid; BINAP for 2,2'-bis(diphenylphosphino)-1,1'-binaphthyl; Boc, BOC, or boc for tert-butoxycarbonyl; BOC-HYP-OH for trans-N-(tert-butoxycarbonyl)-4-hydroxy-L-proline; CDI for 1,1'-carbonyldiimidazole; dba for dibenzylideneacetone; DBU for 1,8-diazabicyclo[5.4.0]

undec-7-ene; DCE for 1,2-dichloroethane; DCM for dichloromethane; DEAD for diethyl azodicarboxylate; DIEA for diisopropylethylamine; DMAP for 4-dimethylaminopyridine; DMF for N,N-dimethylformamide; DMSO for dimethylsulfoxide; Fmoc for 9-fluorenylmethyloxycarbonyl; DPPA for diphenylphosphorylazide; Et for ethyl; EtOAc for ethyl acetate; $Et_3N$ for triethylamine; $Et_2O$ for diethyl ether; HATU for O-(7-azabenzotriazol-1-yl)-N,N,N',N'-tetramethyluronium hexafluorophosphate; HBTU for O-benzotriazol-1-yl-N,N,N',N'-tetramethyluronium hexafluorophosphate; HOAt for 1-hydroxy-7-azabenzotriazole; HOBT or HOBt for 1-hydroxybenzotriazole hydrate; LiHMDS for lithium hexamethyldisilazide; Me for methyl; MeOH for methanol; NMM for N-methylmorpholine; OAc for acetate; Ph for phenyl; $Ph_3PO$ for triphenylphoshphine oxide; PoPd or POPd for $(tert\text{-butyl})_2POH)_2 \cdot PdCl_2$; PyBOP for benzotriazol-1-yloxytripyrrolidinophosphonium hexafluorophosphate; PyBrop for bromotrispyrrolidinophosphonium hexafluorophosphate; TBAF for tetrabutylammonium fluoride; TBME or MTBE for tert-butyl methyl ether; tBu for tert-butyl; TFA for trifluoroacetic acid; and THF for tetrahydrofuran.

The compounds of the present disclosure can be manufactured by methods known to those skilled in the art, see, for example, U.S. Pat. No. 6,323,180 and US Patent Appl. 20020111313 A1. The following methods set forth below are provided for illustrative purposes and are not intended to limit the scope of the claims. It will be recognized that it may be preferred or necessary to prepare such a compound in which a functional group is protected using a conventional protecting group then to remove the protecting group to provide a compound of the present disclosure. The details concerning the use of protecting groups in accordance with the present disclosure are known to those skilled in the art.

The compounds of the present disclosure may, for example, be synthesized according to a general process as illustrated in Scheme I (wherein CPG is a carboxy protecting group and APG is an amino protecting group)

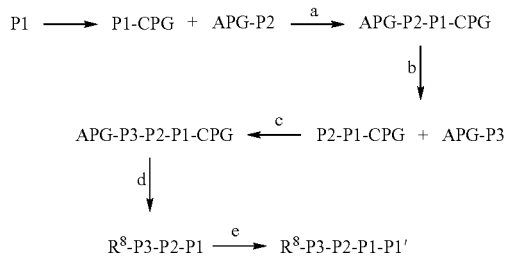

Scheme I

Briefly, the P1, P2, and P3 can be linked by well known peptide coupling techniques. The P1, P2, and P3 groups may be linked together in any order as long as the final compound corresponds to peptides of the disclosure. For example, P3 can be linked to P2-P1; or P1 linked to P3-P2.

Generally, peptides are elongated by deprotecting the α-amino group of the N-terminal residue and coupling the unprotected carboxy group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxy of one reactant with the free amino group of the other reactant in the present of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotrizol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 minutes and 24 hours.

The functional groups of the constituent amino acids generally must be protected during the coupling reactions to avoid formation of undesired bonds. Protecting groups that can be used are listed, for example, in Greene, "Protective Groups in Organic Chemistry", John Wiley & Sons, New York (1981) and "The Peptides: Analysis, Synthesis, Biology", Vol. 3, Academic Press, New York (1981).

The α-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6)trialkylsilyl such as trimethylsilyl; and 7) thiol containing groups such as phenylthiocarbonyl and dithiasuccinoyl. In certain embodiments the α-amino protecting group is either Boc or Fmoc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (rt or RT), usually between 20-22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. When a liquid phase synthesis is used, the protecting groups are removed in whatever manner is dictated by the choice of protecting groups. These procedures are well known to those skilled in the art.

The α-carboxy group of the C-terminal residue is usually protected as an ester (CPG) that can be cleaved to give the carboxylic acid. Protecting groups that can be used include: 1) alkyl esters such as methyl, trimethylsilylethyl and tert-butyl, 2) arylalkyl esters such as benzyl and substituted benzyl, or 3) esters that can be cleaved by mild base treatment or mild reductive means such as trichloroethyl and phenacyl esters. The resulting α-carboxylic acid is coupled with a $R_6SO_2NH_2$ in the presence of a peptide coupling agent.

Compounds of the present disclosure can be prepared by many methods including those described in the examples below and as described in U.S. Pat. No. 6,323,180 and published U.S. Patent Application US20020111313A1.

Scheme II further shows the general process wherein compounds of Formula (I) (2) are constructed by the coupling of tripeptide carboxylic acid intermediate (1) with a P1' sulfonamide. Said coupling reaction requires treatment of carboxylic acid (1) with a coupling reagent such as carbonyl diimidazole in a solvent such as THF, which can be heated to reflux, followed by the addition of the formed derivative of (1), to the P1' sulfonamide, in a solvent such as THF or methylene chloride in the presence of a base such as DBU.

Scheme II

Process P4-P3-P2-P1 $\xrightarrow{P1'}$ P4-P3-P2-P1-P1'

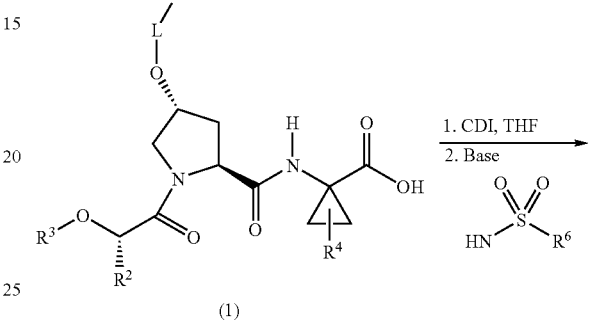

(1)

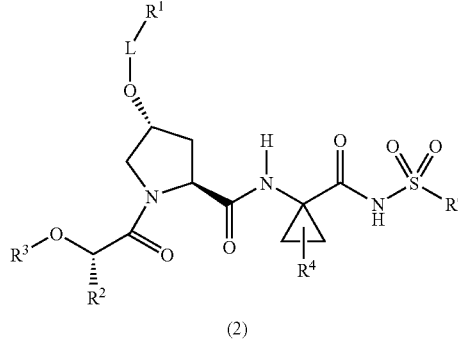

(2)

An alternative process for the construction of compounds of Formula (I) is shown in Scheme III. Therein the P1' sulfonamide element is coupled to the P1 element using the process employed in Scheme I. The resulting P1-P1' moiety can then be deprotected at its amino terminus. In this general example a Boc protecting group is employed but one skilled in the art would recognize that a number of suitable amino protecting groups could be employed in this process. Said Boc protecting group can be removed using acid such as trifluoroacetic acid in a solvent such as dichloroethane to provide the deprotected amine as the TFA salt. Said TFA amine salt can be directly employed in the subsequent coupling reaction or as an alternative the TFA amine salt can be first converted to the HCl amine salt, and this HCl amine salt is used in said coupling reaction as shown in Scheme III. The coupling of said HCl amine salt (3) with the carboxy terminus a P4-P3-P2 intermediate can be achieved using coupling reagents, such as HATU, in solvents such as dichloromethane to provide compounds of formula (4).

Scheme III

Process P1 →(P1') P1-P1' →(P4-P3-P2) P4-P3-P2-P1-P1'

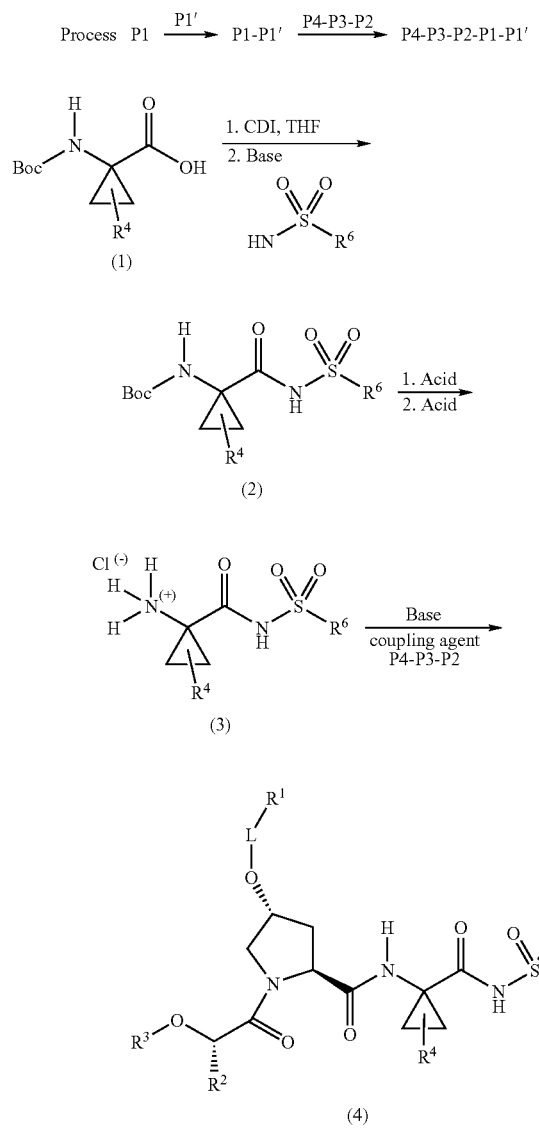

Scheme IV

Process P1-P1' →(P2) P2-P1-P1' →(P4-P3) P4-P3-P2-P1-P1'

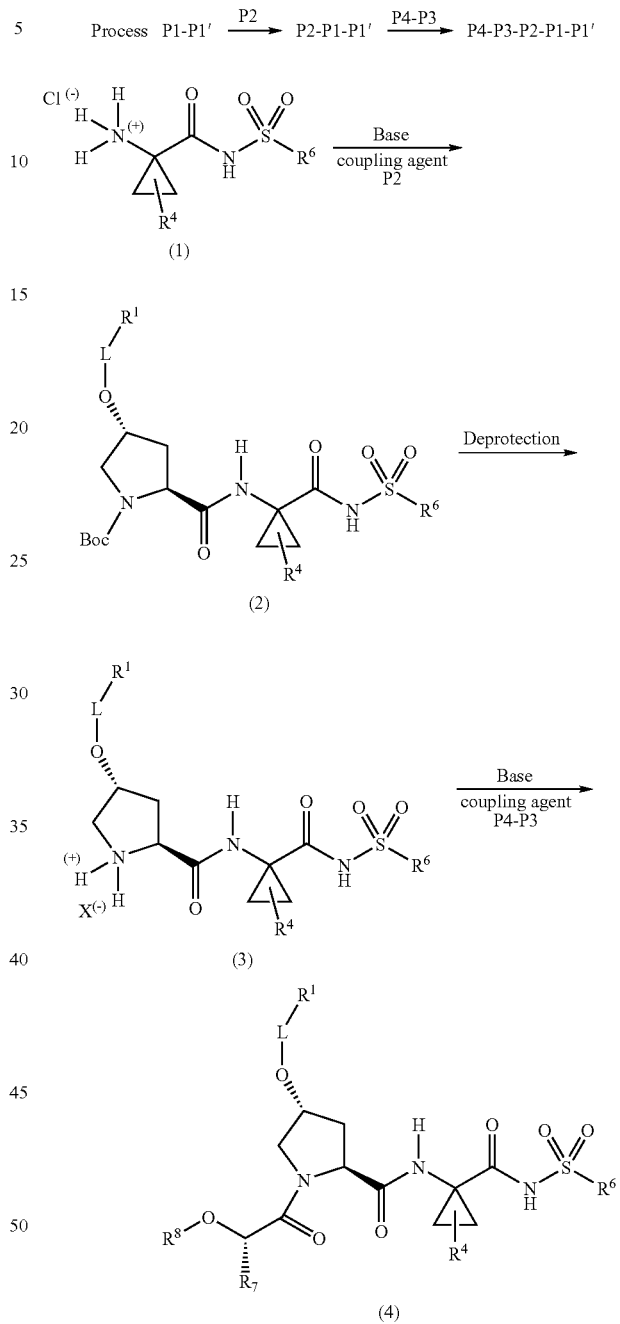

An alternative process for the construction of compounds of Formula (I) is shown in Scheme IV. Herein the hydrochloride salt of the P1-P1' terminal amine (1) is coupled to the free carboxy group of the P2 element using coupling agents such as PyBOP, in the presence of a base such as diisopropylamine, and in a solvent such as methylene chloride. The resulting P2-P1-P1' intermediate can be converted to compounds of Formula (I) (4) in a two step process wherein the first step is deprotection of the P2 amine terminus using an acid such as TFA in a solvent such as methylene chloride. The resulting trifluoroacetic acid salt can be coupled with the carboxy terminus of the P4-P3 element using standard coupling agents such as PyBop in the presence of base such as diisopropylamine, and using solvents such methylene chloride to provide compounds of formula (4).

The P4-P3-P2 intermediate utilized in the above schemes can be constructed as previously described with a further description of this process shown in general Scheme V. Therein the free carboxy terminus of the P4-P3 intermediate (1) can be coupled to the amino terminus of the P2 element to provide the P4-P3-P2 dipeptide (2). The carboxy terminus of the P4-P3-P2 intermediate can be deprotected by saponification of the ester group to provide P4-P3-P2 as the free carboxylic acid (3). Intermediates like (3) can be converted to compounds of Formula (I) using the methods described herein.

Scheme V

Process P4-P3 $\xrightarrow{\text{P2}}$ P4-P3-P2

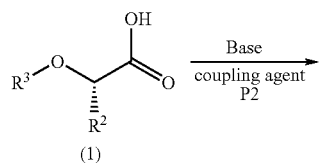

(1)

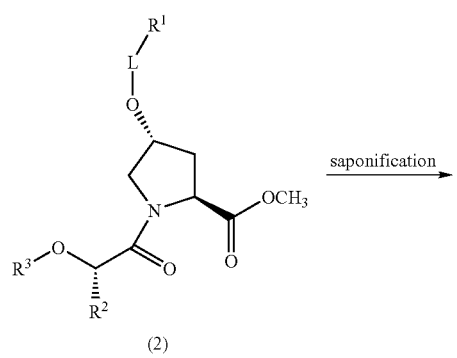

(2)

↓ saponification

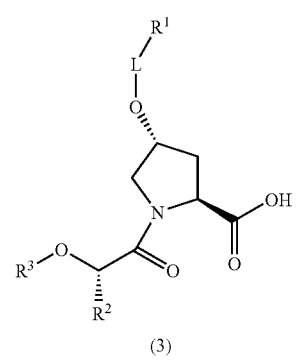

(3)

Compounds of Formula (I) can also be converted into other compounds of Formula (I) as described herein. An example of such a process is shown in Scheme VI wherein a compound of formula (1) which bears a hydroxy group at the P4 position is converted to a compound of formula (2) wherein said compound bears a carbamate group at the P4 position. The conversion of (1) to (2) can be carried by treating (1) with a base such as sodium hydride in a solvent such as THF, followed by the addition of an isocyanate reagent to provide (2). As previously noted one skilled in the art will recognize that intermediate (1) can be used as starting material for the preparation of other compounds of Formula (I).

Scheme VI

Process P4-P3-P2-P1-P1' ⟶ P3-P2-P1-P1' ⟶ P4-P3-P2-P1-P1'

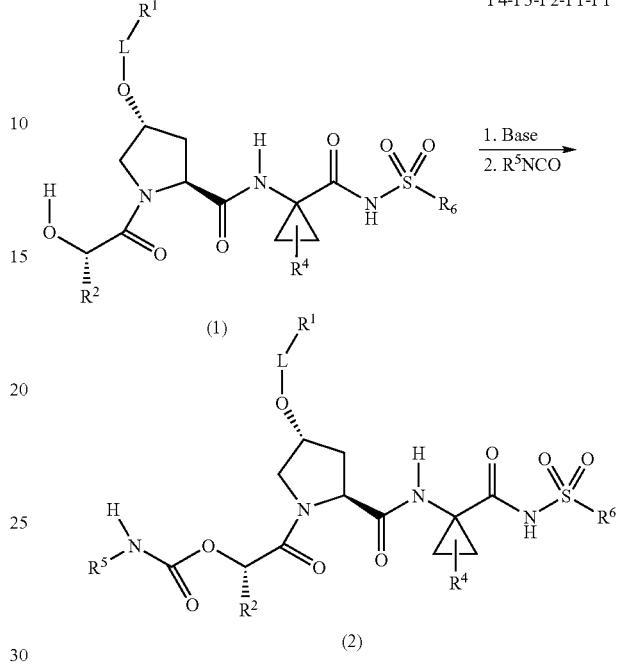

In the construction of compounds of Formula (I), the P1' terminus is incorporated into the molecule using one of the general processes outlined above and described in more detail below. In some examples the P1' elements, that is the cycloalkyl- or alkylsulfonamides, are commercially available or can be prepared from the corresponding alkyl- or cycloalkylsulfonyl chloride by treating said sulfonyl chloride with ammonia. Alternatively, these sulfonamides can be synthesized using the general process outlined in Scheme VII. Therein commercially available 3-chloropropylsulfonyl chloride (1) is converted to a suitable protected sulfonamide as for example by treatment with tert-butylamine. The sulfonamide obtained (2) is then converted to the corresponding cycloalkylsulfonamide by treatment with two equivalents of a base such as butyllithium in a solvent such as THF at low temperature. The resulting cycloalkylsulfonamide can be deprotected by treatment with an acid to provide the desired unprotected cycloalkylsulfoamide.

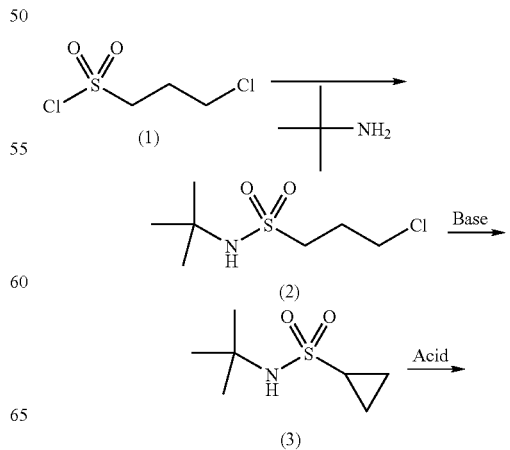

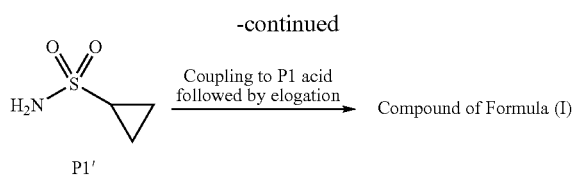

The P1 elements utilized in generating compounds of Formula (I) are in some cases commercially available, but are otherwise synthesized using the methods described herein and subsequently incorporated into compounds of Formula (I) using the methods described herein. The substituted P1 cyclopropylamino acids can be synthesized following the general process outline in Scheme VIII.

Treatment of commercially available or easily synthesized imine (1) with 1,4-dihalobutene (2) in the presence of a base provides the resulting imine (3). Acid hydrolysis of (3) then provides (4), which has an allyl substituent syn to the carboxy group, as the major product. The amine moiety of (4) can protected using a Boc group to provide the fully protected amino acid (5). This intermediate is a racemate which can be resolved by an enzymatic process wherein the ester moiety of (5) is cleaved by a protease to provide the corresponding carboxylic acid. Without being bound to any particular theory, it is believed that this reaction is selective in that one of the enantiomers undergoes the reaction at a much greater rate than its mirror image providing for a kinetic resolution of the intermediate racemate. In the examples cited herein, the more preferred stereoisomer for integration into compounds of Formula (I) is (5a) which houses the (1R,2S) stereochemistry. In the presence of the enzyme, this enantiomer does not undergo ester cleavage and thereby this enantiomer (5a) is recovered from the reaction mixture. However, the less preferred enantiomer, (5b), which houses the (1S,2R) stereochemistry undergoes ester cleavage, i.e., hydrolysis, to provide the free acid (6). Upon completion of this reaction, the ester (5a) can be separated from the acid product (6) by routine methods such as, for example, aqueous extraction methods or chromatography.

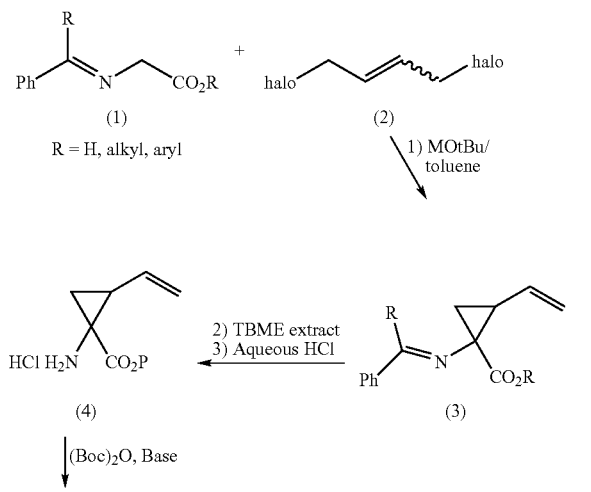

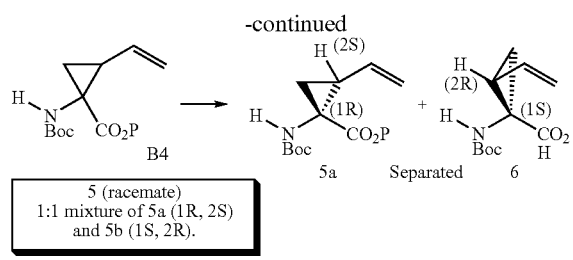

Procedures for making P2 intermediates and compounds of Formula (I) are shown in the schemes below. It should be noted that in many cases reactions are depicted for only one position of an intermediate. However, it is to be understood that such reactions could be used to impart modifications to other positions within this intermediate. Moreover, said intermediates, reaction conditions and methods given in the specific examples are broadly applicable to compounds with other substitution patterns. The general schemes outlined below are followed with examples herein. Both general and specific examples are non-limiting, as for example the isoquinoline nucleus is shown as part of the general scheme, Scheme IX, however, this pathway represents a viable process for the construction of alternate heterocycle substituents as replacements for the isoquinoline element, such as quinolines or quinazolines.

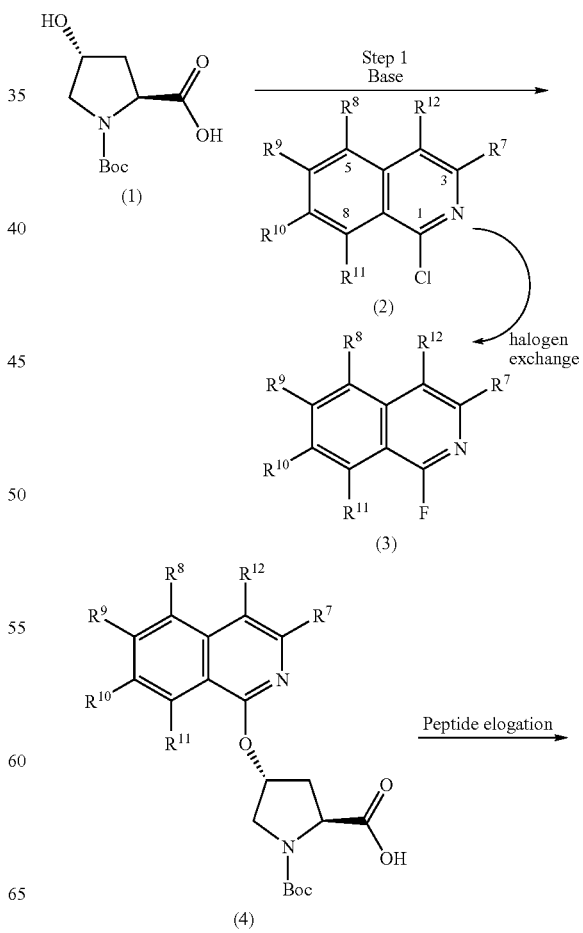

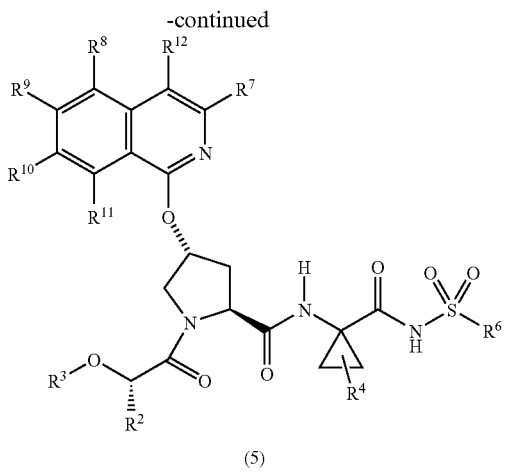

(5)

Scheme IX shows the coupling of an N-protected C4-hydroxyproline moiety with a heterocycle to form intermediate (4) and the subsequent modification of said intermediate (4) to a compound of Formula (I) (5) by the process of peptide elongation as described herein. It should be noted that in the first step, the coupling of the C4-hydroxyproline group with the heteroaryl element, a base is employed. One skilled in the art would recognize that this coupling can be done using bases such as potassium tert-butoxide or sodium hydride in solvent such as DMF or DMSO or THF. This coupling to the isoquinoline ring system occurs at the C1 position (numbering for isoquinoline ring system shown in intermediate 2 of Scheme IX) and is directed by the chloro group which is displaced in the process. It should be noted that alternative leaving groups can be utilized at this position such as a fluoride leaving group as shown in intermediate (3). Said fluoro intermediates (3) are available from the corresponding chloro compound using literature procedures described herein.

It should be further noted that the position of the ring heteroatom(s) in intermediates like (2) of Scheme IX is also variable, as defined by the term heterocycle described herein.

An alternative to the method described above for the coupling of the C4-hydroxyproline to aromatics and heteroaromatics is provided in the Mitsunobu reaction as depicted in step 1 of Scheme X. In this general reaction scheme a C4-hydroxyproline derivative is coupled to a quinazoline ring system. This reaction makes use of reagents such as triphenylphosphine and DEAD (diethylazodicarboxylate) in aprotic solvents such as THF or dioxane and can be used for the formation of aryl and heteroaryl ethers. Note that in the course of this coupling reaction the stereochemistry of the C4 chiral center in the C4-hydroxyproline derivative is inverted and thereby it is necessary to use the C4-hydroxyproline derivative housing the (S) stereochemistry at the C4 position as starting material. It should be noted that numerous modifications and improvements of the Mitsunobu reaction have been described in the literature.

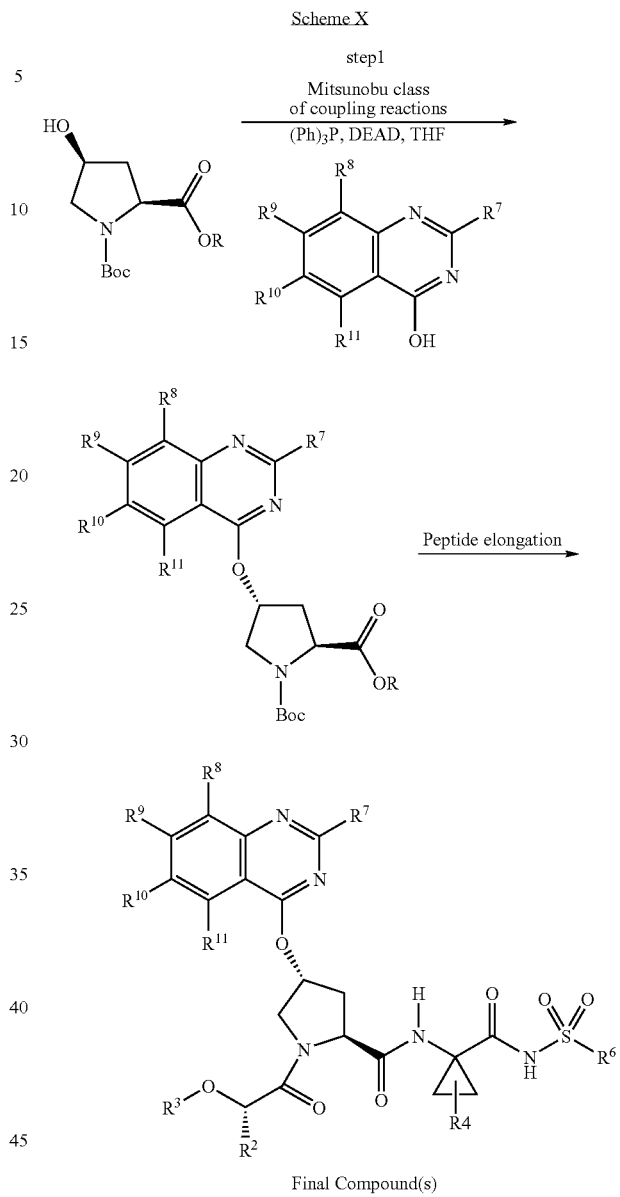

In a subset of examples herein, isoquinolines are incorporated into the final compounds and specifically into the P2 region of said compounds. One skilled in the art would recognize that a number of general methods are available for the synthesis of isoquinolines. Moreoever, said isoquinolines generated by these methods can be readily incorporated into final compounds of Formula (I) using the processes described herein. One general methodology for the synthesis of isoquinolines is shown in Scheme XI, wherein cinnamic acid derivatives, shown in general form as structure (2) are converted to 1-chloroisoquinolines in a four step process. Said chloroisoquinolines can be subsequently used in coupling reactions to C4-hydroxyproline derivatives as described herein. The conversion of cinnamic acids to chloroquinolines begins with the treatment of cinnamic acid with an alkylcholorformate in the presence of a base. The resulting anhydride is then treated with sodium azide which results in the formation of an acylazide (3) as shown in the scheme. Alternate methods are available for the formation of acylazides from carboxylic acids as for example said carboxylic acid can be treated with diphenylphosphorylazide (DPPA) in an aprotic solvent such as methylene chloride in the presence of a base. In the next step of the reaction sequence the acylazide (3) is coverted to the corresponding isoquinolone (4) as shown in the scheme. The acylazide is heated to a temperature of approximately 190° C. in a high boiling solvent such a diphenylmethane. This reaction is general and provides moderate to good yields of substituted isoquinolone from the corresponding cinnamic acid derivatives. It should noted that said cinnamic acid derivatives are available commercially or can be obtained from the corresponding benzaldehyde (1) derivative by direct condensation with malonic acid or derivatives thereof and also by employing a Wittig reaction. The intermediate isoquinolones (4) of Scheme XI can be converted to the corresponding 1-chloroisoquinoline by treatment with phosphorous oxychloride. This reaction is general and can be applied to any of the isoquinolones, quinolones or additional heterocycles as shown herein to covert a hydroxy substituent to the corresponding chloro compound when said hydroxy is in conjugation with a nitrogen atom in said heterocyclic ring systems.

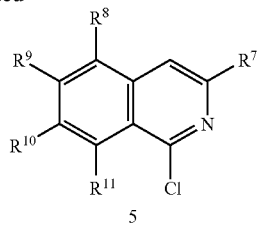

Reference: N. Briet et al, *Tetrahedron*, 2002, 5761

An alternative method for the synthesis of the isoquinoline ring system is the Pomeranz-Fritsh procedure. This general method is outlined in Scheme XII. The process begins with the conversion of a benzaldehyde derivative (1) to a functionalized imine (2). Said imine is then converted to the isoquinoline ring system by treatment with acid at elevated temperature. This isoquinoline synthesis of Scheme XII is general, and it should be noted that this process is particularly useful in procuring isoquinoline intermediates that are substituted at the C8 position. The intermediate isoquinolines (3) can be converted to the corresponding 1-chloroquinolines (5) in a two step process as shown. The first step in this sequence is the formation of the isoquinoline N-oxide (4) by treatment of isoquinoline (3) with meta-chloroperbenzoic acid in an aprotic solvent such as dichloromethane. Intermediate (4) can be converted to the corresponding 1-chloroquinoline by treatment with phosphorous oxychloroide in refluxing chloroform. Note this two step process is general and can be employed to procure chloroisoquinolines and chloroquinolines from the corresponding isoquinolines and quinolines respectively.

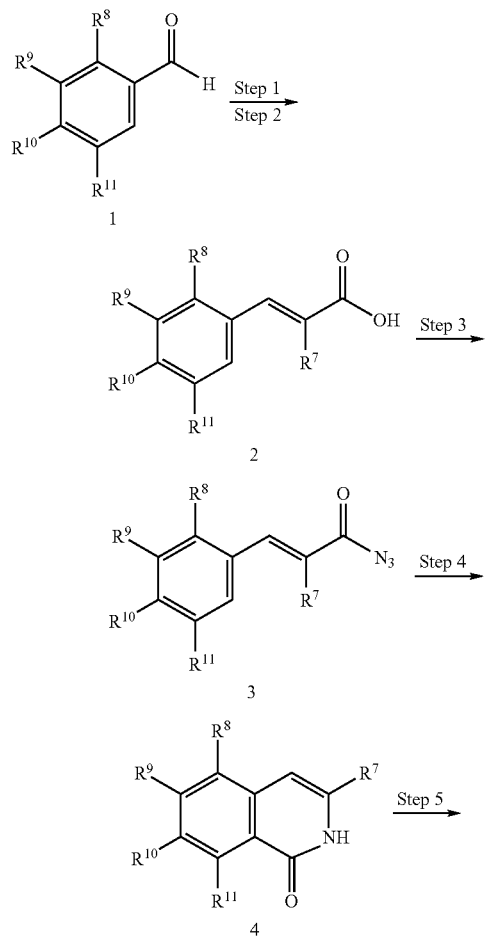

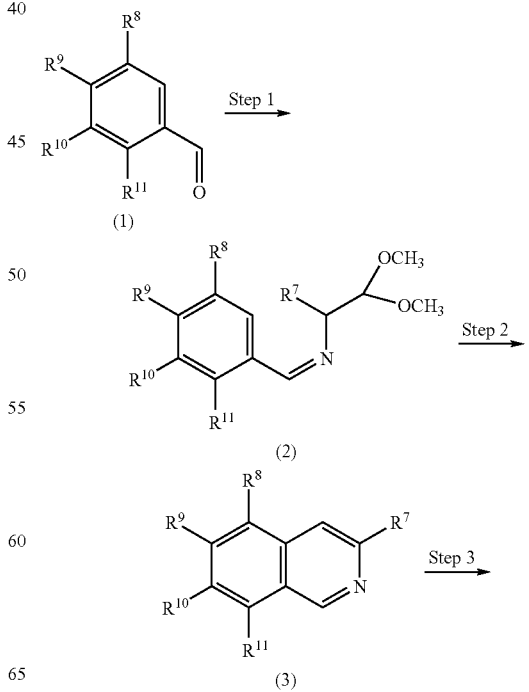

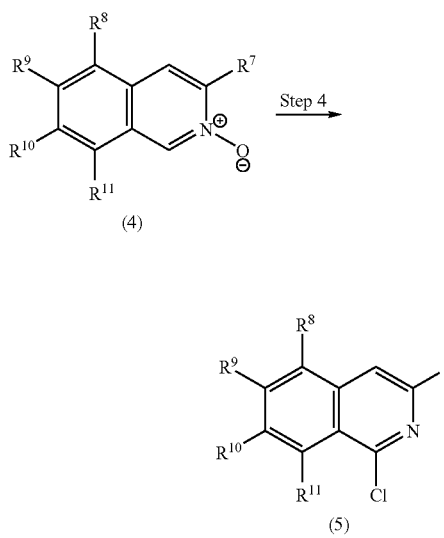

Pomeranz-Fritsch synthesis
K. Hirao, R. Tsuchiya, Y. Yano, H. Tsue, *Heterocycles* 42(1) 1996, 415-422

Another method for the synthesis of the isoquinoline ring system is shown in Scheme XIII. In this process an ortho-alkylbenzamide derivative (1) is treated with a strong base such as tert-butyllithium in a solvent such as THF at low temperature. To this reaction mixture is then added a nitrile derivative, which undergoes an addition reaction with the anion derived from deprotonation of (1), resulting in the formation of (2). This reaction is general and can be used for the formation of substituted isoquinolines. Intermediate (2) of Scheme XIII can be converted to the corresponding 1-chloroquinoline by the methods described herein.

Scheme XIII

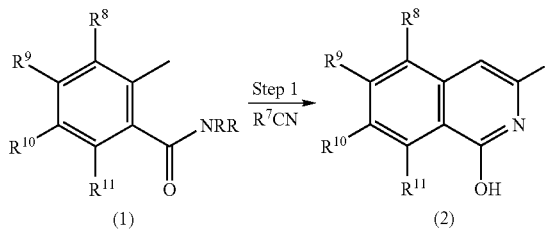

An additional method for the synthesis of isoquinolines is shown in Scheme XIV. The deprotonation of intermediate (1) using tert-butyllithium is described above. In the present method however, said intermediate anion is trapped by an ester, resulting in the formation of intermediate (2) as shown below. In a subsequent reaction ketone (2) is condensed with ammoniumn acetate at elevated temperature providing for the formation of quinolone (3). This reaction is general and can be applied for the construction of substituted isoquinolones which can then be converted to the corresponding 1-chloroisoquinolines as described herein.

Scheme XIV

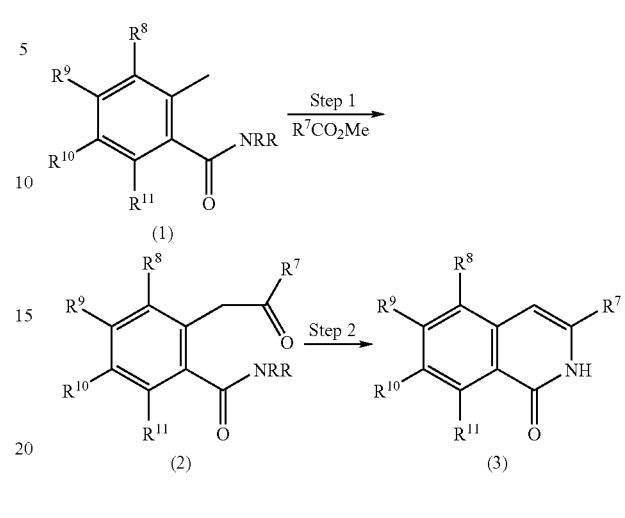

Yet another method for the construction of isoquinolines is found in Scheme XV. In the first step of this process an ortho-alkylarylimine derivatives such as (1) is subjected to deprotonation conditions (sec-butyllithium, THF) and the resulting anion is quenched by the addition of an activated carboxylic acid derivative such as a Weinreb amide. The resulting keto imine (2) can be converted to the corresponding isoquinoline by condensation with ammonium acetate at elevated temperatures. This method is general and can be used for the synthesis of substituted isoquinolines. Said isoquinolines can be converted to the corresponding 1-chloroquinoline by the methods described herein.

Scheme XV

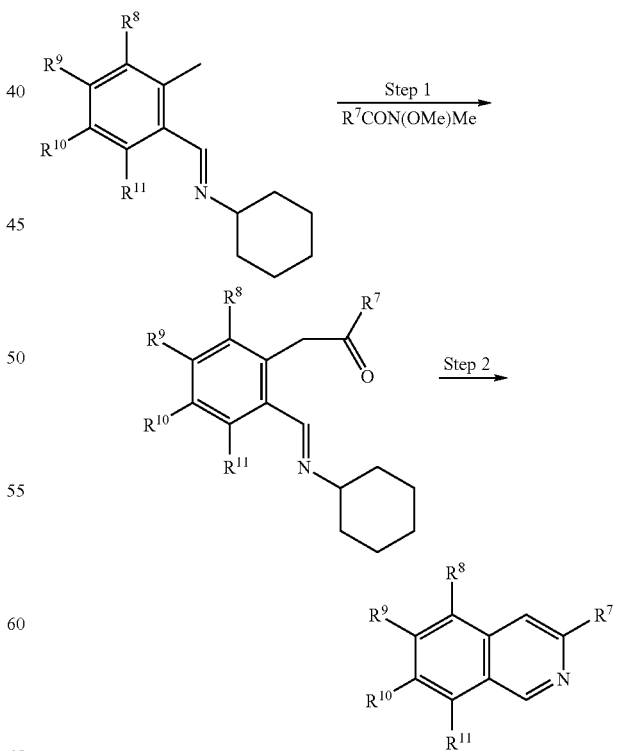

L. Flippin, J. Muchowski, JOC, 1993, 2631-2632

The heterocycles described herein, and which are incorporated into the compounds of Formula (I), can be further functionalized. It is obvious to one skilled in the art that additional functionalization of said heterocycles can be done either before or after incorporation of these functionalities into compounds of Formula (I). The following schemes illustrate this point. For example, Scheme XVI shows the conversion of a 1-chloro-6-fluoroisoquinoline to the corresponding 1-chloro-6-alkoxy-isoquinoline species, by treatment of (1) with a sodium or potassium alkoxide species in the alcohol solvent from which the alkoxide is derived at room temperature. In some cases it may be necessary to heat the reaction to drive it to completion. Said chloroquinoline can be incorporated into a compound of Formula (I) using the art described herein.

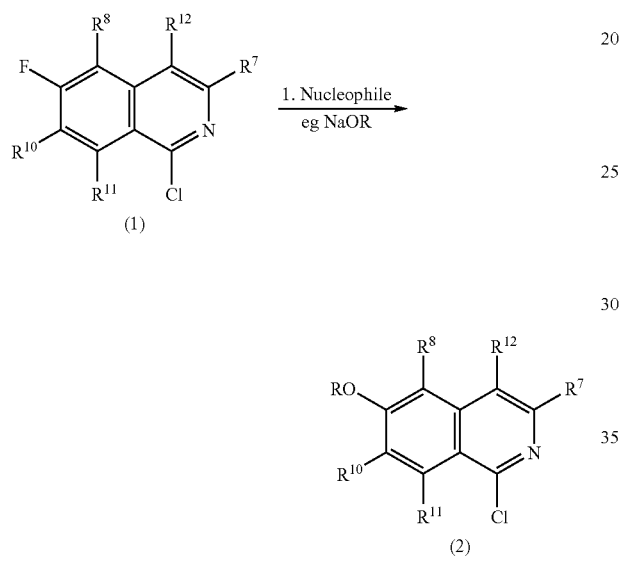

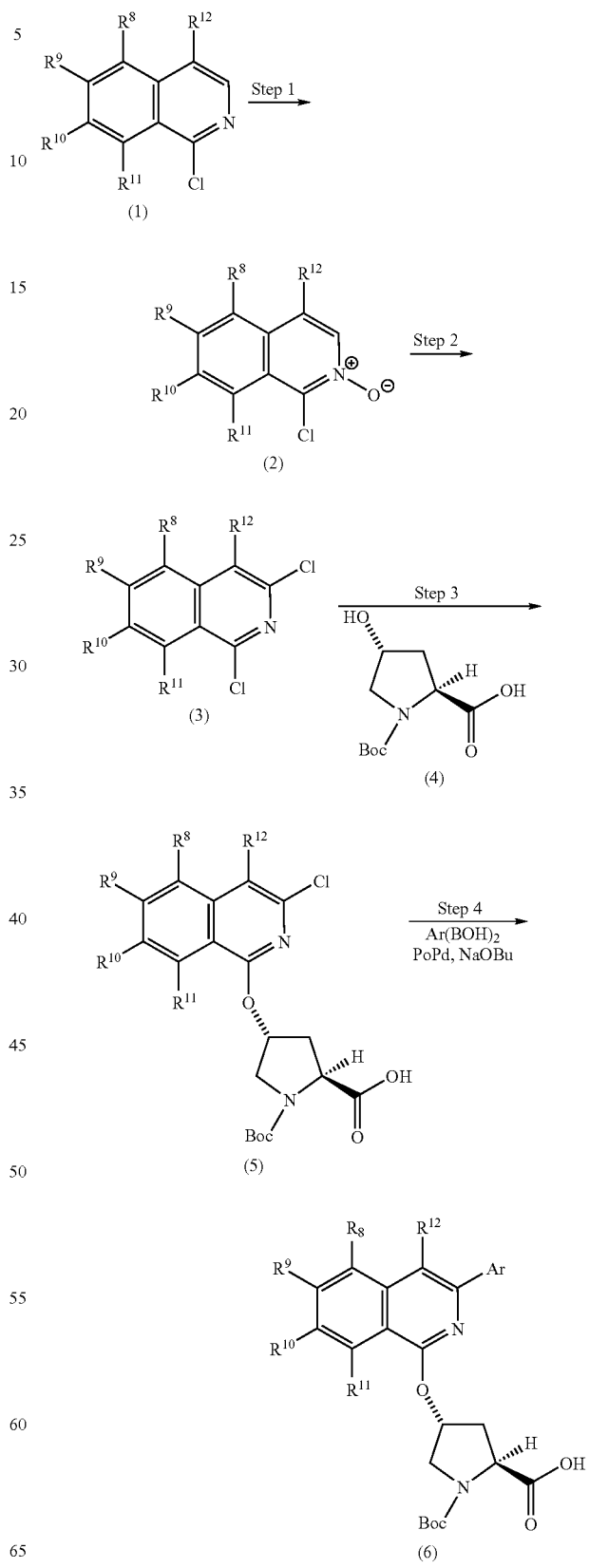

Scheme XVII provides a general example for the modification of heterocycles as defined herein by employing palladium mediated coupling reactions. Said couplings can be employed to functionalize a heterocycle at each position of the ring system providing said ring is suitably activated or functionalized, as for example with a chloride as shown in the scheme. This sequence begins with 1-chloroisoquinoline (1) which upon treatment with metachloroperbenzoic acid can be converted to the corresponding N-oxide (2). Said intermediate (2) can be converted to the corresponding 1,3-dichloroisoquinoline (3) by treatment with phosphorous oxychloride in refluxing chloroform. Intermediate (3) can be coupled with N-Boc-4-hydroxyproline by the methods described herein to provide intermediate (5) as shown in the scheme. Intermediate (5) can undergo a Suzuki coupling with an aryl boronic acid, in the presence of a palladium reagent and base, and in a solvent such as THF or toluene or DMF to provide the C3-arylisoquinoline intermediate (6). Heteroarylboronic acids can also be employed in this Pd mediated coupling process to provide C3-heteroarylisoquinolines. Intermediate (6) can be converted into final compounds of Formula (I) by the methods described herein.

Palladium mediated couplings of heteroaryl systems with aryl or heteroaryl elements can also be employed at a later synthetic stage in the construction of compounds of Formula (I) as shown in Scheme XVIII. Therein tripeptide acylsulfonamide intermediate (1) is coupled to a 1-chloro-3-bromoisoquinoline (2) using the previously described process of alkoxide displacement of an heteroarylhalo moiety to provide intermediate (3). The coupling of (1) and (2) is most efficient in the presence of a catalyst such as lanthanum chloride as described herein. The isoquinoline ring system of intermediate (3) can be further functionalized by employing either Suzuki couplings (Process 1: subjecting (3) to heteroaryl or aryl boronic acids in the presence of a palladium catalyst such as palladium tetra(triphenylphosphine) and a base such as cesium carbonate in solvents such as DMF) or Stille couplings (Process 2: subjecting (3) to heteraryl or aryl tin dervatives in the presence of palladium catalyst such as palladium tetra(triphenylphosphine in solvents such as toluene).

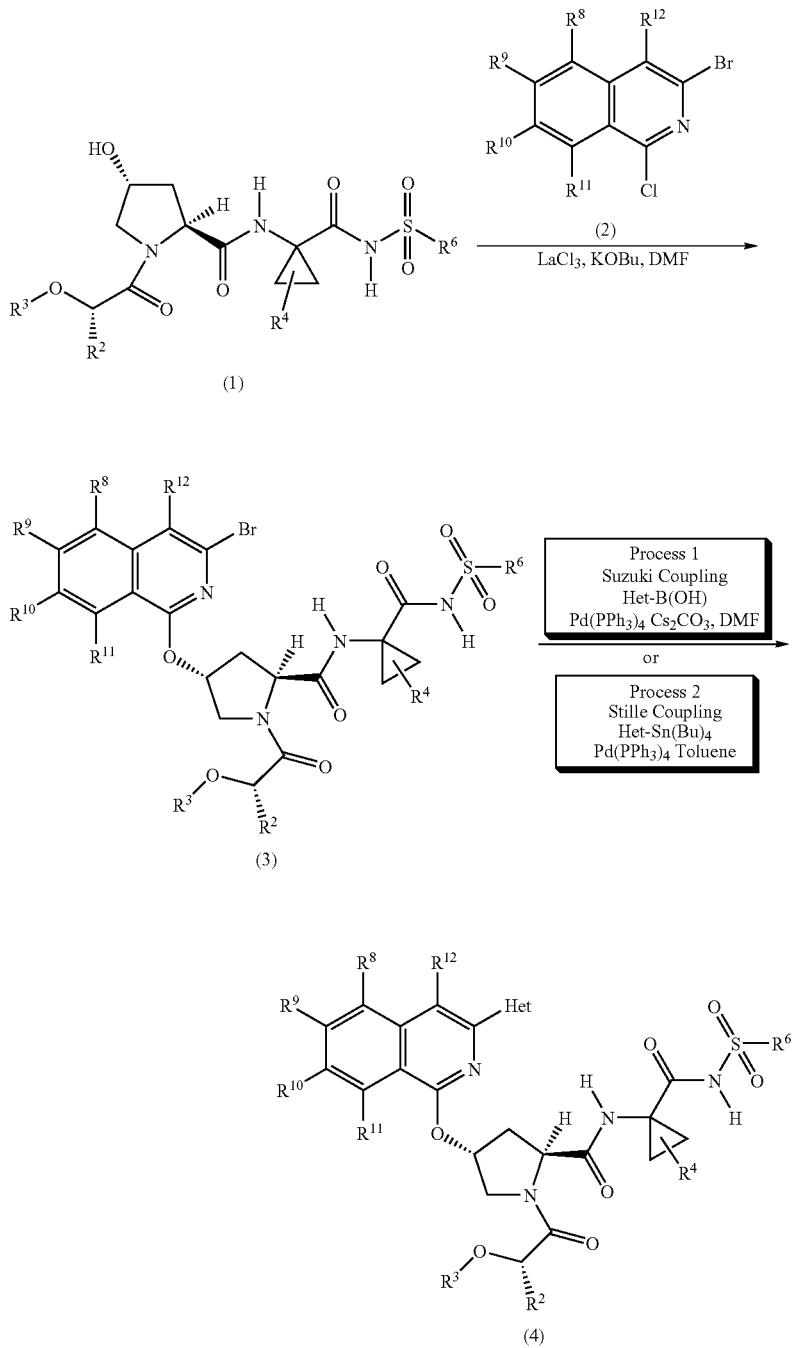

Palladium reactions can also be employed to couple C4-amino proline elements with functionalized heterocycles. Scheme XX shows intermediate (1) coupling with a functionalized isoquinoline in the presence of a palladium catalyst and a base in a solvent such as toluene. Intermediates like (3) can be converted to compounds of Formula (I) using the methods described herein.

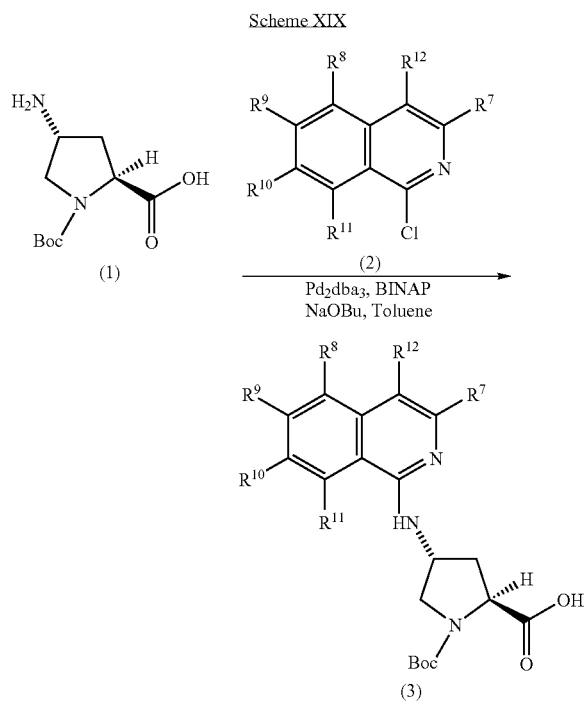

The construction of functionalized isoquinoline ring systems is also possible employing [4+2] cycloaddition reactions. For example, as shown in Scheme XX, the use of vinyl isocyantes (1) in cycloaddition reactions with compounds of formula (2) provides functionalized isoquinolones (3). Said isoquinolines can be incorporated into compounds of Formula (I) using the methods described herein.

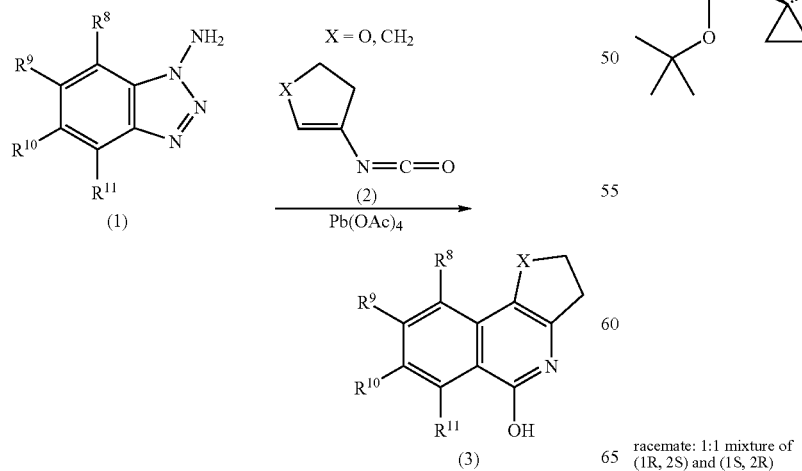

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel ($SiO_2$) by methods evident to one skilled in the art (see *J. Org. Chem.* 1978, 43, 2923).

The compounds and chemical intermediates of the present invention, described in the following examples, were prepared according to the following methods. Example numbers and compound numbers are not contiguous throughout the entire Examples portion of the application.

Section A

I. Preparation of P1 Intermediates

2. Resolution of
N-Boc-(1R,2S)/(1S,2R)-1-amino-2-vinylcyclopropane carboxylic acid ethyl ester

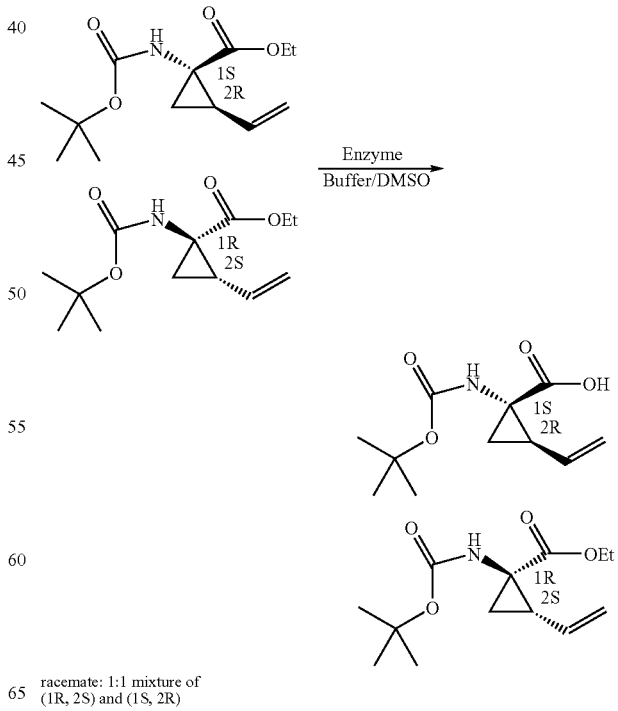

racemate: 1:1 mixture of (1R, 2S) and (1S, 2R)

Resolution A

To an aqueous solution of sodium phosphate buffer (0.1M, 4.25 L, pH 8) housed in a 12 Liter jacked reactor, maintained at 39° C., and stirred at 300 rpm was added 511 grams of Alcalase 2.4L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 minutes. The reaction temperature was then maintained at 40° C. for 24.5 hours during which time the pH of the mixture was adjusted to 8.0 at the 1.5 hour and 19.5 hour time points using 50% NaOH in water. After 24.5 hours, the enantio-excess of the ester was determined to be 97.2%, and the reaction was cooled to room temperature (26° C.) and stirred overnight (16 hours) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% $NaHCO_3$ (3×100 mL), water (3×100 mL), and concentrated in vacuo to give the enantiomerically pure N-Boc-(1R,2S)-1-amino-2-vinylcyclopropane carboxylic acid ethyl ester as light yellow solid (42.55 g; purity: 97% (210 nm, containing no acid; 100% enantiomeric excess ("ee").

The aqueous layer from the extraction process was then acidified to pH 2 with 50% $H_2SO_4$ and extracted with MTBE (2×2 L). The MTBE extract was washed with water (3×100 mL) and concentrated to give the acid as light yellow solid (42.74 g; purity: 99% @ 210 nm, containing no ester).

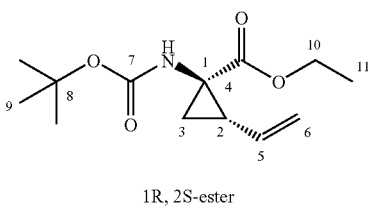

1R, 2S-ester

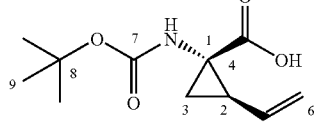

1S, 2R-acid

| | ester | | acid | |
|---|---|---|---|---|
| High Resolution Mass Spec | (+) ESI, $C_{13}H_{22}NO_4$, $[M + H]^+$, calcd. 256.1549, found 256.1542 | | (−) ESI, $C_{11}H_{16}NO_4$, $[M − H]^−$, calcd. 226.1079, found 226.1089 | |

NMR observed chemical shift
Solvent: $CDCl_3$ (proton δ 7.24, C-13 δ 77.0)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = 9.0 Hz) | 35.0 |
| 3a | 1.76 (br) | 23.2 | 1.79 (br) | 23.4 |
| 3b | 1.46 (br) | | 1.51, (br) | |
| 4 | — | 170.8 | — | 175.8 |
| 5 | 5.74 (ddd, J = 9.0, 10.0, 17.0 Hz) | 133.7 | 5.75 (m) | 133.4 |
| 6a | 5.25 (d, J = 17.0 Hz) | 117.6 | 5.28 (d, J = 17.0 Hz) | 118.1 |
| 6b | 5.08 (dd, J = 10.0, 1.5 Hz) | | 5.12 (d, J = 10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J = 7.5 Hz) | 14.2 | — | — |

Resolution B

To 0.5 mL 100 mM Heps.Na buffer (pH 8.5) in a well of a 24 well plate (capacity: 10 mL/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hours, enantio-excess of the ester was determined to be 44.3% as following: 0.1 mL of the reaction mixture was removed and mixed well with 1 mL ethanol; after centrifugation, 10 microliter ("µL") of the supernatant was analyzed with the chiral HPLC. To the remaining reaction mixture, 0.1 mL of DMSO was added, and the plate was incubated for additional 3 days at 250 rpm at 40° C., after which 4 mL of ethanol was added to the well. After centrifugation, 10 µL of the supernatant was analyzed with the chiral HPLC and enantio-excess of the ester was determined to be 100%.

Resolution C

To 0.5 mL 100 mM Heps.Na buffer (pH 8.5) in a well of a 24 well plate (capacity: 10 mL/well), 0.1 mL of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hours, enantio-excess of the ester was determined to be 39.6% as following: 0.1 mL of the reaction mixture was removed and mixed well with 1 mL ethanol; after cenrifugation, 10 µL of the supernatant was analyzed with the chiral HPLC. To the remaining reaction mixture, 0.1 mL of DMSO was added, and the plate was incubated for additional 3 days at 250 rpm at 40° C., after which 4 mL of ethanol was added to the well. After centrifugation, 10 µL of the supernatant was analyzed with the chiral HPLC and enantio-excess of the ester was determined to be 100%.

Samples analysis was carried out in the following manner:
1) Sample preparation: About 0.5 mL of the reaction mixture was mixed well with 10 volume of ethanol. After centrifligation, 10 µL of the supernatant was injected onto HPLC column.
2) Conversion Determination:
Column: YMC ODS A, 4.6×50 mm, S-5 µm
Solvent: A, 1 mM HCl in water; B, acetonitrile
Gradient: 30% B for 1 minute; 30% to 45% B over 0.5 minutes; 45% B for 1.5 minutes; 45% to 30% B over 0.5 minutes.
Flow rate: 2 mL/min
UV Detection: 210 nm
Retention time: acid, 1.2 minutes; ester, 2.8 minutes.
3) Enantio-Excess Determination for the Ester:
Column: CHIRACEL OD-RH, 4.6×150 mm, S-5 µm
Mobile phase: acetonitrile/50 mM $HClO_4$ in water (67/33)

Flow rate: 0.75 mL/minutes.

UV Detection: 210 nm.

Retention Time:

(1S,2R)-1-amino-2-vinylcyclopropane carboxylic acid 5.2 minutes;

Racemate (1R,2S)/(1S,2R)-1-amino-2-vinylcyclopropane carboxylic acid ethyl ester 18.5 minutes and 20.0 minutes;

(1R,2S)-1-amino-2-vinylcyclopropane carboxylic acid ethyl ester 18.5 minutes.

Resolution D

5 L of 0.3M sodium phosphate buffer (pH 8) was maintained at 38° C. in a 20 L jacked reactor, stirred at 130 rpm. Four liters of Alcalase 2.4 L (Novozymes North America Inc.) and 1 liter of DI water were added to the reactor. When temperature of the mixture closed to 38° C., pH was adjusted to 7.8 with 10N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funel. The reaction temperature was then adjusted to 48° C. After 21 hour, enantio-excess of the ester reached 99.3%. Heating was stopped at 24 hours and the reaction was slowly cooled down to room temperature (about 25° C.) and stirred overnight. The pH of the reaction mixture was adjusted to 8.5 with 10N NaOH and the mixture was extracted with MTBE (2×4 L). The combined MTBE extract was washed with 5% NaHCO$_3$ (3×400 mL) and water (3×400 mL), and concentrated to give enantiomerically pure N-Boc-(1R,2S)/-1-amino-2-vinylcyclopropane carboxylic acid ethyl ester as light yellow crystal (259 g; purity: 96.9% @ 210 nm, containing no acid; 100% ee).

Resolution E

10 L of 0.1M sodium phosphate buffer (pH 8) was maintained at 40° C. in a 20 L jacked reactor, and stirred at 360 rpm. 1.5 L of Alcalase 2.4 L (Novozymes North America Inc.) was added to the reactor. When the temperature of the mixture closed to 38° C., the pH was adjusted to 8.0 with 10H NaOH. A solution of the racemic N-Boc-(1R,2S)/(1S,2R)-1-amino-2-vinylcyclopropane carboxylic acid ethyl ester (200 grams) in 2 L DMSO was added to the reactor over a period of 1 hour via an addition funel. The reaction temperature was then adjusted to 40° C. After 3 hours, pH was adjusted to 8.0 with 10N NaOH. After 21 hours, the reaction was cooled down to 25° C. The pH of the reaction mixture was adjusted to 8.5 with 10N NaOH and the mixture was extracted with MTBE (2×5 L). The combined MTBE extract was washed with 5% NaHCO$_3$ (3×500 mL) and water (3×200 mL), and concentrated to give 110 g of yellow oil. The oil was set at room temperature under house vacuum and gave enantiomerically pure N-Boc-(1R,2S)/-1-amino-2-vinylcyclopropane carboxylic acid ethyl ester as colorless long rod crystals (101 g; purity: 97.9% @ 210 nm, containing no acid; 100% ee).

The crystal structure enantiomerically pure N-Boc-(1R,2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N . . . O 3.159 Å).

Structure of N-Boc-(1R,2S)-1-amino-2-vinylcyclopropane carboxylic acid ethyl ester

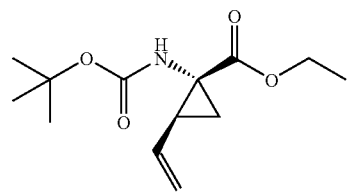

Crystal Data:

Chemical formula: C13H21N1O4

Crystal system: Orthorhombic

Space Group: P2$_1$2$_1$2$_1$ a = 5.2902(1) Å    α = 90°.

b = 13.8946(2) Å    β = 90° c = 19.9768(3) Å    γ = 90°

V = 1468.40(4) Å$^3$

Z = 4    d$_x$ = 1.155 g cm$^{-3}$

No. of reflections for lattice parameters: 6817

θ range for lattice parameters (°): 2.2-65.2

Absorption coefficient (mm$^{-1}$): 0.700

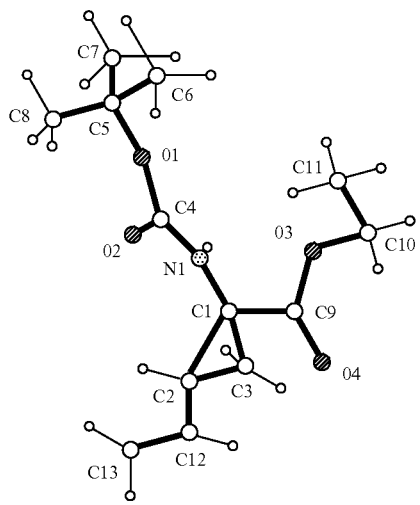

Experimental:

Crystallization

Crystal source: MTBE

Crystal description: Colorless rod

Crystal size (mm): 0.12 × 0.26 × 0.30

Data Collection

Temperature (K): 293

θ$_{max}$ (°): 65.2 (Cu Kα)

No. of reflections measured: 7518

No. of independent reflections: 2390 (R$_{int}$ = 0.0776)

No. of observed reflections (I ≧ 2σ: 2284

Absorption correction (T$_{min}$-T$_{max}$): 0.688-1.000

Resolution F

5 L of 0.2M sodium borate buffer (pH 9) was maintained at 45° C. in a 20 L jacked reactor and stirred at 400 rpm. 3 L of DI water and 4 L of Savinase 16L, type EX (Novozymes North America Inc.) were added to the reactor. When the temperature of the mixture closed to 45° C., the pH was adjusted to 8.5 with 10N NaOH. A solution of the racemic N-Boc-(1R,2S)/(1S,2R)-1-amino-2-vinylcyclopropane carboxylic acid ethyl ester (200 grams) in 2 L DMSO was added to the reactor over a period of 40 minutes via an addition funel. The reaction temperature was then adjusted to 48° C. After 2 hours, the pH was adjusted to pH 9.0 with 10N NaOH. At 18 hours, enantio-excess of the ester reached 72% and the pH was adjusted to 9.0 with 10N NaOH. At 24 hours the temperature was lowered to 35° C. At 42 hours the temperature was raised to 48° C. and the pH was adjusted to 9.0 with 10N NaOH. Heating was stopped at 48 hours and the reaction was slowly cooled down to room temperature (about 25° C.) and stirred overnight. At 66 hours, the pH of the reaction mixture was 8.6. The mixture was extracted with MTBE (2×4 L). The combined MTBE extract was washed with 5% NaHCO$_3$ (6×300 mL) and water (3×300 mL), and concentrated to give enantiomerically pure N-Boc-(1R,2S)/-1-amino-2-vinylcyclopropane carboxylic acid ethyl ester as light yellow crystals (101 A g; purity: 95.9% @ 210 nm, containing no acid; 98.6% ee).

3. Preparation of chiral (1R,2S)-1-amino-2-vinylcyclopropane carboxylic acid ethyl ester hydrochloride

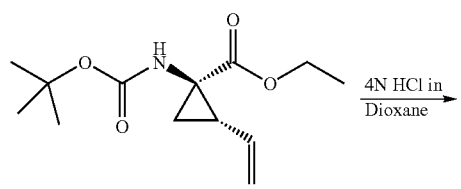

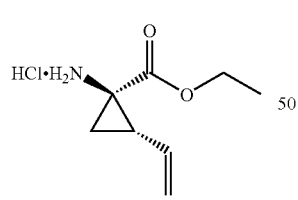

N-BOC-(1R,2 S)-1-amino-2-vinylcyclopropanecarboxylic acid ethyl ester (8.5 g, 33.3 mmol) was stirred under an N$_2$ atmosphere with 200 mL of 4N HCl/dioxane (Aldrich) at room temperature for 3 hours. The solvent was removed under reduced pressure keeping the temperature below 40° C. This gave 6.57 g (~100%) of (1R,2S)-1-amino-2-vinylcyclopropanecarboxylic acid ethyl ester hydrochloride as a light tan solid. $^1$H NMR (300 MHz, CD$_3$OD) δ 1.31 (t, J=7.0 Hz, 3H), 1.69-1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69-5.81 (m, 1H). MS m/z 156 (M$^+$+1).

4. Preparation of N-Boc-(1R,2S)-1-amino-2-cyclopropylcyclopropane carboxylic acid ethyl ester

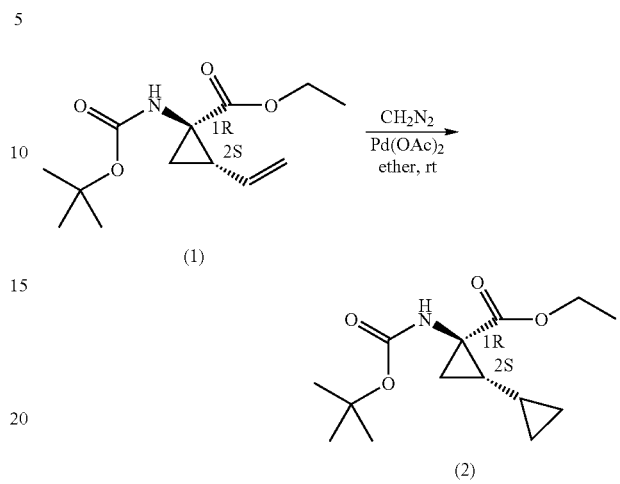

A solution of N-Boc-(1R,2S)-1-amino-2-vinylcyclopropane carboxylic acid (255 mg, 1.0 mmol) in ether (10 mL) was treated with palladium acetate (5 mg, 0.022 mmol). The orange/red solution was placed under an atmosphere of N$_2$. An excess of diazomethane in ether was added dropwise over the course of 1 hour. The resulting solution was stirred at room temperature for 18 hours. The excess diazomethane was removed using a stream of nitrogen. The resulting solution was concentrated by rotary evaporation to give the crude product. Flash chromatography (10% ethyl acetate/hexane) provided 210 mg (78%) of N-Boc-(1R,2S)-1-amino-2-cyclopropylcyclopropane carboxylic acid ethyl ester as a colorless oil. LC-MS (retention time: 2.13, similar to method A except: gradient time 3 minutes, Xterra MS C18 S7 3.0×50 mm column), MS m/e 270 (M$^+$+1).

5. 1-t-Butoxycarbonylamino-cyclopropane-carboxylic acid is commercially available

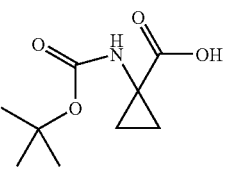

6. Preparation of 1-aminocyclobutanecarboxylic acid methyl ester-hydrochloride

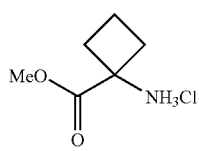

1-Aminocyclobutanecarboxylic acid (100 mg, 0.869 mmol) (Tocris) was dissolved in 10 mL of methanol. HCl gas was bubbled in for 2 hours. The reaction mixture was stirred for 18 hours, and then concentrated in vacuo to give 144 mg of a yellow oil. Trituration with 10 mL of diethyl ether provided 100 mg of the titled product as a white solid. $^1$H NMR (CDCl$_3$) δ 2.10-2.25 (m, 1H), 2.28-2.42 (m, 1H), 2.64-2.82 (m, 4H), 3.87 (s, 3H), 9.21 (br s, 3H).

7. Preparation of racemic (1R,2R)/(1S,2S) 1-Amino-2-ethylcyclopropanecarboxylic acid tert-butyl ester

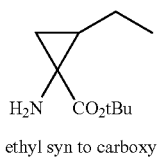

ethyl syn to carboxy

Step 1: Preparation of 2-Ethylcyclopropane-1,1-dicarboxylic acid di-tert-butyl ester, shown below

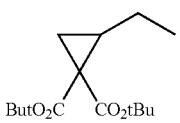

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred 18 hours at room temperature, a mixture of ice and water was then added. The crude product was extracted with dichloromethane (3×) and sequentially washed with water (3×), brine and the organic extracts combined. The organic layer was dried (MgSO$_4$), filtered and concentrated in vacuo. The resulting residue was flash chromatographed (100 g SiO$_2$, 3% diethyl ether in hexane) to afford the titled product (18.3 g, 67.8 mmol, 73% yield) which was used directly in the next reaction.

Step 2: Preparation of racemic 2-Ethylcyclopropane-1,1-dicarboxylic acid tert-butyl ester, shown below

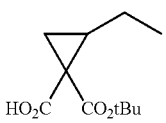

The product of Step 1 (18.3 g, 67.8 mmol) was added to a suspension of potassium tert-butoxide (33.55 g, 299.0 mmol) in dry ether (500 mL) at 0° C., followed by H$_2$O (1.35 mL, 75.0 mmol) and was vigorously stirred overnight at room temperature. The reaction mixture was poured in a mixture of ice and water and washed with diethyl ether (3×). The aqueous layer was acidified with a 10% aq. citric acid solution at 0° C. and extracted with ethyl acetate (3×). The combined organic layers were washed with water (2×), brine, dried (MgSO$_4$), filtered, and concentrated in vacuo to afford the titled product as a pale yellow oil (10 g, 46.8 mmol, 69% yield).

Step 3: Preparation of (1R,2R)/(1S,2S) 2-Ethyl-1-(2trimethylsilanylethoxycarbonylamino)cyclopropane-carboxylic acid tert-butyl ester, shown below

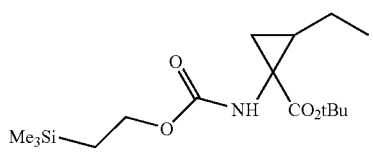

To a suspension of the product of Step 2 (10 g, 46.8 mmol) and 3 g of freshly activated 4 Å molecular sieves in dry benzene (160 mL), was added triethylamine (7.50 mL, 53.8 mmol) and DPPA (11 mL, 10.21 mmol). The reaction mixture was refluxed for 3.5 hours, 2-trimethylsilyl-ethanol (13.5 mL, 94.2 mmol) was then added, and the reaction mixture was refluxed overnight. The reaction mixture was filtered, diluted with diethyl ether, washed with a 10% aqueous citric acid solution, water, saturated aqueous NaHCO$_3$, water (2×), brine (2×), dried (MgSO$_4$), filtered, and concentrated in vacuo. The residue was suspended with 10 g of Aldrich polyisocyanate scavenger resin in 120 mL of dichloromethane, stirred at room temperature overnight and filtered to afford the titled-product (8 g, 24.3 mmol; 52%) as a pale yellow oil: $^1$H NMR (CDCl$_3$) δ 0.03 (s, 9H), 0.97 (m, 5H), 1.20 (br m, 1H), 1.45 (s, 9H), 1.40-1.70 (m, 4H), 4.16 (m, 2H), 5.30 (br s, 1H).

Step 4: Preparation of racemic (1R,2R)/(1S,2S) 1-Amino-2-ethylcyclopropanecarboxylic acid tert-butyl ester, shown below

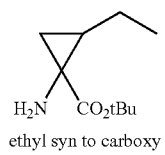

ethyl syn to carboxy

To the product of Step 3 (3 g, 9 mmol) was added a 1.0M TBAF solution in THF (9.3 mL, 9.3 mmol) and the mixture heated to reflux for 1.5 hours, cooled to room temperature and then diluted with 500 mL of ethyl acetate. The solution was successively washed with water (2×100 mL), brine (2×100 mL), dried (MgSO$_4$), filtered, and concentrated in vacuo to provide the title intermediate.

II. Preparation of P1' Intermediates

1. Preparation of Cyclopropylsulfonamide

Method 1 (of 2):

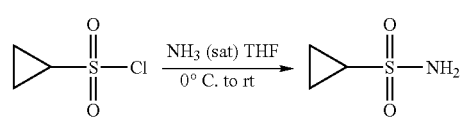

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to room temperature overnight and stirred one additional day. The mixture was concentrated until 1-2 mL of solvent remained, applied on to 30 g plug of $SiO_2$ (eluted with 30% to 60% ethyl acetate/hexanes) to afford 3.45 g (100%) of cyclopropyl sulfonamide as a white solid. $^1$H NMR (methanol-$d_4$) δ 0.94-1.07 (m, 4H), 2.52-2.60 (m, 1H); $^{13}$C NMR (methanol-$d_4$) δ 5.92, 33.01.

Method 2 (of 2):

Step 1: Preparation of N-tert-butyl-(3-chloro)propylsulfonamide

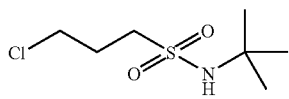

tert-Butylamine (3.0 mol, 315.3 mL) was dissolved in THF (2.5 L). The solution was cooled to −20° C. 3-Chloropropanesulfonyl chloride (1.5 mol, 182.4 mL) was added slowly. The reaction mixture was allowed to warm to room temperature and stirred for 24 hours. The mixture was filtered, and the filtrate was concentrated in vacuo. The residue was dissolved in dichloromethane (2.0 L). The resulting solution was washed with 1N HCl (1.0 L), water (1.0 L), brine (1.0 L) and dried over $Na_2SO_4$. It was filtered and concentrated in vacuo to give a slightly yellow solid, which was crystallized from hexane to afford the product as a white solid (316.0 g, 99%). $^1$H NMR (CDCl$_3$) δ 1.38 (s, 9H), 2.30-2.27 (m, 2H), 3.22 (t, J=7.35 Hz, 2H), 3.68 (t, J=6.2 Hz, 2H), 4.35 (br, 1H).

Step 2: Preparation of Cyclopropanesulfonic acid tert-butylamide

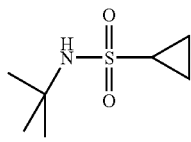

To a solution of N-tert-butyl-(3-chloro)propylsulfonamide (2.14 g, 10.0 mmol) in THF (100 mL) was added n-butyllithium (2.5M in hexane, 8.0 mL, 20.0 mmol) at −78° C. The reation mixture was allowed to warm up to room temperature over period of 1 hour. The volatiles were removed in vacuo. The residue was partitioned between ethyl acetate and water (200 mL, 200 mL). The separated organic phase was washed with brine, dried over $Na_2SO_4$, filtered and concentrated in vacuo. The residue was recrystallized from hexane to yield the desired product as a white solid (1.0 g, 56%). $^1$H NMR (CDCl$_3$) δ 0.98-1.00 (m, 2H), 1.18-1.19 (m, 2H), 1.39 (s, 9H), 2.48-2.51 (m, 1H), 4.19 (br, 1H).

Step 3: Preparation of Cyclopropylsulfonamide

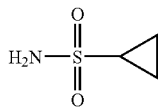

A solution of cyclopropanesulfonic acid tert-butylamide (110.0 g, 0.62 mol) in TFA (500 mL) was stirred at room temperature for 16 hours. The volatiles were removed in vacuo. The residue was recrystallized from ethyl acetate/hexane (60 mL/240 mL) to yield the desired product as a white solid (68.5 g, 91%). $^1$H NMR (DMSO-$d_6$) δ 0.84-0.88 (m, 2H), 0.95-0.98 (m, 2H), 2.41-2.58 (m, 1H), 6.56 (br, 2H).

2. Preparation of Cl-Substituted Cyclopropylsulfonamides

2a. Preparation of N-tert-butyl-(1-methyl)cyclopropyl-sulfonamide

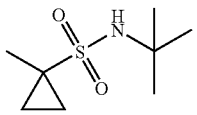

Step 1: Preparation of N-tert-butyl-(3-chloro)propylsulfonamide

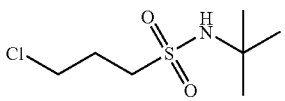

Prepared as described above.

Step 2: Preparation of N-tert-butyl-(1-methyl)cyclopropyl-sulfonamide

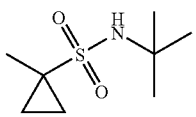

A solution of N-tert-butyl-(3-chloro)propylsulfonamide (4.3 g, 20 mmol) was dissolved in dry THF (100 mL) and cooled to −78° C. To this solution was added n-butyllithium (17.6 mL, 44 mmol, 2.5M in hexane) slowly. The dry ice bath was removed and the reaction mixture was allowed to warm to room temperature over a period of 1.5 hours. This mixture was then cooled to −78° C., and a solution of n-butyllithium (20 mmol, 8 mL, 2.5M in hexane) was added. The reaction mixture was warmed to room temperature, re-cooled to −78° C. over a period of 2 hours and a neat solution of methyl iodide (5.68 g, 40 mmol) was added. The reaction mixture was allowed to warm to room temperature overnight, then quenched with saturated NH$_4$Cl (100 mL) at room temperature. It was extracted with ethyl acetate (100 mL). The organic phase was washed with brine (100 mL), dried (MgSO$_4$), filtered, and concentrated in vacuo to give a yellow oil which was crystallized from hexane to afford the product as a slightly yellow solid (3.1 g, 81%): $^1$H NMR (CDCl$_3$) δ 0.79 (m, 2H), 1.36 (s, 9H), 1.52 (m, 2H), 1.62 (s, 3H), 4.10 (br s, 1H).

Step 3: Preparation of 1-methylcyclopropylsulfonamide

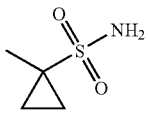

A solution of N-tert-butyl-(1-methyl)cyclopropylsulfonamide (1.91 g, 10 mmol) was dissolved in TFA (30 mL), and the reaction mixture stirred at room temperature for 16 hours. The solvent was removed in vacuo to give a yellow oil which was crystallized from ethyl acetate/hexane (1:4, 40 mL) to yield Example 3, 1-methylcyclopropylsulfonamide, as a white solid (1.25 g, 96%): $^1$H NMR (CDCl$_3$) δ 0.84 (m, 2H), 1.41 (m, 2H), 1.58 (s, 3H), 4.65 (br s, 2H). Anal. Calcd. For C$_4$H$_9$NO$_2$S: C, 35.54; H, 6.71; N, 10.36. Found: C, 35.67; H, 6.80; N, 10.40.

2b. Preparation of 1-Benzylcyclopropylsulfonamide

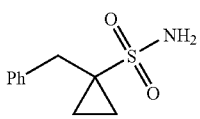

Step 1: Preparation of N-tert-butyl-(1-benzyl)cyclopropylsulfonamide

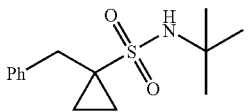

This compound was obtained in 60% yield using the procedure described for the synthesis of N-tert-butyl-(1-methyl)cyclopropylsulfonamide except 1.05 equivalents of benzyl bromide were used, followed by trituration with 10% ethyl acetate in hexane: $^1$H NMR (CDCl$_3$) δ 0.92 (m, 2H), 1.36 (m, 2H), 1.43 (s, 9H), 3.25 (s, 2H), 4.62 (br s, 1H), 7.29-7.36 (m, 5H).

Step 2: Preparation of 1-Benzylcyclopropylsulfonamide

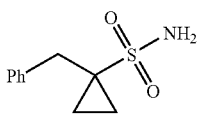

This compound was obtained in 66% yield from N-tert-butyl(1-benzyl)cyclopropylsulfonamide using the procedure described for the synthesis of 1-methylcyclopropylsulfonamide, followed by recrystallization from the minimum amount of 10% ethyl acetate in hexane: $^1$H NMR (CDCl$_3$) δ 0.90 (m, 2H), 1.42 (m, 2H), 3.25 (s, 2H), 4.05 (s, 2H), 7.29 (m, 3H), 7.34 (m, 2H); $^{13}$C NMR (CDCl$_3$) δ 11.1, 36.8, 41.9, 127.4, 128.8, 129.9, 136.5.

2c. Preparation of 1-Propylcyclopropylsulfonamide

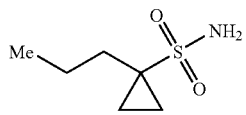

This compound was prepared using the process desribed for the preparation of 1-methylcyclopropylsulfonamide except propyl halide was utilized in place of methyl iodide in the second step of this process.

2d. Preparation of 1-allylcyclopropylsulfonamide

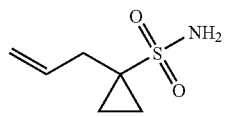

Step 1: Preparation of N-tert-butyl-(1-allyl)cyclopropylsulfonamide

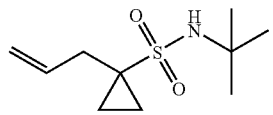

This compound was obtained in 97% yield according to the procedure described in the synthesis of N-tert-butyl-(1-methyl)cyclopropylsulfonamide except 1.25 equivalents of allyl bromide were used as electrophile. The compound was taken directly into the next reaction without purification: $^1$H NMR (CDCl$_3$) δ 0.83 (m, 2H), 1.34 (s, 9H), 1.37 (m, 2H), 2.64 (d, J=7.3 Hz, 2H), 4.25 (br s, 1H), 5.07-5.10 (m, 2H), 6.70-6.85 (m, 1H).

Step 2: Preparation of 1-allylcyclopropylsulfonamide

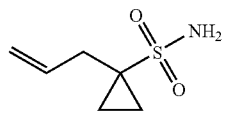

This compound, 1-allylcyclopropylsulfonamide, was obtained in 40% yield from N-tert-butyl-(1-allyl)cyclopropylsulfonamide according to the procedure described in the synthesis of 1-methylcyclopropylsulfonamide. The compound was purified by column chromatography over SiO$_2$ using 2% methanol in dichloromethane as the eluent: $^1$H NMR (CDCl$_3$) δ 0.88 (m, 2H), 1.37 (m, 2H), 2.66 (d, J=7.0 Hz, 2H), 4.80 (s, 2H), 5.16 (m, 2H), 5.82 (m, 1H); $^{13}$C NMR (CDCl$_3$) δ 11.2, 35.6, 40.7, 119.0, 133.6.

2e. Preparation of 1-(1-cyclohexenyl)cyclopropyl-sulfonamide

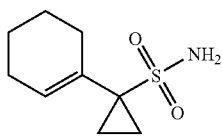

Step 1: Preparation of N-tert-butyl-[1-(1-hydroxy)cyclohexyl]-cyclopropylsulfonamide

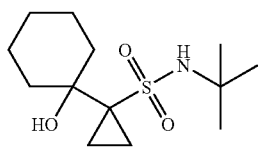

This compound was obtained in 84% yield using to the procedure described for the synthesis of N-tert-butyl-(1-methyl)cyclopropylsul-fonamide except 1.30 equivalents of cyclohexanone were used, followed by recrystallization from the minimum amount of 20% ethyl acetate in hexane: $^1$H NMR (CDCl$_3$) δ 1.05 (m, 4H), 1.26 (m, 2H), 1.37 (s, 9H), 1.57-1.59 (m, 6H), 1.97 (m, 2H), 2.87 (br s, 1H), 4.55 (br s, 1H).

Step 2: Preparation of 1-(1-cyclohexenyl)cyclopropyl-sulfonamide

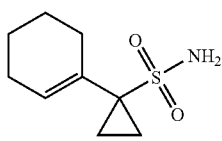

This compound, 1-(1-cyclohexenyl)-cyclopropylsulfonamide was obtained in 85% yield from N-tert-butyl-[1-(1-hydroxy)cyclohexyl]-cyclopropylsulfonamide using the procedure described for the synthesis of 1-methylcyclopropylsulfonamide, followed by recrystallization from the minimum amount of ethyl acetate and hexane: $^1$H NMR (DMSO-d$_6$) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-d$_6$) δ 11.6, 21.5, 22.3, 25.0, 27.2, 46.9, 131.6, 132.2; LR-MS (ESI): 200 (M$^+$–1).

2f. Preparation of 1-benzoylcyclo-propylsulfonamide

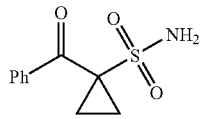

Step 1: Preparation of N-tert-butyl-(1-benzoyl)cyclopropyl-sulfonamide

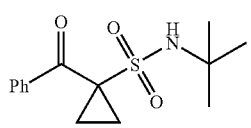

This compound was obtained in 66% yield using the procedure described for the synthesis of N-tert-butyl-(1-methyl)cyclopropylsulfonamide except 1.2 equivalents of methyl benzoate was used as the electrophile. The compound was purified by column chromatography over SiO$_2$ using 30% to 100% dichloromethane in hexane: $^1$H NMR (CDCl$_3$) δ 1.31 (s, 9H), 1.52 (m, 2H), 1.81 (m, 2H), 4.16 (br s, 1H), 7.46 (m, 2H), 7.57 (m, 1H), 8.05 (d, J=8.5 Hz, 2H).

Step 2: Preparation of 1-benzoylcyclo-propylsulfonamide

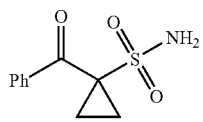

This compound was obtained in 87% yield from N-tert-butyl(1-benzoyl)cyclopropylsul-fonamide using the procedure described for the synthesis of 1-methylcyclopropylsulfonamide, followed by recrystallization from the minimum amount of ethyl acetate in hexane: $^1$H NMR (DMSO-d$_6$) δ 1.39 (m, 2H), 1.61 (m, 2H), 7.22 (s, 2H), 7.53 (t, J=7.6 Hz, 2H), 7.65 (t, J=7.6 Hz, 1H), 8.06 (d, J=8.2 Hz, 2H); $^{13}$C NMR (DMSO-d$_6$) δ 12.3, 48.4, 128.1, 130.0, 133.4, 135.3, 192.0.

2g. Preparation of N-tert-butyl-(1-phenylaminocarboxy)-cyclopropylsulfonamide

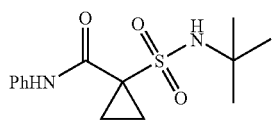

This compound was obtained in 42% yield using the procedure described for the synthesis of N-tert-butyl-(1-methyl)cyclopropylsulfonamide using 1 equivalent of phenylisocyanate, followed by recrystallization from the minimum amount of ethyl acetate in hexane $^1$H NMR (CDCl$_3$) δ 1.38 (s, 9H), 1.67-1.71 (m, 4H), 4.30 (br s, 1H), 7.10 (t, J=7.5 Hz, 1H), 7.34 (t, J=7.5 Hz, 2H), 7.53 (t, J=7.5 Hz, 2H).

3. Preparation of C1-Substituted Cyclopropanesulfonamides the use of an N-Boc Protecting Group

3a. Preparation of Cyclopropylsulfonylamine Tert-butyl Carbamate, a Key Intermediate in the Preparation of C1-substituted Cyclopropylsulfonamides

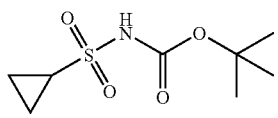

Step 1: Preparation of 3-chloropropylsulfonamide

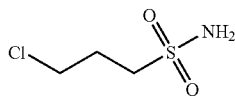

A solution of 3-chloropropanesulfonyl chloride (55 g, 310.7 mmol) was dissolved in THF (200 mL) and added dropwise over 30 minutes to a solution of NH$_4$OH (200 mL) cooled to 0° C. The reaction mixture was warmed to room temperature, stirred 1 hour, and the aqueous layer partioned multiple time with dichloromethane (4×500 mL). The combined dichloromethane layer was washed with 1N HCl (150 mL), water (150 mL), dried over MgSO$_4$, filtered, and concentrated in vacuo. The crude solid was recrystallized from the minimum amount of dichloromethane in hexanes to afford 3-chloropropylsulfonamide as a white solid (45.3 g, 93%). $^1$H NMR (CDCl$_3$) δ 2.34 (m, 2H), 3.32 (t, J=7.3 Hz, 2H), 3.70 (t, J=6.2 Hz, 2H), 4.83 (s, 2H); $^{13}$C NMR (CDCl$_3$) δ 27.10, 42.63, 52.57.

Step 2: Preparation of 3-chloropropylsulfonylamine tert-butylcarbamate

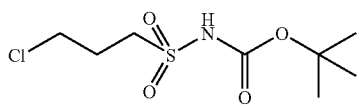

To a solution of 3-chloropropylsulfonamide (30.2 g, 191.5 mmol), triethylamine (30.2 mL, 217.0 mmol), and 4-DMAP (2.40 g, 19.6 mmol) in dichloromethane (350 mL) cooled to 0° C. was added slowly dropwise a solution of di-tert-butyldicarbonate (47.2 g, 216.9 mmol) in dichloromethane (250 mL) over 30 minutes. The reaction mixture was allowed to warm to room temperature, stirred an additional 3 hours and was partioned with 1N HCl (300 mL), water (300 mL), brine (300 mL), dried over MgSO$_4$, filtered, and concentrated in vacuo to afford the crude product. This material was triturated with 70 mL of 5% dichloromethane in hexanes to afford 3-chloropropylsulfonylamine tert-butylcarbamate as an off white solid (47.2 g, 96%): $^1$H NMR (CDCl$_3$) δ 1.51 (s, 9H), 2.33 (m, 2H), 3.60 (t, J=7.3 Hz, 2H), 3.68 (t, J=6.21 Hz, 2H); $^{13}$C NMR (CDCl$_3$) δ 26.50, 27.95, 42.37, 50.40, 84.76, 149.53.

Step 3: Preparation of Cyclopropylsulfonylamine Tert-butyl Carbamate

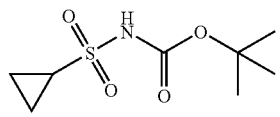

A solution of n-butyllithium (74.7 mL, 119.5 mmol, 1.6M in hexane) was dissolved in dry THF (105 mL) and cooled to –78° C. under a Argon atmosphere. To this solution was added a solution of 3-chloropropylsulfonylamine tert-butyl-carbamate (14 g, 54.3 mmol) in dry THF (105 mL) dropwise over 20-30 minutes. The dry ice bath was removed and the reaction mixture was allowed to warm to room temperature over a period of 2 hours. The reaction mixture was quenched with glacial acetic acid (3.4 mL), concentrated in vacuo, and partitioned between dichloromethane (100 mL) and water (100 mL). The organic phase was washed with brine (100 mL), dried (MgSO$_4$), filtered, and concentrated in vacuo to afford the cyclopropylsulfonylamine tert-butyl carbamate as a waxy off-white solid (12.08 g, 100%): $^1$H NMR (CDCl$_3$) δ 1.10 (m, 2H), 1.34 (m, 2H), 1.50 (s, 9H), 2.88 (m, 1H), 7.43 (s, 1H). $^{13}$C NMR (CDCl$_3$) δ 6.21, 28.00, 31.13, 84.07, 149.82.

3b. Preparation of 1-methoxy-methylcyclopropy-sulfonamide

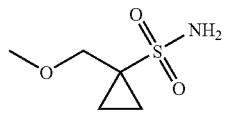

Step 1: Preparation of 1-methoxymethylcycloprotylsulfonylamine tert-butylcarbamate

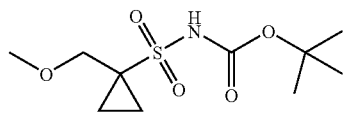

To a solution of cyclopropylsulfonylamine tert-butyl carbamate (1.0 g, 4.5 mmol) dissolved in THF (30 mL) cooled to –78° C., was added n-butyllithium (6.4 mL, 10.2 mmol, 1.6M in hexane) and the reaction mixture was stirred for 1 hour. To this solution was added a neat solution of chloromethyl methyl ether (0.40 mL, 5.24 mmol), and the mixture was slowly allowed to warm to room temperature overnight. The solution pH was adjusted to 3 using 1N aqueous HCl and was then extracted with ethyl acetate (4×50 mL portions). The combined extracts were dried (MgSO$_4$), filtered, and concentrated to afford 1-methoxymethylcyclopropylsulfonylamine tert-butylcarbamate, as a waxy solid (1.20 g, 100%) which was taken directly into the next reaction without further purification: $^1$H NMR (CDCl$_3$) δ 1.03 (m, 2H), 1.52 (s, 9H), 1.66 (m, 2H), 3.38 (s, 3H), 3.68 (s, 2H), 7.54 (s, 1H); $^{13}$C NMR (CDCl$_3$) δ 11.37, 28.29, 40.38, 58.94, 73.43, 83.61, 149.57.

Step 2: Preparation of 1-methoxymethylcyclopropysulfonamide

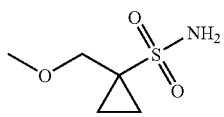

A solution of 1-methoxymethylcyclopropylsulfonylamine tert-butylcarbamate (1.14 g, 4.30 mmol) was dissolved in a solution of 50% TFA/dichloromethane (30 mL) and was stirred stirred at room temperature for 16 hours. The solvent was removed in vacuo and the residue chromatographed over 80 g of SiO$_2$ (eluting with 0% to 60% ethyl acetate/hexanes to 1-methoxymethylcyclopropylsulfonamide as a white solid (0.55 g, 77% overall over two steps): $^1$H NMR (CDCl$_3$) δ 0.95 (m, 2H), 1.44 (m, 2H), 3.36 (s, 3H), 3.65 (s, 2H), 4.85 (s, 2H); $^{13}$C NMR (CDCl$_3$) δ 11.17, 40.87, 59.23, 74.80; LRMS m/z 183 (M$^+$+NH$_4$).

3c. Preparation of 1-cyclopropylmethylcyclopropylsulfonamide

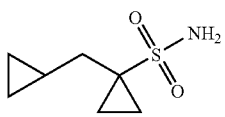

Step 1: Preparation of 1-cyclopropylmethylcyclopropylsulfonylamine tert-butylcarbamate

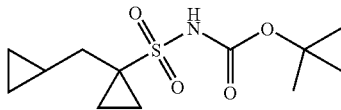

1-Cyclopropylmethylcyclopropylsulfonylamine tert-butylcarbamate was obtained in 92% yield according to the procedure described in the synthesis of 1-methoxymethylcyclopropylsulfonylamine tert-butylcarbamate, except 1.10 equivalents of cyclopropylmethyl bromide were used as electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-cyclopropylmethyl-cyclopropylsulfonamide

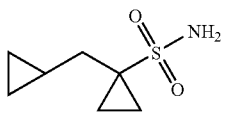

This compound was obtained in 65% yield from 1-cyclopropylmethylcyclopropylsulfonylamine tert-butylcarbamate according to the procedure described for the synthesis of 1-methoxymethylcyclopropylsulfonamide. The compound was purified by column chromatography over SiO$_2$ using 0% to 60% ethyl acetate in hexanes as the eluent: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ4.65, 7.74, 11.26, 35.62, 41.21; LRMS m/z 193 (M$^+$+NH$_4$).

3d. Preparation of 1-propylcarbamoylcyclopropane-sulfonamide

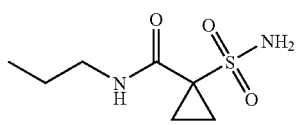

Step 1: Preparation of 1-propylcarbamoylcyclopropane-sulfonamide tert-butylcarbamate

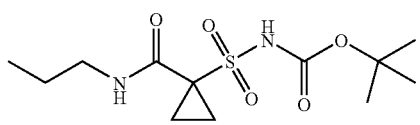

This compound was obtained in a crude 100% yield according to the procedure described for the synthesis of 1-methoxymethylcyclopropylsulfonylamine tert-butyl-carbamate except that 1.10 equivalents of n-propyl isocyanate was used as the electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-propylcarbamoylcyclopropane-sulfonamide

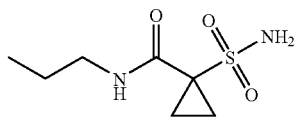

This compound was obtained in an optimized 50% yield from 1-propylcarbamoylcyclopropanesulfonamide tert-butylcarbamate according to the procedure described for the synthesis of 1-methoxymethylcyclopropylsulfonamide, except that no chromatography was used as the material was recrystallized from the minimum amount of dichloromethane/hexanes: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

3e. Preparation of 1-(3,5-dimethylisoxazol-4yl)carbamoylcyclopropanesulfonamide

4. Preparation of Cycloalkylsulfonamides from Cyloalkylbromides

4a. Preparation of Cyclobutylsulfonamide from Cylobutyl Bromide

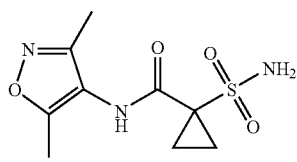

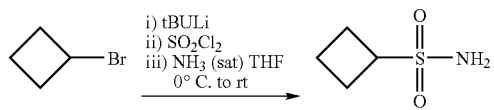

Step 1: Preparation of 1-(3,5-dimethylisoxazol-4-yl)carbamoylcyclopropanesulfonamide tert-butylcarbamate To a solution of 5.0 g (37.0 mmol) of cyclobutyl bromide in 30 mL of anhydrous diethyl ether (diethyl ether) cooled to −78° C. was added 44 mL (74.8 mmol) of 1.7M tert-butyllithium in pentanes and the solution slowly warmed to −35° C. over 1.5 hours. This mixture was cannulated slowly into a solution of 5.0 g (37.0 mmol) of freshly distilled sulfuryl chloride in 100 mL of hexanes cooled to −40° C., warmed to 0° C. over 1 hour and carefully concentrated in vacuo. This mixture was redissolved in diethyl ether, washed once with some ice-cold water, dried (MgSO$_4$), filtered, and concentrated carefully. This mixture was redissolved in 20 mL of THF, added dropwise to 500 mL of saturated NH$_3$ in THF, and was allowed to stir overnight. The mixture was concentrated in vacuo to a crude yellow solid and was recrystallized from the minimum amount of dichloromethane in hexanes with 1-2 drops of methanol to afford 1.90 g (38%) of cyclobutylsulfonamide as a white solid. $^1$H NMR (CDCl$_3$) δ 1.95-2.06 (m, 2H), 2.30-2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M−H)$^-$ calcd for C$_4$H$_8$NSO$_2$: 134.0276, found 134.0282.

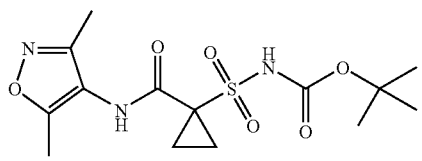

This compound was obtained in a crude 100% yield according to the procedure described for the synthesis of 1-methoxymethylcyclopropylsulfonylamine tert-butylcarbamate except that 1.20 equivalents of 3,5-dimethylisoxazole-4-isocyanate was used as the electrophile. The compound was taken directly into the next reaction without purification.

4b. Preparation of Cyclopentyl Sulfonamide

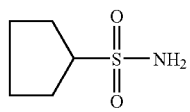

Step 2: Preparation of 1-(3,5-dimethylisoxazol-4yl)carbamoylcyclopropanesulfonamide

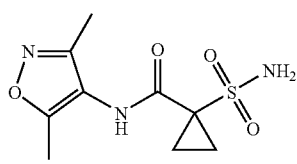

This compound was obtained in 50% yield (580 mg) from 1.62 g (4.52 mmol) of 1-(3,5-dimethylisoxazol-4-yl)carbamoylcyclo-propanesulfonamide tert-butylcarbamate using 30 mL (120 mmol) of 4N HCl/dioxanes, stirring overnight, concentration and chromatography over a Biotage 40M column (eluting with 0% to 5% methanol/dichloromethane: $^1$H NMR (methanol-d$_4$) δ 1.57 (m, 2H), 1.61 (m 2H), 2.15 (s, 3H), 2.30 (s, 3H), 4.84 (s, 3H); $^{13}$C NMR (methanol-d$_4$) δ 9.65, 10.94, 15.01, 46.11, 114.82, 159.45, 165.55, 168.15; LRMS m/z 260 (M$^+$+H).

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and the solution was then concentrated. The residue was recrystallized from the minimum amount of dichloromethane in hexanes with 1-2 drops of methanol to afford 2.49 g (41%) of cyclopentylsulfonamide as a white solid. $^1$H NMR (CDCl$_3$) δ 1.58-1.72 (m, 2H), 1.74-1.88 (m, 2H), 1.94-2.14 (m, 4H), 3.48-3.59 (m, 1H), 4.80 (br s, 2H); $^{13}$C NMR (CDCl$_3$) δ 25.90, 28.33, 63.54; MS m/e 148 (M−H)$^-$.

4c. Preparation of Cyclohexyl Sulfonamide

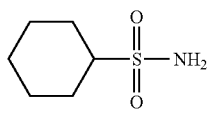

A solution of 18.5 mL (37.0 mmol) of 2M cyclohexylmagnesium chloride (TCI Americas) in diethyl ether was added dropwise to a solution of 3.0 mL (37.0 mmol) freshly distilled sulfuryl chloride in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and was concentrated. The residue was recrystallized from the minimum amount of dichloromethane in hexanes with 1-2 drops of methanol to afford 1.66 g (30%) of cyclohexyl-sulfonamide as a white solid: $^1$H NMR (CDCl$_3$) δ 1.11-1.37 (m, 3H), 1.43-1.56 (m, 2H), 1.67-1.76 (m, 1H), 1.86-1.96 (m, 2H), 2.18-2.28 (m, 2H), 2.91 (tt, J=12, 3.5 Hz, 1H), 4.70 (br s, 2H); $^{13}$C NMR (CDCl$_3$) δ 25.04, 25.04, 26.56, 62.74; MS m/e 162 (M−1)$^-$.

4d. Preparation of Neopentylsulfonamide

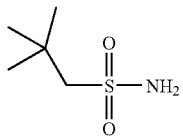

Following the procedure for the preparation of cyclohexylsulfonamide, 49 mL (37 mmol) of 0.75M neopentylmagnesium chloride (Alfa) in diethyl ether was converted to 1.52 g (27%) of neopentylsulfonamide as a white solid. $^1$H NMR (CDCl$_3$) δ 1.17 (s, 9H), 3.12 (s, 2H), 4.74 (brs, 2H); $^{13}$C NMR (CDCl$_3$) δ 29.46, 31.51, 67.38; MS m/e 150 (M−1)$^-$.

4e. Preparation of Cyclobutylcarbinylsulfonamide

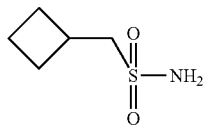

A solution of 12.3 g (83 mmol) of cyclobutylcarbinyl bromide (Aldrich) and 13.7 g (91 mmol) of sodium iodide in 150 mL of acetone was refluxed overnight and then cooled to room temperature. The inorganic solids were filtered off and the acetone and cyclopropylcarbinyl iodide (8.41 g, 46%) distilled off at ambient and 150 torr at 80° C., respectively.

A solution of 4.0 g (21.98 mmol) of cyclobutyl carbinyl iodide in 30 mL of anhydrous diethyl ether (diethyl ether) cooled to −78° C. was cannulated into a solution of 17 mL (21.98 mmol) of 1.3M sec-butyllithium in cyclohexanes and the solution was stirred for 5 minutes. To this mixture was cannulated a solution of 3.0 g (21.98 mmol) of freshly distilled sulfuryl chloride in 110 mL of hexanes cooled to −78° C., the mixture warmed to room temperature over 1 hour and was then carefully concentrated in vacuo. This mixture was redissolved in diethyl ether, washed once with some ice-cold water, dried (MgSO$_4$), filtered, and concentrated carefully. This mixture was redissolved in 30 mL of THF, added dropwise to 500 mL of saturated NH$_3$ in THF and was allowed to stir overnight. The mixture was concentrated in vacuo to a crude yellow solid and was recrystallized from the minimum amount of dichloromethane in hexanes with 1-2 drops of methanol to afford 1.39 g (42%) of cyclobutyl carbinylsulfonamide as a white solid. $^1$H NMR (CDCl$_3$) δ 1.81-2.03 (m, 4H), 2.14-2.28 (m, 2H), 2.81-2.92 (m, 1H), 3.22 (d, J=7 Hz, 2H), 4.74 (brs, 2H); $^{13}$C NMR (CDCl$_3$) δ 19.10, 28.21, 30.64, 60.93; MS m/e 148 (M−1)$^-$. time: 1.73, method B), 818 (M$^+$+H)

4f. Preparation of Cyclopropylcarbinylsulfonamide

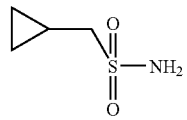

Using the procedure employed for the preparation of cyclobutylcarbinylsulfonamide, cyclopropylcarbinylsulfonamide was prepared from cyclopropylcarbinyl bromide (Aldrich) (see also *JACS* 1981, p. 442-445). $^1$H NMR (CDCl$_3$) δ 0.39-0.44 (m, 2H), 0.67-0.76 (m, 2H), 1.13-1.27 (m, 1H), 3.03 (d, J=7.3 Hz, 2H), 4.74 (brs, 2H); $^{13}$C NMR (CDCl$_3$) δ 4.33, 5.61, 59.93; MS m/e 134 (M−1).

4g. Preparation of 2-thiophenesulfonamide

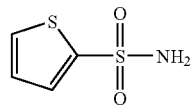

Prepared from 2-thiophenesulfonyl chloride (purchased from Aldrich) using the method of *Justus Liebigs Ann. Chem.*, 501, 1933, p. 174-182.

4h. Preparation of 4-bromobenzenesulfonamide

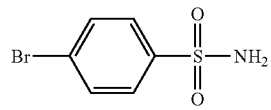

4-Bromophenylsulfonamide was prepared by treatment of commercially available 4-bromosulfonyl chloride with saturated ammonia in THF.

5. General Procedure for the Preparation of Sulfamides

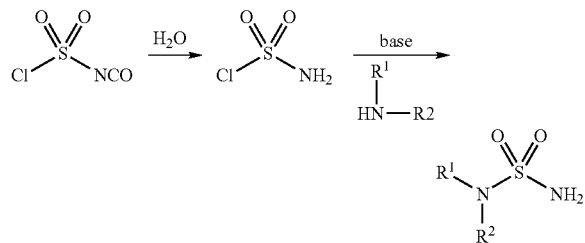

The intermediate sulfamoyl chloride was prepared by addition of water (1 equiv) in THF to a cold (−20° C.) stirred solution of chlorosulfonyl isocyanate (1 equiv) in THF and the resulting solution allowed to warm to 0° C. To this solution was added anhydrous triethylamine (1 equiv) followed by requisite secondary amine (1 equiv). The reaction mixture was warmed to room temperature, then filtered and the filtrate was concentrated to afford the desired sulfamides.

III. Preparation of P1'-P1 Intermediates

1a. Preparation of cyclopropanesulfonic acid (1-(R)-amino-2-(S)-vinyl-cyclopropanecarbonyl)amide HCl salt

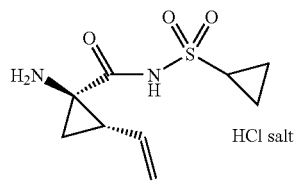

Step 1: Preparation of 1(R)-tert-butoxycarbonylamino-2(S)-vinyl-cyclopropanecarboxylic acid

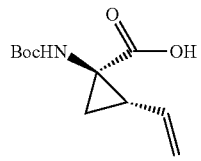

To a solution of 1(R)-tert-butoxycarbonylamino-2(S)-vinyl-cyclopropanecarboxylic acid ethyl ester (3.28 g, 13.2 mmol) in THF (7 mL) and methanol (7 mL) was added a suspension of LiOH (1.27 g, 53.0 mmol) in water (14 mL). The mixture was stirred overnight at room temperature and quenched with 1N NaOH (15 mL) and water (20 mL). The resulting mixture was washed with ethyl acetate (20 mL), and the organic phase was extracted with 20 mL 0.5N NaOH. The combined aqueous phases were acidified with 1N HCl until pH 4 and extracted with ethyl acetate (3×40 mL). The combined organic extracts were washed with brine, dried (MgSO$_4$), filtered and concentrated to yield the title compound as a white solid (2.62 g, 87%). $^1$H NMR: (DMSO-d$_6$) δ 1.22-1.26 (m, 1H), 1.37 (s, 9H), 1.50-1.52 (m, 1H), 2.05 (q, J=9 Hz, 1H), 5.04 (d, J=10 Hz, 1H), 5.22 (d, J=17 Hz, 1H), 5.64-5.71 (m, 1H), 7.18, 7.53 (s, NH (rotamers), 12.4 (br s, 1H)); LC-MS (retention time: 1.67 minutes, method B), MS m/z 228 (M$^+$+H).

Step 2: Preparation of cyclopropanesulfonic acid (1-(R)-tert-butoxycarbonylamino-2-(S)-vinylcyclopropanecarbonyl)-amide

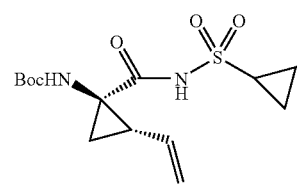

A solution of the product of Step 1 (2.62 g, 11.5 mmol) and CDI (2.43 g, 15.0 mmol) in THF (40 mL) was heated at reflux for 50 minutes under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 hours. The mixture was quenched with 1N HCl to pH 1 and THF was concentrated in vacuo. The suspension was extracted with ethyl acetate (2×50 mL) and the combined organic extracts were dried (Na$_2$SO$_4$), filtered, and concentrated. Purification by recystallization from hexanes-ethyl acetate (1:1) afforded the title compound (2.4 g) as a white solid. The mother liquor was purified by a Biotage 40S column (eluted 9% acetone in dichloromethane) to give a second batch of the title compound (1.1 g). Both batches were combined (total yield 92%). $^1$H NMR (DMSO-d$_6$) δ 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers); LC-MS (retention time: 1.70 minutes, method B), MS m/z 331 (M$^+$+H).

Step 3: Preparation of cyclopropanesulfonic acid (1-(R)-amino-2-(S)-vinylcyclopropanecarbonyl)amide HCl salt

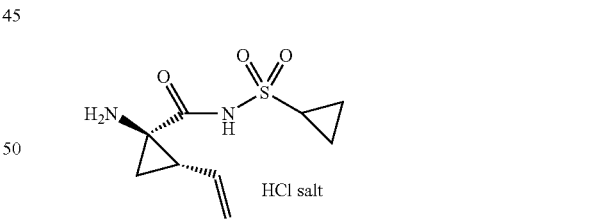

A solution of the product of Step 2 (3.5 g, 10.6 mmol) in dichloromethane (35 mL) and TFA (32 mL) was stirred at room temperature for 1.5 hours. The volatiles were removed in vacuo and the residue suspended in 1N HCl in diethyl ether (20 mL) and concentrated in vacuo. This procedure was repeated once. The resulting mixture was triturated from pentane and filtered to give the title compound as a hygroscopic, off-white solid (2.60 g, 92%). $^1$H NMR: (DMSO-d$_6$) δ 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, 1H), 5.52-5.59 (m, 1H), 9.17 (br s, 3H); LC-MS (retention time: 0.24 minutes, method B), MS m/z 231 (M$^+$+H).

1b. Preparation of P1-P1' Sulfamide Derivative

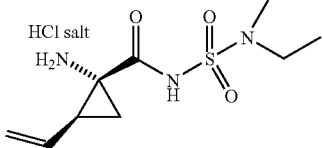

To a solution of (1R,2S) 1-tert-butoxycarbonylamino-2-vinyl-cyclopropanecarboxylic acid (217 mg, 1.194 mmol) in THF (5 mL), was added CDI (290 mg, 1.791 mmol) and the reaction mixture was heated under reflux for 45 minutes. In another round-bottomed flask, LiHMDS (1.0M solution in hexanes, 2.4 mL, 2.4 mmol) was added to a solution of N-ethylmethylsulfamide (330 mg, 2.388 mmol) in THF (5 mL) and the reaction mixture was stirred at room temperature for 1 hour. Two reaction mixtures were added together and stirred at room temperature for 2 hours. Water was added to quench the reaction and the reaction solution was extracted with ethyl acetate. The organic layer was separated and dried over MgSO$_4$. Filtration and concentration of the solvent gave crude product which was purified by preparative HPLC to afford desired N-Boc protected N-acylsulfamide. The Boc protecting group was then removed as the compound was dissolved in 4N HCl solution in dioxane (2 mL) and stirred at room temperature for 4 hours. Evaporation of solution give brownish oil as the HCl salt. (112 mg, 33% yield). $^1$H NMR (400 Mz, CD$_3$OD) δ 1.16 (t, J=7.21 Hz, 3H), 1.68 (dd, J=10.03, 7.83 Hz, 1H), 2.15 (m, 1H), 2.37 (m, 1H), 2.89 (s, 3H), 3.30 (m, 2H), 5.31 (d, J=10.27 Hz, 1H), 5.42 (d, J=17.12 Hz, 3H), 5.68 (m, 1H). LC-MS (retention time: 0.883 minutes.), MS m/z 270 (M+Na$^+$).

Section B

Preparation of Compounds and Examples of Formula I

Example 1

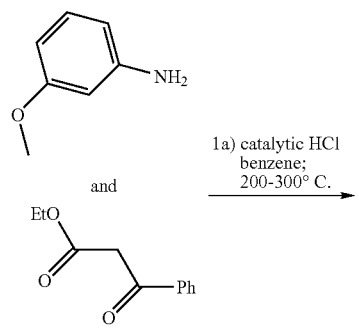

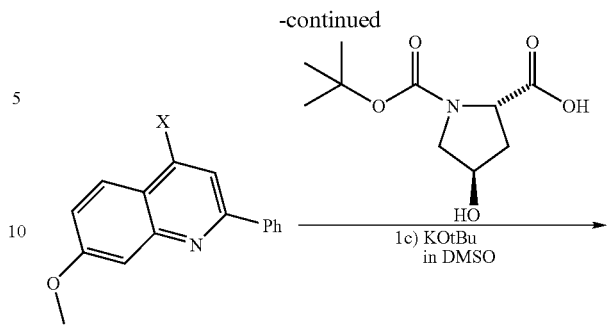

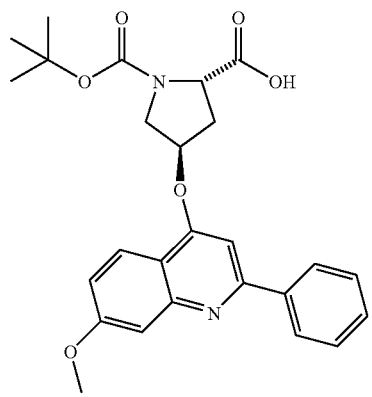

Example 1

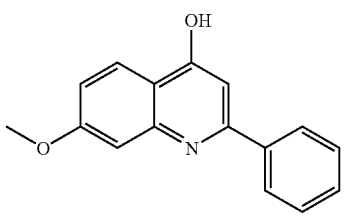

Step 1a

To a solution of m-anisidine (300 g, 2.44 mol) and ethyl benzoylacetate (234.2 g, 1.22 mol) in toluene (2.0 L) was added HCl (4.0N in dioxane, 12.2 mL, 48.8 mmol). The resulting solution was refluxed for 6.5 hours using a Dean-Stark apparatus (about 56 mL of aqueous solution was collected). The mixture was cooled to room temperature, partitioned multiple times with aqueous HCl (10%, 3×500 mL), aqueous NaOH (1.0N, 2×200 mL), water (3×200 mL), and the organic layer dried (MgSO$_4$), filtered, and concentrated in vacuo to supply an oily residue (329.5 g). The crude product was heated in an oil bath (280° C.) for 80 minutes using a Dean-Stark apparatus (about 85 mL liquid was collected). The reaction mixture was cooled down to room temperature, the solid residue triturated with CH$_2$Cl$_2$ (400 mL), the resulting suspension filtered, and the filter cake washed with more CH$_2$Cl$_2$ (2×150 mL). The resulting solid was dried in vacuo (50° C.; 1 torr; 1 day) affording analytically pure product as a light brown solid (60.7 g, 20% overall). $^1$H NMR (DMSO-d$_6$) δ 3.86 (s, 3H), 6.26 (s, 1H), 6.94 (dd, J=9.0, 2.4 Hz, 1H), 7.21 (d, J=2.4 Hz, 1H), 7.55-7.62 (m, 3H), 7.80-7.84 (m, 2H), 8.00 (d, J=9.0 Hz, 1H), 11.54 (s, 1H); $^{13}$C NMR (DMSO-d$_6$) δ 55.38, 99.69, 107.07, 113.18, 119.22, 126.52, 127.17, 128.97, 130.34, 134.17, 142.27, 149.53, 161.92, 176.48. LC-MS (MS m/z 252 (M$^+$+1).

Step 1b

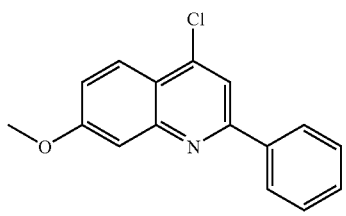

The product of Step 1a (21.7 g, 86.4 mmol) was suspended in POCl$_3$ (240 mL). The suspension was refluxed for 2 hours. After removal of the POCl$_3$ in vacuo, the residue was partitioned between ethyl acetate (1 L), and cold aqueous NaOH (generated from 1.0N 200 mL NaOH and 20 mL 10.0N NaOH) and stirred for 15 minutes. The organic layer was washed with water (2×200 mL), brine (200 mL), dried (MgSO$_4$), and concentrated in vacuo to supply the desired product (21.0 g, 90%) as a light brown solid. $^1$H NMR (DMSO-d$_6$) δ 3.97 (s, 3H), 7.36 (dd, J=9.2, 2.6 Hz, 1H), 7.49-7.59 (m, 4H), 8.08 (d, J=9.2 Hz, 1H), 8.19 (s, 1H), 8.26-8.30 (m, 2H); $^{13}$C NMR (DMSO-d$_6$) δ 55.72, 108.00, 116.51, 119.52, 120.48, 124.74, 127.26, 128.81, 130.00, 137.58, 141.98, 150.20, 156.65, 161.30. LC-MS (MS m/z 270 (M$^+$+1).

Step 1c

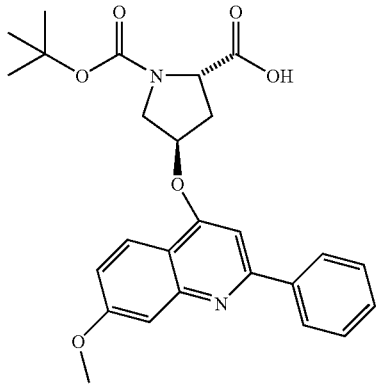

To a suspension of Boc-4R-hydroxyproline (16.44 g, 71.1 mmol) in DMSO (250 mL) was added t-BuOK (19.93 g, 177.6 mmol) at 0° C. The generated mixture was stirred for 1.5 hours and then the product of Step 1b (21.02 g, 77.9 mmol) was added in three portions over 1 hour. The reaction was stirred for one day, poured into cold water (1.5 L) and washed with diethyl ether (4×200 mL). The aqueous solution was acidified to pH 4.6, filtered to obtain a white solid, and dried in vacuo to supply the product (32.5 g, 98%). $^1$H NMR (DMSO-d$_6$) δ 1.32, 1.35 (two s (rotamers) 9H), 2.30-2.42 (m, 1H), 2.62-2.73 (m, 1H), 3.76 (m, 2H), 3.91 (s, 3H), 4.33-4.40 (m, 1H), 5.55 (m, 1H), 7.15 (dd, J=9.2, 2.6 Hz, 1H), 7.37 (d, J=2.6 Hz, 1H), 7.42-7.56 (m, 4H), 7.94-7.99 (m, 1H), 8.25, 8.28 (2s, 2H), 12.53 (brs, 1H); LC-MS, MS m/z 465 (M$^+$+1).

Example 2

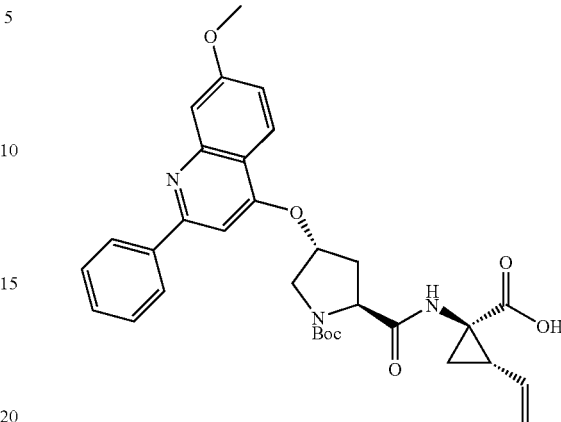

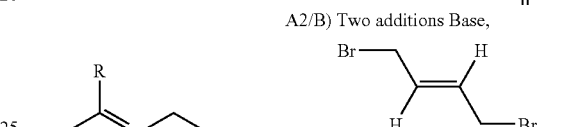

Method A: R = H (From Step A1)
Method B: R = Ph (Aldrich)

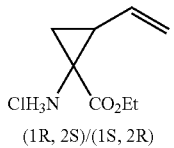
(1R, 2S)/(1S, 2R)

Step 2a (Overall Preparation)
From Method A (steps A1-A3) or
Method B (One-pot procedure)

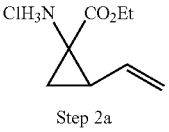

Step 2a

The desired product was made by each of the following methods:

Method A

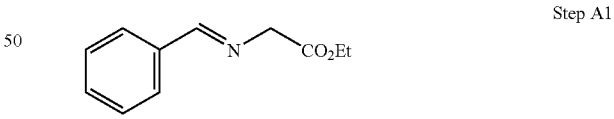

Step A1

Glycine ethyl ester hydrochloride (303.8 g, 2.16 mol) was suspended in tert-butylmethyl ether (1.6 L). Benzaldehyde (231 g, 2.16 mol) and anhydrous sodium sulfate (154.6 g, 1.09 mol) were added and the mixture cooled to 0° C. using an ice-water bath. Triethylamine (455 mL, 3.26 mol) was added dropwise over 30 minutes and the mixture stirred for 48 hours at room temperature. The reaction was then quenched by addition of ice-cold water (1 L) and the organic layer was separated. The aqueous phase was extracted with tert-butylmethyl ether (0.5 L) and the combined organic phases washed with a mixture of saturated aqueous NaHCO$_3$ (1 L) and brine (1 L). The solution was dried over MgSO$_4$, filtered, and concentrated in vacuo to afford 392.4 g of the desired product as a thick yellow oil that was used directly in the next step. ¹H NMR (CDCl₃, 300 MHz) δ 1.32 (t, J=7.1 Hz, 3H), 4.24 (q, J=7.1 Hz, 2H), 4.41 (d, J=1.1 Hz, 2H), 7.39-7.47 (m, 3H), 7.78-7.81 (m, 2H), 8.31 (s, 1H).

Step A2

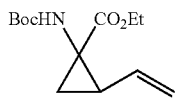

To a suspension of lithium tert-butoxide (84.06 g, 1.05 mol) in dry toluene (1.2 L), was added dropwise a mixture of the product of Step A1 (100.4 g, 0.526 mol) and trans-1,4-dibromo-2-butene (107.0 g, 0.500 mol) in dry toluene (0.6 L) over 60 minutes. After completion of the addition, the deep red mixture was quenched by addition of water (1 L) and tert-butylmethyl ether (TBME, 1 L). The aqueous phase was separated and extracted a second time with TBME (1 L). The organic phases were combined, 1N HCl (1 L) was added, and the mixture stirred at room temperature for 2 hours. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10N NaOH, the organic layer separated, and the aqueous phase extracted with TBME (2×500 mL). The combined organic extracts were dried (MgSO₄), filtered, and concentrated to a volume of 1 L. To this solution was added di-tert-butyldicarbonate (131.0 g, 0.6 mol) and the mixture stirred 4 days at room temperature. Additional di-tert-butyldicarbonate (50 g, 0.23 mol) was added to the reaction, the mixture refluxed for 3 hours, and was then allowed cool to room temperature overnight. The reaction mixture was dried over MgSO₄, filtered, and concentrated in vacuo to afford 80 g of crude material. This residue was purified by flash chromatography (2.5 Kg of SiO₂, eluted with 1% to 2% CH₃OH/CH₂Cl₂) to afford 57 g (53%) of racemic product as a yellow oil which solidified while sitting in the refrigerator. ¹H NMR (CDCl₃, 300 MHz) δ 1.26 (t, J=7.1 Hz, 3H), 1.46 (s, 9H), 1.43-1.49 (m, 1H), 1.76-1.82 (br m, 1H), 2.14 (q, J=8.6 Hz, 1H), 4.18 (q, J=7.2 Hz, 2H), 5.12 (dd, J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M⁺−1).

Step A3

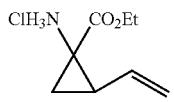

The product of Step A2 (9.39 g, 36.8 mmol) was dissolved in 4N HCl/dioxane (90 mL, 360 mmol) and was stirred for 2 hours at room temperature. The reaction mixture was concentrated to supply the desired product in quantitative yield (7 g, 100%). ¹H NMR (CD₃OD) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26-4.34 (m, 2H), 5.24 (dd, 10.3, 1.3 Hz, 1H) 5.40 (d, J=17.2, 1H), 5.69-5.81 (m, 1H).

Method B

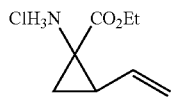

To a solution of potassium tert-butoxide (11.55 g, 102.9 mmol) in THF (450 mL) at −78° C. was added the commercially available N,N-dibenzylimine of glycine ethyl ester (25.0 g, 93.53 mmol) in THF (112 mL). The reaction mixture was warmed to 0° C., stirred for 40 minutes, and was then cooled to −78° C. To this solution was added trans-1,4-dibromo-2-butene (20.0 g, 93.50 mmol). The mixture was stirred for 1 hour at 0° C., and was cooled to −78° C. Potassium tert-butoxide (11.55 g, 102.9 mmol) was added, the mixture immediately warmed to 0° C., and was stirred one more hour before concentrating in vacuo. The crude product was dissolved in diethyl ether (530 mL), 1N aq. HCl solution (106 mL, 106 mmol) added, and the resulting biphasic mixture stirred for 3.5 hours at room temperature. The layers were separated and the aqueous layer was washed with diethyl ether (2×) and basified with a saturated aq. NaHCO₃ solution. The aqueous solution was extracted with diethyl ether (3×) and the combined organic extracts were washed with brine, dried (MgSO₄), filtered, and concentrated in vacuo to obtain the free amine. This material was treated with a 4N HCl solution in dioxane (100 mL, 400 mmol) and concentrated to provide the desired product as a brown semisolid (5.3 g, 34% yield) identical to the material obtained from procedure A, except for the presence of a small unidentified aromatic impurity (8%).

Step 2b

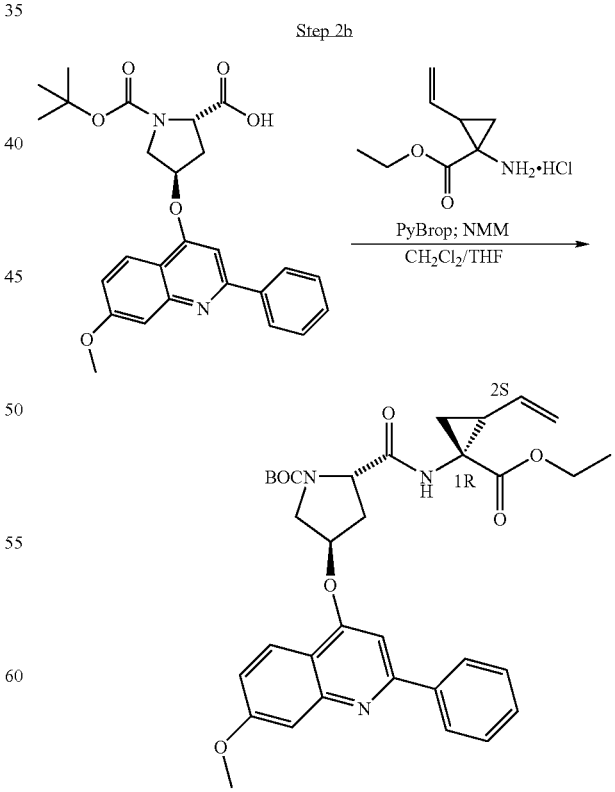

Highest Rf Isomer
and

-continued

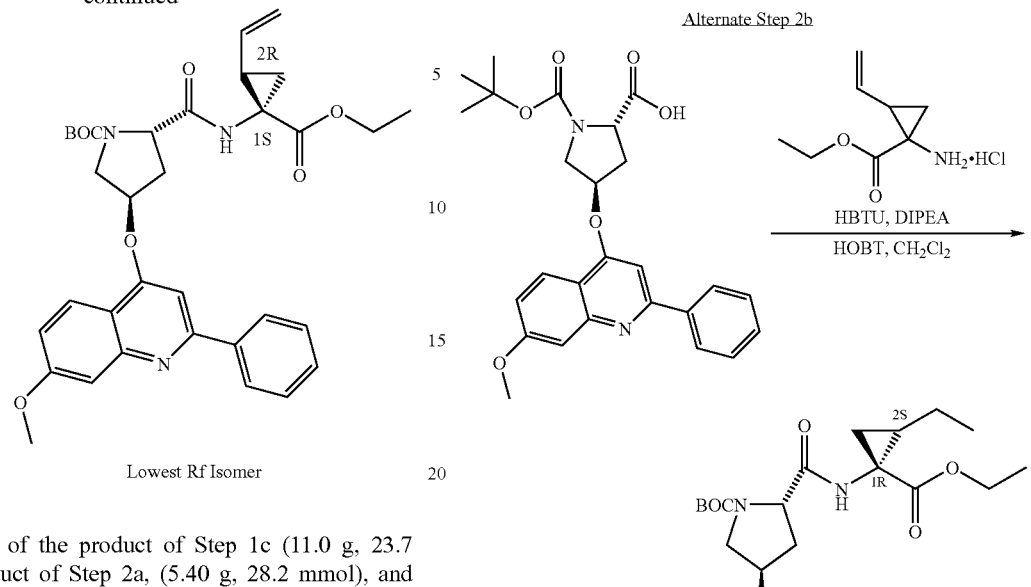

Lowest Rf Isomer

To a solution of the product of Step 1c (11.0 g, 23.7 mmol), the product of Step 2a, (5.40 g, 28.2 mmol), and NMM (20.8 mL; 18.9 mmol) in 500 mL of 50% CH$_2$Cl$_2$/THF was added the coupling reagent bromotrispyrrolidino-phosphonium hexafluorophosphate (Pybrop) (16.0 g, 34.3 mmol) in three portions in 10 minutes at 0° C. The solution was stirred at room temperature for one day and then was washed with pH 4.0 buffer (4×50 mL). The organic layer was washed with saturated aqueous NaHCO$_3$ (100 mL), the aqueous wash extracted with ethyl acetate (150 mL), and the organic layer backwashed with pH 4.0 buffer (50 mL) and saturated aqueous NaHCO$_3$ (50 mL). The organic solution was dried (MgSO$_4$), filtered, concentrated, and purified using a Biotage 65M column (eluted with 50% ethyl acetate/hexanes) to provide over 7.5 g of a 1:1 mixture of (1R,2S) and (1S,2R) P1 isomers of the desired product (50% overall) or, alternatively, eluted over a Biotage 65M column using a slow 15% to 60% ethyl acetate in hexanes gradient to supply 3.54 g (25%) of the high Rf eluted (1R,2S) P1 isomer, and 3.54 g (25%) of the low Rf eluted (1S,2R) P1 isomer.

Data for (1R,2S) P1 isomer: $^1$H NMR (CDCl$_3$) δ 1.21 (t, J=7 Hz, 3H), 1.43 (s, 9H), 1.47-1.57 (m, 1H), 1.88 (m, 1H), 2.05-2.19 (m, 1H), 2.39 (m, 1H), 2.88 (m, 1H), 3.71-3.98 (m, 2H), 3.93 (s, 3H), 4.04-4.24 (m, 2H), 4.55 (m, 1H), 5.13 (d, J=10 Hz, 1H), 5.22-5.40 (m, 1H), 5.29 (d, J=17 Hz, 1H), 5.69-5.81 (m, 1H), 7.02 (brs, 1H), 7.09 (dd, J=9, 2 Hz, 1H), 7.41-7.52 (m, 4H), 7.95 (d, J=9 Hz, 1H), 8.03, 8.05 (2s, 2H); $^{13}$C NMR (CDCl$_3$) δ: 14.22; 22.83, 28.25, 33.14, 33.58, 39.92, 51.84, 55.47, 58.32, 61.30, 75.86, 81.27, 98.14, 107.42, 115.00, 117.84, 118.27, 122.63, 123.03, 127.50, 128.72, 129.26, 133.39, 140.06, 151.23, 159.16, 160.34, 161.35, 169.78, 171.68. LC-MS (MS m/z 602 (M$^+$+1).

Data for the (1S,2R) P1 isomer: $^1$H NMR δ 1.25 (t, J=7 Hz, 3H), 1.44 (s, 9H), 1.46-1.52 (m, 1H), 1.84 (m, 1H), 2.12-2.21 (m, 1H), 2.39 (m, 1H), 2.94 (m, 1H), 3.82 (m, 2H), 3.97 (s, 3H), 4.05-4.17 (m, 2H), 4.58 (m, 1H), 5.15 (d, J=10.8 Hz, 1H), 5.33 (d, J=17 Hz, 1H), 5.30-5.43 (m, 1H), 5.72-5.85 (m, 1H), 7.05 (s, 1H), 7.13 (dd, J=9, 2 Hz, 1H), 7.46-7.60 (m, 4H), 7.98 (d, J=9, 1H), 8.06-8.10 (m, 2H). LC-MS MS m/z 602 (M$^+$+1).

Alternate Step 2b

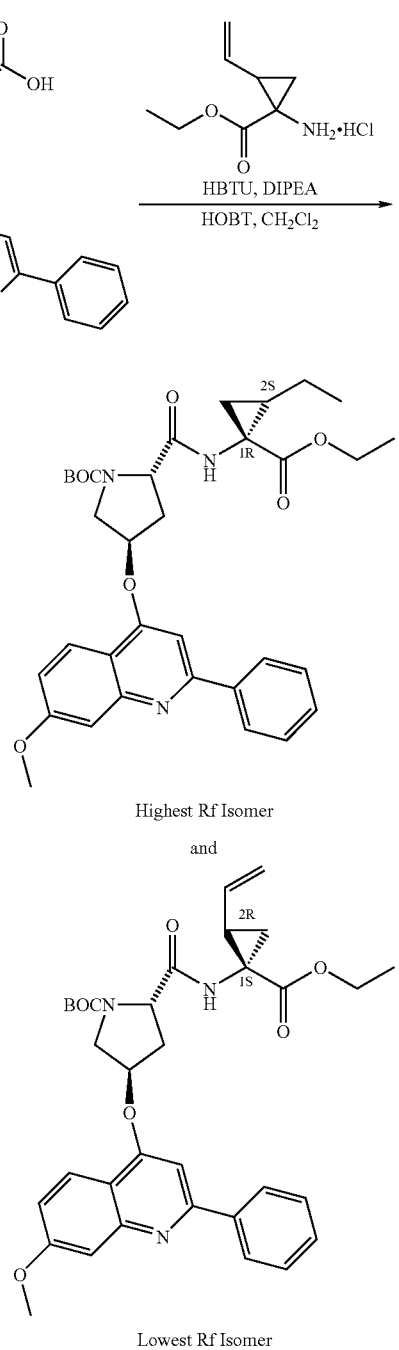

Highest Rf Isomer and

Lowest Rf Isomer

The product of Step 2a (7.5 g, 39.1 mmol) was combined with diisopropylethylamine (32.5 mL, 186 mmol) in dichloromethane (150 mL). To the resulting mixture was added HOBT hydrate (6.85 g, 44.7 mmol) and the product from Step 1c (17.3 g, 37.3 mmol), followed by HBTU (16.96 g, 44.7 mmol). A slight exotherm occurred immediately, and the mixture was stirred at room temperature overnight. The mixture was then concentrated in vacuo and redissolved in ethyl acetate (600 mL). The solution was washed with water (2×200 mL), then with 10% aqueous sodium bicarbonate (2×200 mL), then with water (150 mL) and finally with brine (150 mL). The organic was dried over anhydrous magnesium sulfate and filtered, and the filtrate was concentrated in vacuo to a beige glassy solid. Purification was performed in multiple batches (7 g each) by flash chromatography on a Biotage Flash 75M cartridge (66% hexanes/ethyl acetate) to provide the (1R,2S) P1 isomer as the initial eluted isomer (9.86 g total, 44.0% yield), followed by elution of the (1S,2R) P1 isomer as the second eluted isomer (10.43 g total, 46.5% yield). A total of 1.97 g of mixed fractions were recovered to give an overall conversion of 99.3% to the two diastereomers.

Data for (1R,2S) P1 isomer: $^1$H NMR (methanol-$d_4$) δ 1.23 (t, J=7.2 Hz, 3H), 1.4 (s, 4H), 1.45 (s, 6H), 1.73 (dd, J=7.9, 1.5 Hz, 0.4H), 1.79 (dd, J=7.8, 2.4 Hz, 0.6H), 2.21 (q, J=8.2 Hz, 1H), 2.44-2.49 (m, 1H), 2.66-2.72 (m, 0.4H), 2.73-2.78 (m, 0.6H), 3.93-3.95 (m, 2H), 3.96 (s, 3H), 4.10-4.17 (m, 2H), 4.44 (q, J=7.8 Hz, 1H), 5.13 (d, J=10.7 Hz, 1H), 5.31 (d, J=17.7 Hz, 0.4H), 5.32 (d, J=17.4 Hz, 0.6H), 5.49 (bs, 1H), 5.66-5.82 (m, 1H), 7.16 (dd, J=9.2, 2.5 Hz, 1H), 7.26 (s, 1H), 7.42 (d, J=2.4 Hz, 1H), 7.48-7.55 (m, 3H), 8.02-8.05 (m, 3H); LC-MS (MS m/z 602 (M$^+$+1);

Data for (1S,2R) P1 isomer: $^1$H NMR (methanol-$d_4$) δ 1.23 (t, J=7.2 Hz, 3H), 1.40 (s, 3.5H), 1.43 (s, 6.5H), 1.8 (dd, J=7.2, 5.3 Hz, 0.4H), 1.87 (dd, J=7.8, 5.7 Hz, 0.6H), 2.16 (q, J=8.9 Hz, 0.6H), 2.23 (q, J=8.85 Hz, 0.4H), 2.42-2.50 (m, 1H), 2.67-2.82 (m, 1H), 3.87-3.95 (m, 2H), 3.96 (s, 3H), 4.07-4.19 (m, 3H), 4.41-4.47 (m, 1H), 5.09-5.13 (m, 1H), 5.30 (dd, J=17.09, 0.92 Hz, 1H), 5.48 (s, 1H), 5.70-5.77 (m, 1H), 7.15 (dd, J=9.16, 2.44 Hz, 1H), 7.25 (s, 1H), 7.41 (d, J=2.14 Hz, 1H), 7.48-7.55 (m, 3H), 8.02-8.05 (m, 3H); LC-MS (MS m/z 602 (M$^+$+1).

Step 2c

The (1R,2S) P1 isomer of Step 2b (9.86 g, 16.4 mmol) was treated with 1N NaOH (50 mL, 50 mmol) in a mixture of THF (150 mL) and methanol (80 mL) for 12 hours. The mixture was concentrated in vacuo until only the aqueous phase remained. Water (100 mL) was added and 1N HCl was added slowly until pH 3 was achieved. The mixture was then extracted with ethyl acetate (3×200 mL), and the combined organic extracts were washed with brine, dried over anhydrous sodium sulfate, and filtered. The filtrate was concentrated in vacuo to give the desired product as a white powder (9.2 g, 98% yield). $^1$H NMR (CD$_3$OD) δ 1.41 (s, 2H), 1.45 (s, 9H), 1.77 (dd, J=7.9, 5.5 Hz, 1H), 2.16-2.21 (m, 1H), 2.44-2.51 (m, 1H), 2.74-2.79 (m, 1H), 3.93-3.96 (m, 2H), 3.98 (s, 3H), 4.44 (t, J=7.9 Hz, 1H), 5.11 (d, J=9.5 Hz, 1H), 5.30 (d, J=17.1 Hz, 1H), 5.52 (s, 1H), 5.79-5.86 (m, 1H), 7.22 (dd, J=9.16, 2.14 Hz, 1H), 7.32 (s, 1H), 7.43 (d, J=2.14 Hz, 1H), 7.54-7.60 (m, 3H), 8.04 (dd, J=7.8, 1.4 Hz, 2H), 8.08 (d, J=9.1 Hz, 1H); LC-MS (MS m/z 574 (M$^+$+1).

Example 3

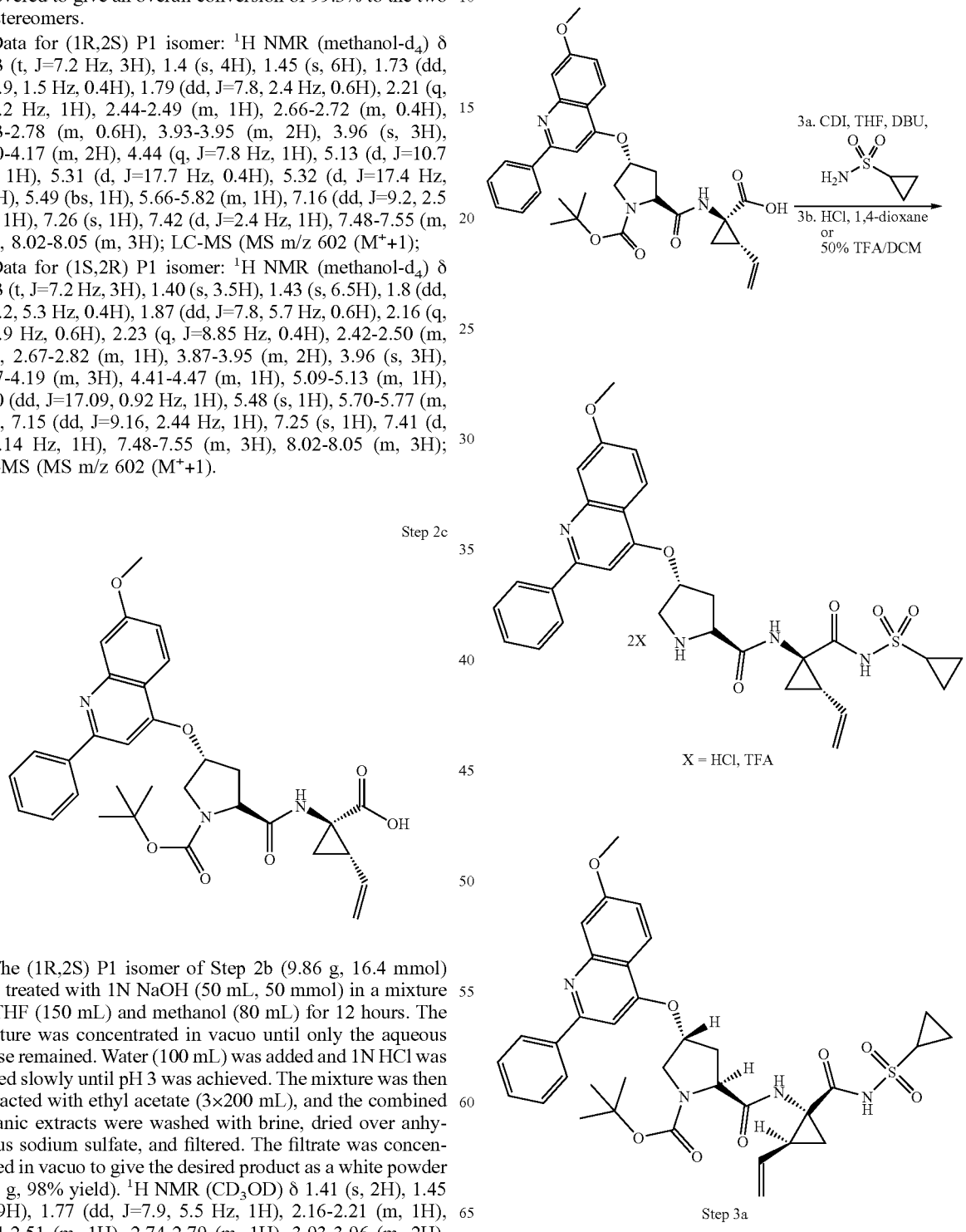

Step 3a

The product of Step 2c (7.54 g, 13.14 mmol) was combined with CDI (3.19 g, 19.7 mmol) and DMAP (2.41 g, 19.7 mmol) in anhydrous THF, and the resulting mixture was heated to reflux for 45 minutes. The slightly opaque mixture was allowed to cool to room temperature, and to it was added cyclopropylsulfonamide (1.91 g, 15.8 g). Upon addition of DBU (5.9 mL, 39.4 mmol), the mixture became clear. The brown solution was stirred overnight. The mixture was then concentrated in vacuo to an oil and was redissolved in ethyl acetate (500 mL). The solution was washed with pH 4 buffer (3×200 mL), and the combined buffer washes were back-extracted with ethyl acetate (200 mL). The combined organics were washed with brine (150 mL) and dried over anhydrous sodium sulfate and filtered. Concentration of the filtrate in vacuo gave a beige solid. The crude product was purified by flash chromatography on a Biotage Flash 75M cartridge (25% hexanes/ethyl acetate) to give the desired product (5.85 g, 66% yield). $^1$H NMR (CD$_3$OD) δ 1.03-1.09 (m, 2H), 1.15-1.28 (m, 2H), 1.40-1.44 (m, 2H), 1.46 (s, 9H), 1.87 (dd, J=8.1, 5.6 Hz, 1H), 2.21-2.27 (m, 1H), 2.36-2.42 (m, 1H), 2.65 (dd, J=13.7, 6.7 Hz, 1H), 2.93-2.97 (m, 1H), 3.90-3.96 (m, 2H), 4.00 (s, 3H), 4.40 (dd, J=9.5, 7.0 Hz, 1H), 5.12 (d, J=10.4 Hz, 1H), 5.31 (d, J=17.4 Hz, 1H), 5.64 (s, 1H), 5.73-5.80 (m, 1H), 7.30 (dd, J=9.2, 2.1 Hz, 1H), 7.40 (s, 1H), 7.47 (s, 1H), 7.61-7.63 (m, 3H), 8.04-8.05 (m, 2H), 8.15 (d, J=9.5 Hz, 1H); LC-MS (MS m/z 677 (M$^+$+1).

Step 3b

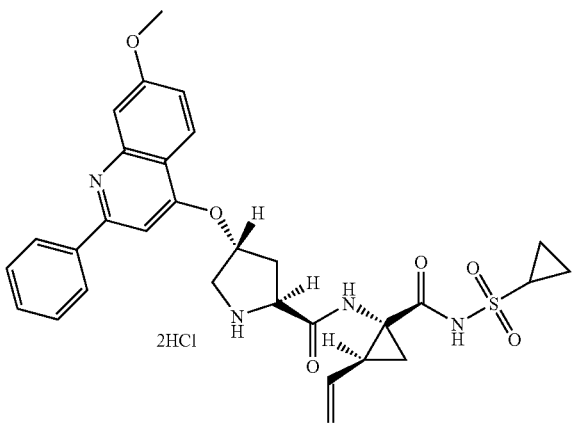

The product of Step 3a (5.78 g, 8.54 mmol) was treated with 4.0M HCl in 1,4-dioxane (50 mL, 200 mmol) overnight. The reaction mixture was concentrated in vacuo and placed in a vacuum oven at 50° C. for several days. The desired product was obtained as a beige powder (5.85 g, quantitative). $^1$H NMR (methanol-d$_4$) δ 1.03-1.18 (m, 3H), 1.26-1.30 (m, 1H), 1.36-1.40 (m, 2H), 1.95 (dd, J=8.2, 5.8 Hz, 1H), 2.37 (q, J=8.9 Hz, 1H), 2.51-2.57 (m, 1H), 2.94-2.98 (m, 1H), 3.09 (dd, J=14.6, 7.3 Hz, 1H), 3.98 (d, J=3.7 Hz, 1H), 3.99 (s, 1H), 4.08 (s, 3H), 4.80 (dd, J=10.7, 7.6 Hz, 1H), 5.15 (dd, J=10.2, 1.4 Hz, 1H), 5.32 (dd, J=17.1, 1.2 Hz, 1H), 5.61-5.69 (m, 1H), 5.99 (t, J=3.7 Hz, 1H), 7.51 (dd, J=9.3, 2.3 Hz, 1H), 7.59 (d, J=2.4 Hz, 1H), 7.65 (s, 1H), 7.72-7.79 (m, 3H), 8.09 (dd, J=7.0, 1.5 Hz, 2H), 8.53 (d, J=9.2 Hz, 1H); LC-MS (MS m/z 577 (M$^+$+1).

Example 4

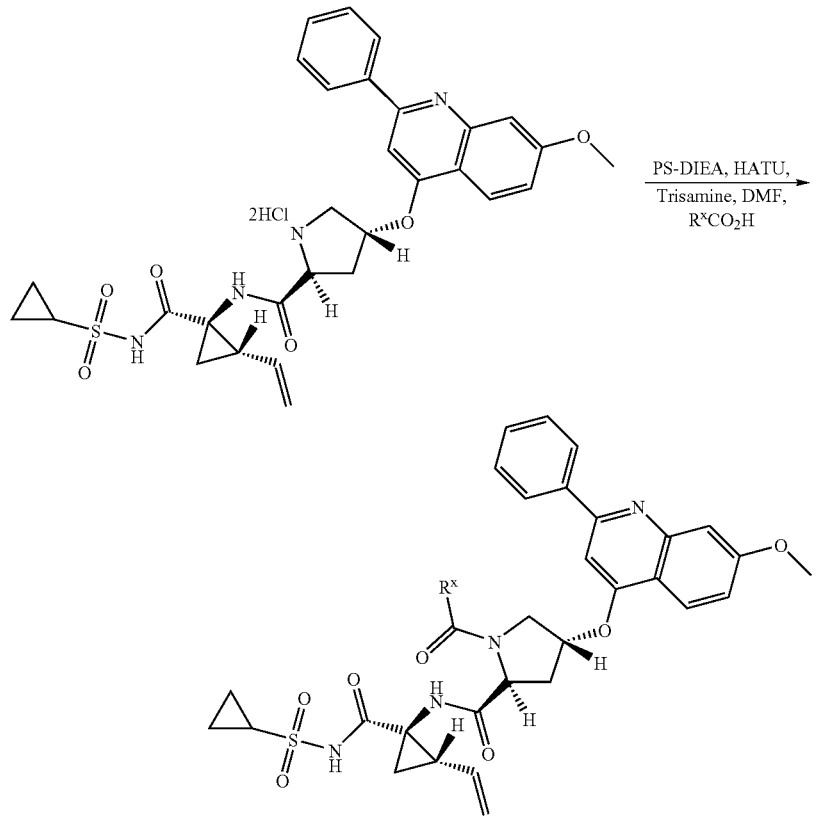

To a reaction vessel containing PS-DIEA resin (Argonaut Technologies, 0.047 g, 0.175 mmol) was added a solution of the appropriately substituted carboxylic acid (as indicated below) (0.044 mmol) in DMF (0.25 mL), followed by the addition of a solution of the product of Step 3b (0.020 g, 0.029 mmol) in DMF (0.50 mL), followed by addition of a solution of HATU (0.017 g, 0.044 mmol) in DMF (0.25 mL). The mixture was shaken for 3 days at room temperature. To the reaction was added PS-trisamine resin (Argonaut Technologies, 0.025 g, 0.086 mmol) and the mixture was shaken for 18 hours at room temperature. The reaction mixture was filtered, and the filtrate was concentrated in vacuo to give crude product, which was purified by preparative HPLC to give the desired product as the trifluoroacetic acid salt.

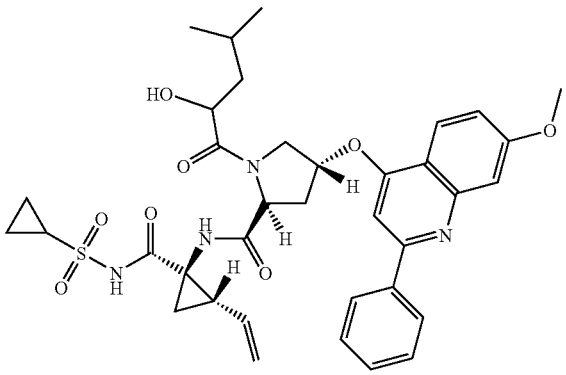

Example 4

Compound 2

Purified by preparative HPLC and isolated as a mixture of two isomers as the mono-trifluoroacetic acid salt. LC-MS (MS m/z 691 (M⁺+1).

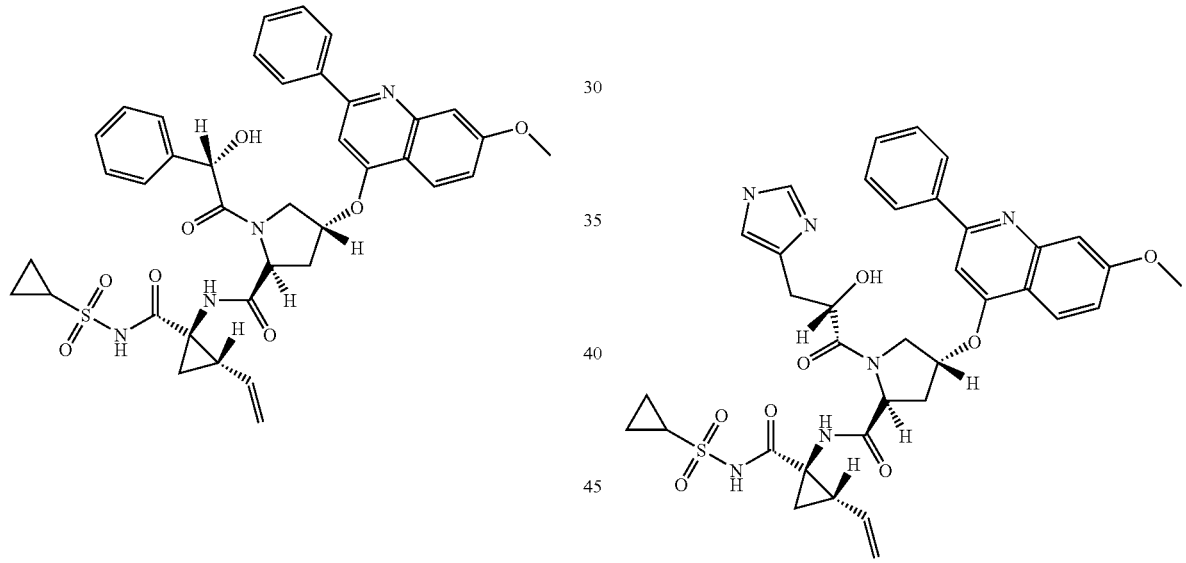

Example 4

Compound 1

Purified by preparative HPLC and isolated as the mono-trifluoroacetic acid salt: $^1$H NMR (CD$_3$OD) δ 1.06-1.14 (m, 2H), 1.18-1.23 (m, 1H), 1.26-1.32 (m, 1H), 1.46 (dd, J=9.5, 5.2 Hz, 1H), 1.96 (dd, J=7.9, 5.2 Hz, 1H), 2.33 (q, J=8.5 Hz, 1H), 2.40-2.46 (m, 1H), 2.69 (s, 1H), 2.69-2.72 (m, 1H), 3.86 (d, J=12.5 Hz, 1H), 3.93 (dd, J=12.5, 2.1 Hz, 1H), 4.09 (s, 3H), 4.69 (dd, J=9.5, 7.6 Hz, 1H), 5.17-5.19 (m, 2H), 5.35-5.39 (dd, J=17.1, 0.9 Hz, 1H), 5.63 (s, 1H), 5.74-5.81 (m, 1H), 6.73-6.81 (m, 3H), 7.18 (d, J=7.0 Hz, 1H), 7.25 (s, 1H), 7.41 (m, 1H), 7.51 (d, J=2.1 Hz, 1H), 7.72-7.77 (m, 3H), 7.84 (d, J=9.2 Hz, 1H), 7.98-7.99 (m, 3H); LC-MS (MS m/z 711 (M⁺+1).

Example 4

Compound 3

Purified by preparative HPLC and isolated as the bis-trifluoroacetic acid salt. $^1$H NMR (CD$_3$OD) δ 1.04-1.19 (m, 4H), 1.24-1.29 (m, 2H), 1.42 (dd, J=9.3, 5.3 Hz, 1H), 1.92 (dd, J=8.1, 5.3 Hz, 1H), 2.27 (q, J=8.7 Hz, 1H), 2.44-2.50 (m, 1H), 2.70 (s, 1H), 2.74-2.79 (m, 1H), 2.93-2.98 (m, 1H), 3.12-3.24 (m, 3H), 4.05 (s, 3H), 4.21 (dd, J=3.5, 12.3 Hz, 1H), 4.48 (d, J=12.2 Hz, 1H), 4.61-4.70 (m, 2H), 5.15 (dd, J=1.5, 10.4 Hz, 1H), 5.33 (dd, J=17.4, 1.5 Hz, 1H), 5.71-5.79 (m, 1H), 5.84-5.91 (m, 1H), 7.35 (s, 1H), 7.39-7.43 (m, 1H), 7.53 (d, J=2.4 Hz, 1H), 7.58 (s, 1H), 7.67-7.75 (m, 4H); LC-MS (MS m/z 715 (M⁺+1).

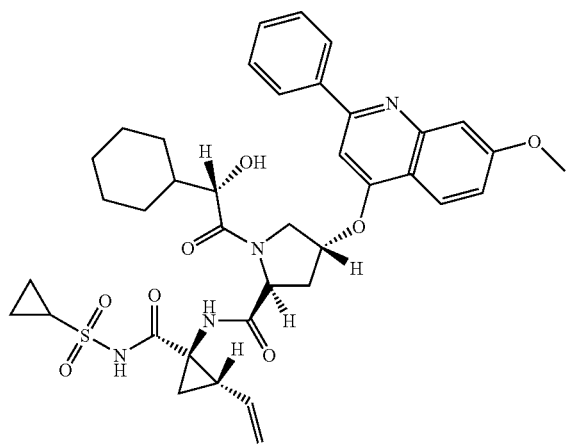

Example 4

Compound 4

Purified by preparative HPLC and isolated as the mono-trifluoroacetic acid salt. LC-MS (MS m/z 717 (M⁺+1).

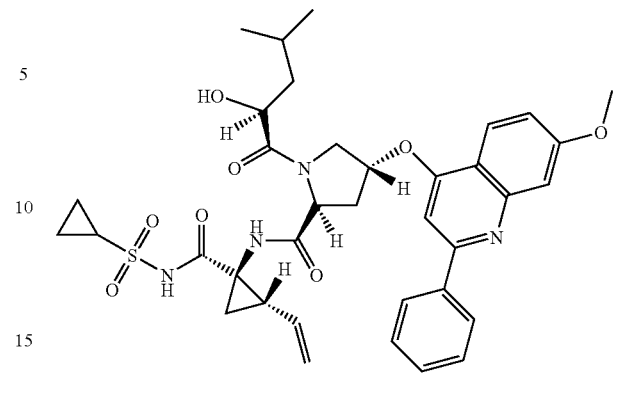

Example 4

Compound 6

Purified by preparative HPLC and isolated as the mono-trifluoroacetic acid salt: LC-MS (MS m/z 691 (M⁺+1).

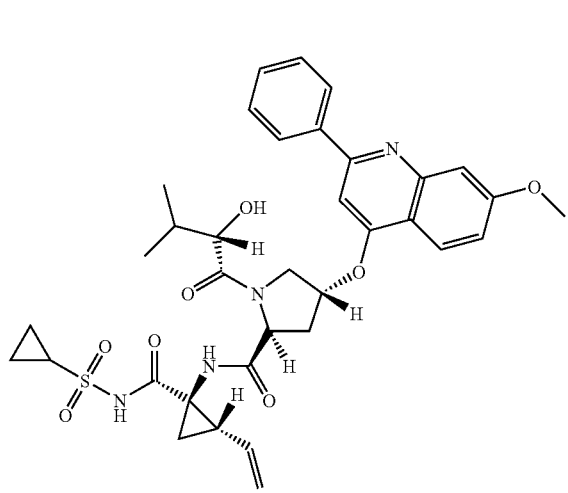

Example 4

Compound 5

Purified by preparative HPLC and isolated as the mono-trifluoroacetic acid salt: $^1$H NMR (CD$_3$OD) δ 0.91 (d, J=6.4 Hz, 3H), 0.98 (d, J=6.7 Hz, 3H), 1.02-1.05 (m, 1H), 1.06-1.10 (m, 2H), 1.15-1.18 (m, 1H), 1.20-1.30 (m, 2H), 1.43 (dd, J=9.3, 5.3 Hz, 1H), 1.91 (dd, J=8.1, 5.3 Hz, 1H), 2.05-2.10 (m, 1H), 2.25 (q, J=8.9 Hz, 1H), 2.41-2.48 (m, 1H), 2.70 (s, 1H), 2.70-2.75 (m, 1H), 2.92-2.98 (m, 1H), 4.06 (s, 3H), 4.14 (dd, J=12.5, 3.1 Hz, 1H), 4.36 (d, J=12.5 Hz, 1H), 4.63 (dd, J=10.2, 6.9 Hz, 1H), 5.14 (d, J=10.4 Hz, 1H), 5.32 (d, J=17.1 Hz, 1H), 5.73-5.81 (m, 1H), 5.85-5.88 (m, 1H), 7.44 (dd, J=9.2, 2.1 Hz, 1H), 7.53 (d, J=2.1 Hz, 1H), 7.61 (s, 1H), 7.70-7.77 (m, 3H), 8.05-8.09 (m, 2H), 8.27 (dd, J=9.2, 2.8 Hz, 1H); LC-MS (MS m/z 677 (M⁺+1).

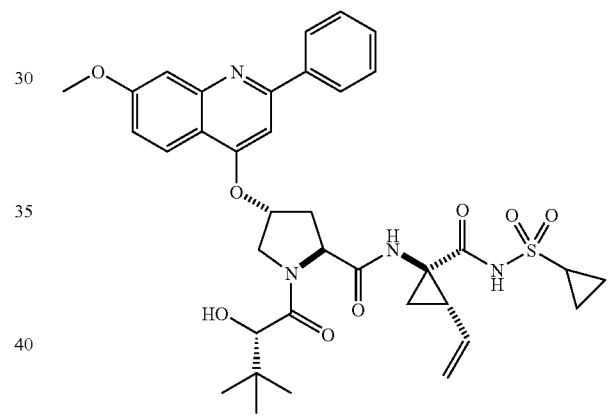

Example 4

Compound 7

To a solution of di-trifluoroacetic acid of Example 3b (prepared according to the Scheme showed in Example 3a, 51.0 mg, 0.063 mmol) in dichloromethane (2 mL) was added DIEA (66 μL, 0.378 mmol), HATU (36 mg, 0.126 mmol), HOAt (13.0 mg, 0.126 mmol), and (S)-(−)-2-hydroxy-3,3-dimethylbutyric acid (13.0 mg, 0.126 mmol). After stirring at room temperature for 16 hours, the solvent was concentrated and the resulting brown viscous oil was purified by reverse phase preparative HPLC to give the desired product (the mono trifluoroacetic acid salt) as a white solid (45.5 mg, 89% yield). $^1$H NMR (CD$_3$OD) δ 0.99 (s, 9H), 1.06-1.09 (m, 2H), 1.22-1.25 (m, 2H), 1.43 (dd, J=9.8, 5.5 Hz, 1H), 1.90 (dd, J=8.2, 5.5 Hz, 1H), 2.24 (q, J=8.7 Hz, 1H), 2.39-2.44 (m, 1H), 2.72 (dd, J=13.7, 7.6 Hz, 1H), 2.91-2.96 (m, 1), 4.04 (s, 1H), 4.07 (s, 3H), 4.16 (dd, J=13.1, 3.4 Hz, 1H), 4.48 (dd, J=13.1, 1.2 Hz, 1H), 4.64 (dd, J=10.2, 6.9 Hz, 1H), 5.14 (dd, J=10.4, 1.5 Hz, 1H), 5.31 (dd, J=17.2, 1.2 Hz, 1H), 5.71-5.78 (m, 1H), 5.86 (bs, 1H), 7.48 (dd, J=9.3, 2.3 Hz, 1H), 7.55 (d, J=2.4 Hz, 1H), 7.65 (s, 1H), 7.72-7.79 (m, 3H), 8.07 (dd, J=8.2, 1.2 Hz, 1H), 8.28 (d, J=9.2 Hz, 1H); LC/MS (MH+, 691)

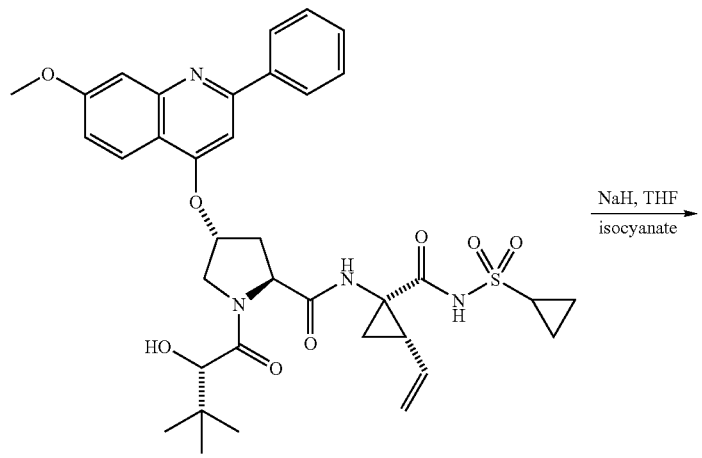

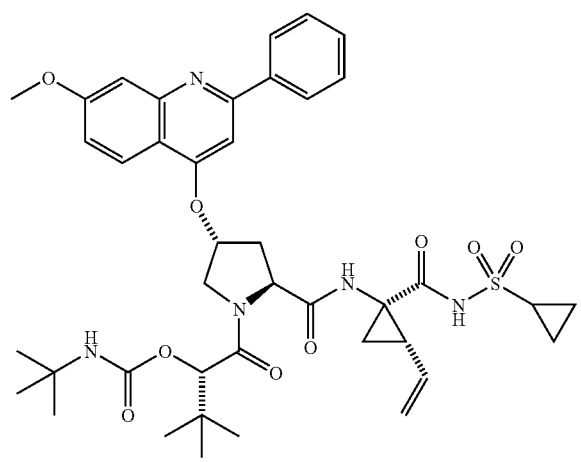

Example 5

Compound 1

To a solution of Example 4, Compound 7 mono trifluoroacetic acid salt (50.0 mg, 0.062 mmol) in THF (1 mL) was added NaH (11.5 mg, 0.279 mmol) followed by tert-butyl isocyanate (24.6 mg, 0.248 mmol). After stirring at room temperature for 14 hours, the reaction was diluted with ethyl acetate (5 mL) and washed with saturated NH$_4$Cl (2 mL). The aqueous layer was extracted with 2×3 mL ethyl acetate. The combined organic layer was dried over MgSO$_4$, filtered, and concentrated to about 1 mL of solvent left. The was added hexanes (15 mL) to affect a white precipitation which was filtered and washed with cold hexanes to give a white solid product (45.2 mg, 92% yield). $^1$H NMR (CD$_3$OD) δ 1.06 (s, 9H), 1.09 (s, 9H), 1.19-1.25 (m, 3H), 1.31-1.42 (m, 2H), 1.88 (t, J=6.7 Hz, 1H), 2.20-2.27 (m, 1H), 2.40-2.45 (m, 1H), 2.72-2.76 (m, 1), 2.94 (br s, 1H), 4.06 (s, 4H), 4.64 (br s, 2H), 5.13 (d, J=9.8 Hz, 1H), 5.30 (t, J=1.7 Hz, 1H), 5.65-5.72 (m, 1H), 5.84 (br s, 1H), 7.37 (d, J=9.8 Hz, 1H), 7.52 (s, 1H), 7.63 (s, 1H), 7.72-7.78 (m, 3H), 8.06 (d, J=7.0 Hz, 2H), 8.51 (d, J=9.5 Hz, 1H); LC/MS (MH+, (790).

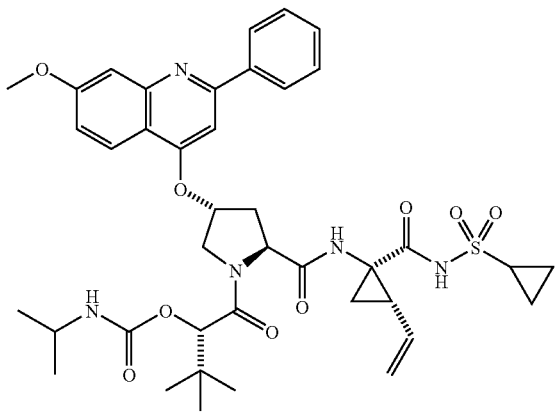

Example 5

Compound 2

The desired product was prepared by substituting isopropyl isocyanate for tert-butyl isocyanate in the procedure for Example 5, Compond 1. LC/MS (MH+, 776).

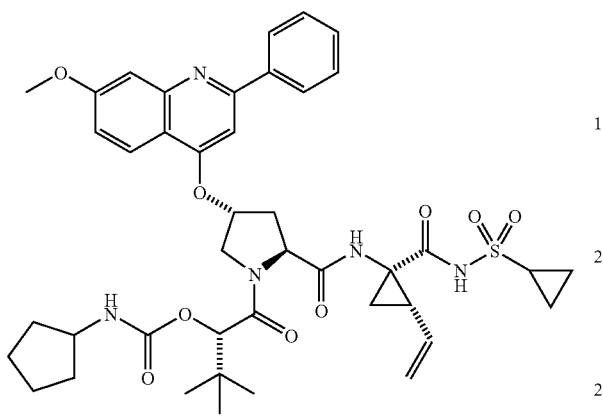

Example 5

Compound 3

The desired product was prepared by substituting cyclopentyl isocyanate for tert-butyl isocyanate in the procedure for Example 5, Compond 1. LH NMR (CD$_3$OD) δ 1.05 (br s, 1H), 1.07 (s, 9H), 1.1-1.16 (m, 2H), 1.23-1.24 (m, 2H), 1.28-1.37 (m, 2H), 1.41 (dd, J=9.5, 5.5 Hz, 1H), 1.50 (br s, 5H), 1.89 (dd, J=8.2, 5.8 Hz, 1H), 2.23 (t, J=8.9 Hz, 1H), 2.40-2.45 (m, 1H), 2.76 (dd, J=12.8, 6.4 Hz, 1H), 2.92-2.97 (m, 1H), 4.82 (s, 4H), 5.14 (dd, J=10.4, 1.5 Hz, 1H), 5.29 (d, J=17.1 Hz, 1H), 5.65-5.73 (m, 1H), 5.85 (br, s, 1H), 7.38 (dd, J=9.2, 1.8 Hz, 1H), 7.53 (d, J=2.4 Hz, 1H), 7.64 (s, 1H), 7.72-7.79 (m, 4H), 8.07 (d, J=7.0 Hz, 2H), 8.50 (d, J=9.2 Hz, 1H). LC/MS (MH+, (802).

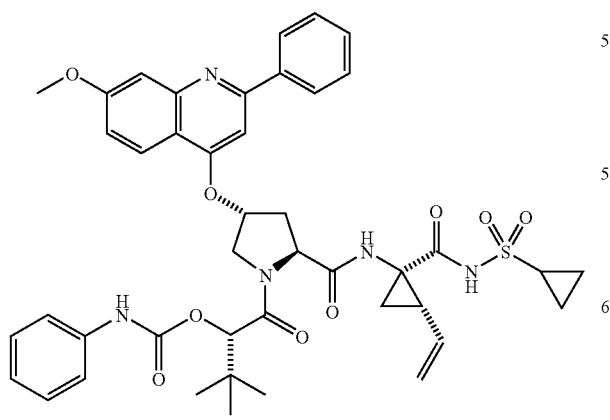

Example 5

Compound 4

The desired product was prepared by substituting phenyl isocyanate for tert-butyl isocyanate in the procedure for Example 5, Compond 1. $^1$H NMR (CD$_3$OD) δ 1.13-1.18 (m, 1H), 1.24 (s, 9H), 1.32-1.38 (m, 3H), 1.51 (dd, J=9.8, 5.8 Hz, 1H), 1.95-2.00 (m, 1H), 2.30-2.61 (m, 1H), 2.89 (dd, J=13.1, 1.8 Hz, 1H), 3.03-3.08 (m, 1H), 4.17 (s, 4H), 4.77 (dd, J=10.4, 7.0 Hz, 1H), 4.87 (t, J=5.9 Hz, 1H), 4.89 (d, J=5.5 Hz, 1H), 4.99 (d, J=5.2 Hz, 1H), 5.24 (dd, J=10.4, 1.8 Hz, 1H), 5.39 (d, J=17.4 Hz, 1H), 5.75-5.83 (m, 1H), 5.98 (br s, 1H), 7.10 (m, 1H), 7.27 (s, 4H), 7.40 (d, J=9.2 Hz, 1H), 7.62 (d, J=2.1 Hz, 1H), 7.76 (d, J=5.2 Hz, 1H), 7.82-7.89 (m, 4H), 8.18 (d, J=9.5 Hz, 2H), 8.60 (d, J=9.2 Hz). LC/MS (MH+, 810).

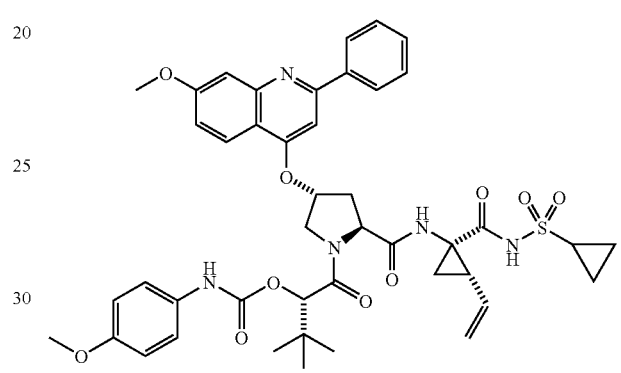

Example 5

Compound 5

The desired product was prepared by substituting 4-methoxyphenyl isocyanate for tert-butyl isocyanate in the procedure for Example 5, Compond 1. LC/MS (MH+, 840.)

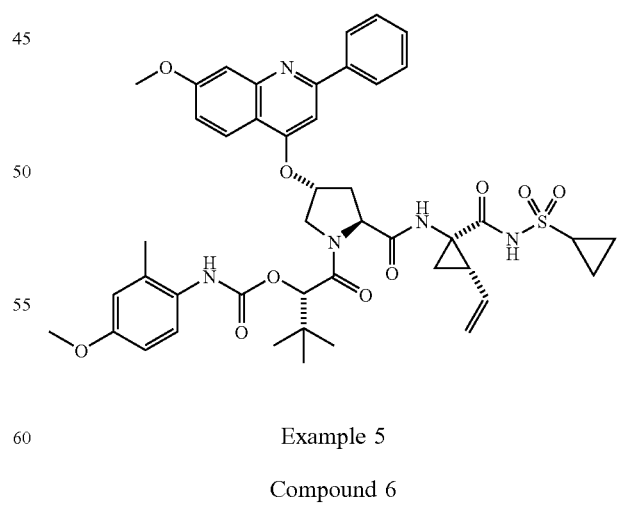

Example 5

Compound 6

The desired product was prepared by substituting 4-methoxy-2-methylphenyl isocyanate for tert-butyl isocyanate in the procedure for Example 5, Compond 1. LC/MS (MH+, 854).

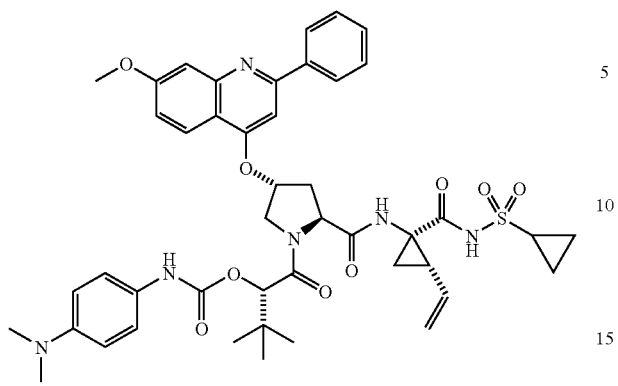

Example 5

Compound 7

The desired product was prepared by substituting 4-N,N-dimethylaminophenyl isocyanate for tert-butyl isocyanate in the procedure for Example 5, Compond 1. LC/MS (MH+, 854).

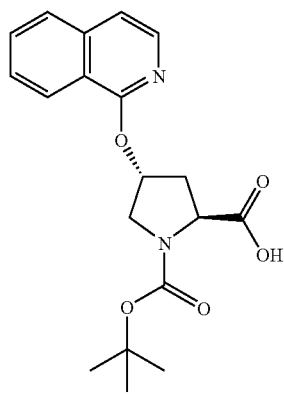

Example 6

To a solution of BOC-HYP-OH (231 mg, 1.0 mmol) in DMSO (10 mL) was added potassium tert-butoxide (336 mg, 3.0 mmol). The formed solution was stirred at ambient temperature for 1 hour before addition of 2-chloroisoquinoline (180 mg, 1.1 mmol). The final solution was stirred for 12 hours at ambient temperature, quenched with ice water, acidified with 1M HCl to pH 4, and extracted with ethyl acetate (2×50 mL). The organic layers were washed with brine, dried over MgSO4, filtered, and concentrated. The residue was purified by prep-HPLC to provide 272 mg (76%) of the desired product as an off-white foam. $^1$H NMR (CD$_3$OD) δ 1.42, 1.44 (rotamers, 1:2, 9H), 2.39-2.44 (m, 1H), 2.68-2.72 (m, 1H), 3.80-3.90 (m, 2H), 4.44-4.52 (m, 1H), 5.78 (b, 1H), 7.31-7.33 (m, 1H), 7.58 (t, J=7.8 Hz, 1H), 7.71 (t, J=7.5 Hz, 1H), 7.81 (d, J=8.0 Hz, 1H), 7.95 (d, J=6.0 Hz, 1H), 8.19 (d, J=8.0 Hz, 1H); LC/MS (MH+, 359).

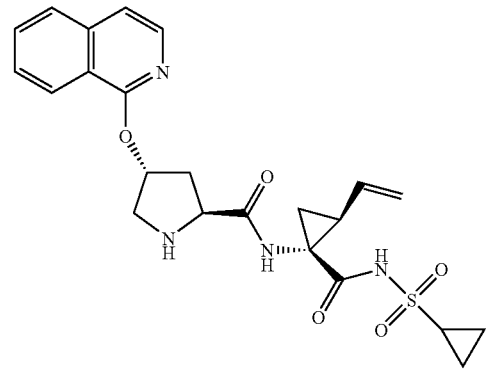

Example 7

Step 7a

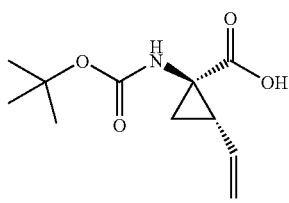

To a solution of 1 (R)-tert-butoxycarbonylamino-2(S)-vinyl-cyclopropanecarboxylic acid ethyl ester (prepared by the procedure described in WO 03/099274, 3.28 g, 13.2 mmol) in THF (7 mL) and methanol (7 mL) was added a suspension of LiOH (1.27 g, 53.0 mmol) in water (14 mL). The mixture was stirred overnight at room temperature and quenched with 1N NaOH (15 mL) and water (20 mL). The resulting mixture was washed with ethyl acetate (20 mL), and the organic phase was extracted with 20 mL 0.5N NaOH. The combined aqueous phases were acidified with 1N HCl to pH 4 and extracted with ethyl acetate (3×40 mL). The combined organic extracts were washed with brine, dried (MgSO$_4$), filtered, and concentrated to provide the desired compound as a white solid (2.62 g, 87%). $^1$H NMR (DMSO-d$_6$) δ 1.22-1.26 (m, 1H), 1.37 (s, 9H), 1.50-1.52 (m, 1H), 2.05 (q, J=9 Hz, 1H), 5.04 (d, J=10 Hz, 1H), 5.22 (d, J=17 Hz, 1H), 5.64-5.71 (m, 1H), 7.18, 7.53 (s, NH (rotamers), 12.4 (br s, 1H); LC/MS (MH+, 228).

Step 7b

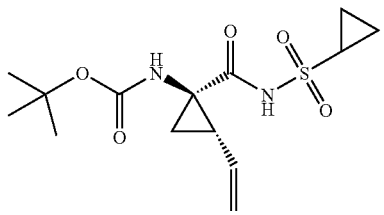

A solution of the product of Step 7a (2.62 g, 11.5 mmol) and CDI (2.43 g, 15.0 mmol) in THF (40 mL) was heated at reflux for 50 minutes under nitrogen. The solution was cooled to room temperature and transferred by cannula to a solution of cyclopropanesulfonic acid amide (1.82 g, 15.0 mmol) in THF (10 mL). To the resulting solution was added DBU (2.40 mL, 16.1 mmol) and stirring was continued for 20 hours. The mixture was quenched with 1N HCl to pH 1 and the THF was evaporated in vacuo. The suspension was extracted with ethyl acetate (2×50 mL) and the combined organic extracts dried ($Na_2SO_4$), filtered, and concentrated. Purification by recrystallization from hexanes-ethyl acetate (1:1) provided the desired compound (2.4 g) as a white solid. The mother liquor was purified by a Biotage 40 S column (eluted 9% acetone in dichloromethane) to provide a second batch of the desired compound (1.1 g). Both batches were combined (total yield 92%). $^1$H NMR (DMSO-$d_6$) δ 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers); LC/MS (MH$^+$, 331).

and concentrated. The residue was triturated with methanol (10 mL) to provide 470 mg (82%) of the desired product. $^1$H NMR (DMSO-$d_6$) δ 1.00-1.09 (m, 4H), 1.35-1.38 (m, 10H), 1.69-1.84 (m, 1H), 2.11-2.66 (m, 3H), 2.89-2.93 (m, 1H), 3.62-3.89 (m, 2H), 4.31 (t, J=8.1 Hz, 1H), 5.12 (d, J=10.8 Hz, 1H), 5.27 (d, J=16.8 Hz, 1H), 5.58-5.70 (m, 1H), 5.76 (b, 1H), 7.43 (d, J=5.7 Hz, 1H), 7.66 (t, J=7.4 Hz, 1H), 7.79 (t, J=7.5 Hz, 1H), 7.92 (d, J=8.1 Hz, 1H), 8.02 (d, J=10 Hz, 1H), 8.13 (d, J=8.1 Hz, 1H), 9.02 (s, 1H); LC/MS (MH$^+$, 571)

Step 7c

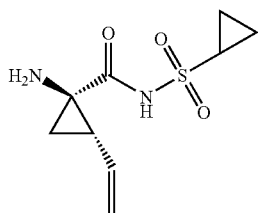

A solution of the product of Step 7b (3.5 g, 10.6 mmol) in dichloromethane (35 mL) and TFA (32 mL) was stirred at room temperature for 1.5 hours. The volatiles were removed in vacuo and the residue suspended in 1N HCl in diethyl ether (20 mL) and concentrated in vacuo. This procedure was repeated once. The resulting mixture was triturated from pentane and filtered to give the desired product as a hygroscopic, off-white solid (2.60 g, 92%). $^1$H NMR (DMSO-$d_6$) δ 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, 1H), 5.52-5.59 (m, 1H), 9.17 (br s, 3H); LC/MS (MH$^+$, (231).

Step 7e

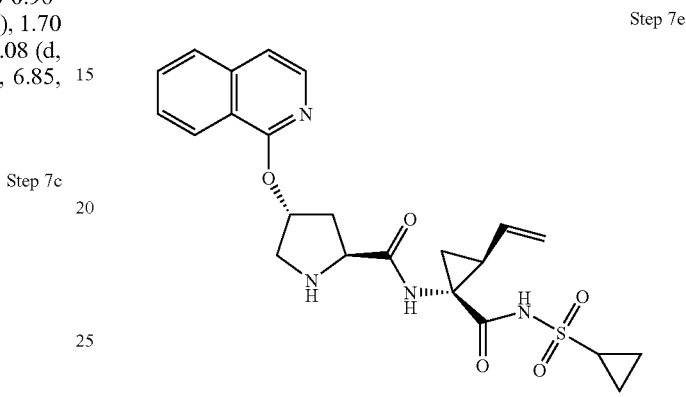

To an iced solution of the product of Step 7d (435 mg, 0.76 mmol) in dichloromethane (5 mL) was added TFA (5 mL). The formed solution was allowed to warm to ambient temperature for 2 hours and the solvent was removed in vacuo. The residue was triturated with 1M HCl in diethyl ether, collected by filtration, and washed with diethyl ether to provide 400 mg (97%) of the desired product as white solid. LC/MS (MH$^+$, 471).

Step 7d

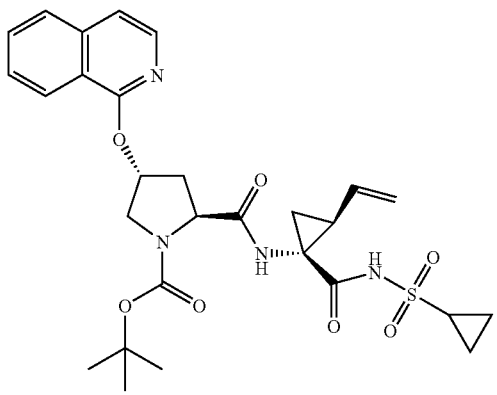

To an iced mixture of the product of Step 6 (358 mg, 1.0 mmol), the product of Step 7c (293 mg, 1.11 mmol) and HATU (570 mg, 1.5 mmol) in DCM (10 mL) was added diisopropylethylamine (387 mg, 3.0 mmol). The formed solution was allowed to warm to ambient temperature for 12 hours, diluted with ethyl acetate (200 mL), washed with 5% citric acid (2×50 mL) and brine, dried over $MgSO_4$, filtered,

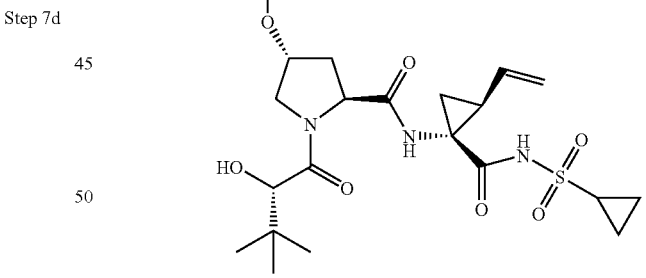

Example 8

The desired product was prepared by substituting Example 7e and (S)-(−)-2-hydroxy-3,3-dimethylbutyric acid for the product of Step 7c and the product of Step 6, respectively, in the procedure for Step 7b. $^1$H NMR (CD$_3$OD) δ 0.98 (s, 9H), 1.05-1.09 (m, 2H), 1.21-1.27 (m, 2H), 1.39-1.44 (m, 1H), 1.87-1.91 (m, 1H), 2.20-2.31 (m, 2H), 2.53-2.62 (m, 1H), 2.90-2.99 (m, 1H), 4.02-4.08 (m, 2H), 4.31 (d, J=12 Hz, 1H), 4.60-4.66 (m, 1H), 5.11-5.15 (m, 1H), 5.29 (d, J=17 Hz, 1H), 5.66-5.79 (m, 1H), 5.88 (b, 1H), 7.34 (d, J=6.0 Hz, 1H), 7.58 (t, J=8.9 Hz, 1H), 7.72 (t, J=8.7

Hz, 1H), 7.82 (d, J=8.1 Hz, 1H), 7.97 (d, J=5.7 Hz, 1H), 8.17 (d, J=8.4 Hz, 1H), 9.24 (s, 1H); LC/MS (MH+, 585).

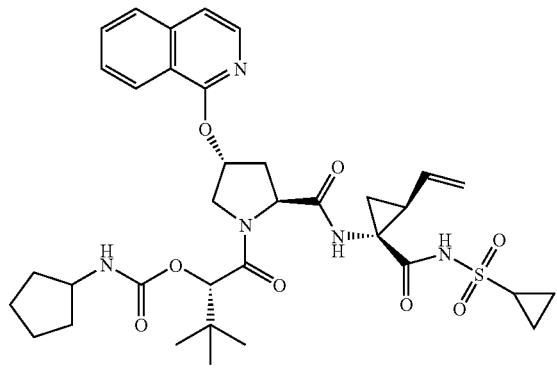

Example 9

To an iced solution of the product of Example 8 (12 mg, 0.02 mmol) in THF (1 mL) was added NaH (60%, 24 mg, 0.08 mmol). The mixture was stirred at this temperature for 1 hour before addition of cyclopentyl isocyanate (9 mg, 0.08 mmol). The final solution was stirred additional 1 hour at 0° C. and then quenched with 5% citric acid and extracted with ethyl acetate (10 mL). The organic layer was washed with 5% citric acid and brine, dried over MgSO$_4$, filtered, and concentrated. The residue was purified by prep-HPLC to provide 5 mg (36%) of the desired product as a white solid. $^1$H NMR (CD$_3$OD) δ 1.06 (s, 9H), 1.23-1.89 (m, 10H), 2.21-2.30 (m, 2H), 2.60-2.69 (m, 1H), 2.92-2.99 (m, 1H), 3.66-3.70 (m, 1H), 3.99-4.03 (m, 1H), 4.51-4.60 (m, 2H), 4.76 (s, 1H), 5.12 (d, J=10 Hz, 1H), 5.28 (d, J=17.5 Hz, 1H), 5.65-5.75 (m, 1H), 5.87 (b, 1H), 7.33 (d, J=6.0 Hz, 1H), 7.54 (t, J=8.9 Hz, 1H), 7.72 (t, J=8.7 Hz, 1H), 7.81 (d, J=8.1 Hz, 1H), 7.95 (d, J=5.7 Hz, 1H), 8.34 (d, J=8.4 Hz, 1H), 8.99 (s, 1H); LC/MS (MH+, 696).

Example 50

Preparation of Compound 50

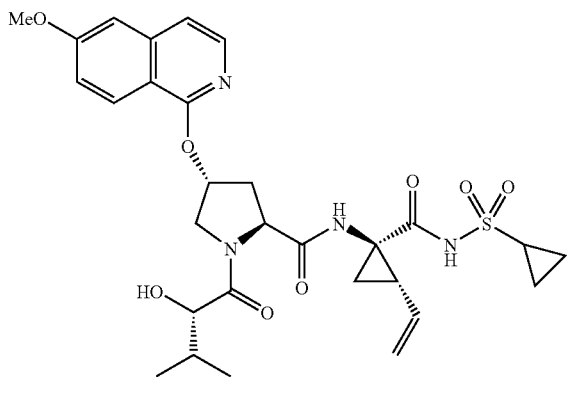

Compound 50

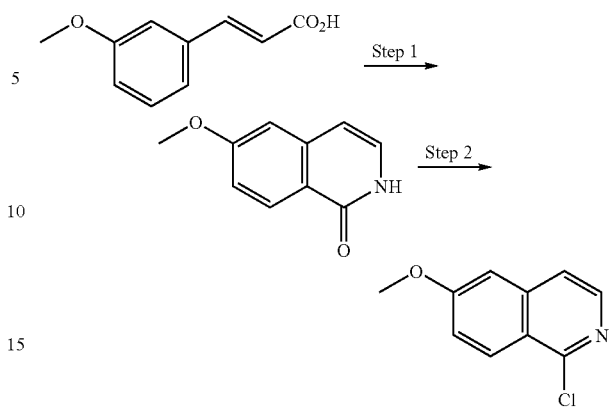

Step 1

To a solution of 3-methoxy cinnamic acid (11.04 g, 62 mmol) and triethylamine (12.52 g, 124 mmol) in acetone (80 mL) was added ethyl chloroformate (approximately 1.5 equivalents) dropwise at 0° C. After stirring at this temperature for 1 h, aqueous NaN$_3$ (6.40 g, 100 mmol in 35 mL H$_2$O) was added dropwise and the reaction mixture was stirred for 16 hours at ambient temperature. Water (100 mL) was added to the mixture and volatiles were removed in vacuo. The resulting slurry was extracted with toluene (3×50 mL) and the combined organic layers were dried over MgSO$_4$, filtered, and concentrated. The dried solution was added dropwise to a heated solution of diphenylmethane (50 mL) and tributylamine (30 mL) at 190° C. The toluene was distilled off during the addition. After complete addition, the reaction temperature was raised to 210° C. for 2 hours. Upon cooling, the precipitated product was collected by filtration, washed with hexane (2×50 mL), and dried to yield the desired product as a white solid (5.53 g, 51%) (Nicolas Briet at el, *Tetrahedron*, 2002, 5761-5766).

LC-MS, MS m/z 176 (M++H).

Step 2

6-Methoxy-2H-isoquinolin-1-one (5.0 g, 28.4 mmol) in POCl$_3$ (10 mL) was heated to gentle reflux for 3 hours and the mixture was then concentrated in vacuo (Nicolas Briet at el, *Tetrahedron*, 2002, 5761-5766). The residue was poured into ice water (20 mL) and brought to pH 10 by addition of 10 M NaOH. The resulting mixture was extracted with CHCl$_3$. The organic layer was washed with brine, dried over MgSO$_4$, filtered, and concentrated. The residue was purified by flash chromatography (1:1 hexane-EtOAc) to afford 4.41 g (80%) of the desired product as a white solid.

$^1$H NMR (CD$_3$OD) δ ppm 3.98 (s, 3H), 7.34-7.38 (m, 2H), 7.69 (d, J=5.5 Hz, 1H), 8.10 (d, J=6.0 Hz, 1H), 8.23 (d, J=9.5 Hz, 1H); LC-MS, MS m/z 194 (M++H).

Scheme 2.

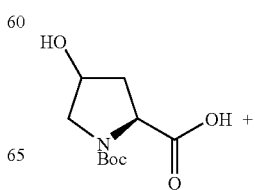

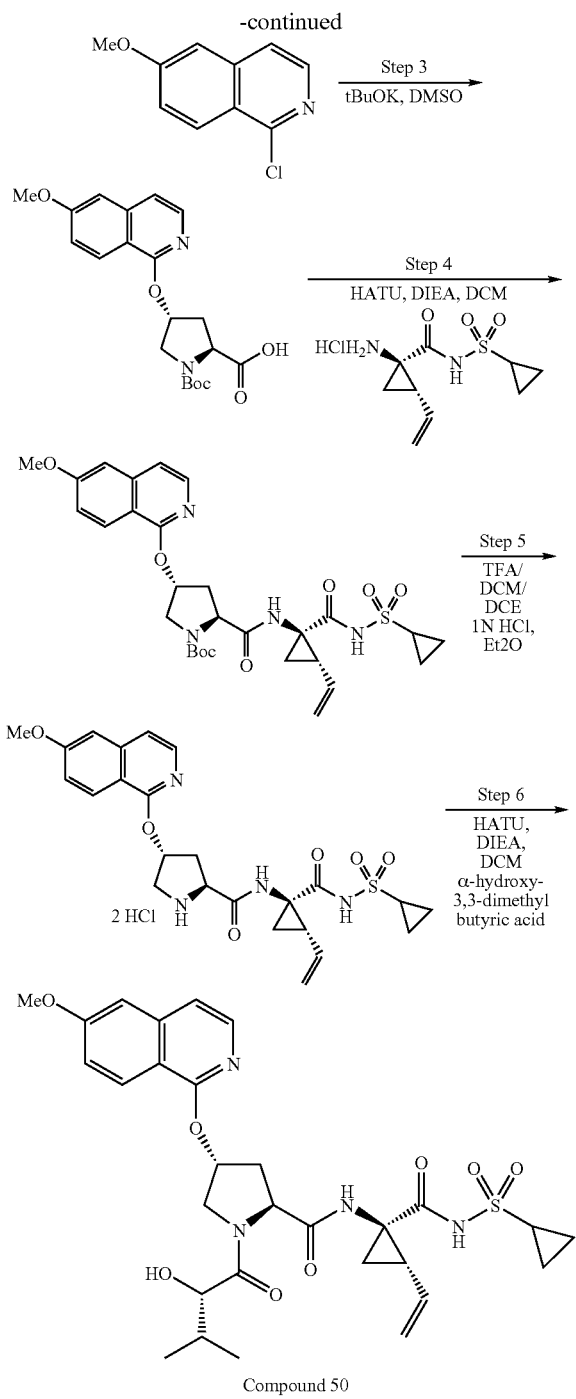

Compound 50

Step 3

To a solution of N-BOC-3-(R)-hydroxy-L-proline (892 mg, 3.89 mmol) in DMSO (40 mL) at ambient temperature was added solid potassium tert-butoxide (1.34 g, 12.0 mmol) in one portion. The suspension was stirred at room temperature for 30 min before being cooled to 10° C. 1-chloro-6-methoxy-isoquinoline (product of step 2, Example 50) (785 mg, 4.05 mmol) was added as a solid in one portion and the resulting mixture was stirred at ambient temperature for 12 hours. The mixture was quenched with ice cold 5% citric acid (aq) and then extracted with EtOAc (100 mL). The aqueous phase was extracted with EtOAc once more. The combined organic layers were washed with 5% citric acid (aq) and brine respectively, dried over $MgSO_4$ and filtered. The filtrate was concentrated in vacuo to dryness to yield 1.49 g (99%) of the desired product as an off-white foam. This crude material was used in the next reaction step without further purification. $^1$H NMR ($CD_3OD$) δ 1.42, 1.44 (rotamers, 9H), 2.38-2.43 (m, 1H), 2.66-2.72 (m, 1H), 3.80-3.87 (m, 2H), 3.92 (s, 3H), 4.44-4.52 (m, 1H), 5.73 (b, 1H), 7.16-7.18 (m, 2H), 7.24-7.25 (m, 1H), 7.87-7.88 (m, 1H), 8.07 (d, J=8.5 Hz, 1H); LC-MS, MS m/z 389 ($M^++H$).

Step 4

To a mixture of the product of Example 50, step 3 (1.49 g, 3.84 mmol), HATU (2.19 g, 5.76 mmol), and cyclopropanesulfonic acid (1-(R)-amino-2-(S)-vinyl-cyclopropanecarbonyl)-amide HCl salt, the product of step 7c, Example 7, (1.12 g, 4.22 mmol) in $CH_2Cl_2$ (50 mL) was added DIPEA (1.29 g, 11.5 mmol) at 0° C. After stirring at ambient temperature for 12 h, the resulting solution was diluted with $CH_2Cl_2$ (50 mL) and washed with iced 5% citric acid (aq). The organic layer was washed with 5% citric acid (aq) and brine respectively, dried over $MgSO_4$ and filtered. The filtrate was concentrated in vacuo to dryness. The residue was recrystallized from methanol to yield 1.60 g (70%) of the desired product as a white solid. $^1$H NMR ($CD_3OD$) δ 1.05-1.08 (m, 2H), 1.16-1.20 (m, 1H), 1.24-1.27 (m, 1H), 1.42-1.45 (m, 10H), 1.88 (dd, J=8.09, 5.34 Hz, 1H), 2.24-2.30 (m, 2H), 2.53-2.57 (m, 1H), 2.94-2.98 (m, 1H), 3.80 (d, J=12.5 Hz, 1H), 3.86-3.89 (m, 1H), 3.93 (s, 3H), 4.40-4.42 (m, 1H), 5.13 (d, J=10.5 Hz, 1H), 5.32 (d, J=18.0 Hz, 1H), 5.72-5.81 (m, 2H), 7.17-7.20 (m, 2H), 7.26 (d, J=6.0 Hz, 1H), 7.88 (d, J=6.0 Hz, 1H), 8.07 (d, J=9.0 Hz, 1H); LC-MS, MS m/z 601 ($M^++H$).

Step 5

To an ice cold solution of the product of Example 50, Step 4 (1.50 g, 2.50 mmol) in $CH_2Cl_2$ (10 mL) was added TFA (10 mL). The resulting solution was allowed to warm to ambient temperature and was stirred for 2 hours. The solvent was removed in vacuo. The residue was triturated with 1M HCl in ether, filtered and washed with ether to yield 1.43 g (99.8%) of the desired product as a hygroscopic white solid. $^1$H NMR ($CD_3OD$) δ ppm 1.03-1.208 (m, 4H), 1.26-1.31 (m, 1H), 1.37-1.40 (m, 1H), 1.95-1.97 (m, 1H), 2.32-2.37 (m, 1H), 2.42-2.48 (m, 1H), 2.95-2.99 (m, 1H), 3.88 (d, J=12.5 Hz, 2H), 3.98 (s, 3H), 4.40-4.42 (m, 1H), 5.16 (d, J=10.5 Hz, 1H), 5.33 (d, J=18.0 Hz, 1H), 5.62-5.69 (m, 1H), 5.97 (b, 1H), 7.30-7.34 (m, 2H), 7.47 (d, J=6.0 Hz, 1H), 7.90 (d, J=6.5 Hz, 1H), 8.34 (d, J=9.0 Hz, 1H), 9.14 (b, 1H); LC-MS, MS m/z 501 ($M^++H$).

Step 6

To a mixture of the product of step 5, Example 50, (0.50 g, 0.872 mmol), DIPEA (1.29 g, 11.5 mmol), and (S)-(+)-α-hydroxy-3-methylbutyric acid (0.156 g, 1.13 mmol) in $CH_2Cl_2$ (9 mL) was added HATU (0.597 g, 1.57 mmol). After stirring at ambient temperature for 16 h, the white precipitate byproduct HOAT was removed by vaccum filtrarion and washed with EtOAc (25 mL). The liquid filtrate was concentrated and the resulting residue was redissolved in EtOAc (75 mL) and washed with 2×10 mL 0.1 aqueous HCl. The aqueous layers were combined and extracted with EtOAc (50 mL). The organic layer was washed with 10% $Na_2CO_3$ (aq), brine, dried over $MgSO_4$, and filtered. The filtrate was concentrated in vacuo to dryness. The residue was purified by flash column chromatography ($SiO_2$, 97:3, DCM:MeOH) to yield 0.436 g (88%) of Compound 50 as a white foamy solid. ¹H NMR (CD₃OD) δ ppm 0.93 (d, J=6.72 Hz, 3H), 1.00 (d, J=6.72 Hz, 3H), 1.10 (dd, J=7.9, 2.4 Hz, 2H), 1.23-1.30 (m, 2H), 1.45 (dd, J=9.3, 5.4 Hz, 1H), 1.93 (dd, J=9.3, 5.4 Hz, 1H), 2.06-2.12 (m, 1H), 2.28 (q, J=8.9 Hz, 1H), 2.37-2.43 (m, 1H), 2.69 (dd, J=13.7, 6.4 Hz, 1H), 2.94-2.99 (m, 1H), 4.08 (d, J=5.5 Hz, 1H), 4.11 (dd, J=12.5, 3.5 Hz, 1H), 4.32 (d, J=12.5 Hz, 1H), 4.65 (dd, J=10.1, 7.0 Hz, 1H), 5.16 (dd, J=10.4, 1.5 Hz, 1H), 5.34 (dd, J=17.2, 1.4 Hz, 1H), 5.76-5.83 (m, 1H), 5.91 (br s, 1H), 7.33 (dd, J=9.2, 2.4 Hz, 1H), 7.37 (d, J=2.5 Hz, 1H), 7.50 (d, J=6.1 Hz, 1H), 7.92 (d, J=6.4 Hz, 1H), 8.22 (d, J=9.2 Hz, 1H); LC-MS, MS m/z 601 (M⁺+H).

Example 51

Preparation of Compound 51

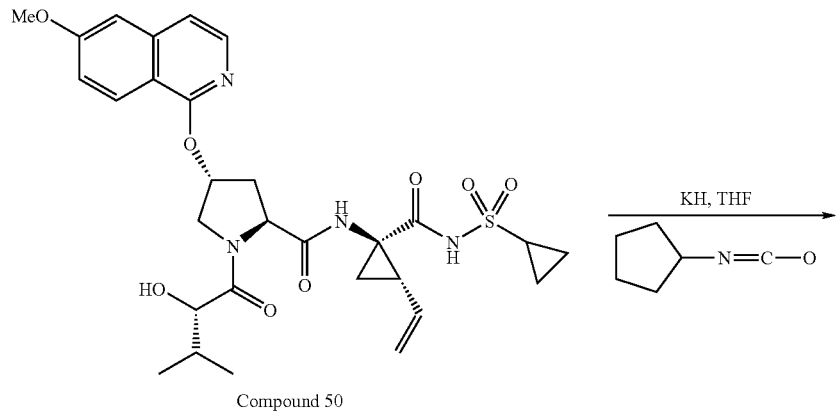

Compound 50

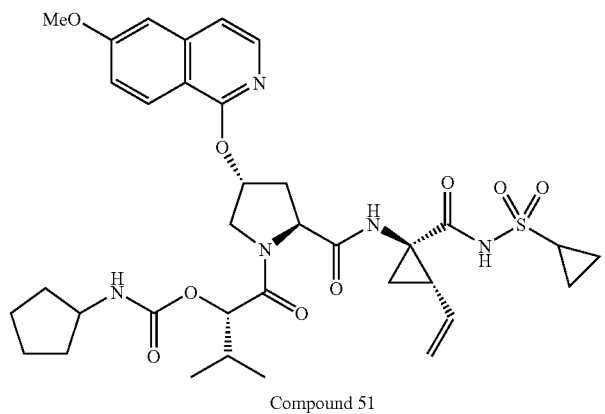

Compound 51

To a 0° C. solution of Compound 50 (0.249 g, 0.415 mmol) in THF (5 mL) was added KH (pre-washed with hexanes and dried in vacuo, 58.2 mg, 1.45 mmol). After stiring for 5 minutes, cyclopentyl isocyanate (142.6 mg, 1.25 mmol) was added. The resulting mixture was stirred at ambient temperature over 5 h, at which time the reaction was diluted with EtOAc (40 mL) and washed with 1N aqueous HCl (3 mL). The aqueous layer was extracted with EtOAc (15 mL). The combined organic layer was washed with 10% aqueous Na₂CO₃ (5 mL), brine, dried over MgSO₄, filtered, and concentrated. The crude mixture was purified by reverse phase HPLC to give a yellow solid (95.6 mg, 31% yield). ¹H NMR (500 MHz, MeOD) δ ppm 1.01 (dd, J=12.67, 6.56 Hz, 6H) 1.07-1.11 (m, 2H) 1.19-1.36 (m, 4H) 1.42 (dd, J=9.46, 5.49 Hz, 1H) 1.46-1.54 (m, 2H) 1.58-1.78 (m, 4H) 1.92 (dd, J=8.24, 5.49 Hz, 1H) 2.19-2.33 (m, 2H) 2.37-2.47 (m, 1H) 2.72 (dd, J=113.58, 6.56 Hz, 1H) 2.98 (ddd, J=12.82, 8.09, 4.73 Hz, 1H) 3.38-3.44 (m, 1H) 4.01 (s, 3H) 4.02-4.08 (m, 1H) 4.58-4.66 (m, 2H) 4.70 (d, J=12.21 Hz, 1H) 5.16 (dd, J=10.38, 1.53 Hz, 1H) 5.33 (dd, J=17.09, 1.22 Hz, 1H) 5.76 (ddd, J=17.24, 10.22, 9.16 Hz, 1H) 5.88 (s, 1H) 7.28 (dd, J=9.16, 2.44 Hz, 1H) 7.37 (s, 1H) 7.50 (d, J=6.41 Hz, 1H) 7.91 (d, J=6.41 Hz, 1H) 8.35 (d, J=9.16 Hz, 1H); LC-MS, MS m/z 712 (M⁺+H).

Example 52

Preparation of Compound 52

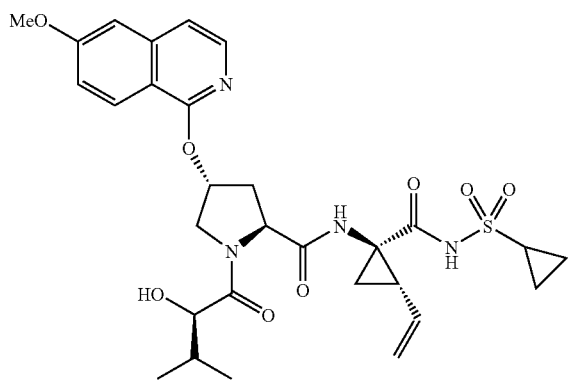

Compound 52

Compound 52 was prepared in 67% yield by the same procedure as described in step 6, example 50, except D-α-hydroxyvaleric acid was used instead of (S)-(+)-α-hydroxy-3-methylbutyric acid. $^1$H NMR (500 MHz, MeOD) δ ppm 0.90 (d, J=6.71 Hz, 6H) 1.04-1.16 (m, 3H) 1.18-1.24 (m, 1H) 1.26-1.33 (m, 2H) 1.43 (dd, J=9.31, 5.34 Hz, 1H) 1.85-1.96 (m, 2H) 2.30 (q, J=8.85 Hz, 1H) 2.45 (ddd, J=13.81, 9.23, 4.12 Hz, 1H) 2.70 (dd, J=13.89, 7.17 Hz, 1H) 2.98 (ddd, J=12.74, 8.01, 4.58 Hz, 1H) 4.01 (s, 3H) 4.06 (d, J=5.80 Hz, 1H) 4.14 (dd, J=12.36, 3.20 Hz, 1H) 4.33 (d, J=12.51 Hz, 1H) 4.62 (t, J=8.24 Hz, 1H) 5.16 (dd, J=10.38, 1.22 Hz, 1H) 5.35 (dd, J=17.09, 1.22 Hz, 1H) 5.73-5.84 (m, 1H) 5.93 (s, 1H) 7.33 (dd, J=9.16, 2.14 Hz, 1H) 7.38 (d, J=2.14 Hz, 1H) 7.51 (d, J=6.41 Hz, 1H) 7.92 (d, J=6.41 Hz, 1H) 8.16 (d, J=9.16 Hz, 1H). LC-MS, MS m/z 601 (M$^+$+H).

Example 53

Preparation of Compound 53

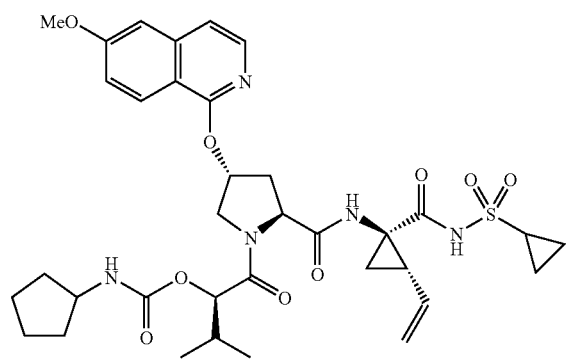

Compound 53

Compound 53 was prepared in 25% yield from Compound 52 by the same procedure as described for the preparation of Compound 51. $^1$H NMR (500 MHz, MeOD) δ ppm 0.81 (d, J=6.71 Hz, 3H) 0.98 (d, J=6.41 Hz, 3H) 1.05-1.15 (m, 2H) 1.21-1.33 (m, 2H) 1.35-1.44 (m, 2H) 1.47 (dd, J=12.51, 5.80 Hz, 1H) 1.51-1.61 (m, 2H) 1.63-1.75 (m, 2H) 1.77-1.87 (m, 2H) 1.87-1.95 (m, 1H) 1.99-2.09 (m, 1H) 2.37 (q, J=8.85 Hz, 1H) 2.45 (ddd, J=13.89, 9.16, 4.73 Hz, 1H) 2.76 (dd, J=13.89, 7.78 Hz, 1H) 2.95 (ddd, J=112.67, 8.09, 4.88 Hz, 1H) 3.80-3.90 (m, 1H) 3.97 (s, 3H) 4.20-4.30 (m, 2H) 4.62-4.70 (m, 2H) 5.17 (d, J=11.29 Hz, 1H) 5.33 (d, J=17.09 Hz, 1H) 5.75 (ddd, J=17.24, 10.07, 8.70 Hz, 1H) 5.89 (s, 1H) 7.25 (dd, J=9.16, 2.14 Hz, 1H) 7.29 (d, J=2.14 Hz, 1H) 7.39 (d, J=6.10 Hz, 1H) 7.92 (d, J=6.10 Hz, 1H) 8.10 (d, J=8.85 Hz, 1H); LC-MS, MS m/z 712 (M$^+$+H).

Example 54

Preparation of Compound 54

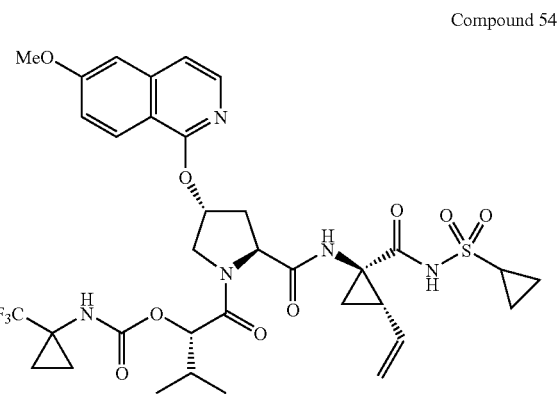

Compound 54

Compound 54 was prepared in 70% yield from Compound 50 by the same procedure as described for the preparation of Compound 51, except NaH and trifluoromethyl cyclopropyl isocyanate (prepared from trifluoromethyl cyclopropyl carboxylic acid via a Curtis rearrangement, T. Shioiri et al. *JACS*, 1972, 94, 6203) were used instead of KH and cyclopentyl isocyanate, respectively. $^1$H NMR (500 MHz, MeOD) δ ppm 0.92-1.16 (m, 12H) 1.18-1.35 (m, 3H) 1.91 (dd, J=7.93, 5.19 Hz, 1H) 2.25 (q, J=8.75 Hz, 2H) 2.37 (ddd, J=13.81, 10.45, 3.20 Hz, 1H) 2.67 (dd, J=14.50, 7.17 Hz, 1H) 2.98 (ddd, J=12.74, 8.16, 5.04 Hz, 1H) 3.98 (s, 3H) 4.04 (dd, J=12.21, 3.36 Hz, 1H) 4.55-4.63 (m, 1H) 4.69 (d, J=8.55 Hz, 1H) 5.15 (dd, J=10.38, 1.22 Hz, 1H) 5.32 (dd, J=17.09, 0.92 Hz, 1H) 5.75 (ddd, J=17.09, 9.92, 9.31 Hz, 1H) 5.87 (s, 1H) 7.22 (d, J=9.16 Hz, 1H) 7.30 (s, 1H) 7.41 (d, J=6.10 Hz, 1H) 7.90 (d, J=6.10 Hz, 1H) 8.07 (s, 0.5H) 8.33 (d, J=9.16 Hz, 1H) 9.25 (s, 0.5H); LC-MS, MS m/z 752 (M$^+$+H).

Example 55

Preparation of Compound 55

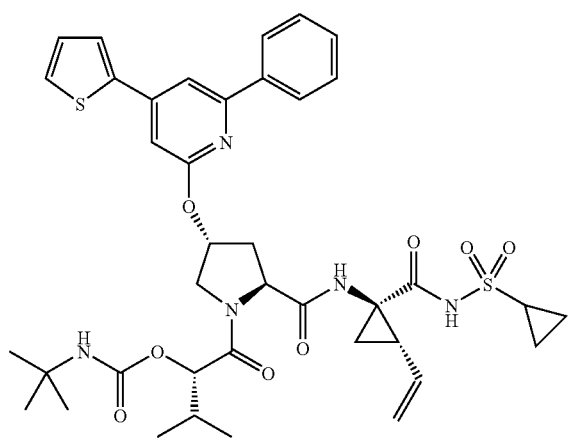

Compound 55

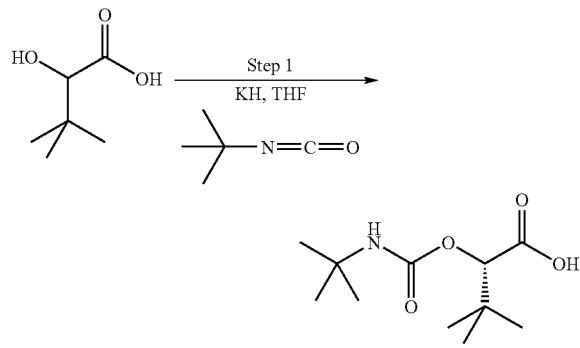

Scheme 1

Step 1.

To a 0° C. slurry of KH (0.640 g, 16.0 mmol) and THF (32 mL) was added (S)-(−)-a-hydroxy-3,3-dimethylbutyric acid (1.10 g, 7.98 mmol). The ice bath was removed and after stirring at ambient temperature for 20 mins, the reaction was again chilled to 0° C. and treated dropwise with tert-butyl isocyanate (2.03 g, 23.94 mmol). After stirring at room temperature for 14 h, the reaction was diluted with EtOAc (50 mL), slowly quenched with 1N NaOH (25 mL), and the layers were separated. The organic layer was extracted with 3×25 mL H$_2$O and discarded. The combined aqeous layer was acidified to about pH=5 with concentrated HCl, then extracted with 3×50 mL EtOAc. The combined organic layer was dried over MgSO$_4$, filtered, and concentrated to give a yellow solid (1.8 g, 98% yield) which was used without further purification. $^1$HNMR (CD$_3$OD) δ ppm 1.05 (s, 9H), 1.33 (s, 9H), 4.60 (s, 1H), 4.84 (s, 1H), 10.50 (br s, 1H); LC-MS, MS m/z 232 (M$^+$+Na).

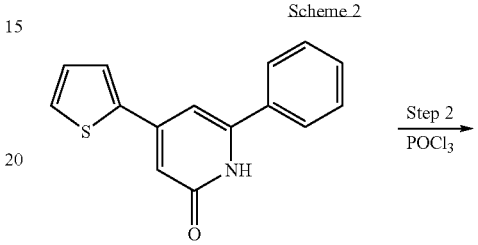

Scheme 2

S. Wang et at, Synthesis 4, 487-490, 2003

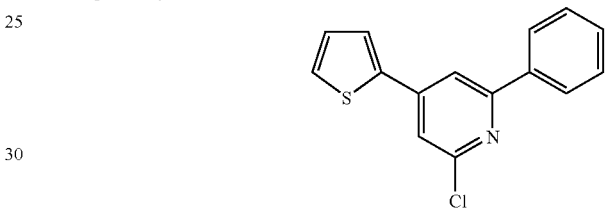

Step 2.

A solution of 6-phenyl-4-(thiophen-2-yl)pyridin-2(1H)-one (1.07 mg, 4.23 mmol) (prepared according to S. Wang et al., *Synthesis* 4, 487-490, 2003) in phosphorus oxychloride (15 mL) was heat to reflux for three days. The excess phosphorus oxychloride was removed in vacuo and the residue was triturated with ice-water. The triturant was made basic with aqueous NaOH and the product was extracted into DCM. The organic layer was washed with brine, dried, filtered through diatomaceous earth (Celite®), and concentrated. Crude product was purified by flash column chromatography to give a white solid product (624 mg, 54% yield). $^1$H NMR (CDCl$_3$) δ ppm 7.16 (dd, J=5.13, 3.7 Hz, 1H), 7.44-7.52 (m, 5H), 7.55 (dd, J=3.7, 1.1 Hz, 1H), 7.79 (d, J=1.5 Hz, 1H), 8.02 (dd, J=8.1, 1.5 Hz, 2H); LC-MS, MS m/z 272 (M$^+$+H).

Scheme 3

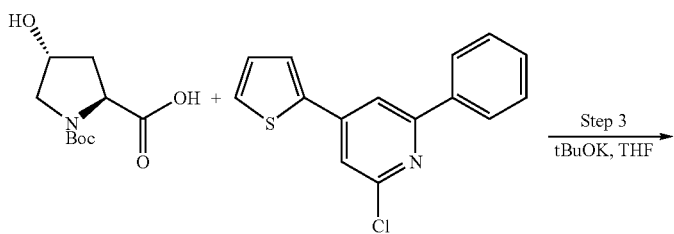

-continued
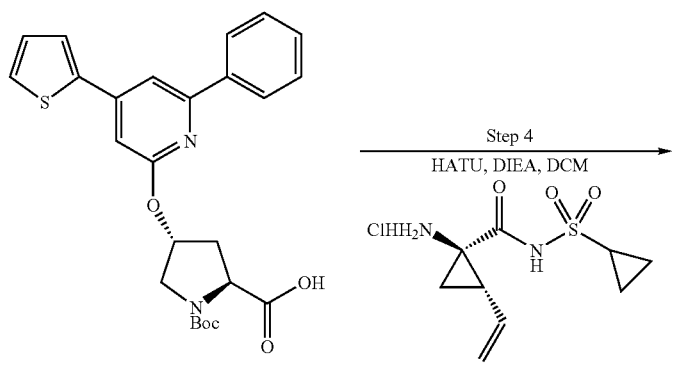
Step 4
HATU, DIEA, DCM
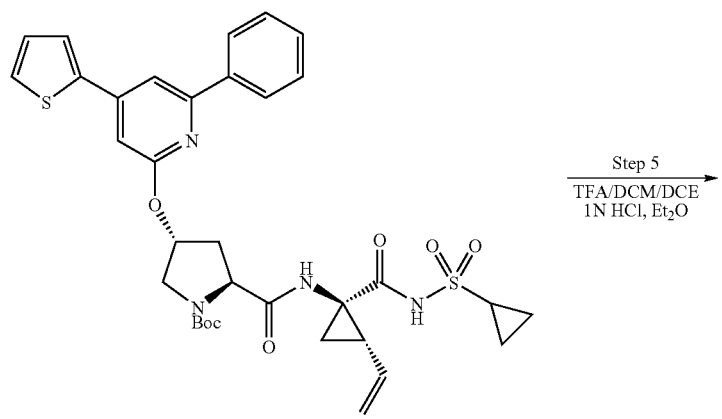
Step 5
TFA/DCM/DCE
1N HCl, Et₂O
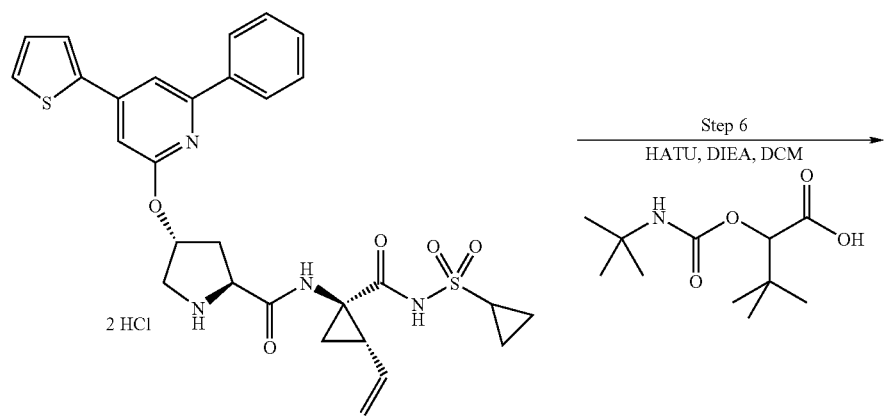
Step 6
HATU, DIEA, DCM

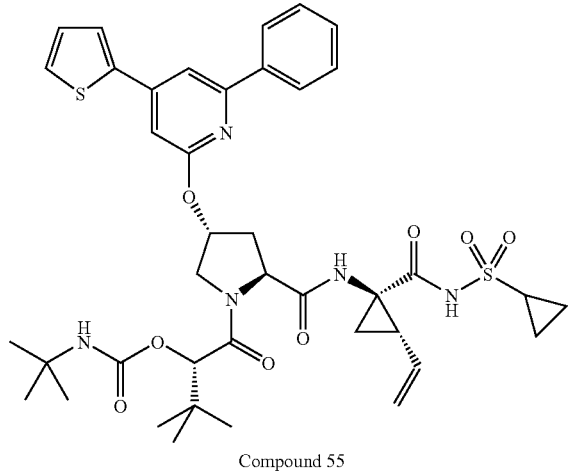

Compound 55

Step 3.

To a solution of Boc-Hyp-OH (254 mg, 1.1 mmol) in DMSO (5 mL) was added potassium tert-butoxide (295 mg, 2.5 mmol). After stirring at room temperature for 1 hour, the chloropyridine product from step 2, Example 55 was added and the resulting mixture was stirred at room temperature overnight. The reaction mixture was partitioned between EtOAc and aqueous citric acid. The organic phase was washed with H$_2$O and brine, and was then dried over MgSO$_4$, filtered, and concentrated in vacuo. LC/MS of crude mixture showed a 2.5:1 mixture of product:chloropyridine starting material. The crude mixture was purified by a flash column chromatography (SiO$_2$, 90:10 DCM:MeOH) to give a solid product (270 mg, 58% yield). $^1$H NMR (CD$_3$OD) δ 1.45 (s, 9H), 2.37-2.42 (m, 1H), 2.63 (q, J=13.9 Hz, 1H), 3.79 (d, J=11.9 Hz, 1H), 3.88 (d, J=12.2 Hz, 1H), 4.41-4.46 (m, 1H), 5.70 (br s, 1H), 6.92 (br s, 1H), 7.15 (d, J=3.4 Hz, 1H), 7.40 (t, J=6.1 Hz, 1H), 7.45 (q, J=6.7 Hz, 2H), 7.51 (d, J=4.0 Hz, 1H), 7.65 (br s, 2H), 8.05 (d, J=7.0 Hz, 2H); LC-MS, MS m/z 467 (M$^+$+H).

Step 4.

The product from step 3, Example 55, (260 mg, 0.56 mmol) was combined with N-methylmorpholine (284 mg, 2.79 mmol), cyclopropanesulfonic acid (1-(R)-amino-2-(S)-vinyl-cyclopropanecarbonyl)-amide HCl salt, the product of step 7c, Example 7, (202 mg, 0.61 mmol) and HATU (276 mg, 0.73 mmol) in DCM (5 mL). After stirring at room temperature for 2 hours, the reaction mixture was poured into aqueous citric acid and the product was extracted with EtOAc. The organic layer was washed with aqueous bicarbonate, and brine, and was then dried over MgSO$_4$, filtered, and concentrated in vacuo. The crude mixture was purified by flash column chromatography (SiO$_2$, 1.5% MeOH in DCM) to give a white solid product (250 mg, 66% yield). NMR (CD$_3$OD) δ 1.07 (q, J=7.1 Hz, 2H), 1.18 (dd, J=9.5, 4.3 Hz, 1H), 1.23-1.29 (m, 1H), 1.43 (q, J=6.1 Hz, 1H), 1.47 (s, 9H), 1.88 (q, J=5.5 Hz, 1H), 2.25 (q, J=8.5 Hz, 1H), 2.30 (dd, J=9.5, 4.6 Hz, 1H), 2.51 (dd, J=13.5 Hz, 1H), 2.93-2.97 (m, 1H), 3.77 (d, J=11.9 Hz, 1H), 3.89 (dd, J=11.6, 4.1 Hz, 1H), 4.32 (t, J=8.3 Hz, 1H), 5.12 (d, J=10.4 Hz, 1H), 5.31 (d, J=17.1 Hz, 1H), 5.76 (br s, 1H), 6.93 (s, 1H), 7.16 (t, J=4.3 Hz, 1H), 7.41 (t, J=6.9 Hz, 1H), 7.46 (t, J=7.5 Hz, 2H), 7.54 (d, J=4.9 Hz, 1H), 7.68 (br s, 2H), 8.06 (d, J=7.6 Hz, 2H); LC-MS, MS m/z 678 (M$^+$+H).

Step 5.

To a solution of the product of step 4, Example 55, (0.707 g, 1.04 mmol) in 1:1 DCM:DCE (20 mL) was added TFA (10 mL). After stirring at room temperature for 0.5 h, the reaction was concentrated in vacuo. The resulting residue was redissolved in DCE (20 mL) and re-concentrated. The resulting brown viscous oil was then dissolved in DCM (3 mL) and was added dropwise to a rapidly stirred solution of 1N HCl in Et$_2$O (100 mL). The resulting precipitate, an off-white solid (0.666 g, 98% yield) was obtained by vacuum filtration and was washed with Et$_2$O.

LC-MS, MS m/z 579 (M$^+$+H).

Step 6.

To a mixture of the product of step 5, Example 55, (0.200 g, 0.307 mmol) and DIEA (0.139 g, 1.07 mmol) in DCM (3 mL) was added the product of step 1, Example 55, followed by addition of HATU (0.140 g, 0.368 mmol). After stirring at room temperature for 8 hours, solvent was removed and the residue was re-dissolved with EtOAc (30 mL) followed by washing with 2×3 mL 1N aqueous HCl. The aqueous layer was extracted with EtOAc (30 mL). The combined organic layer was washed with 10% aqueous Na$_2$CO$_3$ and brine, and was then dried over MgSO$_4$, filtered, and concentrated. The resulting brown viscous oil was purified by a flash column chromatography (SiO$_2$, 97:3 and 95:5 DCM:MeOH) to give Compound 55 as a white solid (0.170 g, 70% yield). $^1$H NMR (500 MHz, MeOD) δ ppm 1.08 (s, 11H) 1.22 (s, 9H) 1.24-1.29 (m, 2H) 1.42 (dd, J=9.46, 5.49 Hz, 1H) 1.90 (dd, J=8.24, 5.49 Hz, 1H) 2.25-2.37 (m, 2H) 2.58 (dd, J=13.58, 7.48 Hz, 1H) 2.98 (ddd, J=12.82, 8.09, 4.73 Hz, 1H) 4.09 (dd, J=11.75, 3.81 Hz, 1H) 4.41 (d, J=11.60 Hz, 1H) 4.62 (t, J=8.39 Hz, 1H) 4.74 (s, 1H) 5.15 (dd, J=10.38, 1.22 Hz, 1H) 5.32 (dd, J=17.24, 1.07 Hz, 1H) 5.68-5.79 (m, 1H) 5.91 (s, 1H) 6.97 (s, 1H) 7.20 (dd, J=4.88, 3.66 Hz, 1H) 7.45 (t, J=7.32 Hz, 1H) 7.51 (t, J=7.32 Hz, 2H) 7.57 (d, J=5.19 Hz, 1H) 7.71 (d, J=3.05 Hz, 1H) 7.74 (d, J=1.22 Hz, 1H) 8.12 (d, J=7.32 Hz, 2H); LC-MS, MS m/z 792 (M$^+$+H).

Example 56

Preparation of Compound 56

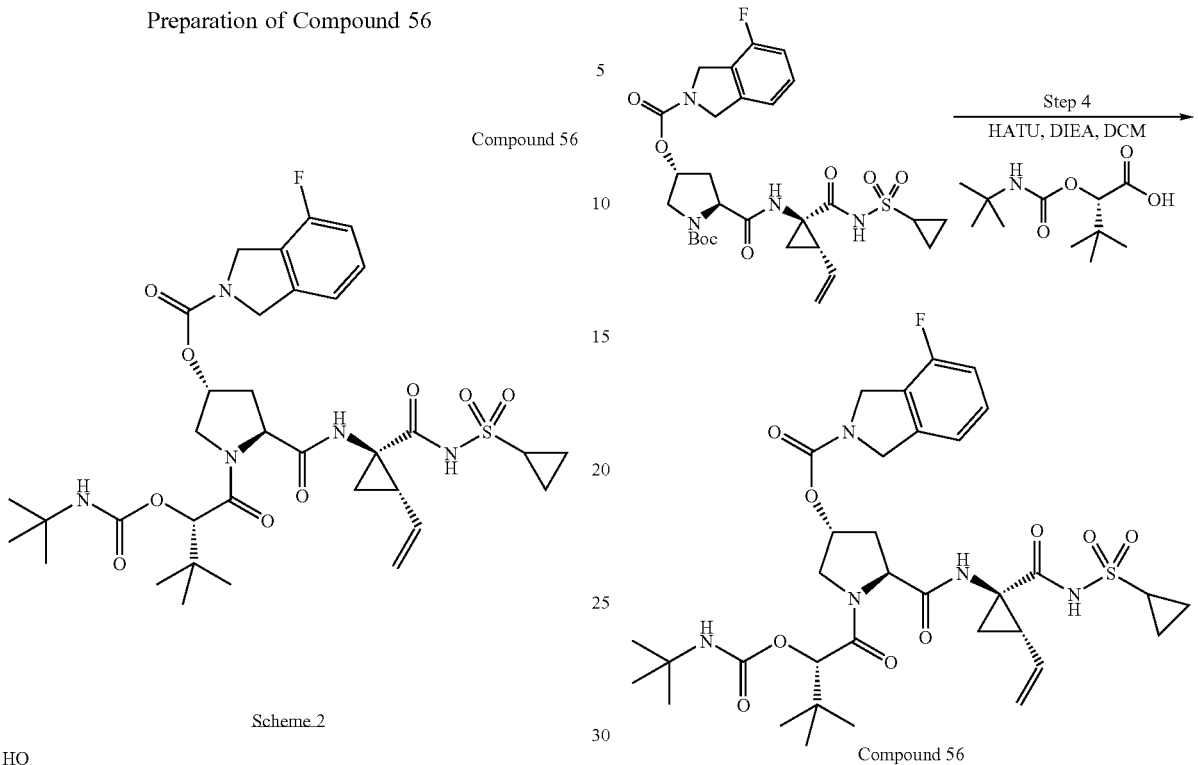

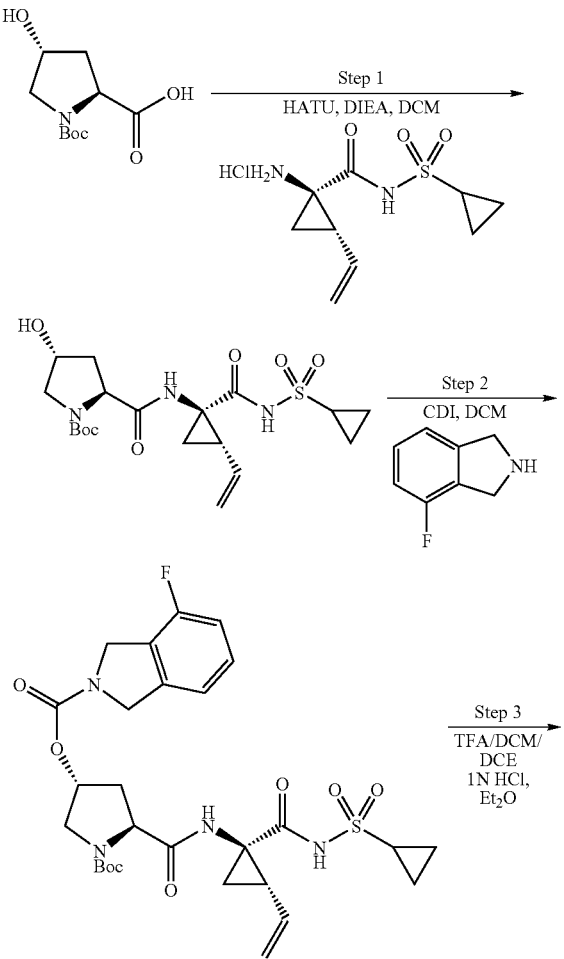

Step 1.

The product of step 1, Example 56, was prepared by the same procedure as the product of step 4, Example 50, starting with Boc-Hyp-OH instead of the product of step 3, Example 50. $^1$H NMR (500 MHz, MeOD) δ ppm 1.09 (d, J=7.63 Hz, 2H) 1.16-1.22 (m, 1H) 1.25-1.32 (m, 1H) 1.42 (dd, J=9.46, 5.49 Hz, 1H) 1.47 (s, 1.7H) 1.50 (s, 7.3H) 1.88 (dd, J=8.09, 5.34 Hz, 1H) 1.94-2.03 (m, 1H) 2.13 (dd, J=12.97, 6.87 Hz, 1H) 2.26 (q, J=8.85 Hz, 1H) 2.97 (ddd, J=12.51, 8.09, 4.73 Hz, 1H) 3.47 (d, J=11.60 Hz, 1H) 3.56-3.62 (m, 1H) 4.25 (dd, J=9.61, 6.87 Hz, 1H) 4.42 (s, 1H) 5.15 (d, J=10.38 Hz, 1H) 5.34 (d, J=17.09 Hz, 1H) 5.74-5.85 (m, 1H); LCMS, MS m/z=442 (M−H)⁻.

Step 2.

To a solution of the product from step 1, Example 56, (1.0 g, 2.25 mmol) in DCM (20 mL) was added 1,1'-carbonyldiimidazole (439 mg, 2.71 mmol). After stirring at room temperature for 3 hours, 4-fluoroisoindoline (prepared according to procedure found in: L. M. Blatt et al. *PCT Int. Appl.* (2005), 244 pp, WO 2005037214) (617 mg, 4.50 mmol) was added and the resulting mixture was stirred at room temperature overnight. The reaction mixture was diluted with EtOAc (100 mL) and washed with 2×10 mL 1N aqueous HCl. The aqueous layer was extracted with 2×50 mL EtOAc. The combined organic layer was washed with brine, dried over MgSO₄, filtered, and concentrated to a dark brown viscous oil. The crude mixture was purified by flash column chromatography (SiO₂, 97:3 and 95:5 DCM:MeOH) to give a grey foamy solid (1.3 g, 95% yield). $^1$H NMR (500 MHz, CDCl₃) δ ppm 1.29-1.37 (m, 2H) 1.38-1.45 (m, 2H) 1.47 (s, 9H) 1.95-2.00 (m, 1H) 2.07-2.14 (m, 1H) 2.28-2.35 (m, 1H) 2.37-2.46 (m, 1H) 2.90-2.97 (m, 1H) 3.65 (d, J=12.80 Hz, 1H) 3.72 (d, J=12.50 Hz, 1H) 4.26 (t, J=7.02

Hz, 1H) 4.68 (d, J=9.46 Hz, 2H) 4.77 (d, J=9.16 Hz, 2H) 5.15 (d, J=10.38 Hz, 1H) 5.29 (d, J=17.10 Hz, 1H) 5.33 (s, 1H) 5.73-5.84 (m, 1H) 6.97 (t, J=8.70 Hz, 1H) 7.01 (d, J=7.63 Hz, 1H) 7.28 (dd, J=8.09, 2.90 Hz, 1H) 10.00 (s, 1H); LC-MS, MS m/z 629 (M$^+$+Na).

Step 3.

The product of step 3, Example 56, was prepared in 94% yield from the product of step 2, Example 56, by the same procedure as described for the preparation of the product of step 5, Example 55. $^1$H NMR (500 MHz, MeOD) δ ppm 1.05-1.11 (m, 1H) 1.11-1.17 (m, 1H) 1.18-1.23 (m, 1H) 1.27-1.34 (m, 1H) 1.40 (dd, J=9.61, 5.65 Hz, 1H) 1.98 (dd, J=7.93, 5.80 Hz, 1H) 2.27-2.33 (m, 1H) 2.36 (q, J=8.80 Hz, 1H) 2.75 (dd, J=14.34, 7.32 Hz, 1H) 2.96-3.03 (m, 1H) 3.65-3.75 (m, 2H) 4.61-4.67 (m, 1H) 4.78 (s, 2H) 5.19 (d, J=10.38 Hz, 1H) 5.36 (d, J=17.09 Hz, 1H) 5.48 (s, 1H) 5.64-5.73 (m, 1H) 7.06 (t, J=8.70 Hz, 1H) 7.17 (dd, J=16.17, 7.63 Hz, 1H) 7.37 (q, J=7.63 Hz, 1H); LC-MS, MS m/z 507 (M$^+$+H).

Step 4.

Compound 56, Example 56, was prepared in 55% yield from the product of step 3, Example 56, by the same procedure as described for the preparation of the product of step 6, Example 55. $^1$H NMR (500 MHz, MeOD) δ ppm 1.02 (s, 5H) 1.05-1.14 (m, 16H) 1.22-1.28 (m, 2H) 1.42 (dd, J=9.46, 5.49 Hz, 1H) 1.87-1.92 (m, 1H) 2.15-2.22 (m, 1H) 2.26 (q, J=8.85 Hz, 1H) 2.44-2.52 (m, 1H) 2.97 (ddd, J=12.82, 8.09, 4.73 Hz, 1H) 3.82 (d, J=11.60 Hz, 1H) 4.42 (d, J=11.29 Hz, 1H) 4.53-4.64 (m, 2H) 4.71-4.79 (m, 3H) 5.15 (dd, J=10.38, 1.22 Hz, 1H) 5.32 (dd, J=17.09, 1.22 Hz, 1H) 5.35 (s, 1H) 5.67-5.77 (m, 1H) 6.51 (d, J=23.19 Hz, 1H) 6.99-7.08 (m, 1.4H) 7.16 (d, J=7.63 Hz, 0.6H) 7.31-7.38 (m, 1H); LC-MS, MS m/z 720 (M$^+$+H).

Example 57

Preparation of Compound 57

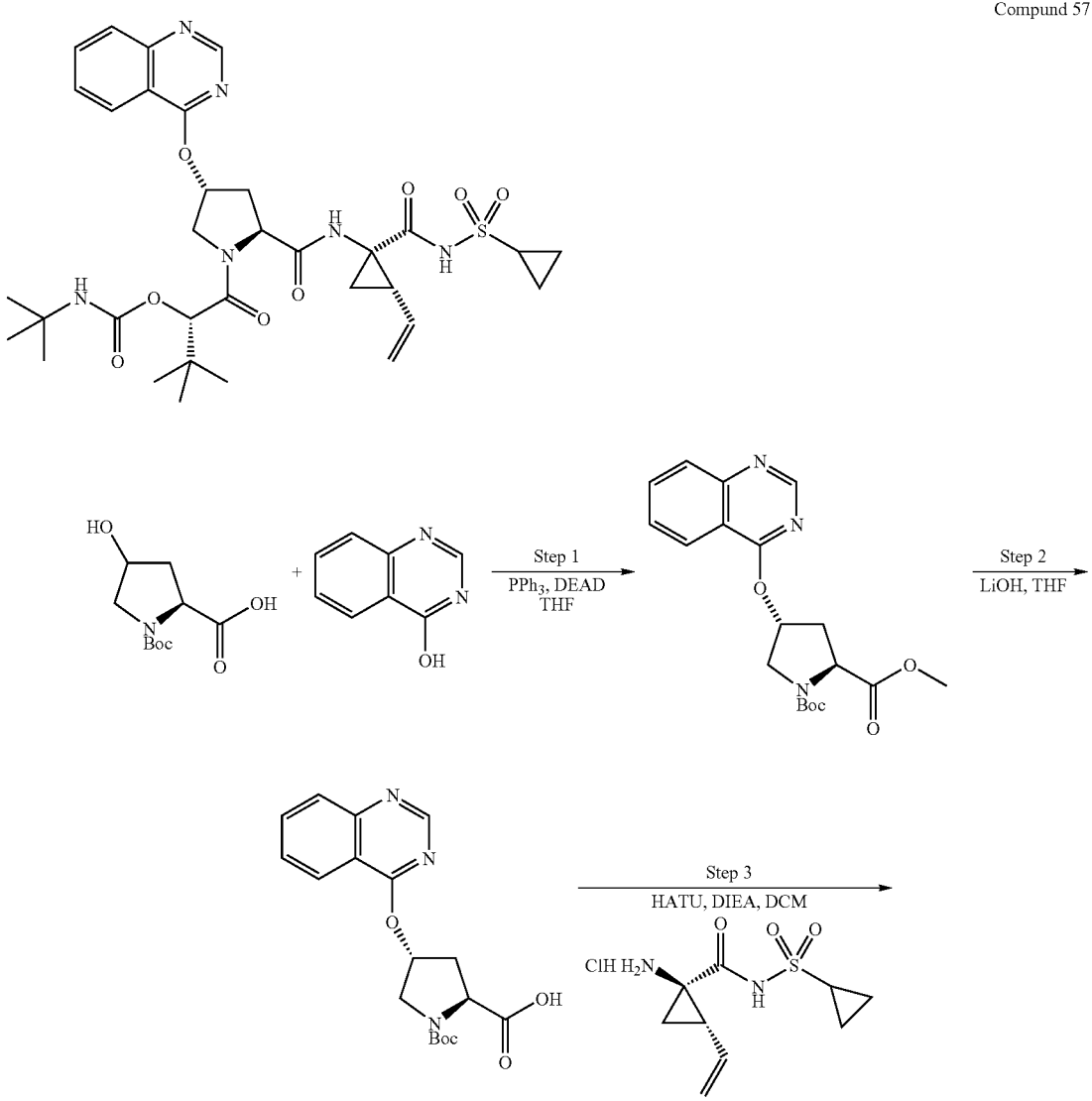

Compound 57

-continued
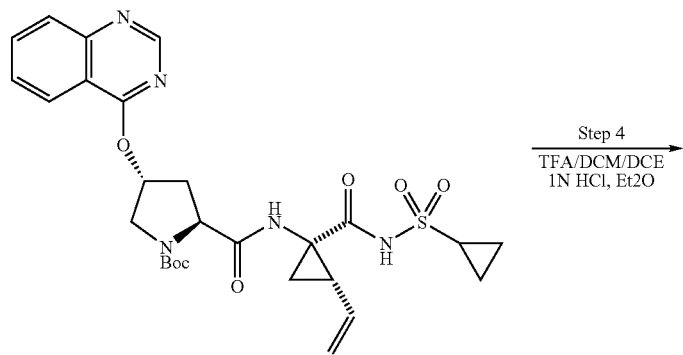
Step 4
TFA/DCM/DCE
1N HCl, Et2O
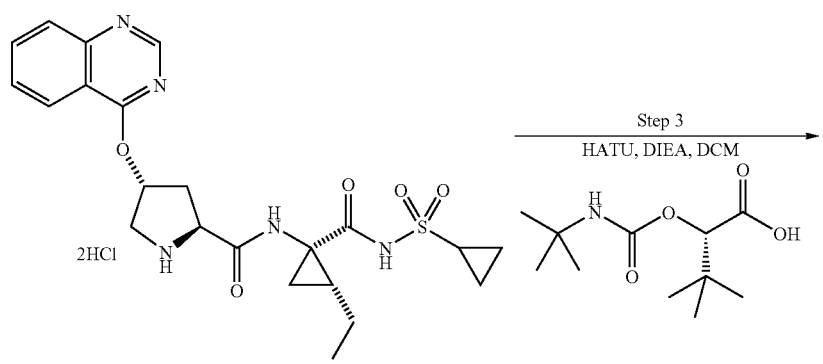
Step 3
HATU, DIEA, DCM
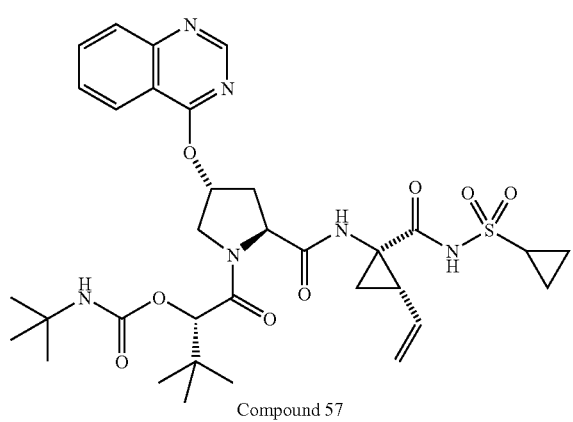
Compound 57

Step 1.

To a solution of cis-Boc-Hyp-OH (4.95 g, 20.2 mmol) and PPh$_3$ (10.6 g, 40.4 mmol) in THF (100 mL) was added diethylazodicarboxylate (7.4 g, 42.4 mmol) dropwise. After stirring at room temperature for 15 min was added 4-hydroxyquinoline (3.7 g, 25.3 mmol). After aqueous work up the product was used as crude with some triphenylphosphine oxide by-product contaimination still present for the next step.

Step 2.

To a solution of the crude product from step 1, Example 57, (assumed 20.2 mmol) in THF was added a solution of LiOH (2.54 g, 60.54 mmol) in H$_2$O (18 ml). The mixture was stirred at room temperature for 2 hours. The reaction mixture was then extracted with Et$_2$O and the organic layer was subsequently washed with H$_2$O (50 ml). The combined aqueous layer was diluted with DCM (50 mL) and acidified to pH=4. The mixture was shaken and the layers separated. The aqueous layer was extracted with 3×50 mL DCM. The combined DCM layer was washed with brine, dried over MgSO$_4$, filtered, and concentrated to give a light orange solid (5.8 g, 80% yield). LC-MS, MS m/z 360 (M$^+$+H)

Step 3.

The product of step 3, Example 57, was prepared in 76% yield from the product of step 2, Example 57, by the same procedure as described for the preparation of the product of step 4, Example 55. $^1$H NMR (500 MHz, MeOD) δ ppm 0.81-0.98 (m, 2H) 1.07 (s, 2H) 1.23-1.31 (m, 1H) 1.39 (d, J=6.41 Hz, 4H) 1.46 (s, 9H) 1.87 (d, J=2.75 Hz, 1H) 2.06-2.20 (m, 1H) 2.63-2.80 (m, 2H) 3.96 (d, J=13.73 Hz, 1H) 4.04 (d, J=11.90 Hz, 1H) 4.43 (q, J=7.60 Hz, 1H) 5.05 (d, J=9.16 Hz, 1H) 5.26 (d, J=17.09 Hz, 1H) 5.94 (s, 1H) 5.96-6.05 (m, 1H) 7.70 (t, J=7.63 Hz, 1H) 7.90-8.00 (m, 2H) 8.20 (d, J=8.24 Hz, 1H) 8.79 (s, 1H); LC-MS, MS m/z 572 (M$^+$+H)

Step 4.

The product of step 4, Example 57, was prepared in 83% yield from the product of step 3, Example 57, by the same procedure as described for the preparation of the product of step 5, Example 55. $^1$H NMR (500 MHz, MeOD) δ ppm 1.03-1.10 (m, 1H) 1.10-1.17 (m, 1H) 1.17-1.24 (m, 1H) 1.27-1.35 (m, 1H) 1.37-1.45 (m, 2H) 1.99 (dd, J=7.78, 5.65 Hz, 1H) 2.40 (q, J=8.75 Hz, 1H) 2.52-2.61 (m, 1H) 2.95-3.03 (m, 1H) 3.10 (dd, J=14.80, 7.48 Hz, 1H) 3.99 (s, 2H) 5.19 (d, J=10.38 Hz, 1H) 5.37 (d, J=17.09 Hz, 1H) 5.63-5.74 (m, 1H) 6.29 (s, 1H) 8.00 (t, J=7.63 Hz, 1H) 8.10 (d, J=8.24 Hz, 1H) 8.28 (t, J=7.93 Hz, 1H) 8.61 (d, J=8.24 Hz, 1H) 9.28 (s, 1H); LC-MS, MS m/z 472 (M$^+$+H).

Step 5.

Compound 57, Example 57, was prepared in 78% yield from the product of step 4, Example 57, by the same procedure as described for the preparation of the product of step 6, Example 55. $^1$H NMR (500 MHz, MeOD) δ ppm 1.02-1.08 (m, 3H) 1.09 (s, 9H) 1.07-1.14 (m, 9H) 1.22-1.28 (m, 3H) 1.30-1.34 (m, 1H) 1.90 (dd, J=7.78, 5.65 Hz, 1H) 2.25 (q, J=8.65 Hz, 1H) 2.36 (t, J=12.36 Hz, 1H) 2.72 (dd, J=13.73, 6.41 Hz, 1H) 2.93-3.00 (m, 1H) 4.02 (dd, J=11.90, 2.14 Hz, 1H) 4.60-4.77 (m, 1H) 5.15 (d, J=10.38 Hz, 1H) 5.31 (d, J=17.70 Hz, 1H) 5.67-5.77 (m, 1H) 5.98 (s, 1H) 7.64 (t, J=7.02 Hz, 1H) 7.90-7.99 (m, 2H) 8.38 (d, J=7.93 Hz, 1H) 8.80 (s, 1H); LC-MS, MS m/z 685 (M$^+$+H).

Example 58

Preparation of Compound 58

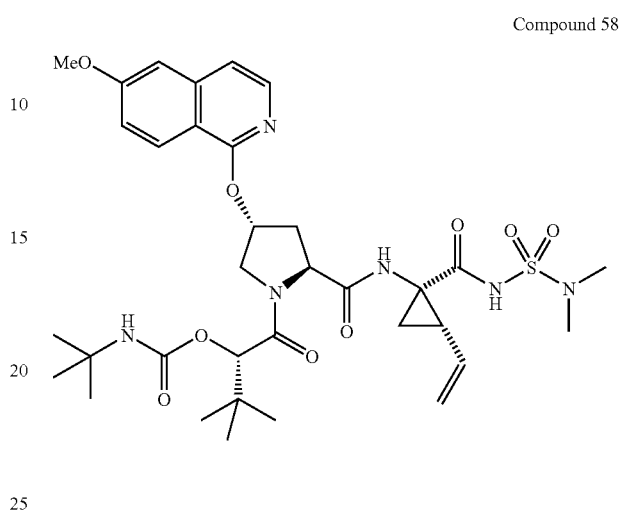

Compound 58

Scheme 1.

Step 1.

To a solution N-Boc-vinylcyclopropane carboxylic acid, the product of step 7a, Example 7, (1.83 g, 8.05 mmol) and THF (32 mL) was added 1,1'-carbonyldiimidazole (1.44 g, 8.86 mmol). After stirring at room temperature for 3 hours, the reaction mixture was treated with N,N-dimethylsulfamide (1.0 g, 8.05 mmol) followed by DBU (2.45 g, 16.1 mmol) and it was stirred at room temperature for an additional 15 hours. The reaction was then diluted with EtOAc (50 mL) and was washed with 2×25 mL 1N aqueous HCl. The aqueous layer was extracted with 2×50 mL EtOAc. The combined organic portion was washed with H$_2$O (25 mL) and brine, dried over MgSO$_4$, filtered, and concentrated to a light yellow solid (2.6 g, 97% yield) which was used without further purification. LC-MS, MS m/z 356 (M$^+$+Na).

Step 2.
To a solution of the product of step 2, Example 58, (1.42 g, 4.26 mmol) in 1:1 DCM:DCE (20 mL) was added TFA (10 mL). After stirring at room temperature for 0.5 hours, the solvent and excess TFA were removed and the residue was redisolved in DCE (20 mL) and concentrated again to give a yellow solid (1.46 g, 99% yield). LC-MS, MS m/z 234 (M$^+$+H).
Scheme 2
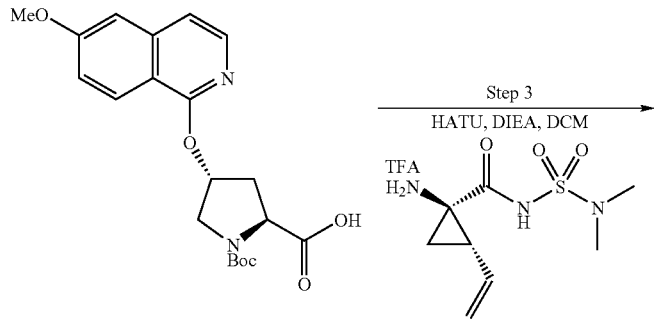
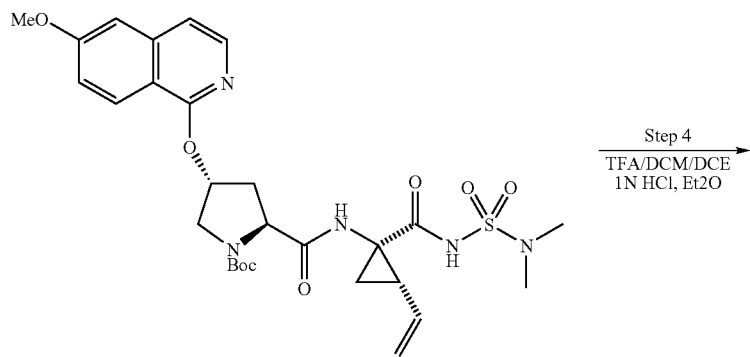
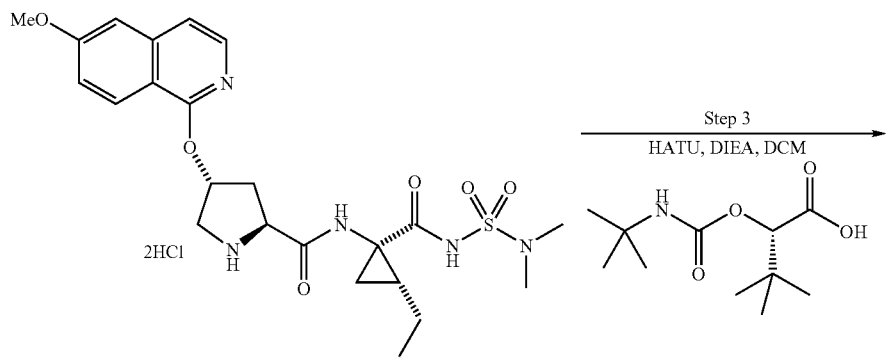

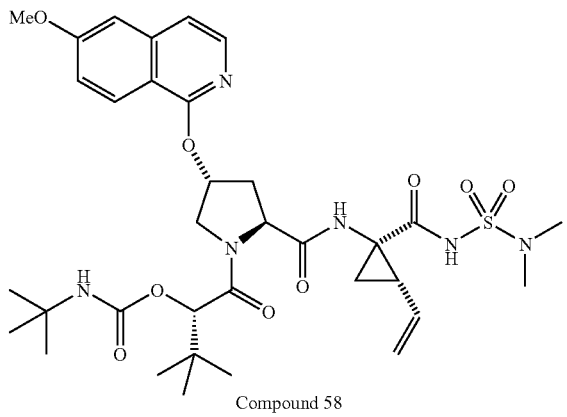

Compound 58

Step 3.

The product of step 3, Example 58, was prepared in 91% yield from the product of step 2, Example 58, by the same procedure as described for the preparation of the product of step 4, Example 55. $^1$H NMR (500 MHz, CDCl$_3$) δ ppm 1.38 (dd, J=7.78, 4.43 Hz, 1H) 1.46 (s, 9H) 1.95 (dd, J=8.09, 5.65 Hz, 1H) 2.08 (q, J=8.65 Hz, 1H) 2.49-2.55 (m, 2H) 2.91 (s, 6H) 3.77-3.87 (m, 2H) 3.93 (s, 3H) 4.38 (t, J=6.87 Hz, 1H) 5.16 (d, J=10.38 Hz, 1H) 5.29 (d, J=17.40 Hz, 1H) 5.71-5.79 (m, 1H) 5.80 (s, 1H) 7.02 (d, J=2.44 Hz, 1H) 7.13-7.16 (m, J=5.50 Hz, 1H) 7.90 (d, J=5.80 Hz, 1H) 8.02 (d, J=9.16 Hz, 1H) 9.83 (s, 1H); LC-MS, MS m/z 604 (M$^+$+H)

Step 4.

The product of step 4, Example 58, was prepared in 95% yield from the product of step 3, Example 58, by the same procedure as described for the preparation of the product of step 5, Example 55. LC-MS, MS m/z 504 (M$^+$+H).

Step 5.

Compound 58, Example 58, was prepared in 83% yield from the product of step 4, Example 58, by the same procedure as described for the preparation of the product of step 6, Example 55. $^1$H NMR (500 MHz, MeOD) δ ppm 1.08 (s, 9H) 1.24 (s, 9H) 1.32-1.39 (m, 1H) 1.81-1.89 (m, 1H) 2.17-2.30 (m, 2H) 2.65 (dd, J=13.12, 6.41 Hz, 1H) 2.87-2.92 (m, 6H) 3.91-3.96 (m, 3H) 3.96-4.03 (m, 1H) 4.53-4.63 (m, 2H) 4.74 (s, 1H) 5.15 (dd, J=10.38, 1.83 Hz, 1H) 5.29 (d, J=17.09 Hz, 1H) 5.62-5.74 (m, 1H) 5.82 (d, J=2.75 Hz, 1H) 6.61 (s, 1H) 7.11 (d, J=8.85 Hz, 1H) 7.20 (d, J=2.44 Hz, 1H) 7.23-7.29 (m, 1H) 7.86-7.92 (m, 1H) 8.29 (d, J=8.85 Hz, 1H); LC-MS, MS m/z 717 (M$^+$+H).

Example 59

Preparation of Compound 59

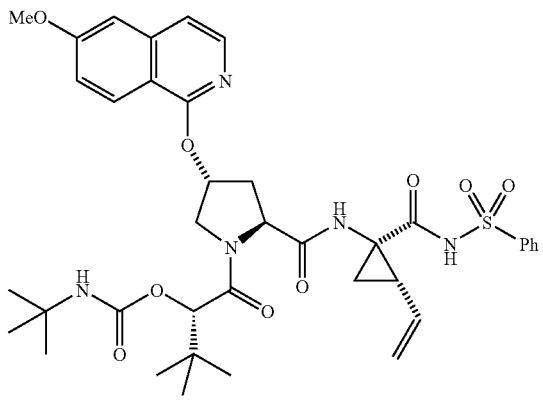

Compound 59

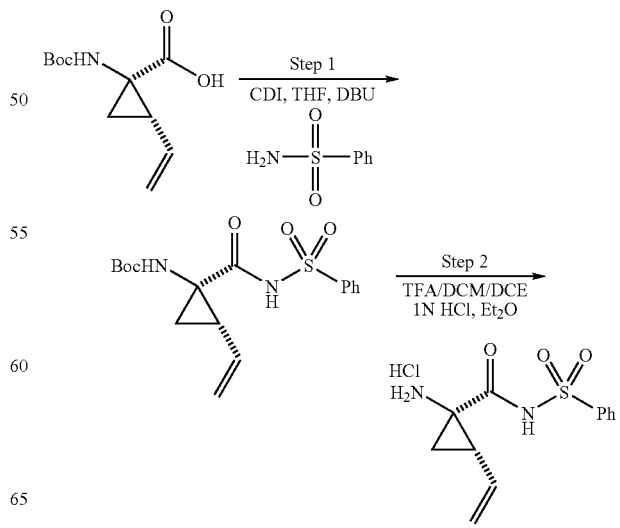

Scheme 1.

Step 1.

The product of step 1, Example 59, was prepared in 92% yield from N-Boc-vinylcyclopropane carboxylic acid, the product of step 7a, Example 7, and benzenesulfamide by the same procedure as described for the preparation of the product of step 1, Example 58. LC-MS MS m/z 389 (M$^+$+Na).

Step 2.

The product of step 2, Example 59, was prepared in 86% yield from the product of step 1, Example 59, by the same procedure as described for the preparation of the product of step 2, Example 58. LC-MS, MS m/z 267 (M$^+$+H).

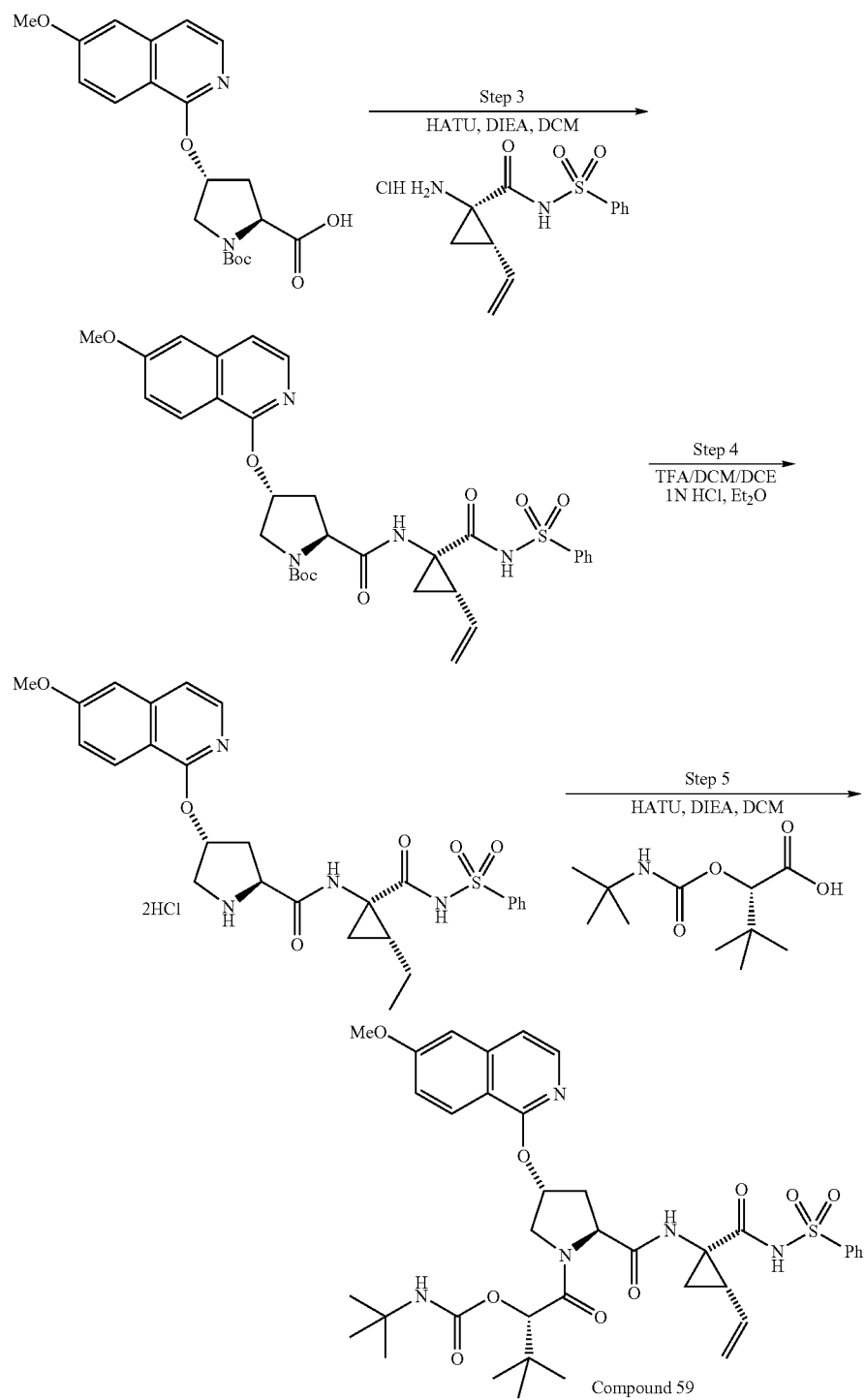

Step 3.

The product of step 3, Example 59, was prepared in 75% yield from the product of step 2, Example 59, by the same procedure as described for the preparation of the product of step 4, Example 55. LC-MS, MS m/z 637 (M++H)

Step 4.

The product of step 4, Example 59, was prepared in 87% yield from the product of step 3, Example 59, by the same procedure as described for the preparation of the product of step 5, Example 55. $^1$H NMR (500 MHz, MeOD) δ ppm 1.32 (dd, J=9.46, 5.49 Hz, 1H) 1.82 (dd, J=7.78, 5.65 Hz, 1H) 2.28 (q, J=8.44 Hz, 1H) 2.44-2.52 (m, 1H) 3.00 (dd, J=14.34, 7.32 Hz, 1H) 3.92 (s, 2H) 4.01 (s, 3H) 4.80 (dd, J=10.38, 7.63 Hz, 1H) 4.89 (dd, J=11.60, 1.83 Hz, 1H) 5.18 (dd, J=17.10, 2.14 Hz, 1H) 5.21-5.30 (m, 1H) 6.00 (s, 2H) 7.35 (d, J=2.14 Hz, 0.5H) 7.37 (d, J=2.13 Hz, 0.5H) 7.37-7.40 (m, 1H) 7.52 (d, J=6.41 Hz, 1H) 7.58 (t, J=7.78 Hz, 2H) 7.70 (t, J=7.48 Hz, 1H) 7.93 (d, J=6.41 Hz, 1H) 8.01 (d, J=8.24 Hz, 2H) 8.41 (d, J=8.85 Hz, 1H); LC-MS, MS m/z 537 (M++H).

Step 5.

Compound 59, Example 59, was prepared in 85% yield from the product of step 4, Example 59, by the same procedure as described for the preparation of the product of step 6, Example 55. $^1$H NMR (500 MHz, MeOD) δ ppm 1.11 (s, 9H) 1.26 (s, 9H) 1.31 (dd, J=9.61, 5.34 Hz, 1H) 1.72 (dd, J=7.93, 5.49 Hz, 1H) 2.18 (q, J=8.55 Hz, 1H) 2.22-2.31 (m, 1H) 2.65 (dd, J=13.73, 7.32 Hz, 1H) 3.95 (s, 3H) 4.00 (dd, J=10.99, 2.44 Hz, 1H) 4.55-4.64 (m, 2H) 4.78 (s, 1H) 4.94 (d, J=11.60 Hz, 1H) 5.18 (d, J=17.09 Hz, 1H) 5.33-5.45 (m, 1H) 5.84 (s, 1H) 7.12 (d, J=8.85 Hz, 1H) 7.20 (d, J=2.44 Hz, 1H) 7.27 (d, J=5.80 Hz, 1H) 7.57 (t, J=7.63 Hz, 2H) 7.68 (t, J=7.48 Hz, 1H) 7.90 (d, J=5.80 Hz, 1H) 8.01 (d, J=8.24 Hz, 2H) 8.29 (d, J=8.85 Hz, 1H); LC-MS, MS m/z 750 (M++H).

Example 60

Preparation of Compound 60

Compound 60

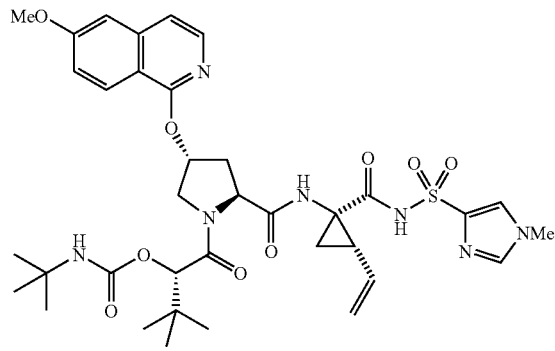

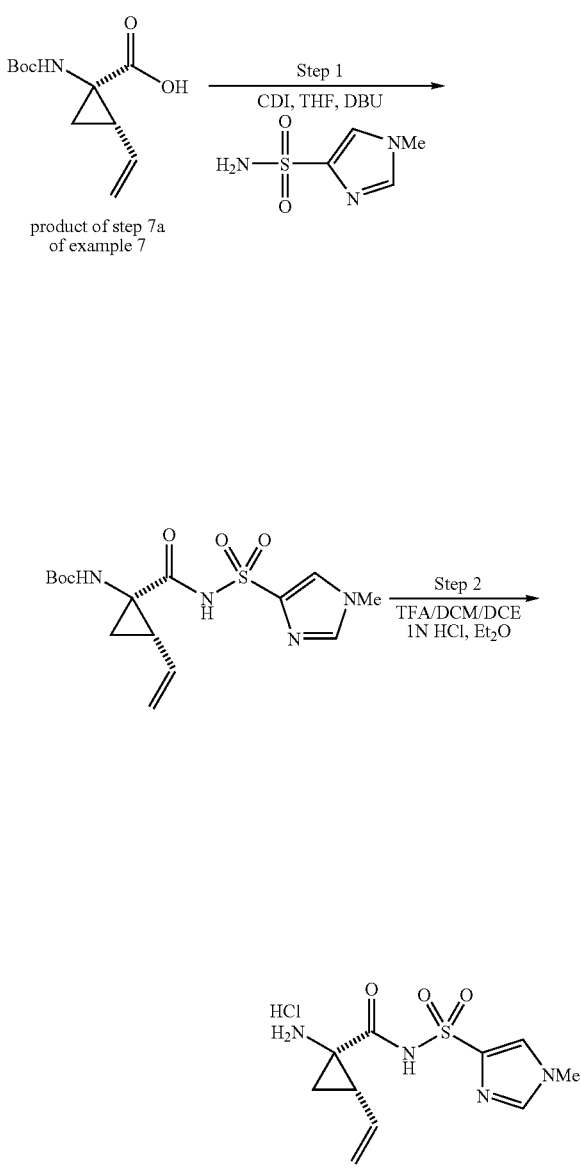

Step 1.

The product of step 1, Example 60, was prepared in 79% yield from N-Boc-vinylcyclopropane carboxylic acid, the product of step 7a, Example 7, and 1-methylimidazole-4-sulphonimide by the same procedure as described for the preparation of the product of step 1, Example 58. LC-MS, MS m/z 371 (M++Na).

Step 2.

The product of step 2, Example 60, was prepared in 83% yield from the product of step 1, Example 60, by the same procedure as described for the preparation of the product of step 2, Example 58. LC-MS, MS m/z 271 (M++H).

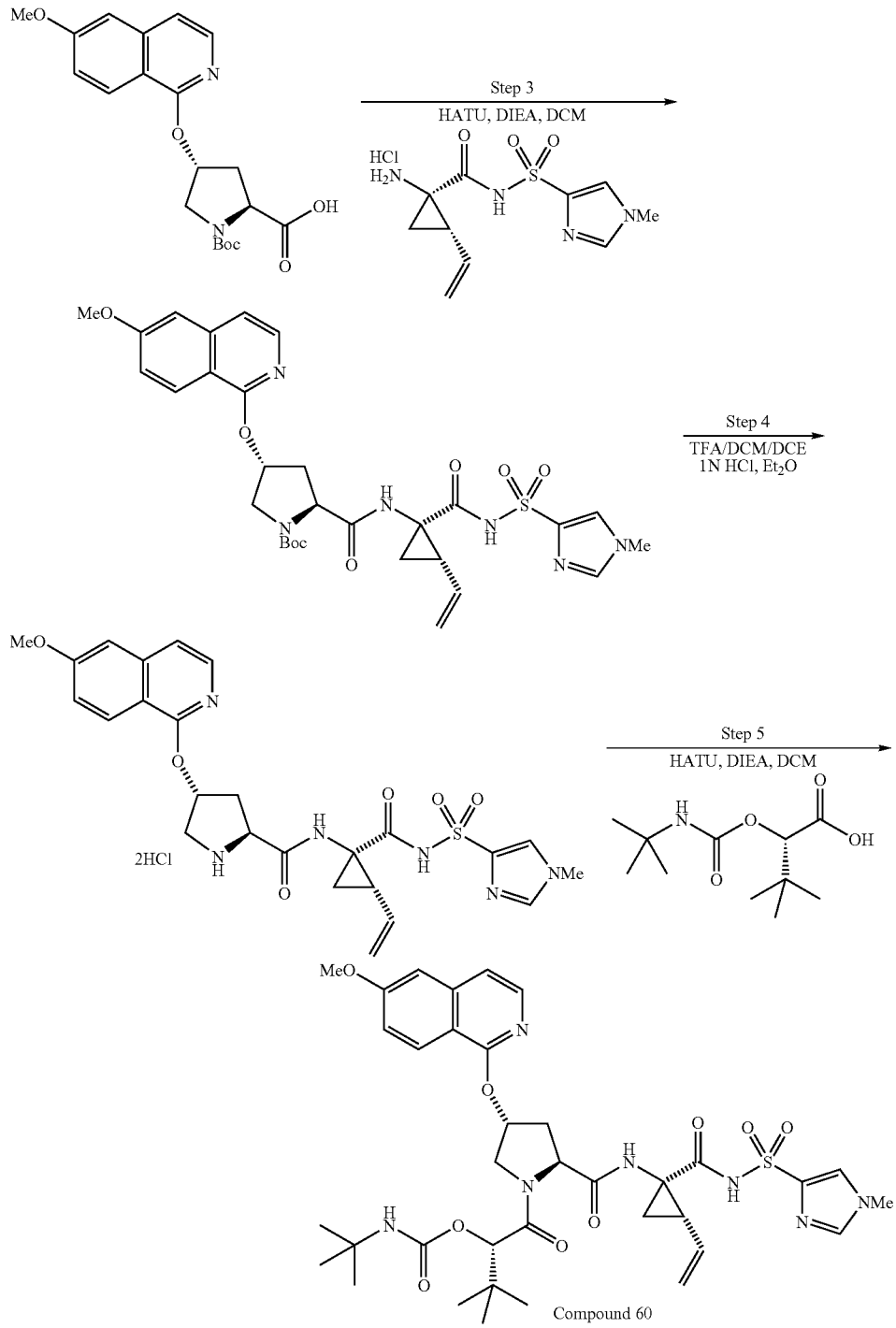

Step 3.

The product of step 3, Example 60, was prepared in 76% yield from the product of step 2, Example 60, by the same procedure as described for the preparation of the product of step 4, Example 55. $^1$H NMR (500 MHz, MeOD) δ ppm 1.26 (q, 1H) 1.33-1.38 (m, 1H) 1.44 (s, 9H) 1.76-1.87 (m, 1H) 2.03-2.11 (m, 1H) 2.51-2.70 (m, 2H) 3.25 (q, J=7.53 Hz, 2H) 3.71-3.79 (m, 4H) 3.95 (s, 3H) 4.33-4.47 (m, 1H) 4.91 (d, J=11.30 Hz, 1H) 5.15 (d, J=17.09 Hz, 1H) 5.70 (s, 1H) 5.72-5.82 (m, 1H) 7.18 (d, J=9.16 Hz, 1H) 7.21 (s, 1H) 7.26 (s, 1H) 7.68 (s, 1H) 7.91 (d, J=5.80 Hz, 1H) 8.06 (d, J=8.85 Hz, 1H); LC-MS, MS m/z 641 (M$^+$+H).

Step 4.

The product of step 4, Example 60, was prepared in 85% yield from the product of step 3, Example 60, by the same procedure as described for the preparation of the product of step 5, Example 55. ¹H NMR (500 MHz, MeOD) δ ppm 1.20 (t, J=7.02 Hz, 1H) 1.35 (dd, J=9.46, 5.80 Hz, 1H) 1.38-1.42 (m, 4H) 1.86 (dd, J=7.78, 5.65 Hz, 1H) 2.31 (q, J=8.55 Hz, 1H) 2.40-2.49 (m, 1H) 2.92 (dd, J=14.19, 7.78 Hz, 1H) 3.21-3.28 (m, 1H) 3.71-3.79 (m, 1H) 3.88 (s, 3H) 3.99 (s, 3H) 4.73 (dd, J=9.92, 7.78 Hz, 1H) 5.07 (d, J=10.38 Hz, 1H) 5.27 (d, J=16.79 Hz, 1H) 5.42-5.52 (m, 1H) 5.97 (s, 1H) 7.41 (d, J=6.10 Hz, 1H) 7.93 (d, J=6.10 Hz, 1H) 8.03 (s, 1H) 8.18 (s, 1H) 8.29 (d, J=8.85 Hz, 1H); LC-MS, MS m/z 541 (M⁺+H).

Step 5.

Compound 60, Example 60, was prepared in 91% yield from the product of step 4, Example 60, by the same procedure as described for the preparation of the product of step 6, Example 55. ¹H NMR (500 MHz, MeOD) δ ppm 0.93 (s, 9H) 1.11 (s, 9H) 1.17-1.24 (m, 2H) 1.63 (t, J=6.20 Hz, 1H) 2.02 (d, J=7.30 Hz, 1H) 2.20-2.35 (m, 1H) 2.52 (dd, J=13.43, 7.63 Hz, 1H) 3.64 (s, 3H) 3.82 (s, 3H) 3.84-3.92 (m, 1H) 4.43 (d, J=11.60 Hz, 1H) 4.48 (dd, J=9.77, 7.93 Hz, 1H) 4.56 (s, 1H) 4.81 (d, J=7.02 Hz, 1H) 5.02 (d, J=16.79 Hz, 1H) 5.69 (s, 1H) 6.98 (dd, J=9.16, 1.83 Hz, 1H) 7.07 (d, J=2.44 Hz, 1H) 7.13 (d, J=6.10 Hz, 1H) 7.57 (s, 1H) 7.78 (d, J=6.10 Hz, 1H) 8.14 (d, J=8.85 Hz, 1H); LC-MS, MS m/z 754 (M⁺+H).

Example 61

Preparation of Compound 61

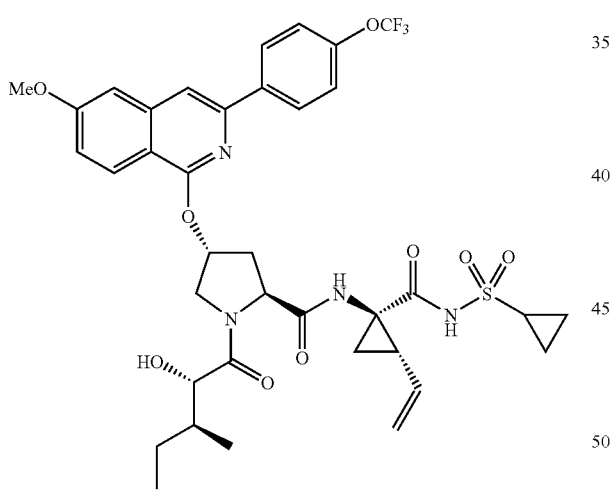

Compound 61

Compound 61, Example 61, was prepared similarly to Compound 50. ¹H NMR (500 MHz, MeOD) δ ppm 0.87 (t, J=7.32 Hz, 3H) 0.95 (d, J=7.02 Hz, 3H) 1.07-1.13 (m, 2H) 1.13-1.19 (m, 1H) 1.20-1.26 (m, 1H) 1.28-1.35 (m, 1H) 1.45 (dd, J=9.46, 5.19 Hz, 1H) 1.56-1.65 (m, 1H) 1.78-1.87 (m, 1H) 1.93 (dd, J=7.93, 5.49 Hz, 1H) 2.28 (q, J=8.75 Hz, 1H) 2.37-2.46 (m, 1H) 2.69 (dd, J=13.73, 7.32 Hz, 1H) 2.94-3.02 (m, 1H) 3.98 (s, 3H) 4.09 (d, J=6.41 Hz, 1H) 4.16 (dd, J=12.21, 3.66 Hz, 1H) 4.31 (d, J=12.51 Hz, 1H) 4.65 (dd, J=10.07, 7.32 Hz, 1H) 5.15 (d, J=10.38 Hz, 1H) 5.34 (d, J=17.09 Hz, 1H) 5.74-5.85 (m, 1H) 6.10 (s, 1H) 7.19 (dd, J=9.16, 2.44 Hz, 1H) 7.32 (d, J=2.14 Hz, 1H) 7.40 (d, J=8.24 Hz, 2H) 7.86 (s, 1H) 8.10 (d, J=9.16 Hz, 1H) 8.28 (d, J=8.85 Hz, 2H); LC-MS, MS m/z 775 (M⁺+H).

Example 62

Preparation of Compound 62

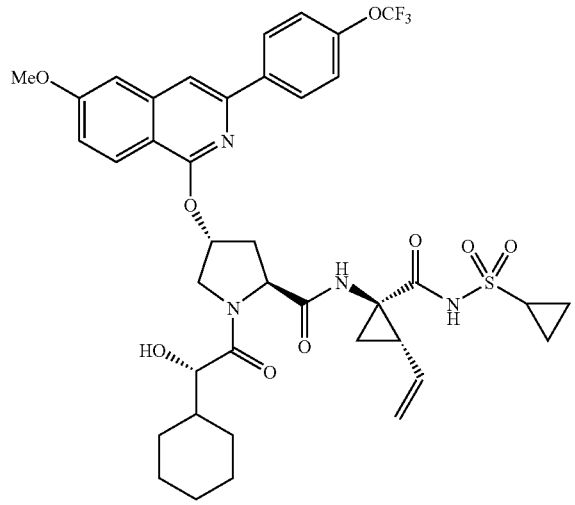

Compound 62

Compound 62, Example 62, was prepared similarly to Compound 50. ¹H NMR (500 MHz, MeOD) δ ppm 1.05-1.12 (m, 3H) 1.18 (dd, J=13.12, 10.07 Hz, 4H) 1.22-1.27 (m, 1H) 1.28-1.34 (m, 1H) 1.45 (dd, J=9.46, 5.19 Hz, 1H) 1.59-1.72 (m, 4H) 1.76 (d, J=14.04 Hz, 2H) 1.92 (dd, J=8.09, 5.34 Hz, 1H) 2.27 (q, J=8.65 Hz, 1H) 2.38-2.46 (m, 1H) 2.69 (dd, J=13.73, 7.32 Hz, 1H) 2.93-3.02 (m, 1H) 3.98 (s, 3H) 4.07 (d, J=6.10 Hz, 1H) 4.14 (dd, J=12.21, 3.97 Hz, 1H) 4.31 (d, J=12.21 Hz, 1H) 4.65 (dd, J=10.07, 7.32 Hz, 1H) 5.15 (d, J=10.38 Hz, 1H) 5.33 (d, J=17.09 Hz, 1H) 5.75-5.85 (m, 1H) 6.09 (s, 1H) 7.18 (dd, J=9.00, 2.59 Hz, 1H) 7.31 (d, J=2.44 Hz, 1H) 7.40 (d, J=8.24 Hz, 2H) 7.85 (s, 1H) 8.09 (d, J=9.16 Hz, 1H) 8.27 (d, J=8.85 Hz, 2H); LC-MS, MS m/z 801 (M⁺+H).

Example 63

Preparation of Compound 63

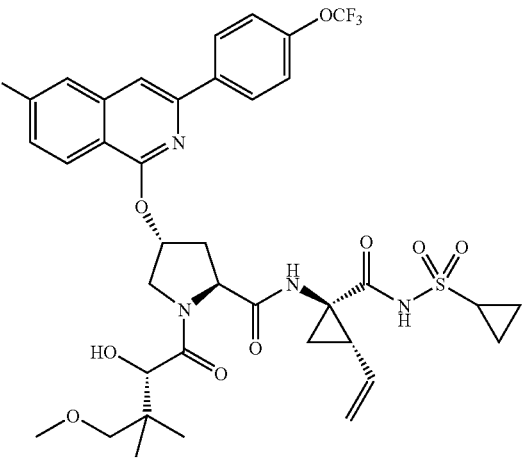

Compound 63

Compound 63, Example 63, was prepared similarly to Compound 50. ¹H NMR (500 MHz, MeOD) δ ppm 0.98 (s, 3H) 1.06 (s, 3H) 1.08-1.13 (m, 2H) 1.24-1.30 (m, 2H) 1.45 (dd, J=9.46, 5.49 Hz, 1H) 1.92 (dd, J=7.93, 5.49 Hz, 1H) 2.28 (q, J=8.55 Hz, 1H) 2.35-2.43 (m, 1H) 2.68 (dd, J=13.73, 7.32 Hz, 1H) 2.94-3.01 (m, 1H) 3.17 (d, J=8.85 Hz, 1H) 3.31 (s, 3H) 3.98 (s, 3H) 4.21 (dd, J=12.36, 3.81 Hz, 1H) 4.31 (d, J=11.90 Hz, 1H) 4.34 (s, 1H) 4.65 (dd, J=9.46, 7.32 Hz, 1H) 5.15 (d, J=10.38 Hz, 1H) 5.33 (d, J=18.62 Hz, 1H) 5.72-5.82 (m, 1H) 6.06 (s, 1H) 7.18 (dd, J=9.16, 2.44 Hz, 1H) 7.31 (d, J=2.14 Hz, 1H) 7.39 (d, J=8.24 Hz, 2H) 7.85 (s, 1H) 8.10 (d, J=9.16 Hz, 1H) 8.27 (d, J=8.55 Hz, 2H); LC-MS, MS m/z 805 (M⁺+H).

Examples below further describe the preparation of P2 intermediates. These intermediates can be used to make compounds of Formula I by using the teachings described, or referenced, in this document.

Example 70

Preparation of Intermediate 70

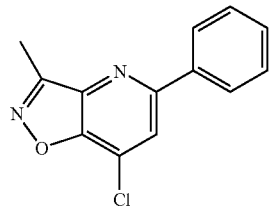

Intermediate 70

Scheme 1

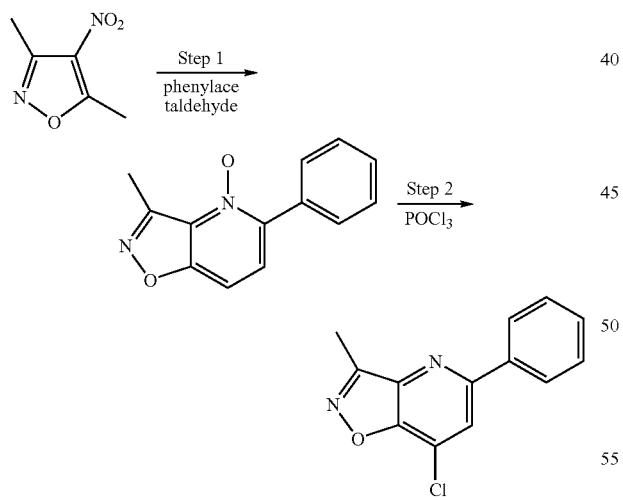

Step 1:
A mixture of 3,5-dimethyl-4-nitro-isoxazole (1.42 g, 10.0 mmol), phenylacetaldehyde (1.32 g, 11.0 mmol) in piperidine (1 mL) and ethanol (10 mL) was heated to reflux for 16 hours. After cooling down to the ambient temperature, the product precipitated out was collected by filtration. The cake was washed with cold ethanol thoroughly to afford 1.20 g (53%) of the desired product as a white solid. ¹H NMR (CDCl₃) δ 2.87 (s, 3H), 7.46-7.50 (m, 3H), 7.56 (d, J=8.5 Hz, 1H), 7.7-7.80 (m, 2H); MS m/z 227 (M⁺+H).

Step 2:
A solution of 3-methyl-5-phenyl-isoxazolo[4,5-b]pyridine 4-oxide (1.00 g, 4.40 mmol) and POCl₃ (2.71 g, 17.7 mmol) in chloroform (10 mL) was heated to reflux for 1 hour. After cooling down to the ambient temperature, the final solution was diluted with chloroform (50 mL) and washed with NaHCO₃ (aq.) (two 50 mL portions) and brine, dried over MgSO₄, filtered, and concentrated. The residue was purified by flash chromatography (4:1 hexane-EtOAc) to afford 790 mg (73%) of the desired product as a white solid.
¹H NMR (CDCl₃) δ 2.72 (s, 3H), 7.46-7.54 (m, 3H), 7.91 (s, 1H), 8.00-8.03 (m, 2H); MS m/z 245, 247 (M⁺+H).

Intermediate 70 can be used to make compounds of Formula I as follows:

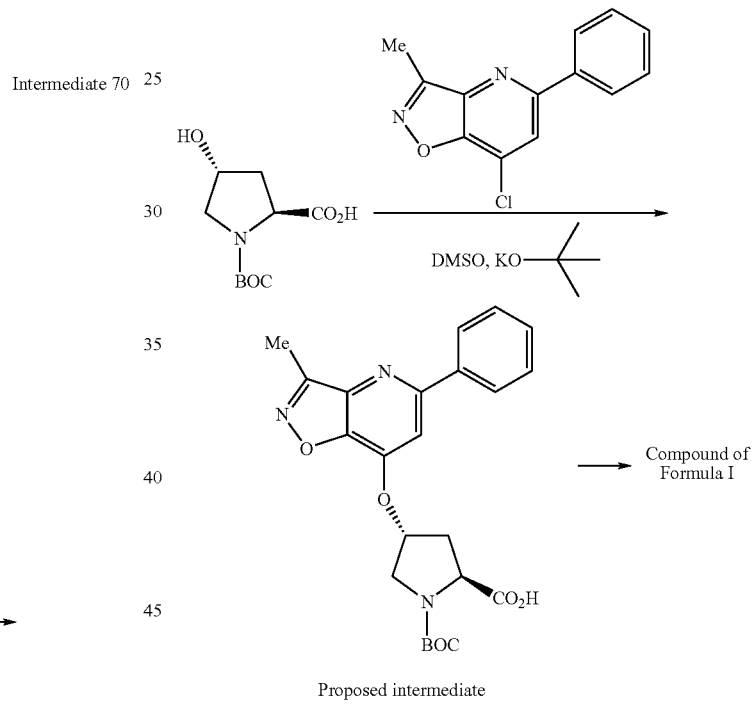

Proposed intermediate

Example 71

Preparation of Intermediate 71

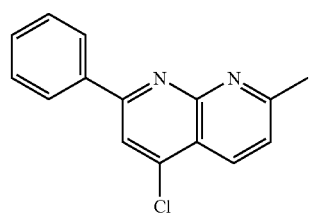

Intermediate 71

Scheme 1

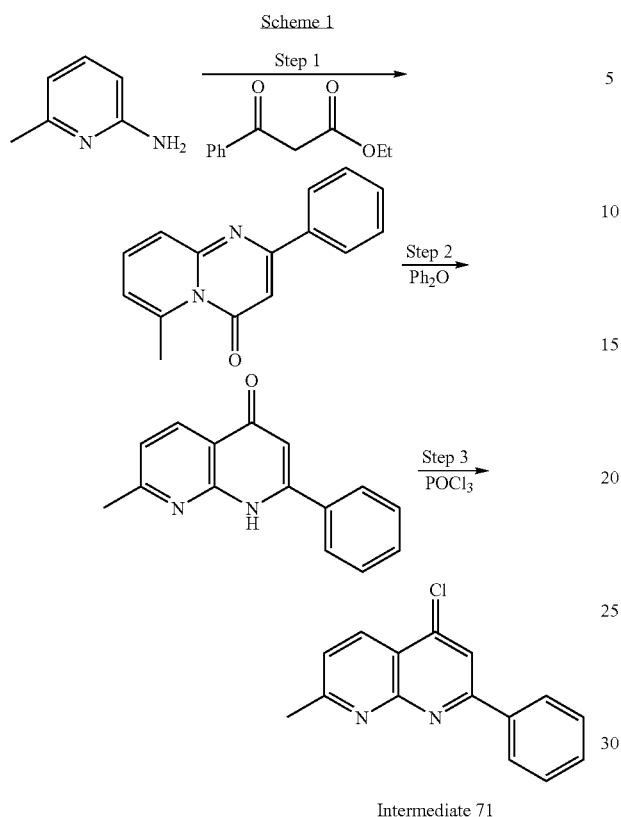

Intermediate 71

Step 1:
A mixture of 2-amino-6-methylpyridine (1.08 g, 10.0 mmol), ethyl benzoylacetate (2.30 g, 12.0 mmol) and polyphosphoric acid (6.00 g, 61.2 mmol) was heated to 110° C. for 5 hours. After cooling to the ambient temperature, the mixture was poured into iced water (20 mL) and neutralized to pH 7 with 10 M NaOH. Extracted with $CHCl_3$. The organic layer was washed with brine, dried over $MgSO_4$, filtered, concentrated. The residue was purified by flash chromatography (1:1 hexane-EtOAc) to afford 510 mg (22%) of the desired product as a pale yellow solid. $^1H$ NMR ($CDCl_3$) δ 3.08 (s, 3H), 6.64 (d, J=7.0 Hz, 1H), 6.71 (s, 1H), 7.42-7.52 (m, 5H), 8.04-8.06 (m, 2H); MS m/z 237 ($M^+$+H).

Step 2:
A solution of 6-methyl-2-phenyl-pyrido[1,2a]pyrimidin-4-one (489 mg, 2.07 mmol) in melted diphenyl ether (5 mL) was heated to gentle reflux for 5 hours. After cooling to the ambient temperature, the formed suspension was diluted with diethyl ether (10 mL), filtered. The cake was washed with diethyl ether thoroughly to afford 450 mg (92%) of the desired product as a brownish solid. MS m/z 237 ($M^+$+H).

Step 3:
A suspension of 7-methyl-2-phenyl-1H-[1,8]naphthyridin-4-one (450 mg, 1.91 mmol) in $POCl_3$ (10 mL) was heated to gentle reflux for 3 hours. Then concentrated in vacuo. The residue was poured into iced water (20 mL) and neutralized to pH 10 with 10 M NaOH. The mixture was then extracted with $CHCl_3$ and the organic layer was washed with brine, dried over $MgSO_4$, filtered and concentrated. The residue was purified by flash chromatography (2:1 hexane-EtOAc) to afford 450 mg (92%) of the desired product as a pink solid. $^1H$ NMR ($CD_3OD$) δ 2.80 (s, 3H), 7.54-7.56 (m, 3H), 7.61 (d, J=8.4 Hz, 1H), 8.25-8.30 (m, 3H), 8.58 (d, J=8.4 Hz, 1H); MS m/z 255, 257 ($M^+$+H).

Intermediate 71 can be used to make compounds of Formula I as follows:

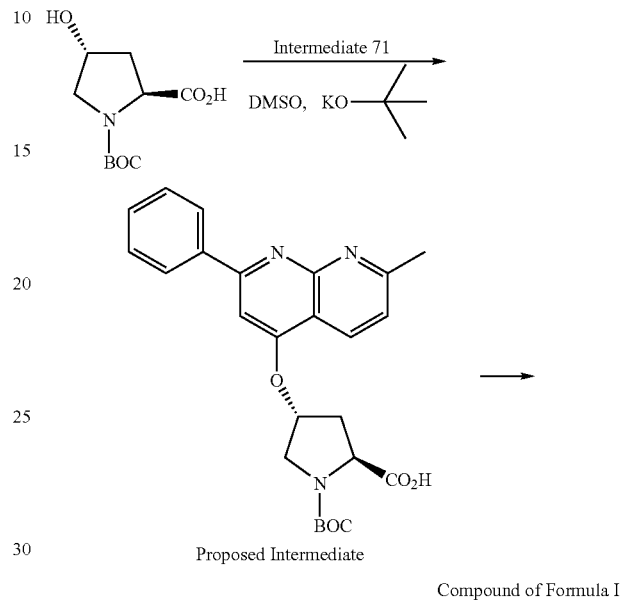

Example 72

Preparation of Intermediate 72

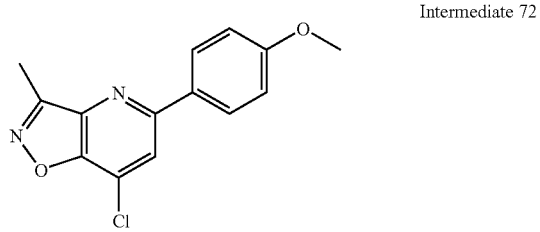

Intermediate 72

Scheme 1

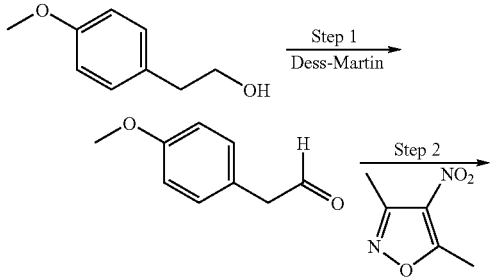

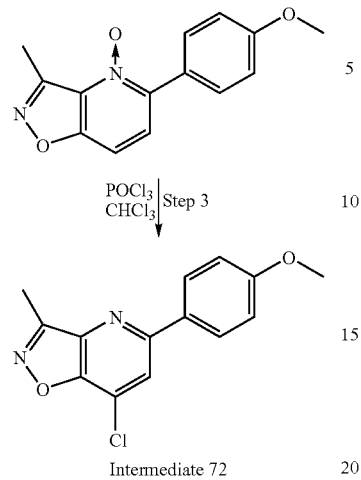

Intermediate 72

Step 1:

To a solution of 4-methoxyphenethyl alcohol (1.52 g, 10.0 mmol) in $CH_2Cl_2$ (50 mL) at 0° C. was added Dess-Martin reagent (4.45 g, 10.5 mmol) in one portion. The formed mixture was allowed to warm to the ambient temperature for 1 hour. Washed with sat. $Na_2S_2O_3$ (aq) and 1M NaOH, brine respectively. Dried over $MgSO_4$, filtered, and concentrated in vacuo to give 1.50 g (100%) of the desired aldehyde as a viscous oil. This product was used as crude without any further purification.

Step 2:

A solution of 3,5-dimethyl-4-nitro-isoxazole (142 mg, 1.0 mmol), 4-methoxy-phenylacetaldehyde from Example 3, Step 1 (180 mg, 1.1 mmol) in piperidine (0.1 mL) and ethanol (2 mL) was heated to reflux for 12 hours ours After cooling down to the ambient temperature, the product precipitated out was collected by filtration. The cake was washed with cold ethanol thoroughly to afford 130 mg (51%) of the desired product as a grayish solid. $^1$H NMR ($CDCl_3$) δ 2.88 (s, 3H), 3.87 (s, 3H), 7.02 (d, J=8.5 Hz, 2H), 7.50 (d, J=9.0 Hz, 1H), 7.57 (d, J=9.0 Hz, 1H), 7.81 (d, J=8.5 Hz, 2H); MS m/z 257 ($M^+$+H).

Step 3:

This product was prepared by the same procedure as described in Example 70, Step 2.

$^1$H NMR ($CDCl_3$) δ 2.70 (s, 3H), 3.87 (s, 3H), 7.00-7.03 (m, 2H), 7.84 (s, 1H), 7.96-7.98 (m, 2H); MS m/z 275, 277 ($M^+$+H).

Intermediate 72 can be used to make compounds of Formula I as follows:

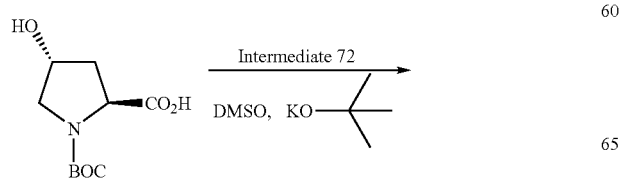

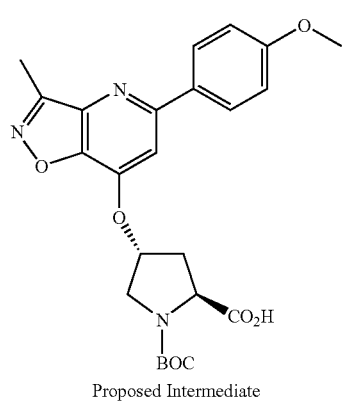

Proposed Intermediate

Compound of Formula I

Example 73

Preparation of Intermediate 73

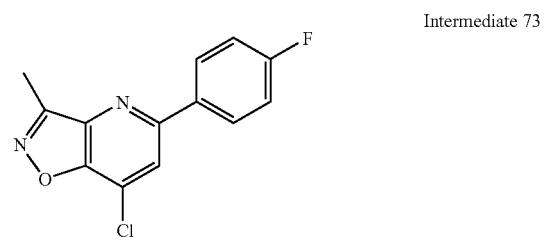

Intermediate 73

Scheme 1

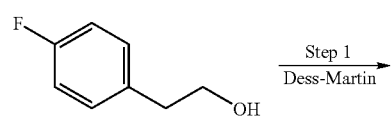

Step 1
Dess-Martin

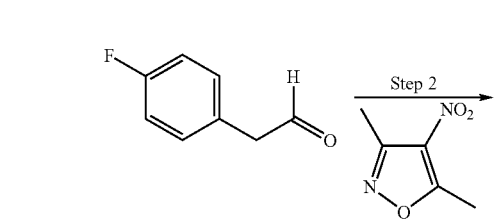

Step 2

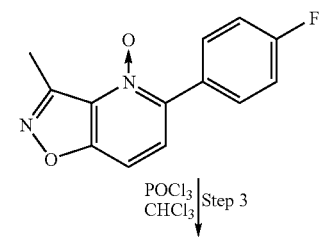

POCl$_3$ / CHCl$_3$ Step 3

-continued

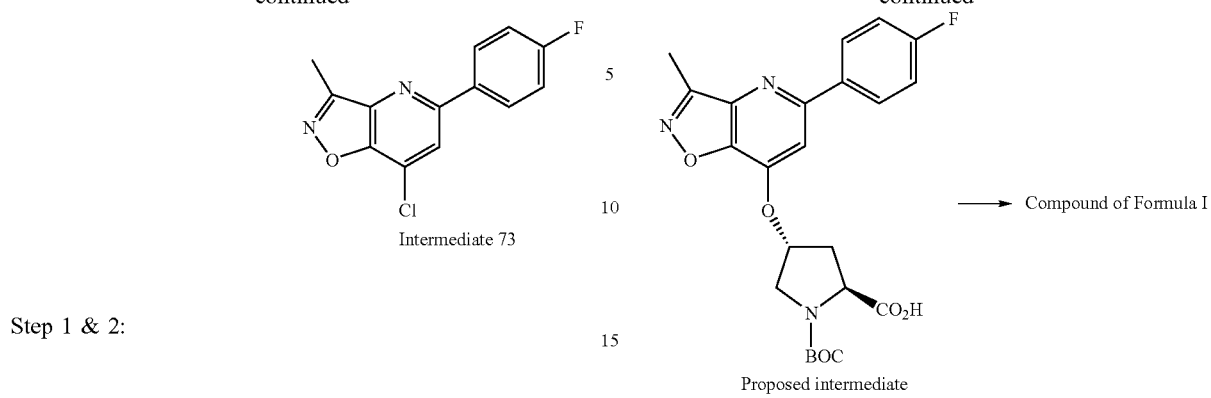

Intermediate 73

Step 1 & 2:

This product was prepared by the same procedure as described in Example 72, Step 1 & 2, except using 4-fluorophenethyl alcohol instead. MS m/z 245 (M$^+$+H).

Step 3:

This product was prepared by the same procedure as described in step 2 of Example 70.

$^1$H NMR (CDCl$_3$) δ 2.71 (s, 3H), 7.17-7.20 (m, 2H), 7.86 (s, 1H), 8.00-8.02 (m, 2H); MS m/z 263, 265 (M$^+$+H).

Intermediate 73 can be used to make compounds of Formula I as follows:

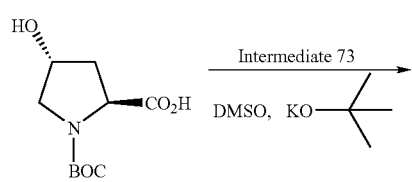

-continued

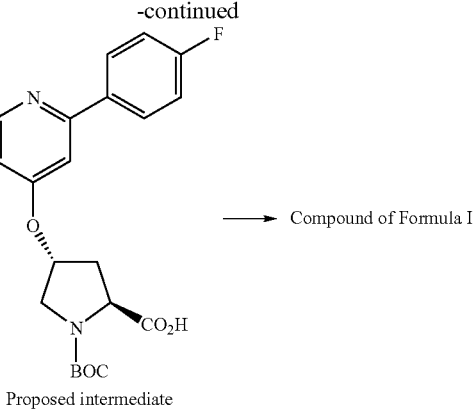

Proposed intermediate

→ Compound of Formula I

Example 74

Preparation of Intermediate 74

Intermediate 74

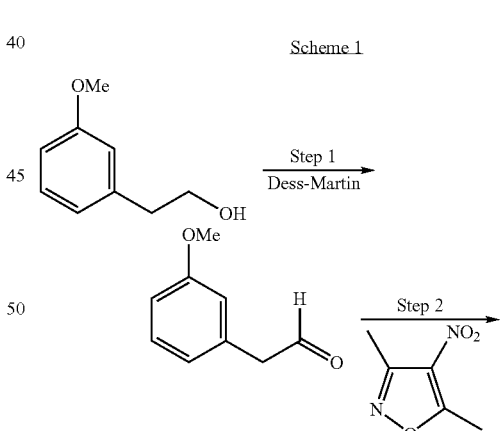

Scheme 1

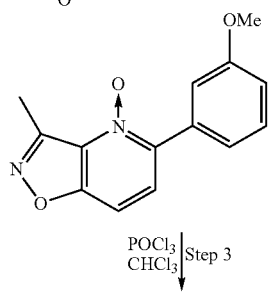

-continued

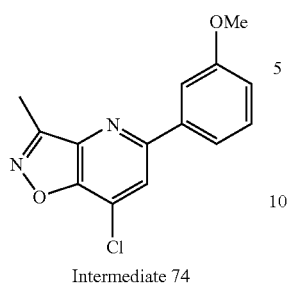

Intermediate 74

Step 1 & 2:

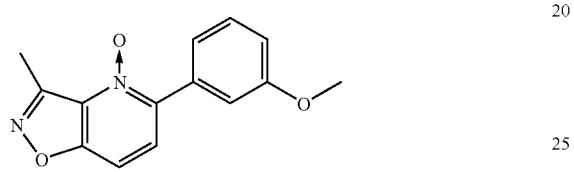

This product was prepared by the same procedure as described in Example 72, Step 1 & 2, except using 3-methoxy-phenethyl alcohol as starting material. MS m/z 257 (M$^+$+H).

Step 3:

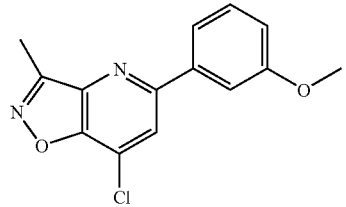

This product was prepared by the same procedure as described in Example 70 step 2. $^1$H NMR (CDCl$_3$) δ 2.72 (s, 3H), 3.90 (s, 3H), 7.00-7.02 (m, 1H), 7.41 (t, J=8.0 Hz, 1H), 7.55 (d, J=7.5 Hz, 1H), 7.59 (d, J=2.0 Hz, 1H), 7.89 (s, 1H); MS m/z 275, 277 (M$^+$+H).

Intermediate 74 can be used to make compounds of Formula I as follows:

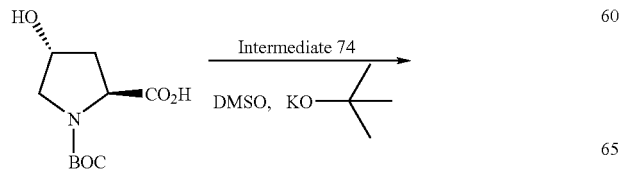

-continued

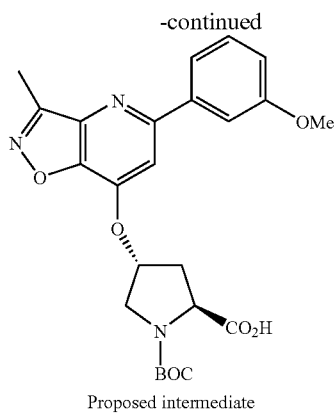

Proposed intermediate

Compound of Formula I

Example 75

Preparation of Intermediate 75

Intermediate 75

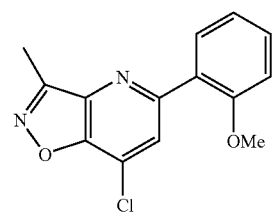

Scheme 1

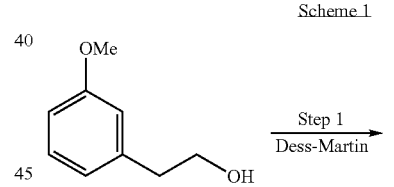

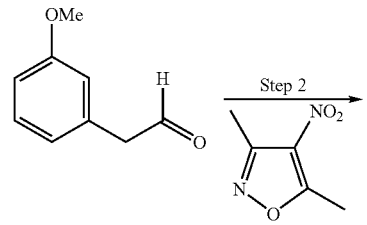

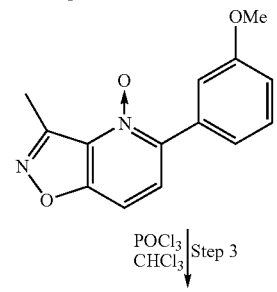

-continued

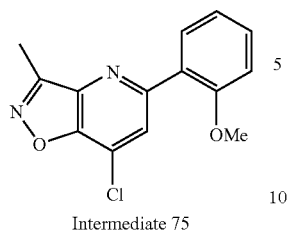
Intermediate 75

Step 1 & 2:

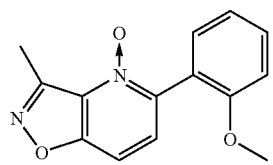

This product was prepared by the same procedure as described in Example 72, Step 1 & 2, except using 2-methoxy-phenethyl alcohol as starting material. MS m/z 257 (M$^+$+H).

Step 3:

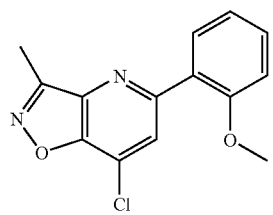

This product was prepared by the same procedure as described in Example 70, Step 2.

$^1$H NMR (CDCl$_3$) δ 2.721 (s, 3H), 3.88 (s, 3H), 7.03 (d, J=8.0 Hz, 1H), 7.11 (t, J=7.5 Hz, 1H), 7.41-7.44 (m, 1H), 7.79-7.81 (m, 1H), 8.04 (s, 1H); MS m/z 275, 277 (M$^+$+H).

Intermediate 75 can be used to make compounds of Formula I as follows:

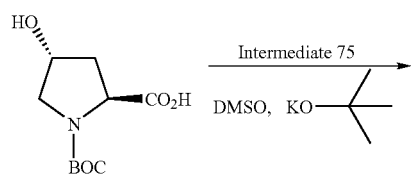

-continued

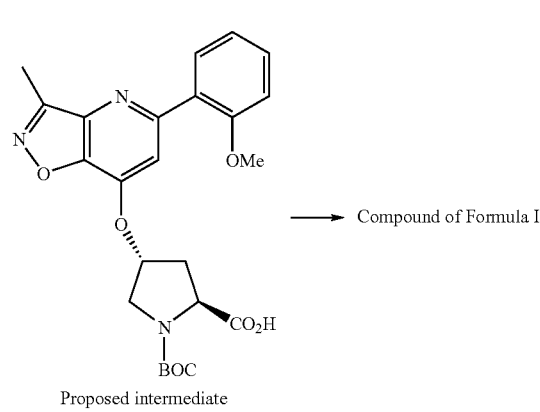
Proposed intermediate

→ Compound of Formula I

Example 76

Preparation of Intermediate 76

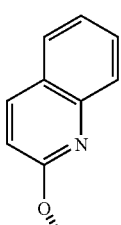
Intermediate 76

Intermediate 76 is commercially available

Intermediate 76 can be used to make compounds of Formula I as follows:

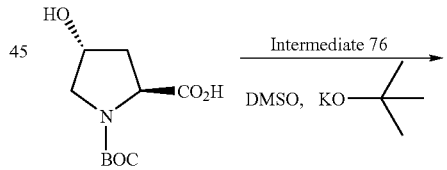
Proposed intermediate

→ Compound of Formula I

Example 77

Preparation of Intermediate 77

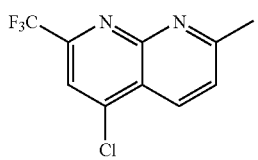
Intermediate 77

Intermediate 77 was prepared as described by P. Ferrarini et al, in J Heterocyclic Chem, 1983, p1053.

Intermediate 77 can be used to make compounds of Formula I as follows:

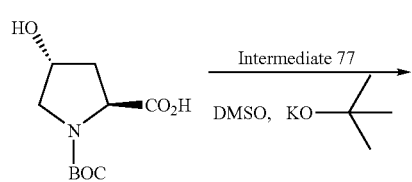

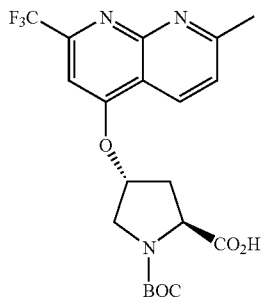
Proposed intermediate

Example 78

Preparation of Intermediate 78

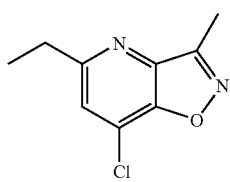
Intermediate 78

Intermediate 78 was prepared as described by R. Nesi et al, Synth Comm. 1992, 22(16), 2349.

Intermediate 78 can be used to make compounds of Formula I as follows:

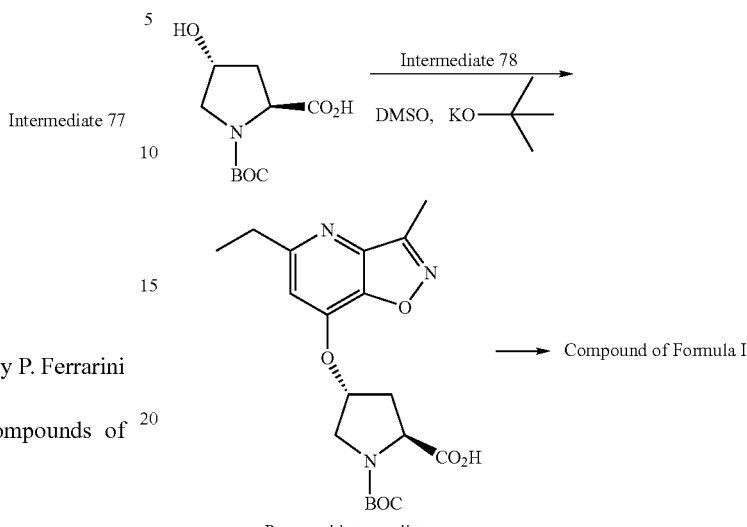

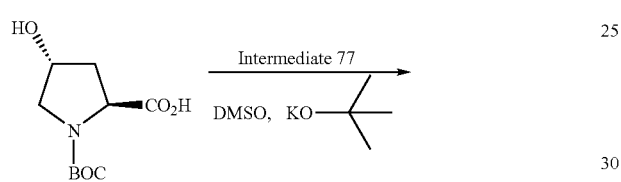

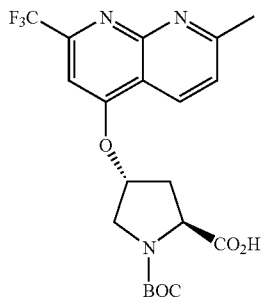
Proposed intermediate

Example 79

Preparation of Intermediate 79

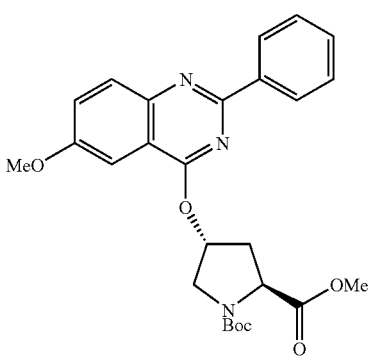
Intermediate 79

Scheme 1

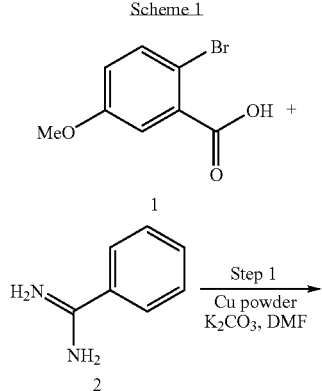

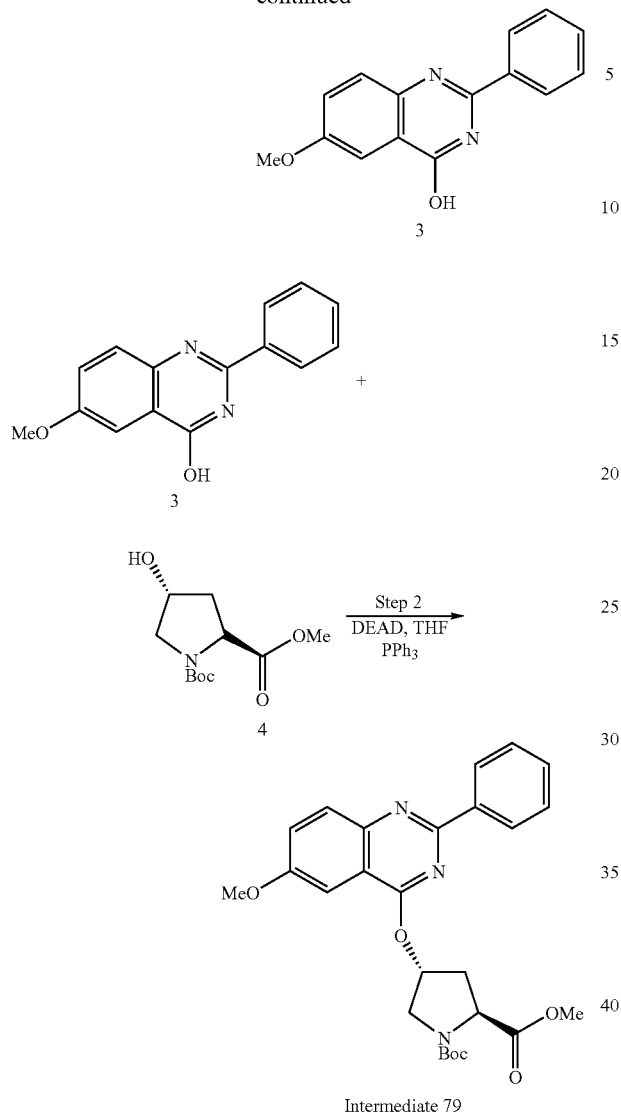

3

Intermediate 79

Step 1:

To a solution of 2-bromo-5-methoxybenzoic acid (1.68 g, 7.27 mmol) in DMF (50 mL) in a medium pressure flask (Chemglass) was added benzamidine (1.25 g, 8.00 mmol), $K_2CO_3$ (6.0 g, 43.6 mmol), and copper powder (336 mg, 1.45 mmol). The reaction mixture was heated to 180° C. for 1 hour. Copper and excess $K_2CO_3$ were removed by vacuum filtration and washed with MeOH. The filtrate was concentrated and the resulting crude was purified by flash column chromatography ($SiO_2$, 5% MeOH in DCM) to give a light green solid (1.55 g, 84% yield): $^1H$ NMR (DMSO-$d_6$) δ 3.84 (s, 3H), 7.26 (d, J=7.8 Hz, 1H), 7.46 (br s, 5H), 7.57 (s, 1H), 8.38 (br s, 1H); MS m/z (MH$^+$) 253.

Step 2:

To a 0° C. slurry of Boc-cis-Hydroxyproline-OMe (2.0 g, 8.15 mmol) and 3 (2.26 g, 8.97 mmol) in THF (82 mL) was added $Ph_3P$ and diisopropyl azocarboxylate (1.98 g, 8.97 mmol). After stirring at room temperature for 17 hours, the reaction mixture was diluted with EtOAc (100 mL) and washed with $H_2O$ (50 mL). The aqueous layer was separated and back-extracted with EtOAc (2×50 mL). The combined organic layer was washed with brine, dried over $MgSO_4$, filtered, and concentrated to give a viscous oil which was redissolved in minimal amount of EtOAc and hexanes was added to effect the precipitation of most of the $Ph_3PO$ by-product. $Ph_3PO$ was removed by vacuum filtration and the liquid filtrate was concentrated. The resulting viscous oil was purified by a flash column chromatography ($SiO_2$, 4:1 hex:EtOAc) to give a white solid product (1.76 g, 45% yield): $^1H$ NMR (60/40 rotomers, $CDCl_3$) δ 1.47 (s, 9H), 2.49-2.55 (m, 1H), 2.73-2.83 (m, 1H), 3.80 (s, 1.8H), 3.81 (s, 1.2H), 3.96 (s, 3H), 4.03-4.09 (m, 0.1H), 4.54 (t, J=8.0 Hz, 0.6H), 4.66 (t, J=7.8 Hz), 4.96-5.06 (m, 1H), 5.97 (br s, 0.6H), 6.04 (br s, 0.4H), 7.33 (dd, J=6.1, 2.7 Hz, 1H), 7.46-7.51 (m, 4H), 7.91 (d, J=9.2 Hz, 1H), 8.49 (t, J=8.5 Hz, 2H); $^{13}C$ NMR (rotomers, $CDCl_3$) δ 21.7, 22.0, 28.3, 28.4, 35.8, 36.8, 52.3, 52.4, 52.6, 55.8, 55.9, 57.9, 58.3, 74.5, 74.9, 80.6, 101.2, 101.3, 115.7, 125.8, 126.0, 128.1, 128.5, 129.7, 130.2, 137.9, 147.8, 153.8, 157.7, 158.0, 158.0, 164.8, 173.1, 173.3; MS m/z (MH$^+$) 480.

Intermediate 79 can be used to make compounds of Formula I as follows:

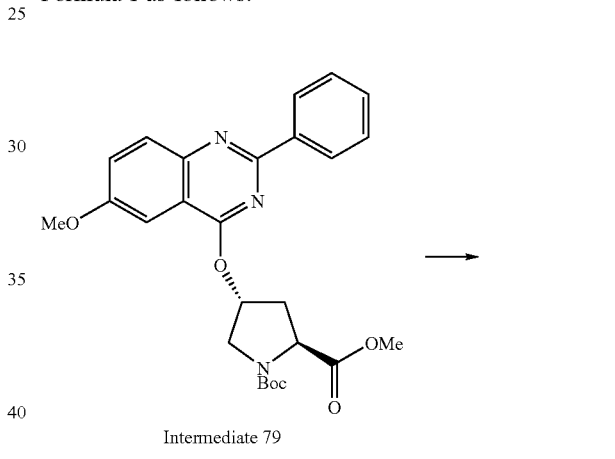

Intermediate 79

Compound of Formula I

Example 80

Preparation of Intermediate 80

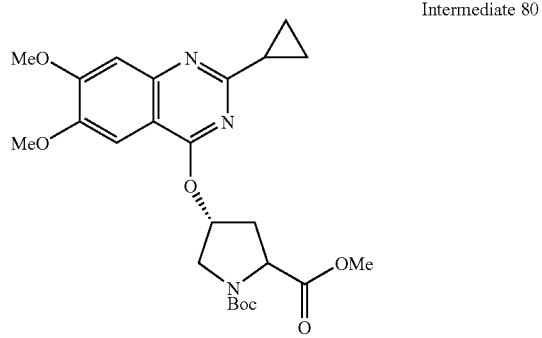

Intermediate 80

Step 1:

As described for Example 79

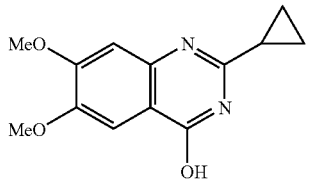

Data: ¹H NMR (DMSO-d₆) δ 0.97-1.01 (m, 2H), 1.03-1.06 (m, 2H), 1.90-1.94 (m, 1H), 3.84 (s, 3H), 3.87 (s, 3H), 6.93 (s, 1H), 7.37 (s, 3H), 12.28 (s, 1H); ¹³C NMR (DMSO-d₆) 9.03, 13.17, 55.47, 55.73, 104.81, 107.27, 113.26, 145.16, 147.48, 154.44, 157.21, 160.89; MS m/z (MH⁺) 247.

Step 2:

As described for Example 79

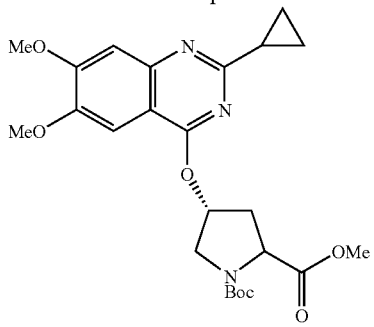

Data: ¹H NMR (CDCl₃) δ 1.00-1.04 (m, 2H), 1.07-1.11 (m, 2H), 1.43 (s, 5.4H), 1.46 (s, 3.6H), 2.17-2.21 (m, 1H), 2.37-2.43 (m, 1H), 2.62-2.69 (m, 1H), 3.75 (s, 1.8H), 3.78 (s, 1.2H), 3.92 (d, J=2.8 Hz, 1H), 4.00 (s, 3.6H), 4.01 (s, 2.4H), 4.48 (t, J=8.0 Hz, 0.6H), 4.59 (t, J=7.6 Hz, 0.4H), 5.7 (br s, 0.6H), 5.74 (br s, 0.4H), 7.18 (s, 1H), 7.20 (s, 1H); ¹³C NMR (CDCl₃) δ 9.6, 9.7, 18.1, 28.3, 28.4, 35.8, 36.7, 52.2, 52.4, 56.3, 57.8, 58.2, 74.0, 74.5, 80.5, 80.6, 101.0, 101.1, 106.3, 108.6, 148.8, 149.1, 153.8, 155.4, 164.4, 165.9, 172.9, 173.2; LC-MS m/z (MH⁺) 474.

Intermediate 80 can be used to make compounds of Formula I as follows:

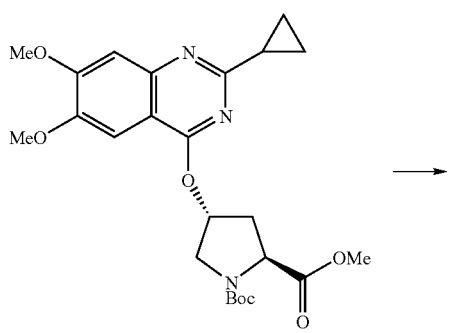

Intermediate 80

⟶ Compound of Formula I

Example 80

Preparation of Intermediate 81

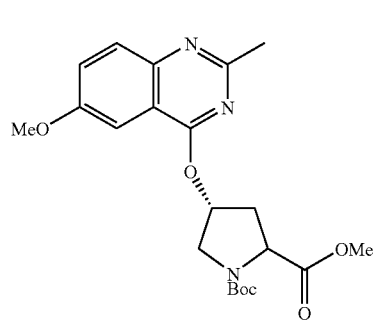

Intermediate 81

Step 1:
As described in Example 79 wherein acetamidine hydrochloride and 2-bromo-5-methoxybenzoic acid were utilized as starting materials.

Product:

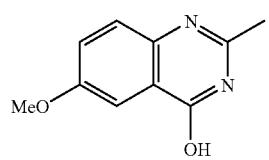

Data: ¹H NMR (DMSO) δ 2.31 (s, 3H), 3.85 (s, 3H), 7.36 (d, J=6.2 Hz, 1H), 7.37 (s, 1H), 7.51 (d, J=7.8 Hz, 1H), 12.15 (s, 1H); ¹³C NMR (DMSO) δ 21.11, 55.41, 105.57, 121.22, 123.59, 128.12, 143.34, 151.68, 157.00, 161.45; LC-MS m/e (MH⁺) 191.

Step 2:
As described in Example 79.

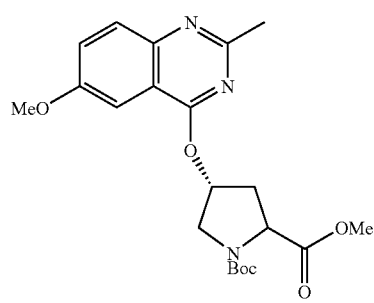

Intermediate 81

Data: ¹H NMR (CDCl₃) δ 1.43 (s, 5.4H), 1.45 (s, 3.6H), 2.38-2.45 (m, 1H), 2.62-2.71 (m, 1H), 2.66 (s, 1.8H), 2.68 (s, 1.2H), 3.77 (1.8H), 3.79 (s, 1.2H), 3.92 (s, 3H), 3.93-3.98 (m, 2H), 4.49 (t, J=8.0 Hz, 0.6H), 4.61 (t, J=7.8 Hz, 0.4H), 5.82 (t, J=2.1 Hz, 0.6H), 5.89 (t, J=2.3 Hz, 0.4H), 7.26 (dd, J=4.7, 3.2 Hz, 1H), 7.42 (dd, J=6.3, 2.8 Hz, 1H), 7.75 (d, J=9.15 Hz, 1H); ¹³C NMR (CDCl₃) δ 26.1, 28.3, 28.4, 35.8, 36.7, 52.2, 52.2, 52.4, 52.5, 55.755.8, 57.9, 58.2, 74.1, 74.7, 80.6, 101.0, 101.2, 114.9, 125.6, 125.9, 128.6, 147.3, 153.8, 154.5, 157.6, 157.6, 161.2, 164.6, 173.0, 173.3; LC-MS m/e (MH⁺) 418.

Intermediate 81 can be used to make compounds of Formula I as follows:

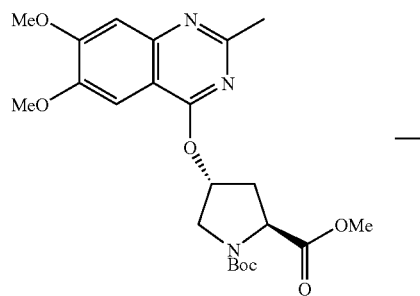

Intermediate 81

↓

Compound of Formula I

Example 82

Preparation of Intermediate 82

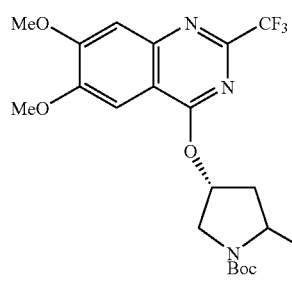

Intermediate 82

Step 1:

Prepared as described in Example 79 and using 2-bromo-4,5-dimethoxybenzoic acid and trifluoroamidine as starting materials.

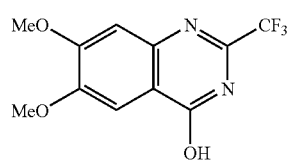

Data: $^1$H NMR (DMSO) δ 3.92 (s, 3H), 3.94 (s, 3H), 7.33 (s, 1H), 7.50 (s, 1H), 13.40 (br s, 1H); $^{13}$C NMR (DMSO) δ 55.8, 56.1, 104.9, 108.7, 150.2, 155.0; LC-MS m/e (MH$^+$) 275.

Step 2:

As described in Example 79

Product:

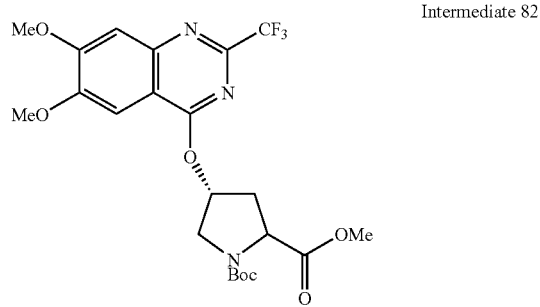

Intermediate 82

Data: $^1$H NMR (CDCl$_3$) δ 1.42 (s, 3.6H), 1.44 (s, 5.4H), 2.42-2.49 (m, 1H), 2.67-2.73 (m, 1H), 3.37 (s, 1.2H), 3.78 (s, 1.8H), 3.97 (t, J=6.5 Hz, 1H), 4.02 (s, 2.4H), 4.04 (s, 3.6H), 4.48 (t, J=7.9 Hz, 0.6H), 4.60 (t, J=7.7 Hz, 0.4H), 5.86 (br s, 0.6H), 5.90 (br s, 0.4H), 7.27-7.29 (m, 1H), 7.38-7.44 (m, 1H); $^{13}$C NMR (CDCl$_3$) δ 8.2, 28.3, 35.7, 36.7, 52.1, 52.2, 52.4, 56.5, 57.8, 58.2, 75.5, 76.0, 80.7, 100.8, 107.6, 111.0, 119.7, 148.2, 150.2, 151.4, 153.8, 154.5, 156.4, 165.1, 172.7, 173.0; LC-MS m/e (MH$^+$) 502.

Intermediate 82 can be used to make compounds of Formula I as follows:

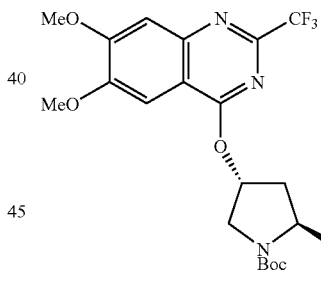

Intermediate 82

↓

Compound of Formula I

Example 83

Preparation of Intermediate 83

Intermediate 83

Intermediate 83 is commercially available and can be used to make compounds of Formula I.

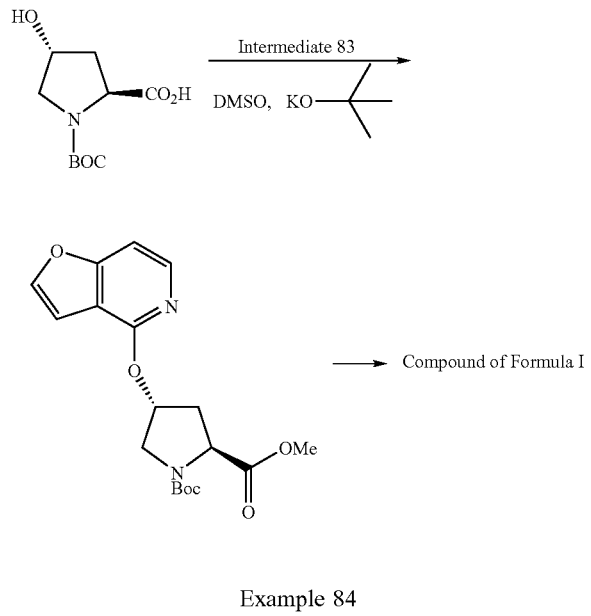

Example 84

Preparation of Intermediate 84

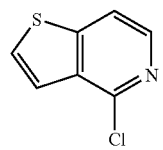
Intermediate 84

Intermediate 84 is commercially available and can be used to make compounds of Formula I.

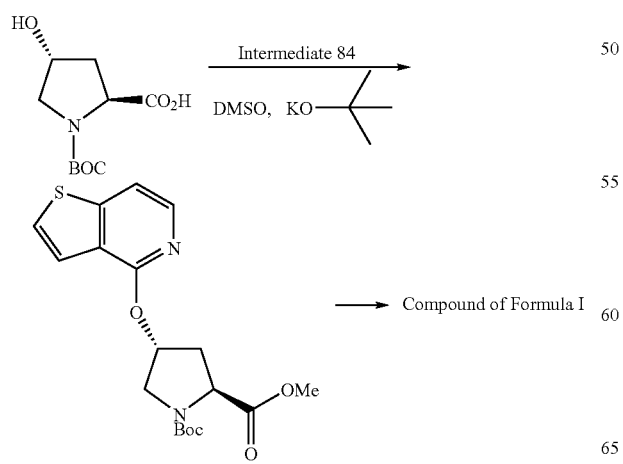

Example 85

Preparation of Intermediate 85

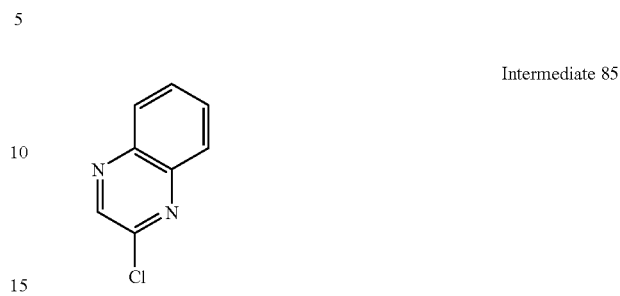
Intermediate 85

Intermediate 85 is commercially available and can be used to make compounds of Formula I.

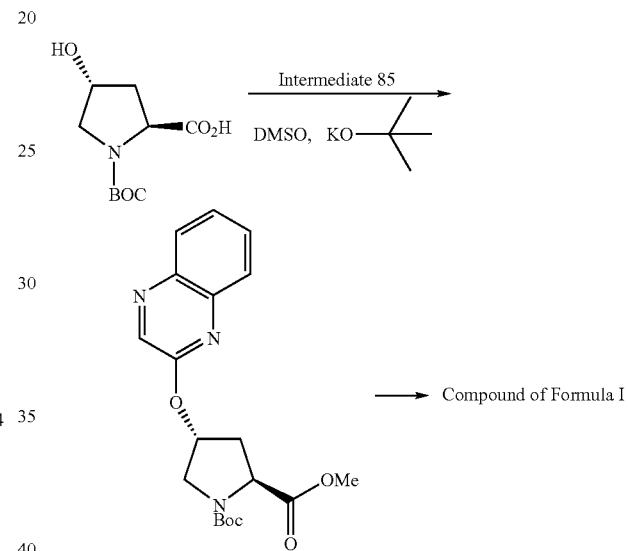

Example 86

Preparation of Intermediate 86

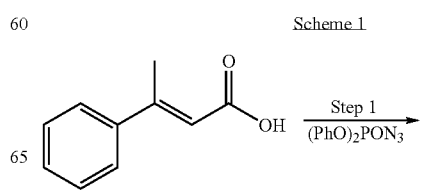
Intermediate 86

Reference scheme for preparation of Intermediate 86

Scheme 1

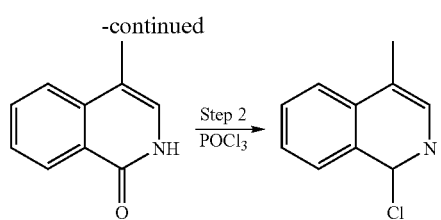

Step 1:

A solution of 3-phenyl-but-2-enoic acid (16.2 g), diphenylphosphoryl azide (27.5 g), and triethylamine (10.1 g) in benzene (100 mL) was stirred for 1 hour. After filtration through a silica gel plug washing with benzene and concentration, the residue was dissolved in diphenylmethane (80 mL) and refluxed for 3 hours. After cooling to room temperature, solids were collected through a plug washing with benzene and dried to give 10 g (63%) of the desired product as a solid. $^1$H NMR (400 MHz, CD$_3$OD) δ ppm 2.30 (s, 3H), 7.00 (s, 1H), 7.54 (m, 1H), 7.77 (m, 2H), 8.33 (d, J=7.34 Hz, 1H).

Step 2:

A solution of 4-methyl-2H-isoquinolin-1-one (4.8 g) in POCl$_3$ (50 mL) was refluxed for 3 hours. After cooling and concentration, the residue was based with 5 N NaOH and extracted with CH$_2$Cl$_2$. The organic layer was washed with brine and dried over MgSO$_4$. After filtration and concentration, purification by flash chromatography of Biotage with 5% ethyl acetate in hexanes gave 4.8 g (90%) of the desired product as a solid. $^1$H NMR (400 MHz, CDCl$_3$) δ ppm 2.59 (s, 3H), 7.68 (t, J=7.70 Hz, 1H), 7.78 (m, 1H), 7.94 (d, J=8.31 Hz, 1H), 8.11 (s, 1H), 8.35 (d, J=8.31 Hz, 1H).

Chemistry for Preparation of Intermediate 86

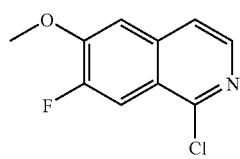

Intermediate 86

Step 1:

Preparation of 7-fluoro-6-methoxy-2H-isoquinolin-1-one. As shown in step 1 of this example using 19.6 g 4-fluoro-3-methoxycinnamic acid as starting material. 9.5 g product obtained (48% yield).

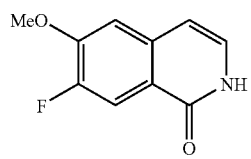

Data: $^1$H NMR (400 MHz, CD$_3$COCD$_3$) δ ppm 4.00 (s, 1H), 6.49 (d, J=7.34 Hz, 1H), 7.19 (d, J=7.09 Hz, 1H), 7.29 (d, J=8.07 Hz, 1H), 7.86 (d, J=11.74 Hz, 1H).

Step 2:

Preparation of 1-chloro-7-fluoro-6-methoxyisoquinoline: As shown in step 2 of this example using 7-fluoro-6-methoxy-2H-isoquinolin-1-one (9 g) as starting material. 7 g of desired product obtained (70% yield).

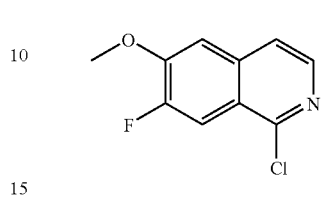

Intermediate 86

Data: $^1$H NMR (400 MHz, CDCl$_3$) δ ppm 4.04 (s, 3H), 7.17 (d, J=8.07 Hz, 1H), 7.48 (d, J=5.62 Hz, 1H), 7.94 (d, J=11.49 Hz, 1H), 8.20 (d, J=5.62 Hz, 1H).

Intermediate 86 can be used to make compounds of Formula I.

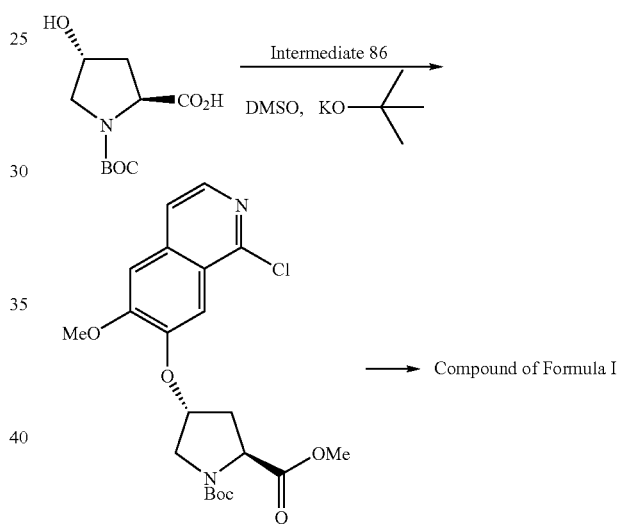

Example 87

Preparation of Intermediate 87

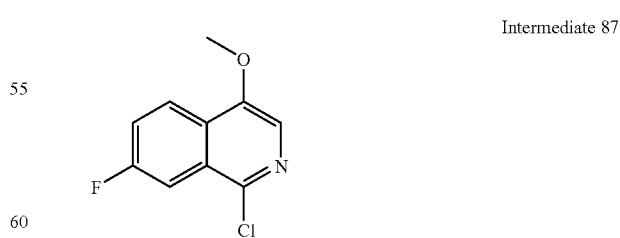

Intermediate 87

Step 1:

As in Example 86 step 1 but with 3.82 g of 3-(4-Fluorophenyl)-3-methoxy-acrylic acid as starting material. 198 mg product obtained (5% yield).

145

Product:

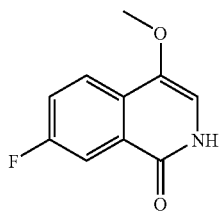

Data: MS: (M+H)+ 194.

Step 2:

As in Example 86, step 1, but with 193 mg 7-fluoro-4-methoxy-2H-isoquinolin-1-one as starting material. 199 mg product obtained (94% yield).

Product:

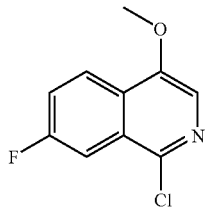

Data: $^1$H NMR (400 MHz, CDCl$_3$) δ ppm 4.05 (s, 3H), 7.49 (m, 1H), 7.78 (s, 1H), 7.86 (dd, J=9.66, 2.57 Hz, 1H), 8.23 (dd, J=9.29, 5.38 Hz, 1H); MS: (M+H)+ 212.

Intermediate 87 can be used to make compounds of Formula I.

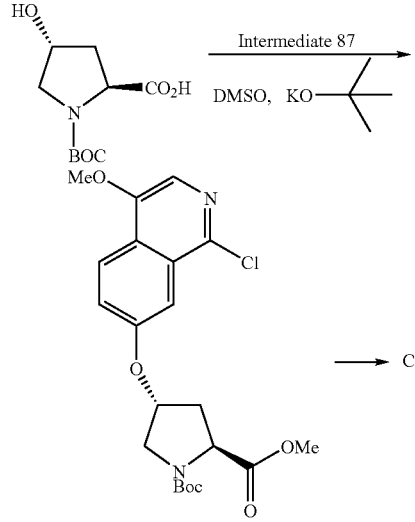

146

Example 88

Preparation of Intermediate 88

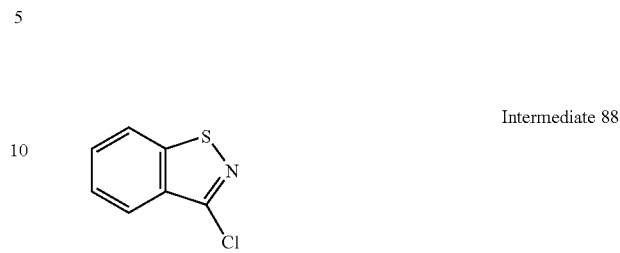

Intermediate 88

Intermediate 88 can be used to make compounds of Formula I.

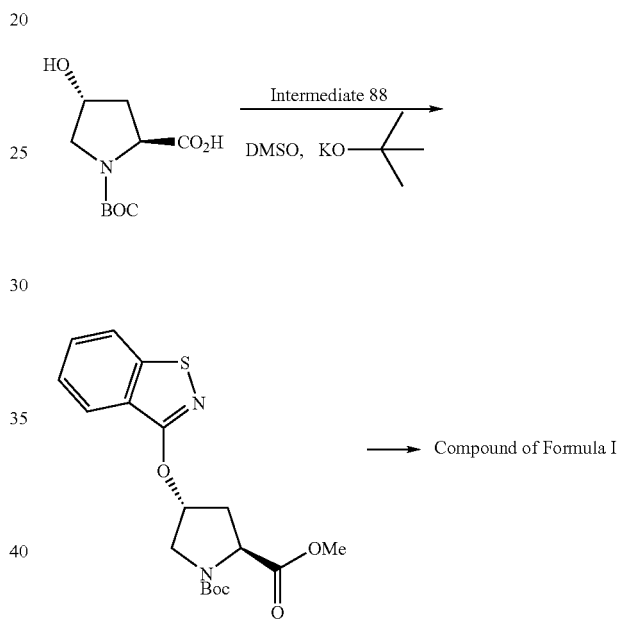

→ Compound of Formula I

Example 89

Preparation of Intermediate 89

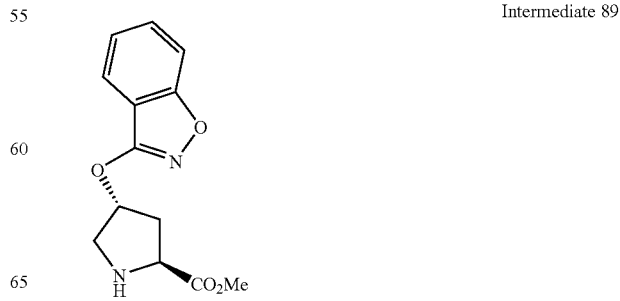

Intermediate 89

-continued

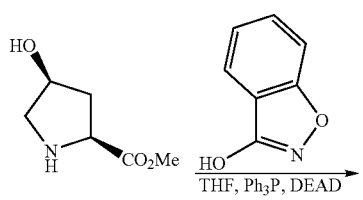

Example 90

Preparation of Intermediate 90

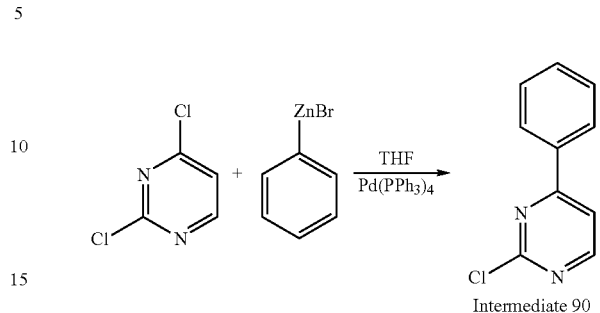

Intermediate 90

To a solution of 2,4-dichloropyrimidine (149 mg, 1 mmol) in THF (5 mL), tetrakis(triphenylphosphine)palladium (23 mg, 2 mol %) and 0.5M solution of phenylzinc bromide (2.1 mL, 1.05 mmol) in THF were added. The reaction mixture was stirred at 50° C. for overnight. Then it was added saturated ammonium chloride solution and extracted with EtOAc twice. The organic layers were combined, washed with water and dried (MgSO$_4$). Filtration and concentration of solvent gave a yellow residue which was purified by Prep. HPLC to afford a yellowish oil as 2-chloro-4-phenyl-pyrimidine.

Intermediate 90 can be used to make compounds of Formula I.

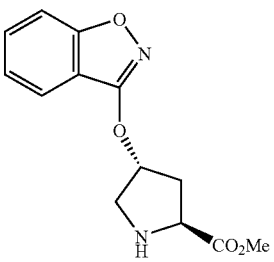

Intermediate 89

To a solution of Boc-cis-HYP-OMe (122.6 mg, 0.5 mmol) in THF (15 mL) at 0° C., triphenylphosphine (196.7 mg, 0.75 mmol) and benzo[d]isoxazol-3-ol (81 mg, 0.6 mmol) were added. Then DEAD (0.118 mL, 0.75 mmol) was added. The reaction mixture was warmed to room temperature and stirred for 3 hr. Then solvent was concentrated and the residue was purified by Prep. HPLC to give a colorless thick oil. (117 mg, 54% yield)

$^1$H NMR (400 MHz, CD$_3$OD) δ 1.41 (m, 9H), 2.38 (m, 1H), 2.75 (m, 1H), 3.75 (m, 3H), 3.81 (m, 1H), 3.90 (m, 1H), 4.47 (m, 1H), 5.44 (m, 1H), 7.31 (t, J=7.46 Hz, 1H), 7.47 (d, J=8.56 Hz, 1H), 7.59 (t, J=7.83 Hz, 1H), 7.66 (d, J=8.07 Hz, 1H). LC-MS (retention time: 2.65 min.), MS m/z 363 (MH$^+$).

Intermediate 89 can be used to make compounds of Formula I.

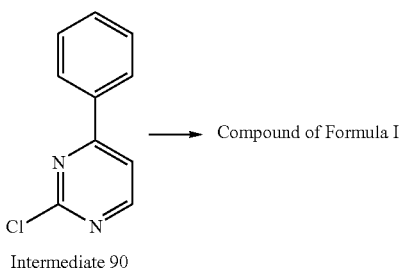

Intermediate 90

⟶ Compound of Formula I

Example 91

Preparation of Intermediate 91

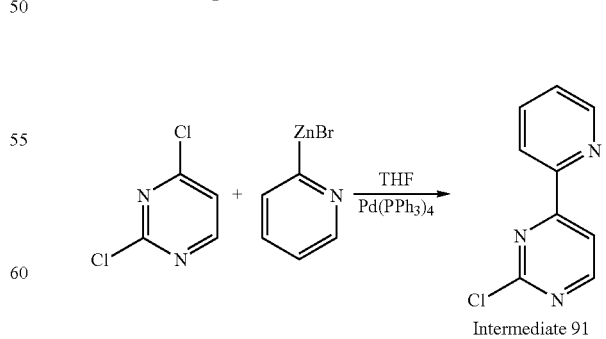

Intermediate 91

To a solution of 2,4-dichloropyrimidine (149 mg, 1 mmol) in THF (5 mL), tetrakis(triphenylphosphine)palladium (58 mg, 5 mol %) and 0.5M solution of 2-pyridinylzinc bromide

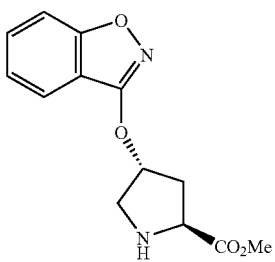

Intermediate 89

⟶ Compound of Formula I (2.4 mL, 1.2 mmol) in THF were added. The reaction mixture was stirred at 50° C. for overnight. Then it was added saturated ammonium chloride solution and extracted with EtOAc twice. The organic layers were combined, washed with water and dried (MgSO$_4$). Filtration followed by concentration of solvent gave a yellow residue which was purified by Prep. HPLC to afford a yellowish oil as product. (Intermediate 60, 11 mg, 3.6% yield) $^1$H NMR (500 MHz, CD$_3$OD) δ 7.61 (m, 1H), 8.07 (m, 1H), 8.36 (d, J=5.19 Hz, 1H), 8.50 (d, J=7.94 Hz, 1H), 8.75 (d, J=3.97 Hz, 1H), 8.82 (d, J=5.19 Hz, 1H). MS m/z 192 (MH$^+$).

Intermediate 91 can be used to make compounds of Formula I.

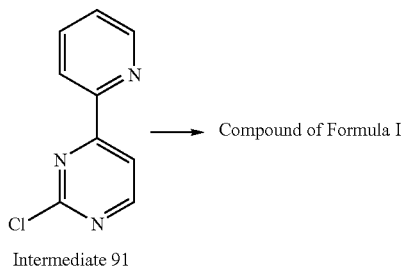

Intermediate 91

Example 92

Preparation of Intermediate 92

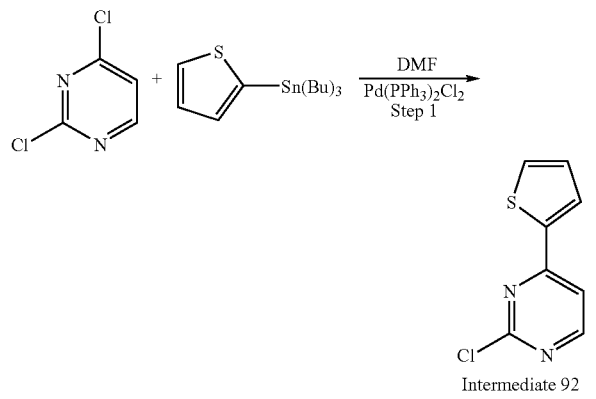

Intermediate 92

To a solution of 2,4-dichloropyrimidine (149 mg, 1 mmol) in DMF (5 mL), dichloro bis(triphenylphosphine)palladium (II) (35 mg, 5 mol %) and 2-(tributylstannyl)thiophene (0.38 mL, 1.2 mmol) were added. The reaction mixture was heated at 70° C. for 3 hours. Then it was added saturated KF solution in methanol (20 mL) and stirred at room temperature for 4 hr. The reaction mixture was concentrated with a small amount of silica gel and the residue was filtered through filter paper and washed with EtOAc. The filtrate was then concentrated and the residue was purified by Prep. HPLC to afford an off-white solid as product. (110 mg, 35% yield) $^1$H NMR (400 MHz, CD$_3$OD) δ 7.20 (dd, J=5.01, 3.79 Hz, 1H), 7.74 (dd, J=5.01, 1.10 Hz, 1H), 7.77 (d, J=5.38 Hz, 1H), 7.98 (dd, J=3.79, 1.10 Hz, 1H), 8.55 (d, J=5.38 Hz, 1H). MS m/z 197 (MH$^+$).

Intermediate 92 can be used to make compounds of Formula I.

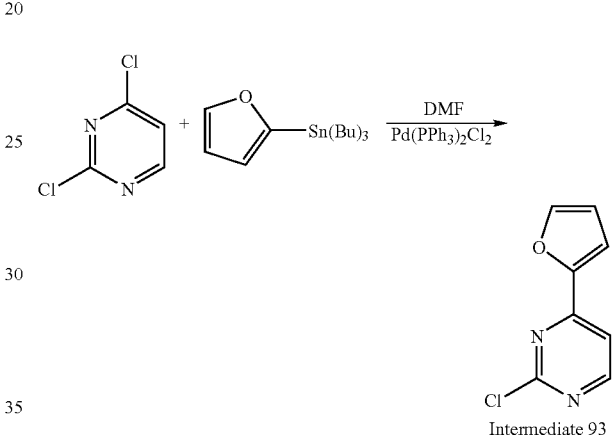

Intermediate 92

Example 93

Preparation of Intermediate 93

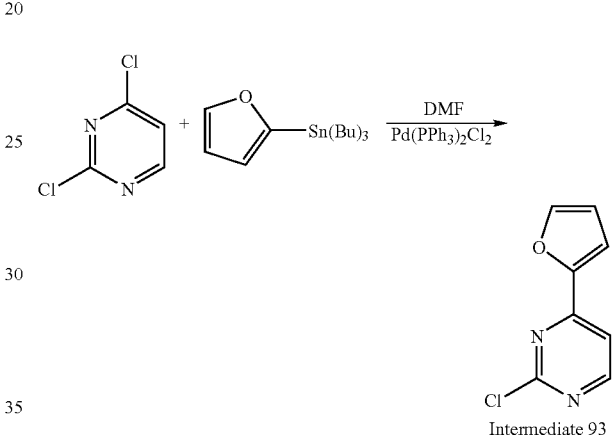

Intermediate 93

To a solution of 2,4-dichloropyrimidine (149 mg, 1 mmol) in DMF (5 mL), dichloro bis(triphenylphosphine)palladium (II) (35 mg, 5 mol %) and 2-(tributylstannyl)furan (0.35 mL, 1.1 mmol) were added. The reaction mixture was heated at 70° C. for 3 hours. Then it was added saturated KF solution in methanol (20 mL) and stirred at room temperature for 4 hours. The reaction mixture was concentrated with a small amount of silica gel and the residue was filtered through filter paper and washed with EtOAc. The filtrate was then concentrated and the residue was purified by Prep. HPLC to afford a brownish solid as product. (80 mg, 27% yield) $^1$H NMR (400 MHz, CD$_3$OD) δ 6.68 (dd, J=3.67, 1.71 Hz, 1H), 7.42 (d, J=3.67 Hz, 1H), 7.67 (d, J=5.13 Hz, 1H), 7.30 (d, J=1.71 Hz, 1H), 8.62 (d, J=5.14 Hz, 1H). MS m/z 181 (MH$^+$).

Intermediate 62 can be used to make compounds of Formula I.

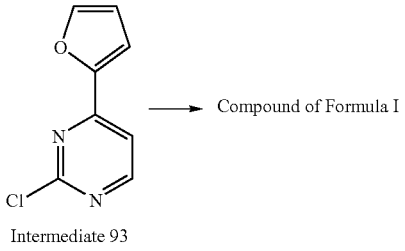

Intermediate 93

Example 94

Preparation of Intermediate 94

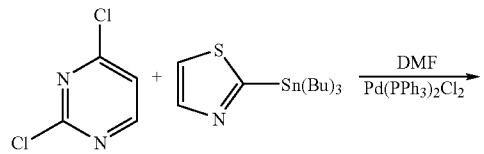

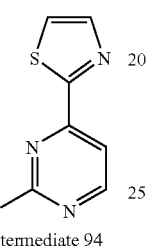

Intermediate 94

To a solution of 2,4-dichloropyrimidine (149 mg, 1 mmol) in DMF (5 mL), dichloro bis(triphenylphosphine)palladium (II) (35 mg, 5 mol %) and 2-(tributylstannyl)thiazole (412 mg, 1.1 mmol) were added. The reaction mixture was heated at 80° C. for 3 hours. Then it was added saturated KF solution in methanol (20 mL) and stirred at room temperature for 4 hours. The reaction mixture was concentrated with a small amount of silica gel and the residue was filtered through filter paper and washed with EtOAc. The filtrate was then concentrated and the residue was purified by Prep. HPLC to afford a brownish solid as product. (9 mg, 3% yield). MS m/z 198 (MH$^+$).

Intermediate 63 can be used to make compounds of Formula I.

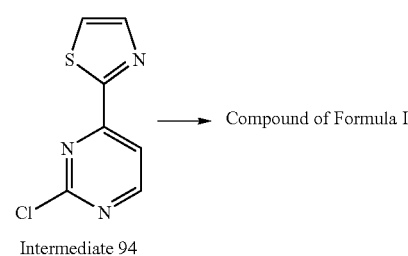

Intermediate 94 → Compound of Formula I

Example 95

Preparation of Intermediate 95

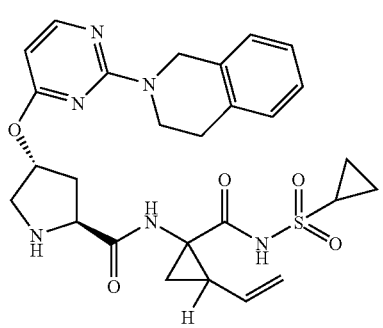

Intermediate 95

Scheme 1

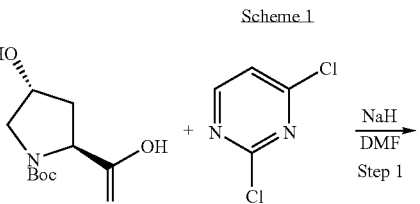

Step 1

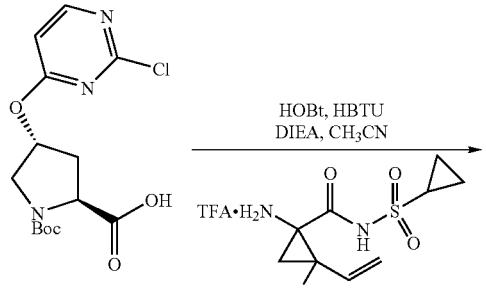

Step 2

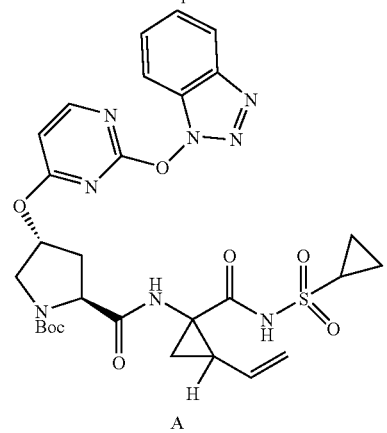

A

3) CH$_2$Cl$_2$, Et$_3$N    4) HCl, dioxane

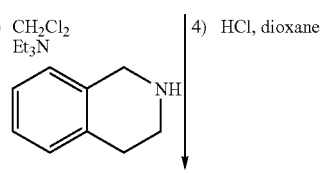

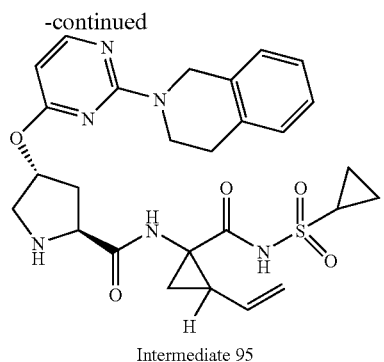

Intermediate 95

Step 1:

To a solution of Boc-HYP-OH (1.0 g, 4.324 mmol) in DMF (20 mL), NaH (0.38 g of 60% dispersion in mineral oil, 9.513 mmol) was added at 0° C. The reaction mixture was stirred for 1 hr. Then 2,4-dichloropyrimidine (0.709 g, 0.0289 mmol) was added. The reaction mixture was warmed to room temperature and stirred for overnight. It was then quenched with 1N HCl solution and extracted with EtOAc. The organic layer was separated, washed with brine and dried (MgSO$_4$). Filtration followed by concentration of solvent gave crude product which was then purified by Prep. HPLC to give colorless oil as product. (0.4 g, 27% yield)

$^1$H NMR(CD$_3$OD, 300 MHz) δ 1.13 (m, 9H), 2.37 (m, 1H), 2.62 (m, 1H), 3.70-3.84 (m, 2H), 4.38 (m, 1H), 5.65 (m, 1H), 6.88 (d, J=5.86 Hz, 1H), 8.37 (d, J=5.86 Hz, 1H). MS m/z 344 (MH$^+$).

Step 2:

To a solution of (2S,4R) 4-(2-Chloro-pyrimidin-4-yloxy)-pyrrolidine-1,2-dicarboxylic acid 1-tert-butyl ester (0.34 g, 0.99 mmol) in CH$_3$CN (20 mL) was added (1R,2S)/(1S,2R) (1-cyclopropanesulfonyl-aminocarbonyl-2-vinyl-cyclo-propyl)-carbamic acid (0.511 g, 1.48 mmol), DIEA (0.86 mL, 4.95 mmol) and the coupling reagent HOBt (0.226 g, 1.48 mmol) and HBTU (0.561 g, 1.48 mmol). The solution was stirred at room temperature overnight. Then it was concentrated, washed with water and extracted with ethyl acetate twice. The combined organic layers were washed with brine, dried over MgSO$_4$, filtered, and concentrated. It was then purified by Prep. HPLC column to give a yellow solid (A). (0.33 g, 41% yield). MS m/z 655 (MH$^+$).

Step 3:

To a solution of intermediate 4 (50 mg, 0.061 mmol) in CH$_2$Cl$_2$ (2.5 mL), 1,2,3,4-tetrahydroisoquinoline (0.011 mL, 0.0915 mmol) and Et$_3$N (0.021 mL, 0.153 mmol) were added. The reaction mixture was stirred at room temperature for overnight and at 40° C. for 1 day. The solvent was stripped and the residue was purified by Prep. HPLC to give a colorless oil. It was then dissolved in 4N HCl in dioxane (1 mL) and stirred for overnight. Evaporation of solvent gave a colorless oil as hydrochloride salt. (20 mg, 52% yield). MS m/z 553 (MH$^+$).

Step 4:

To a solution of 4-[2-(3,4-Dihydro-1H-isoquinolin-2-yl)-pyrimidin-4-yloxy]-pyrrolidine-2-carboxylic acid (1-cyclopropanesulfonylaminocarbonyl-2-vinyl-cyclopropyl)-amide hydrochloride (20 mg, 0.032 mmol) in CH$_3$CN (5 mL) was added 2-methoxycarbonylamino-3,3-dimethyl-butyric acid (9.1 mg, 0.048 mmol), DIEA (0.028 mL, 0.16 mmol) and the coupling reagent HOBt (7.3 mg, 0.048 mmol) and HBTU (18.2 mg, 0.048 mmol). The solution was stirred at room temperature overnight. Then it was concentrated, washed with water and extracted with ethyl acetate twice. The combined organic layers were washed with brine, dried over MgSO$_4$, filtered, and concentrated to give yellowish oil. It was purified by Prep. HPLC column to give a colorless oil as TFA salt (Intermediate 64). (16 mg, 60% yield)

$^1$H NMR(CD$_3$OD, 500 MHz) δ 0.98-1.06 (m, 13H), 1.13 (m, 1H), 1.22-1.32 (m, 1H), 1.35-1.44 (m, 1H), 1.82 (dd, J=8.24, 5.19 Hz, 0.5H), 1.90 (dd, J=8.24, 5.49 Hz, 0.5H), 2.26 (m, 1H), 2.32-2.43 (m, 1H), 2.56 (m, 1H), 2.96 (m, 1H), 3.11 (m, br, 2H), 3.56 (s, 3H), 4.14 (m, 1H), 4.21 (m, 1H), 4.38 (m, 1H), 4.47 (m, 1H), 5.15 (m, 1H), 5.31 (m, 1H), 5.75 (m, 1H), 5.94 (s, 1H), 6.47 (d, J=7.02 Hz, 1H), 7.29 (s, 4H), 7.49 (m, 1H), 7.56 (m, 1H), 7.74 (d, J=8.24 Hz, 1H), 7.88 (d, J=8.24 Hz, 1H), 8.11 (d, J=7.02 Hz, 1H). MS m/z 724 (MH$^+$).

Intermediate 95 can be used to make compounds of Formula I.

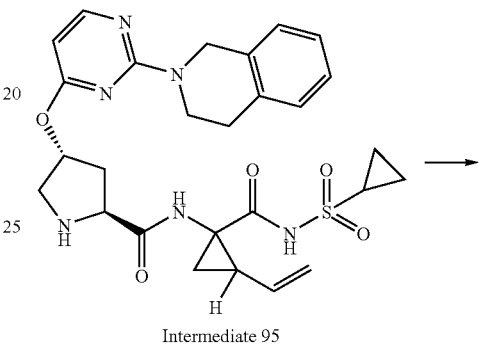

Intermediate 95      Compound of Formula I

Example 96

Preparation of Intermediate 96

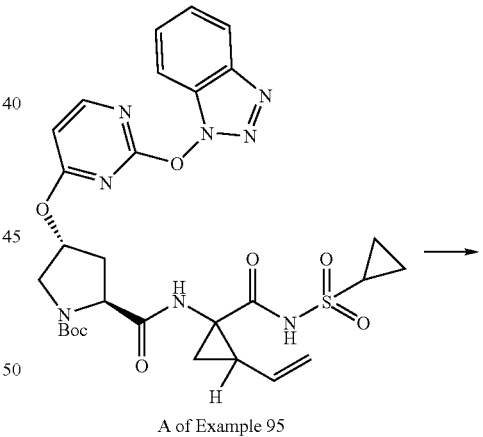

A of Example 95

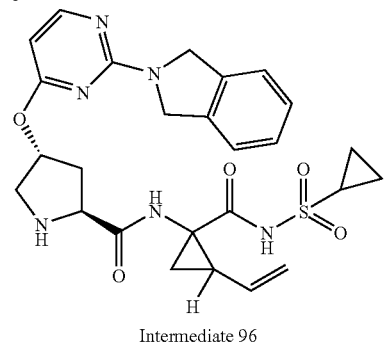

Intermediate 96

To a solution of A (50 mg, 0.061 mmol) in CH$_2$Cl$_2$ (2.5 mL), isoindoline (0.013 mL, 0.115 mmol) and Et$_3$N (0.026 mL, 0.19 mmol) were added. The reaction mixture was stirred at room temperature for 2 days. The solvent was stripped and the residue was purified by Prep. HPLC to give a colorless oil. It was then dissolved in 4N HCl in dioxane (1 mL) and stirred for overnight. Evaporation of solvent gave crude product which was purified by Prep. HPLC again to afford yellowish solid as TFA salt. (8.5 mg, 14% yield). MS m/z 539 (MH$^+$).

Intermediate 65 can be used to make compounds of Formula I.

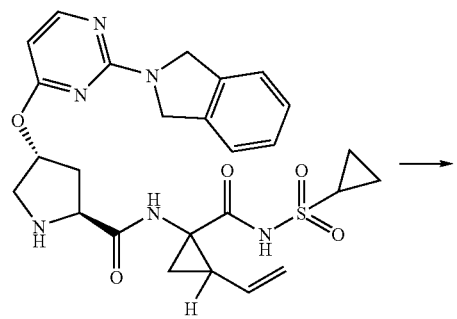

Intermediate 96

↓

Compound of Formula I

Example 97

Preparation of Intermediate 97

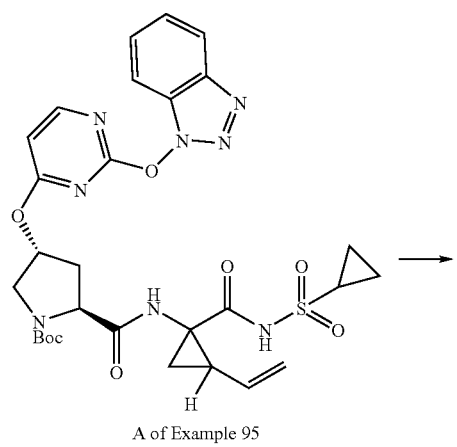

A of Example 95

↓

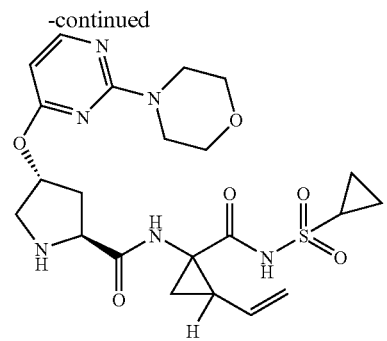

Intermediate 97

To a solution of A of Example 95 (50 mg, 0.061 mmol) in CH$_2$Cl$_2$ (2.5 mL), morpholine (0.008 mL, 0.0915 mmol) and Et$_3$N (0.021 mL, 0.153 mmol) were added. The reaction mixture was stirred at room temperature for overnight and at 40° C. for 1 day. The solvent was stripped and the residue was purified by Prep. HPLC to give a colorless oil. It was then dissolved in 4N HCl in dioxane (1 mL) and stirred for overnight. Evaporation of solvent gave a colorless oil as hydrochloride salt. (12.6 mg, 36% yield); MS m/z 507 (MH$^+$).

Intermediate 66 can be used to make compounds of Formula I.

Intermediate 97

↓

Compound of Formula I

Example 98

Preparation of Intermediate 98

Scheme 1

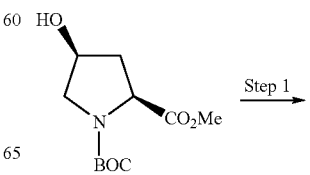

Step 1 →

-continued

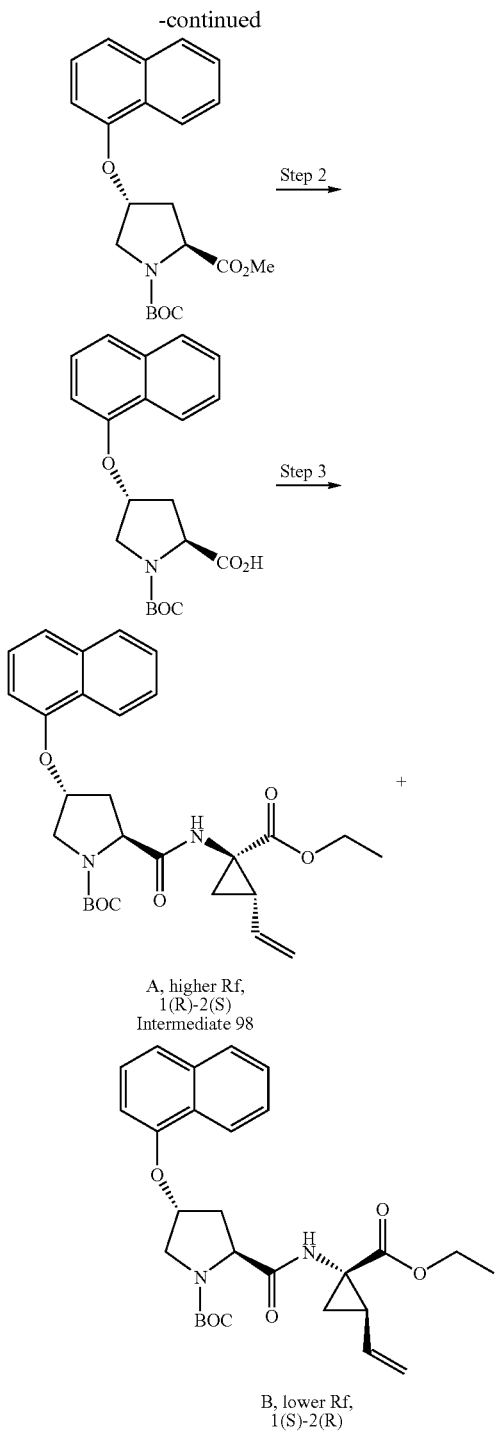

A, higher Rf,
1(R)-2(S)
Intermediate 98

B, lower Rf,
1(S)-2(R)

Step 1:

To a solution of commercially available N-Boc-(4S)-(cis)-Hydroxyproline-OMe (200 mgs, 0.82 mmole), triphenylphosphine (320 mgs, 1.22 mmole) and 1-naphthol (176 mgs, 1.22 mmole) in 2.5 mL tetrahydrofuran was added dropwise a solution of diethyldiazodicarboxylate (190 µL, 1.22 mmole) in 1.0 mL THF over 10 minutes. After stirring for 5.5 days, the reaction was concentrated in vacuo. The crude yellow oil was chromatographed on a 20×40 cM preparative TLC plate (Analtech SiO2) eluting with 6-1 hexanes-ethyl acetate to yield the desired product as a pale yellow oil (150 mgs, 33%).

$^1$H NMR (CDCl$_3$, 500 MHz) δ 1.44 (s, 9H) 2.33 (1H, m), 2.72 (1H, m), 3.77 and 3.38 (2s, 3H, rotamers), 3.88 (dd, 1H, J=4.3, 12.4 Hz), 3.97 (bd, 1H), 4.53 and 4.62 (2t, 1H, J=7.8 Hz, rotamers), 5.10 (bd, 1H), 6.76 (t, 1H, J=9.5 Hz), 7.37 (m, 1H), 7.46 (m, 3H), 7.80 (d, 1H, J=7.7 Hz), 8.18 (m, 1H); MS m/z 394 (M+Na)$^+$ Step 2:

To a stirred solution of Boc-(4R)-naphthal-1-oxo)-Pro-OEt (150 mgs, 0.40 mmole) in 1.5 mL THF and 0.5 mL water was added lithium hydroxide (10 mgs). The solution was stirred for 21 hours at room temperature and then diluted with 0.5N NaHCO$_3$. The basic solution was extracted with ethyl acetate and then the aqueous layer was acidified to pH 2 with the dropwise addition of conc. HCl. This acidified layer was then extracted again with ethyl acetate. This second ethyl acetate layer was dried with magnesium sulfate, filtered and then concentrated in vacuo to yield Boc-(4R)-naphthal-1-oxo)-Pro-OH as pale-pink crystals (147 mgs, 100%).

$^1$H NMR (CDCl$_3$, 500 MHz) δ 1.47 and 1.48 (2s, 9H, rotamers), 2.40 and 2.52 (2m, 1H), 2.68 and 2.78 (2m, 1H), 3.78-4.07 (m, 2H), 4.57 and 4.69 (2t, 1H, J=7.6 and 8.0 Hz, rotamers), 5.12 (bd, 1H), 6.77 (dd, 1H, J=7.6, 21.2 Hz), 7.37 (m, 1H), 7.46 (m, 3H), 7.81 (t, 1H, J=5.8 Hz), 8.19 (m, 1H); MS m/z 358 (M+H)$^+$ Step 3:

To a solution of Boc-((4R)-naphthal-1-oxo)-Pro-OH (147 mgs, 0.41 mmole) and racemic (1R/2S)/(1S/2R)-1-amino-2-vinylcyclopropane carboxylic acid ethyl ester hydrochloride salt (79 mgs, 0.41 mmole) in 2.8 mL methylene chloride was added DIPEA (250 µL, 1.44 mmole) and TBTU (158 mgs, 0.49 mmole). The resulting solution was stirred under nitrogen for 20 hours and then diluted with 40 mL methylene chloride. The organic layer was washed with water, 1N NaHCO$_3$, 1N HCl, water and brine. The solution was then dried with sodium sulfate and concentrated in vacuo. Purification by preparative TLC yielded two separate diastereomers, higher Rf diastereomer A (P2[Boc(4R)-(naphthal-1-oxo)proline]-P1(1R,2S Vinyl Acca)-OEt, 78 mgs, 38%) and lower Rf diastereomer B (P2[Boc(4R)-(naphthal-1-oxo)proline]-P1(1S,2R Vinyl Acca)-OEt, 91 mgs, 45%) as off white solids:

Diastereomer A: P2[Boc(4R)-(naphthal-1-oxo)proline]-P1(1R,2S Vinyl Acca)-OEt: $^1$H NMR (CDCl$_3$, 500 MHz) δ 1.24 (t, 3H), 1.43 (s, 9H), 1.52 (m, 1H), 1.84 (m, 1H), 2.02 (m, 1H), 2.14 (m, 1H), 2.81 (m, 1H), 3.88 (m, 2H), 4.11 (q, 1H, J=7.15), 4.19 (m, 1H), 4.54 (m, 1H), 5.15 (m, 1H), 5.31 (dd, 1H, J=17, 0.8 Hz), 5.77 (m, 1H), 6.83 (m, 1H), 7.36 (t, 1H, J=7.8 Hz), 7.46 (m, 3H), 7.78 (d, 1H, J=7.6 Hz), 8.14 (d, 1H, J=8.15 Hz); MS m/z 495 (M+H)$^+$ Diastereomer B, Example 10B: P2[Boc(4R)-(naphthal-1-oxo)proline]-P1(1S,2R Vinyl Acca)-OEt: $^1$H NMR (d1-CHCl$_3$, 500 MHz) δ 1.24 (t, 3H), 1.42 (s, 9H), 1.85 (m, 1H), 2.15 (q, 1H, J=8.9 Hz), 2.40 (m, 1H), 2.78 (m, 1H), 3.78 (m, 1H), 4.12 (m, 2H), 4.52 (m, 1H), 5.15 (m, 1H), 5.31 (m, 1H), 5.79 (m, 1H), 6.80 (m, 1H), 7.35 (t, 1H, J=7.6 Hz), 7.46 (m, 3H), 7.78 (d, 1H, J=7.6 Hz), 8.14 (d, 1H, J=8.10 Hz). MS m/z 495 (M+H)$^+$ Intermediate 98 can be used to make compounds of Formula I.

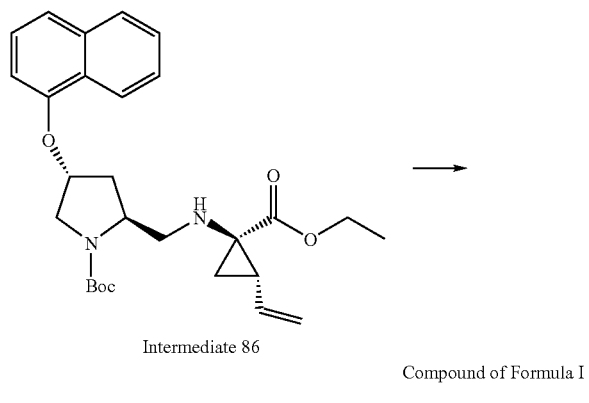

Intermediate 86 → Compound of Formula I

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and hours Marsden, J. Clin. Microbiol., 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16), 8738-8743 (1997); AF054247, see Yanagi, M., St Claire, M., Shapiro, M., Emerson, S. U., Purcell, R. H. and Bukh, J, Virology 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. Biochemistry. 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in Escherichia coli strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-NA-(2-Ethane Sulfonic acid) (HEPES), pH 7.5, 20% glycerol, 500 mM Sodium Chloride (NaCl), 0.5% Triton X-100, 1 microgram/milliliter ("μg/mL") lysozyme, 5 mM Magnesium Chloride ($MgCl_2$), 1 μg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 hour at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activty

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate;

AnaSpec, Inc. cat # 22991) (FRET peptide), described by Taliani et al. in Anal. Biochem. 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 μM final concentration (from a 2 mM stock solution in DMSO stored at −20° C.). HCV NS3/4A protease type 1a (1b), 2-3 nM final concentration (from a 5 μM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 μg/ml Bovine Serum Albumin (Sigma) to the assay buffer and reducing the end protease concentration to 300 pM.

The assay was performed in a 96-well polystyrene black plate from Falcon. Each well contained 25 μl NS3/4A protease complex in assay buffer, 50 μl of a compound of the present disclosure in 10% DMSO/assay buffer and 25 μl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+((B-A)/(1+((C/x)^D)))$.

All of the compounds tested were found to inhibit the activity of the NS3/4A protease complex with IC50's of 8 μM or less. Further, compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases, a 96-well plate format protocol using colorimetric p-nitroaniline (pNA) substrate or fluorometric Amino-Methyl-Coumarin (AMC) substrate, specific for each enzyme was used as described previously (PCT Patent Application No. WO 00/09543) with some modifications. All enzymes were purchased from Sigma or EMDbiosciences while the substrates were from Bachem.

Each pNA assay included a 2 hours enzyme-inhibitor pre-incubation at room temperature followed by addition of substrate and hydrolysis to ~15% conversion as measured on a Spectramax Pro microplate reader. The cathepsin B assay was initiated by adding substrate to a 10 min enzyme-inhibitor pre-incubation at room temperature, and the assay plate measured immediately using the Cytofluor Series 4000. Compound concentrations varied from 100 to 0.4 μM depending on their potency.

The final conditions for each assay were as follows: 50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with:

133 μM succ-AAA-pNA and 20 nM HNE or 8 nM PPE; 100 μM succ-AAPF-pNA and 250 pM Chymotrypsin.

100 mM $NaHPO_4$ (Sodium Hydrogen Phosphate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 μM Z-FR-AMC diluted in $H_2O$.

The percentage of inhibition was calculated using the formula:

$$[1-((UV_{inh}-UV_{blank})/(UV_{ctl}-UV_{blank}))]\times 100$$

A non-linear curve fit was applied to the inhibition-concentration data, and the 50% effective concentration ($IC_{50}$) was calculated by the use of Excel XLfit software.

Generation of HCV Replicon

An HCV replicon whole cell system was established as described by Lohmann V, Korner F, Koch J, Herian U, Theilmann L, Bartenschlager R., Science 285(5424): 110-3 (1999). This system enabled us to evaluate the effects of our HCV Protease compounds on HCV RNA replication. Briefly, using the HCV strain 1b sequence described in the Lohmann paper (Assession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomycin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a $CC_{50}$ reading. The toxicity of compound ($CC_{50}$) was determined by adding $\frac{1}{10}^{th}$ volume of alamarBlue to the media incubating the cells. After 4 h, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 µl). The cells were lysed with 25 µl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 µM final from a 2 mM stock in 100% DMSO. The plate was then placed into the Cytofluor 4000 instrument which had been set to 340 nm excitation/490 nm emissions, automatic mode for 21 cycles and the plate read in a kinetic mode. $EC_{50}$ determinations were carried out as described for the $IC_{50}$ determinations.

HCV Replicon Luciferase Reporter Assay

As a secondary assay, $EC_{50}$ determinations from the replicon FRET assay were confirmed in a replicon luciferase reporter assay. Utilization of a replicon luciferase reporter assay was first described by Krieger et al (Krieger N, Lohmann V, and Bartenschlager R, J. Virol. 75(10):4614-4624 (2001)). The replicon construct described for our FRET assay was modified by inserting cDNA encoding a humanized form of the *Renilla* luciferase gene and a linker sequence fused directly to the 3'-end of the luciferase gene. This insert was introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, Science 290(5498): 1972-1974). A stable cell line constitutively expressing this HCV replicon construct was generated as described above. The luciferase reporter assay was set up as described for the HCV replicon FRET assay with the following modifications. Following 4 days in a 37° C./5% $CO_2$ incubator, cells were analyzed for *Renilla* Luciferase activity using the Promega Dual-Glo Luciferase Assay System. Media (100 µl) was removed from each well containing cells. To the remaining 50 µl of media, 50 µl of Dual-Glo Luciferase Reagent was added, and plates rocked for 10 min to 2 hours at room temperature. Dual-Glo Stop & Glo Reagent (50 µl) was then added to each well, and plates were rocked again for an additional 10 min to 2 hours at room temperature. Plates were read on a Packard TopCount NXT using a luminescence program.

The percentage inhibition was calculated using the formula below:

$$\% \text{ control} = \frac{\text{average luciferase signal in experimental wells}(+\text{compound})}{\text{average luciferase signal in } DMSO \text{ control wells}(-\text{compound})}$$

The values were graphed and analyzed using XLfit to obtain the $EC_{50}$ value.

Representative compounds of the disclosure were assessed in the HCV enzyme assays, HCV replicon cell assay and/or in several of the outlined specificity assays. For example, Compound 56 was found to have an $IC_{50}$ of 99 nanomolar (nM) against the NS3/4A BMS strain in the enzyme assay. Similar potency values were obtained with the published H77 ($IC_{50}$ of 17 nM) and J4L6S ($IC_{50}$ of 9.8 nM) strains. The $EC_{50}$ value in the replicon FRET assay was 742 nM and 247 nM in the replicon Luciferase assay.

In the specificity assays, the same compound was found to have the following activity: HLE>100 µM; PPE>100 µM; Chymotrypsin>100 µM; Cathepsin B>100 µM. These results indicate this family of compounds is highly specific for the NS3 protease and many of these members inhibit HCV replicon replication.

The compounds of the current disclosure were tested and found to have activities in the ranges as follow:

$IC_{50}$ Activity Range (for compounds tested): A is >1 µM; B is 0.1-1 µM; C is <0.1

$EC_{50}$ Activity Ranges (NS3/4A BMS Strain): A is >5 µM; B is 0.5-5 µM; C is <0.5 µM.

In accordance with one embodiment of the present disclosure, the compounds have a biological activity ($EC_{50}$) of 5 µM or less, and in another embodiment, 0.5 µM or less.

Table 1 shows the IC50 and EC50 values for representative compounds. Those examples which are not contained within the earlier examples can be prepared by following the procedures described in the examples and schemes by substituting the appropriate starting materials.

TABLE 1

Biological Data for Representative Compounds

| Example | Structure | IC50 Range | EC50 Range |
| --- | --- | --- | --- |
| Example 4, Compound 8 | 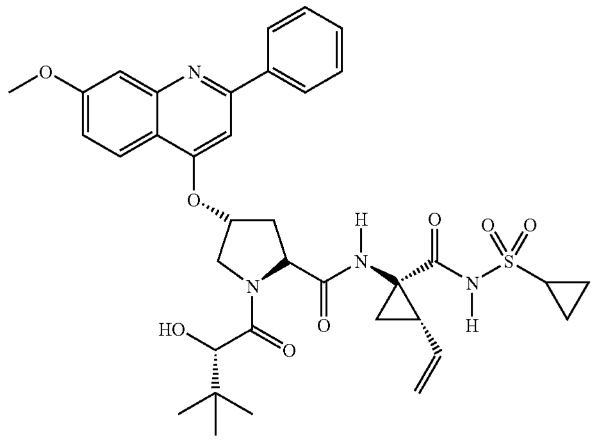 | C | B |
| Example 4, Compound 5 | Chiral | C | B |
| Example 10 | Chiral | C | B |

TABLE 1-continued
Biological Data for Representative Compounds
| Example | Structure | IC50 Range | EC50 Range |
|---|---|---|---|
| Example 11 | 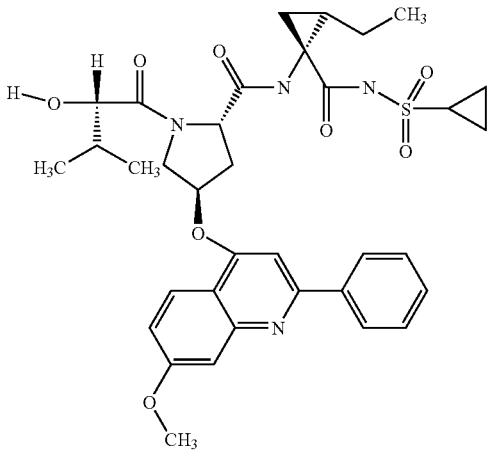 Chiral | C | B |
| Example 12 | 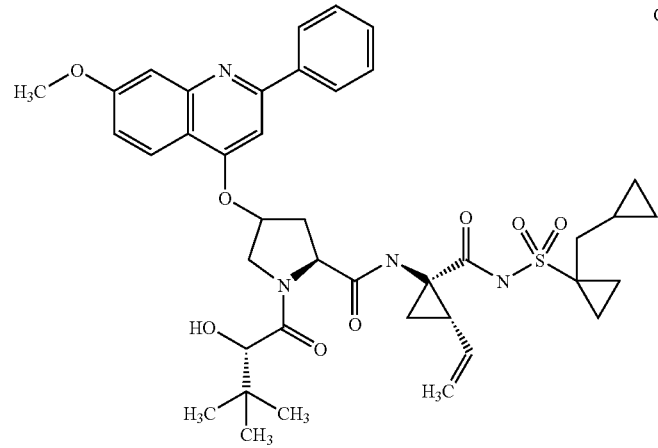 Chiral | C | B |
| Example 4, Compound 4 | 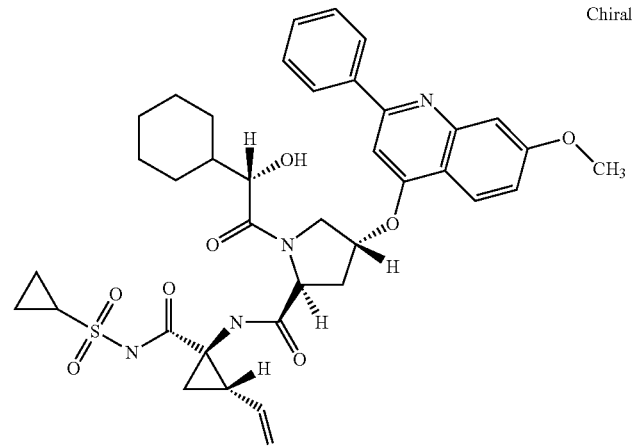 Chiral | C | B |

TABLE 1-continued

Biological Data for Representative Compounds

| Example | Structure | | IC50 Range | EC50 Range |
|---|---|---|---|---|
| Example 4, Compound 6 | [structure] | Chiral | C | B |
| Example 13 | [structure] | Chiral | C | B |
| Example 4, Compound 2 | [structure] | Chiral | B | B |

TABLE 1-continued

Biological Data for Representative Compounds

| Example | Structure | IC50 Range | EC50 Range |
|---|---|---|---|
| Example 4, Compound 3 | Chiral | B | A |
| Example 14 | Chiral | B | A |
| Example 15 | Chiral | B | B |

TABLE 1-continued

Biological Data for Representative Compounds

| Example | Structure | IC50 Range | EC50 Range |
|---|---|---|---|
| Example 16 | 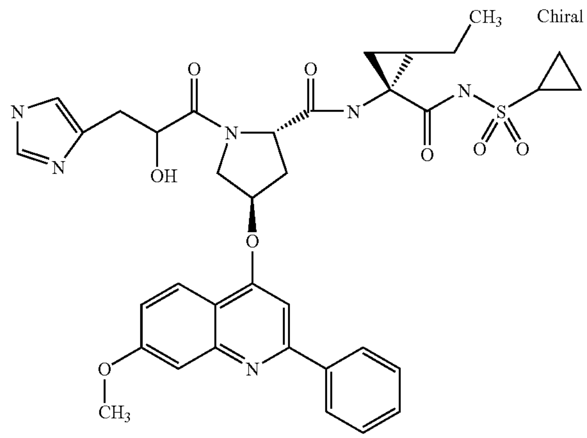 | B | A |
| Example 17 | 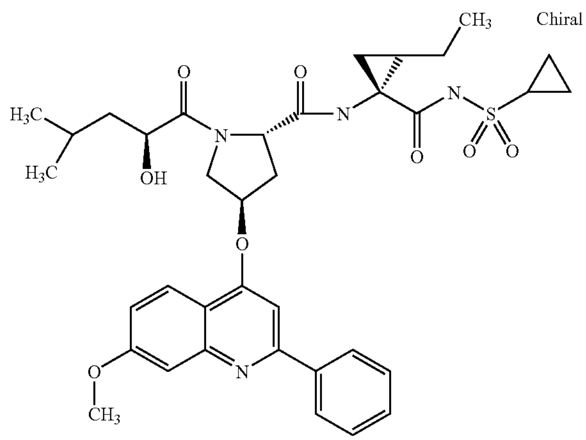 | B | B |
| Example 4, Compound 1 | 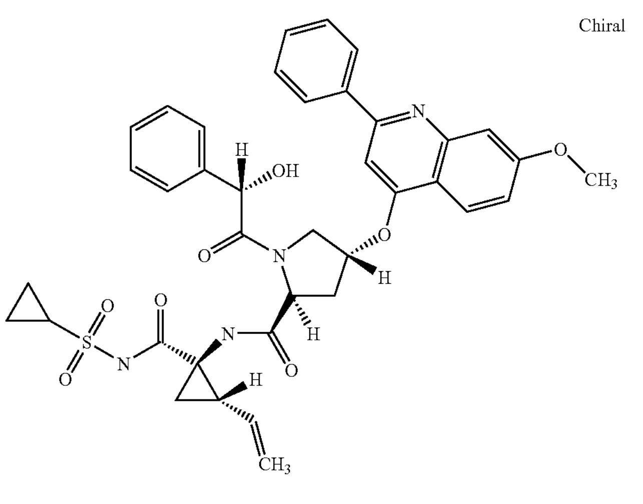 | B | A |

TABLE 1-continued

Biological Data for Representative Compounds

| Example | Structure | | IC50 Range | EC50 Range |
|---|---|---|---|---|
| Example 18 | 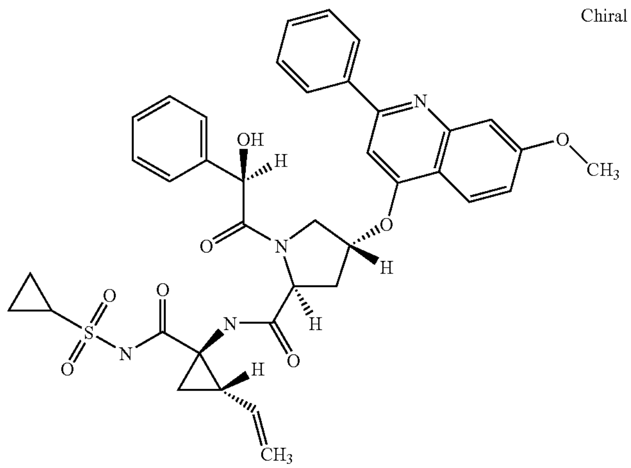 | Chiral | B | A |
| Example 19 | 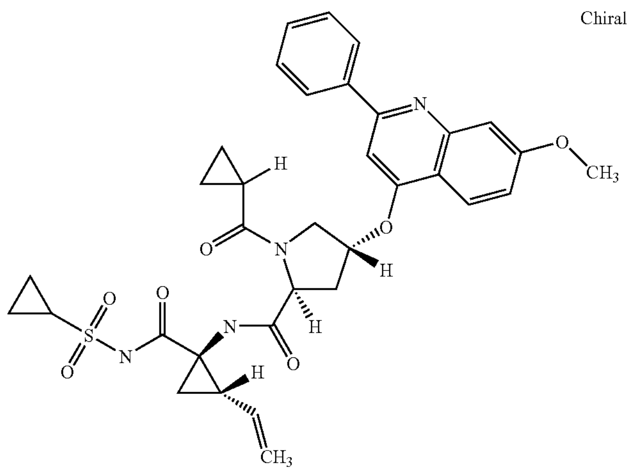 | Chiral | B | — |
| Example 20 | 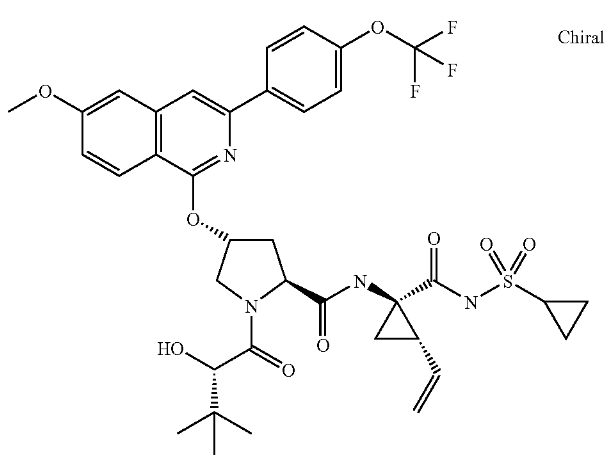 | Chiral | C | B |

TABLE 1-continued

Biological Data for Representative Compounds

| Example | Structure | | IC50 Range | EC50 Range |
|---|---|---|---|---|
| Example 8 | 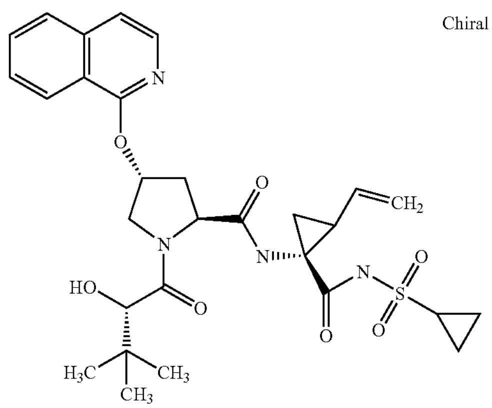 | Chiral | B | B |
| Example 21 | 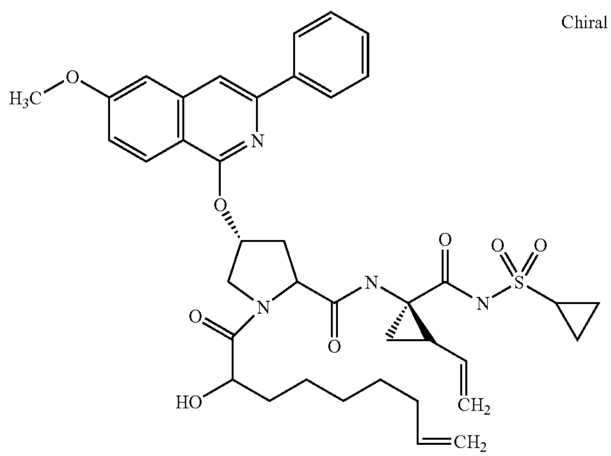 | Chiral | B | — |
| Example 22 | 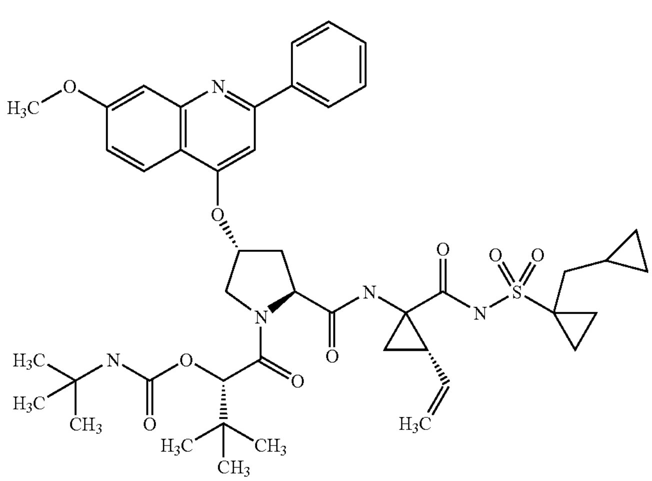 | | C | B |

TABLE 1-continued

Biological Data for Representative Compounds

| Example | Structure | | IC50 Range | EC50 Range |
|---|---|---|---|---|
| Example 5, Compound 1 | 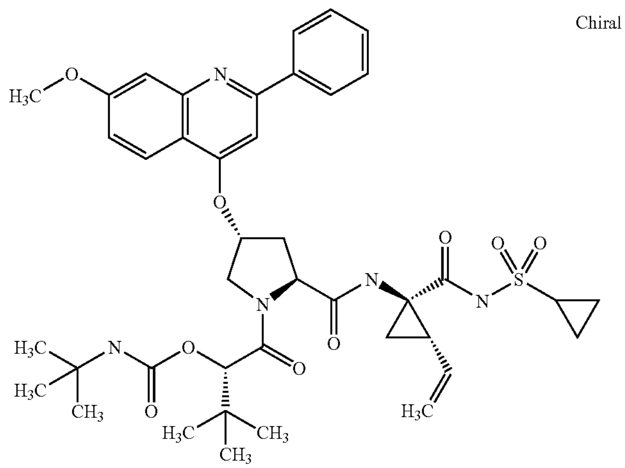 | Chiral | C | C |
| Example 5, Compound 3 | 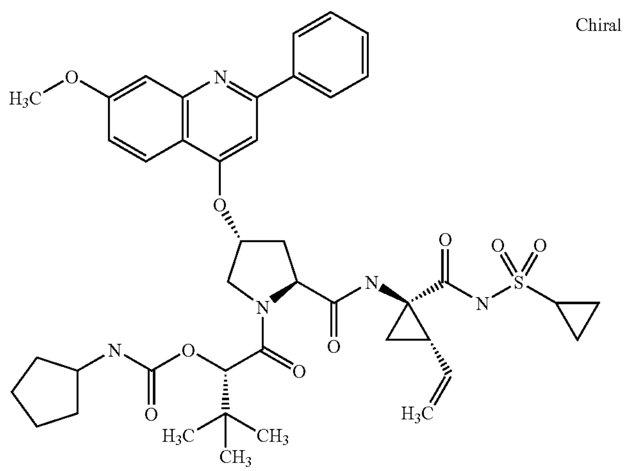 | Chiral | C | C |
| Example 5, Compound 2 | 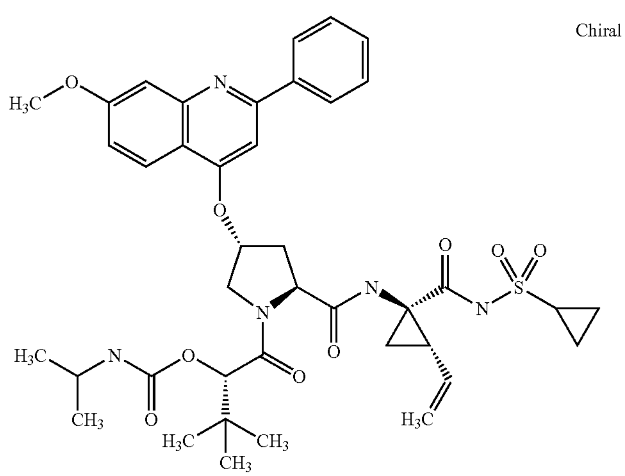 | Chiral | C | C |

TABLE 1-continued

Biological Data for Representative Compounds

| Example | Structure | | IC50 Range | EC50 Range |
|---|---|---|---|---|
| Example 5, Compound 4 | 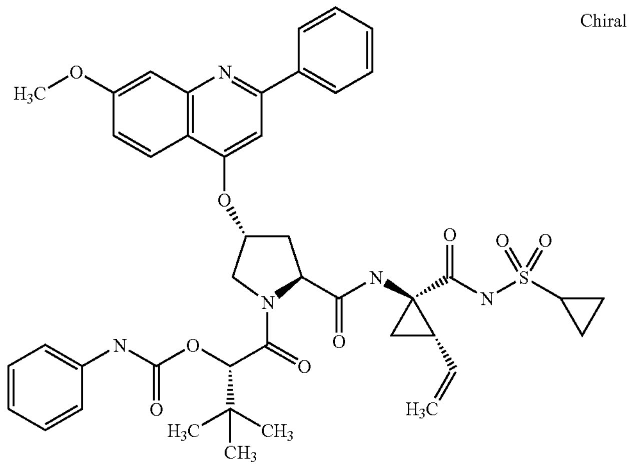 | Chiral | C | C |
| Example 5, Compound 7 | 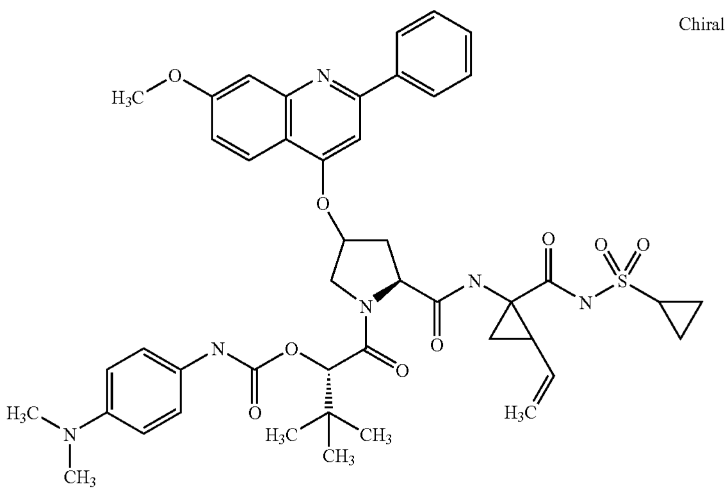 | Chiral | B | B |
| Example 5, Compound 5 | 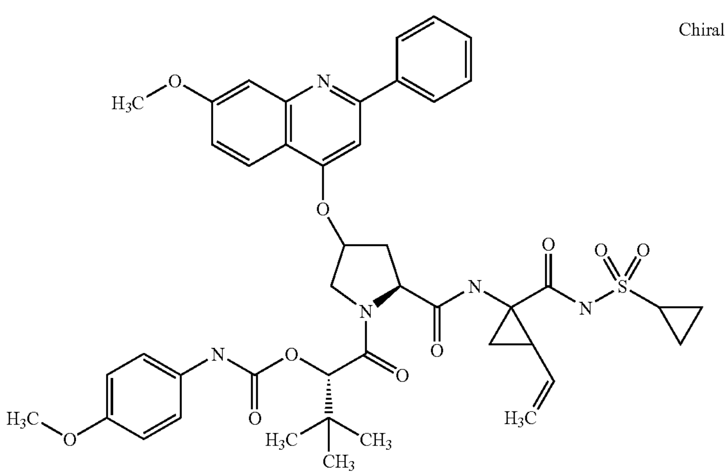 | Chiral | B | B |

TABLE 1-continued

Biological Data for Representative Compounds

| Example | Structure | | IC50 Range | EC50 Range |
|---|---|---|---|---|
| Example 5, Compound 6 | (chemical structure) | Chiral | B | B |
| Example 23 | (chemical structure) | Chiral | C | B |
| Example 9 | (chemical structure) | Chiral | B | B |

TABLE 1-continued

Biological Data for Representative Compounds

| Example | Structure | IC50 Range | EC50 Range |
|---|---|---|---|
| Example 24 | Chiral | B | B |
| Example 25 | Chiral | B | B |
| Example 26 | Chiral | B | B |

TABLE 1-continued
Biological Data for Representative Compounds
| Example | Structure | | IC50 Range | EC50 Range |
|---|---|---|---|---|
| Example 27 | 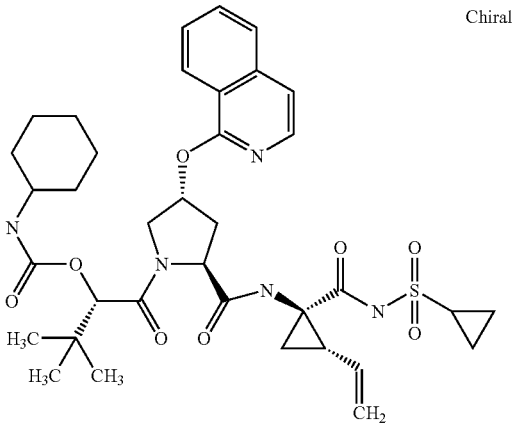 | Chiral | C | B |
| Example 28 | 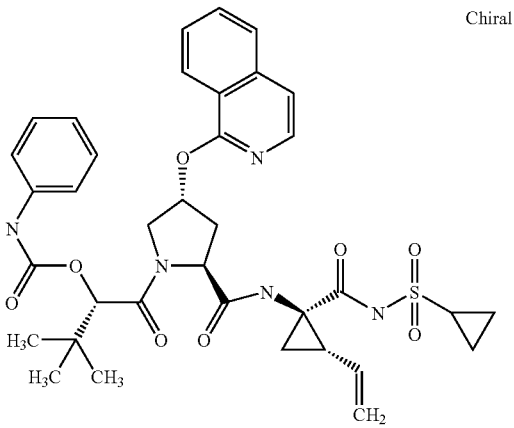 | Chiral | B | B |
| Example 29 | 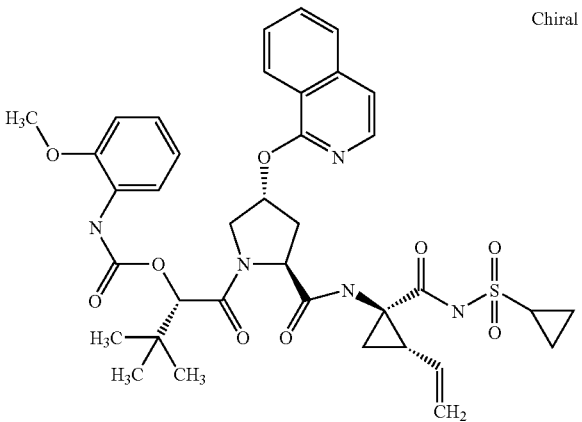 | Chiral | B | B |

TABLE 1-continued

Biological Data for Representative Compounds

| Example | Structure | IC50 Range | EC50 Range |
|---|---|---|---|
| Example 30 | Chiral | B | B |
| Example 31 | Chiral | B | B |
| Example 32 | Chiral | B | B |

TABLE 1-continued

Biological Data for Representative Compounds

| Example | Structure | | IC50 Range | EC50 Range |
|---|---|---|---|---|
| Example 33 | | Chiral | B | B |
| Example 50 Compound 50 | | Chiral | B | B |
| Example 51 Compound 51 | | Chiral | C | B |

TABLE 1-continued

Biological Data for Representative Compounds

| Example | Structure | | IC50 Range | EC50 Range |
|---|---|---|---|---|
| Example 52 Compound 52 | 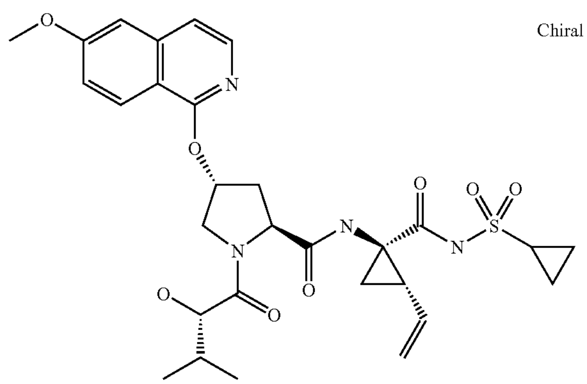 | Chiral | B | A |
| Example 53 Compound 53 | 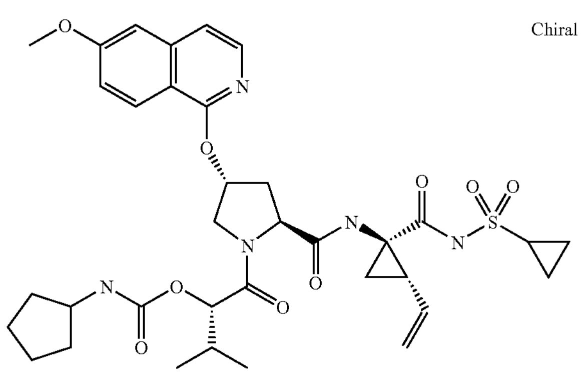 | Chiral | A | A |
| Example 54 Compound 54 | 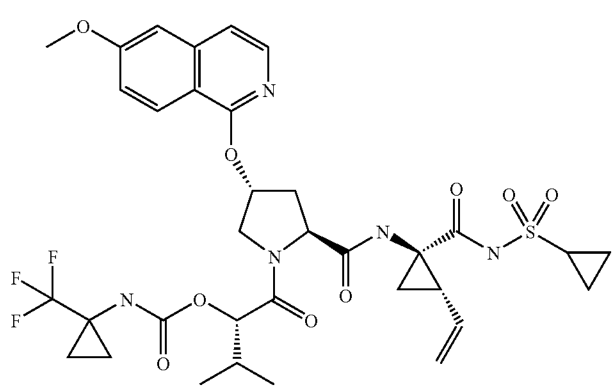 | | B | B |

TABLE 1-continued

Biological Data for Representative Compounds

| Example | Structure | | IC50 Range | EC50 Range |
|---|---|---|---|---|
| Example 55 Compound 55 | | Chiral | C | B |
| Example 56 Compound 56 | | Chiral | C | B |
| Example 57 Compound 57 | | Chiral | B | B |

TABLE 1-continued
Biological Data for Representative Compounds
| Example | Structure | | IC50 Range | EC50 Range |
|---|---|---|---|---|
| Example 58 Compound 58 | 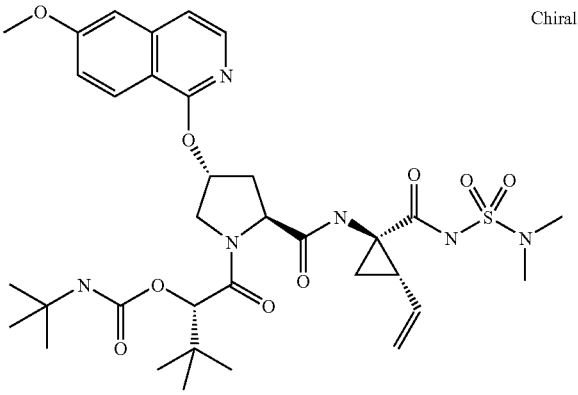 | Chiral | C | B |
| Example 59 Compound 59 | 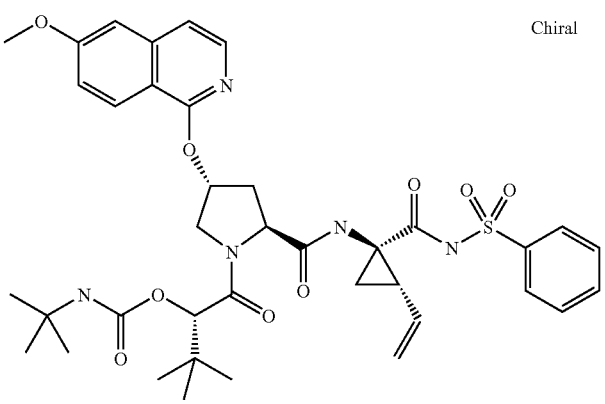 | Chiral | B | B |
| Example 60 Compound 60 | 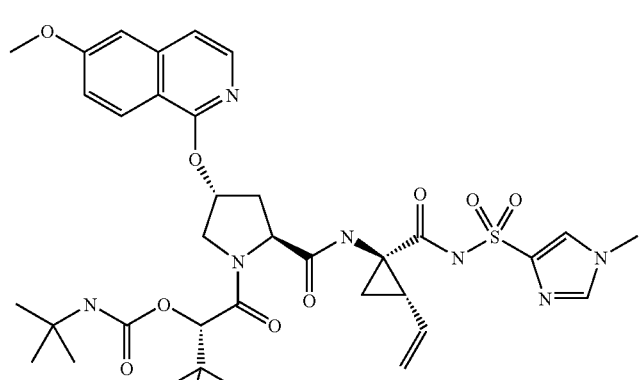 | | A | A |

TABLE 1-continued

Biological Data for Representative Compounds

| Example | Structure | | IC50 Range | EC50 Range |
|---|---|---|---|---|
| Example 61 Compound 61 | | Chiral | B | B |
| Example 62 Compound 62 | | Chiral | B | B |
| Example 63 Compound 63 | | Chiral | C | B |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

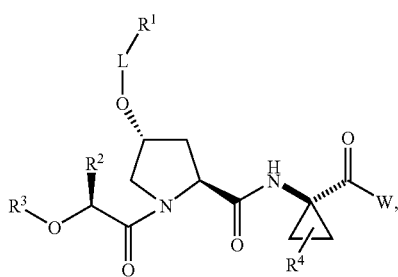

or a pharmaceutically acceptable salt thereof, wherein

L is absent or —C(O)—;

$R^1$ is heteroaryl or heterocyclyl wherein the heteroaryl and heterocyclyl are optionally substituted with one, two, three, four, five, or six substituents independently selected from alkoxy, alkoxycarbonyl, alkoxycarbonyloxy, alkyl, alkylsulfanyl, aryl, arylalkoxy, carboxy, cyano, cycloalkyl, halo, haloalkoxy, haloalkyl, heteroaryloxy, heteroaryl, heteroarylcarbonyl, heterocyclyl, hydroxy, mercapto, —$NR^aR^b$, ($NR^aR^b$)alkyl, and ($NR^cR^d$)carbonyl;

$R^2$ is selected from hydrogen, alkenyl, alkoxyalkyl, alkoxycarbonylalkyl, alkyl, alkylaminoalkyl, aminoalkyl, aryl, arylalkyl, cycloalkyl, (cycloalkyl)alkyl, dialkylaminoalkyl, haloalkoxyalkyl, haloalkyl, heteroaryl, heteroarylalkyl, heterocyclyl, and heterocyclylalkyl;

$R^3$ is selected from hydrogen and $R^5$—NH—C(O)—;

$R^4$ is selected from hydrogen, alkenyl, alkyl, cycloalkyl, haloalkenyl, and haloalkyl;

$R^5$ is selected from alkyl, aryl, arylalkyl, carboxyalkyl, cycloalkyl, (cycloalkyl)alkyl, haloalkoxyalkyl, haloalkyl, heteroaryl, heteroarylalkyl, heterocyclyl, and heterocyclylalkyl;

one of $R^a$ and $R^b$ is selected from hydrogen, alkoxycarbonyl, alkyl, alkylcarbonyl, alkylsulfonyl, arylalkyl, arylcarbonyl, arylsulfonyl, cycloalkyl, formyl, and ($NR^cR^d$)carbonyl and the other is selected from hydrogen, alkyl, and cycloalkyl;

$R^c$ and $R^d$ are each independently selected from hydrogen and alkyl; and

W is selected from hydroxy and —NH—$SO_n$—$R^6$, wherein n is 1 or 2 and $R^6$ is selected from alkyl, aryl, cycloalkyl, (cycloalkyl)alkyl, heteroaryl, heterocyclyl, and —$NR^aR^b$.

2. The compound of claim 1 wherein $R^3$ is hydrogen.

3. The compound of claim 1 wherein $R^3$ is $R^5$—NH—C(O)—.

4. The compound of claim 3 wherein W is —NH—$SO_n$—$R^6$.

5. The compound of claim 4 wherein L is —C(O)—.

6. The compound of claim 5 wherein $R^1$ is

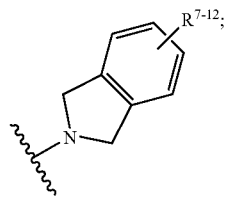

wherein $R^7$, $R^8$, $R^9$, $R^{10}$, $R^{11}$, and $R^{12}$ are independently selected from hydrogen, alkoxy, alkoxycarbonyl, alkoxycarbonyloxy, alkyl, alkylsulfanyl, aryl, arylalkoxy, carboxy, cyano, cycloalkyl, halo, haloalkoxy, haloalkyl, heteroaryloxy, heteroaryl, heteroarylcarbonyl, heterocyclyl, hydroxy, mercapto, —$NR^aR^b$, ($NR^aR^b$)alkyl, and ($NR^cR^d$)carbonyl.

7. The compound of claim 6 wherein one of $R^7$, $R^8$, $R^9$, $R^{10}$, $R^{11}$, and $R^{12}$ is halo an the rest are hydrogen.

8. The compound of claim 4 wherein L is absent.

9. The compound of claim 8 wherein $R^1$ is

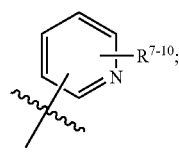

wherein $R^7$, $R^8$, $R^9$, a-d $R^{10}$ are independently selected from hydrogen, alkoxy, alkoxycarbonyl, alkoxycarbonyloxy, alkyl, alkylsulfanyl, aryl, arylalkoxy, carboxy, cyano, cycloalkyl, halo, haloalkoxy, haloalkyl, heteroaryloxy, heteroaryl, heteroarylcarbonyl, heterocyclyl, hydroxy, mercapto, —$NR^aR^b$, ($NR^aR^b$)alkyl, and ($NR^cR^d$)carbonyl.

10. The compound of claim 8 wherein $R^1$ is

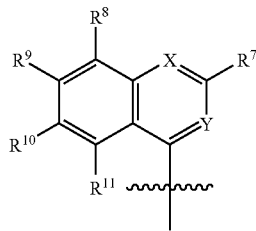

wherein

X is selected from N and $CR^{12}$;

Y is selected from N and CH; and $R^7$, $R^8$, $R^9$, $R^{10}$, $R^{11}$ and $R^{12}$ are independently selected from hydrogen, alkoxy, alkoxycarbonyl, alkoxycarbonyloxy, alkyl, alkylsulfanyl, aryl, arylalkoxy, carboxy, cyano, cycloalkyl, halo, haloalkoxy, haloalkyl, heteroaryloxy, heteroaryl, heteroarylcarbonyl, heterocyclyl, hydroxy, mercapto, —$NR^aR^b$, ($NR^aR^b$)alkyl, and ($NR^cR^d$)carbonyl.

11. A compound of formula (II)

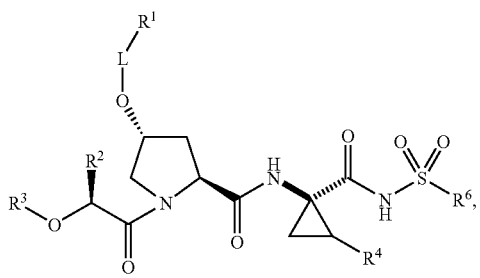

(II)

or a pharmaceutically acceptable salt thereof, wherein R$^1$ is selected from

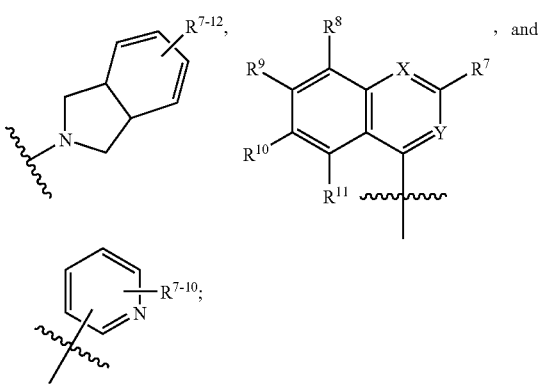

, and

L is absent or —C(O)—;
X is selected from N and CR$^{12}$;
Y is selected from N and CH; and
R$^7$, R$^8$, R$^9$, R$^{10}$, R$^{11}$ and R$^{12}$ are each independently selected from hydrogen, alkoxy, aryl, halo, and heteroaryl;
R$^2$ is selected from alkoxyalkyl, alkyl, aryl, cycloalkyl, (cycloalkyl)alkyl, and heteroarylalkyl;
R$^3$ is selected from hydrogen and R$^5$—NH—C(O)—;
R$^4$ is alkenyl or alkyl;
R$^5$ is selected from alkenyl, alkyl, aryl, cycloalkyl, and heteroarylalkyl;

R$^6$ is selected from aryl, cycloalkyl, heteroaryl, and —NR$^a$R$^b$; and
R$^a$ and R$^b$ are alkyl.

12. The compound of claim 11 wherein R$^3$ is hydrogen.
13. The compound of claim 11 wherein R$^3$ is R$^5$—NH—C(O)—.
14. A composition comprising a compound of claim 1 and a pharmaceutically acceptable carrier.
15. The composition according to the claim 14 further comprising an interferon and ribavirin.
16. The composition according to claim 14 further comprising a second compound having anti-HCV activity.
17. The composition according to claim 16 wherein the second compound having anti-HCV activity is an interferon.
18. The composition according to claim 17 wherein the interferon is selected from interferon alpha 2B, pegylated interferon alpha, consensus interferon, interferon alpha 2A, and lymphoblastiod interferon tau.
19. The composition according to claim 16 wherein the second compound having anti-HCV activity is selected from interleukin 2, interleukin 6, interleukin 12, Imiqimod, ribavirin, an inosine 5'-monophospate dehydrogenase inhibitor, amantadine, and rimantadine.
20. A method of inhibiting the function of HCV serine protease comprising contacting the HCV serine protease with a compound of claim 1.
21. A method of treating an HCV infection in a patient, comprising administering to the patient a therapeutically effective amount of a compound of claim 1.
22. The method of claim 21 wherein the compound is effective to inhibit the function of the HCV serine protease.
23. The method of claim 22 further comprising administering a second compound having anti-HCV activity prior to, after or simultaneously with the compound of claim 1.
24. The method of claim 23 wherein the second compound having anti-HCV activity is an interferon.
25. The method of claim 24 wherein the interferon is selected from interferon alpha 2B, pegylated interferon alpha, consensus interferon, interferon alpha 2A, and lymphoblastiod interferon tau.
26. The method of claim 23 wherein the second compound having anti-HCV activity is selected from interleukin 2, interleukin 6, interleukin 12, Imiqimod, ribavirin, an inosine 5'-monophospate dehydrogenase inhibitor, amantadine, and rimantadine.

* * * * *

UNITED STATES PATENT AND TRADEMARK OFFICE
CERTIFICATE OF CORRECTION

PATENT NO. : 7,323,447 B2  Page 1 of 1
APPLICATION NO. : 11/348721
DATED : January 29, 2008
INVENTOR(S) : Ny Sin et al.

It is certified that error appears in the above-identified patent and that said Letters Patent is hereby corrected as shown below:

Column 5, line 40 and Column 6, line 7, "Imiqimod" should be --Imiquimod--.

Column 202, Claim 9, line 37, "a-d" should be --and--.

Column 204, Claim 19, line 21 and Claim 26, line 44, "Imiqimod" should be --Imiquimod--.

Signed and Sealed this

Twenty-ninth Day of July, 2008

JON W. DUDAS
*Director of the United States Patent and Trademark Office*